US011781183B2

(12) United States Patent
Sadeh et al.

(10) Patent No.: US 11,781,183 B2
(45) Date of Patent: Oct. 10, 2023

(54) DIAGNOSTIC USE OF CELL FREE DNA CHROMATIN IMMUNOPRECIPITATION

(71) Applicant: YISSUM RESEARCH DEVELOPMENT COMPANY OF THE HEBREW UNIVERSITY OF JERUSALEM LTD., Jerusalem (IL)

(72) Inventors: Ronen Sadeh, Tel Aviv (IL); Nir Friedman, Mevaseret Zion (IL); Alon Appleboim, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 34 days.

(21) Appl. No.: 16/980,497

(22) PCT Filed: Mar. 13, 2019

(86) PCT No.: PCT/IL2019/050281
§ 371 (c)(1),
(2) Date: Sep. 14, 2020

(87) PCT Pub. No.: WO2019/175876
PCT Pub. Date: Sep. 19, 2019

(65) Prior Publication Data
US 2021/0024994 A1      Jan. 28, 2021

Related U.S. Application Data
(60) Provisional application No. 62/642,158, filed on Mar. 13, 2018, provisional application No. 62/667,528, filed on May 6, 2018.

(51) Int. Cl.
C12Q 1/68        (2018.01)
C12Q 1/6869      (2018.01)
C12N 15/10       (2006.01)

(52) U.S. Cl.
CPC ....... *C12Q 1/6869* (2013.01); *C12N 15/1006* (2013.01)

(58) Field of Classification Search
CPC ...................................................... C12Q 1/68
(Continued)

(56) References Cited

U.S. PATENT DOCUMENTS

2001/0053533 A1* 12/2001 Aguzzi .................. A61P 25/00
                                                              436/526
2013/0017958 A1*  1/2013 Benz .................... G01N 33/574
                                                              506/2
(Continued)

FOREIGN PATENT DOCUMENTS

EP       1668368 B1    10/2008
WO    WO-0214550 A2 *   2/2002  .......... C12N 15/1034
(Continued)

OTHER PUBLICATIONS

Ren et al, Use of chromatin immunoprecipitation assays in genome-wide location analysis of mammalian transcription factors, Methods Enzymol. 2004;376:304-15. doi: 10.1016/50076-6879(03)76020-0.*

(Continued)

*Primary Examiner* — Aaron A Priest
(74) *Attorney, Agent, or Firm* — The Roy Gross Law Firm, LLC; Roy Gross

(57) ABSTRACT

Methods of determining the origin of cell free DNA (cfDNA), for detecting death of a cell type or tissue in a subject, for determining a cellular state of a cell as it died, and combinations thereof, are provided. As are computer program products for doing same.

18 Claims, 49 Drawing Sheets

(58) Field of Classification Search
USPC .......................................................... 435/6
See application file for complete search history.

(56) References Cited

U.S. PATENT DOCUMENTS

| | | | | |
|---|---|---|---|---|
| 2013/0310260 | A1* | 11/2013 | Kim | G16B 30/10 |
| | | | | 702/19 |
| 2014/0322719 | A1* | 10/2014 | Micallef | C12Q 1/6804 |
| | | | | 435/6.19 |
| 2015/0087529 | A1 | 3/2015 | Lo | |
| 2016/0145685 | A1* | 5/2016 | Jensen | C12Q 1/6811 |
| | | | | 506/16 |
| 2017/0211143 | A1* | 7/2017 | Shendure | G16B 40/10 |
| 2018/0024141 | A1* | 1/2018 | Micallef | G01N 33/6875 |
| | | | | 435/6.14 |
| 2019/0064184 | A1* | 2/2019 | Eccleston | G01N 33/6875 |
| 2020/0143907 | A1* | 5/2020 | Engreitz | C12N 15/1034 |
| 2021/0074378 | A1* | 3/2021 | Zhou | G16B 15/30 |

FOREIGN PATENT DOCUMENTS

| | | | | |
|---|---|---|---|---|
| WO | 03/070894 | † | 8/2003 | |
| WO | 2003070894 | A2 | 8/2003 | |
| WO | WO-03070894 | A2 * | 8/2003 | .......... C12Q 1/6809 |
| WO | 2005019826 | † | 3/2005 | |
| WO | 2005019826 | A1 | 3/2005 | |
| WO | WO-2005019826 | A1 * | 3/2005 | .......... G01N 33/564 |
| WO | WO-2006095041 | A1 * | 9/2006 | .............. A61P 25/28 |
| WO | WO-2010145035 | A1 * | 12/2010 | .......... C12Q 1/6886 |
| WO | 2016067029 | A1 | 5/2016 | |
| WO | 2017068371 | A1 | 4/2017 | |
| WO | WO-2017195153 | A1 * | 11/2017 | .......... A61K 31/337 |

OTHER PUBLICATIONS

Lara-Astiaso et al, Chromatin state dynamics during blood formation, Science. Aug. 22, 2014; 345(6199): 943-949.*

Gezer U, Ustek D, Yörüker EE, Cakiris A, Abaci N, Leszinski G, Dalay N, Holdenrieder S. Characterization of H3K9me3- and H4K20me3-associated nucleosomal circulating DNA by high-throughput sequencing in colorectal cancer. Tumour Biol. Feb. 2013;34(1):329-36. doi: 10.1007/s13277-012-0554-5. Epub Oct. 20, 2012. PMID: 23086575.

Lehmann-Werman, Roni et al. "Identification of tissue-specific cell death using methylation patterns of circulating DNA." Proceedings of the National Academy of Sciences of the United States of America vol. 113,13 (2016): E1826-34. doi:10.1073/pnas.1519286113 Epub Mar. 14, 2016. PMID: 26976580; PMCID: PMC4822610.

Bauden M, Pamart D, Ansari D, Herzog M, Eccleston M, Micallef J, Andersson B, Andersson R. Circulating nucleosomes as epigenetic biomarkers in pancreatic cancer. Clin Epigenetics. Oct. 7, 2015;7:106. doi: 10.1186/s13148-015-0139-4. PMID: 26451166; PMCID: PMC4597435.

McAnena P, Brown JA, Kerin MJ. Circulating Nucleosomes and Nucleosome Modifications as Biomarkers in Cancer. Cancers (Basel). Jan. 8, 2017;9(1):5. doi: 10.3390/cancers9010005. PMID: 28075351; PMCID: PMC5295776.

Deligezer U, Akisik EE, Erten N, Dalay N. Sequence-specific histone methylation is detectable on circulating nucleosomes in plasma. Clin Chem. Jul. 2008;54(7):1125-31. doi: 10.1373/clinchem. 2007.101766. Epub May 16, 2008. PMID: 18487283.

Snyder MW, Kircher M, Hill AJ, Daza RM, Shendure J. Cell-free DNA Comprises an In Vivo Nucleosome Footprint that Informs Its Tissues-Of-Origin. Cell. Jan. 14, 2016;164(1-2):57-68. doi: 10.1016/j.cell.2015.11.050. PMID: 26771485; PMCID: PMC4715266.

Rasmussen L, Herzog M, Rømer E, Micallef J, Bulut O, Wilhelmsen M, Christensen IJ, Nielsen HJ. Pre-analytical variables of circulating cell-free nucleosomes containing 5-methylcytosine DNA or histone modification H3K9Me3. Scand J Clin Lab Invest. Oct. 2016;76(6):448-53. doi: 10.1080/00365513.2016 1190862. Epub Jun. 13, 2016. PMID: 27291394.

Sadeh R, Launer-Wachs R, Wandel H, Rahat A, Friedman N. Elucidating Combinatorial Chromatin States at Single-Nucleosome Resolution. Mol Cell. Sep. 15, 2016;63(6):1080-8. doi: 10.1016/j.molcel.2016.07.023. Epub Aug. 2, 2016. PMID: 27496019; PMCID: PMC5031555.

De Vlaminck I, Valantine HA, Snyder TM, Strehl C, Cohen G, Luikart H, Neff NF, Okamoto J, Bernstein D, Weisshaar D, Quake SR, Khush KK. Circulating cell-free DNA enables noninvasive diagnosis of heart transplant rejection. Sci Transl Med. Jun. 18, 2014;6(241):241ra77. doi: 10.1126/scitranslmed.3007803. PMID: 24944192; PMCID PMC4326260.

Schwarzenbach H, Hoon DS, Pantel K. Cell-free nucleic acids as biomarkers in cancer patients. Nat Rev Cancer. Jun. 2011;11(6):426-37. doi: 10.1038/nrc3066. Epub May 12, 2011. PMID: 21562580.

Sun K, Jiang P, Chan KC, Wong J, Cheng YK, Liang RH, Chan WK, Ma ES, Chan SL, Cheng SH, Chan RW, Tong YK, Ng SS, Wong RS, Hui DS, Leung TN, Leung TY, Lai PB, Chiu RW, Lo YM. Plasma DNA tissue mapping by genome-wide methylation sequencing for noninvasive prenatal, cancer, and transplantation assessments. Proc Natl Acad Sci U S A. Oct. 6, 2015;112(40):E5503-12. doi: 10.1073/pnas.1508736112. Epub Sep. 21, 2015. PMID: 26392541; PMCID: PMC4603482.

Lu JL, Liang ZY. Circulating free DNA in the era of precision oncology: Pre- and post-analytical concerns. Chronic Dis Transl Med. Dec. 22, 2016;2(4):223-230. doi: 10.1016/j.cdtm.2016.12.001. PMID: 29063046; PMCID: PMC5643833.

Wan JCM, Massie C, Garcia-Corbacho J, Mouliere F, Brenton JD, Caldas C, Pacey S, Baird R, Rosenfeld N. Liquid biopsies come of age: towards implementation of circulating tumour DNA. Nat Rev Cancer. Apr. 2017;17(4):223-238. doi: 10.1038/nrc.2017.7. Epub Feb. 24, 2017. PMID: 28233803.

Dwivedi DJ, Toltl LJ, Swystun LL, Pogue J, Liaw KL, Weitz JI, Cook DJ, Fox-Robichaud AE, Liaw PC; Canadian Critical Care Translational Biology Group. Prognostic utility and characterization of cell-free DNA in patients with severe sepsis. Crit Care. Aug. 13, 2012;16(4):R151. doi: 10.1186/cc11466. PMID: 22889177; PMCID: PMC3580740.

Ulz P, Thallinger GG, Auer M, Graf R, Kashofer K, Jahn SW, Abete L, Pristauz G, Petru E, Geigl JB, Heitzer E, Speicher MR. Inferring expressed genes by whole-genome sequencing of plasma DNA. Nat Genet. Oct. 2016;48(10):1273-8. doi: 10.1038/ng.3648. Epub Aug. 29, 2016. PMID: 27571261.

Guo S, Diep D, Plongthongkum N, Fung HL, Zhang K, Zhang K. Identification of methylation haplotype blocks aids in deconvolution of heterogeneous tissue samples and tumor tissue-of-origin mapping from plasma DNA. Nat Genet. Apr. 2017;49(4):635-642. doi: 10.1038/ng.3805. Epub Mar. 6, 2017. PMID: 28263317; PMCID: PMC5374016.

Reinius LE, Acevedo N, Joerink M, Pershagen G, Dahlén SE, Greco D, Söderhäll C, Scheynius A, Kere J. Differential DNA methylation in purified human blood cells: implications for cell lineage and studies on disease susceptibility. PLoS One. 2012;7(7):e41361. doi: 10.1371/journal.pone.0041361. Epub Jul. 25, 2012. PMID: 22848472; PMCID: PMC3405143.

Allum F, et al. Characterization of functional methylomes by next-generation capture sequencing identifies novel disease-associated variants. Nat Commun. May 29, 2015;6:7211. doi: 10.1038/ncomms8211. Erratum in: Nat Commun. 2015;6:8016. PMID: 26021296; PMCID: PMC4544751.

Visel A, Blow MJ, Li Z, Zhang T, Akiyama JA, Holt A, Plajzer-Frick I, Shoukry M, Wright C, Chen F, Afzal V, Ren B, Rubin EM, Pennacchio LA. ChIP-seq accurately predicts tissue-specific activity of enhancers. Nature. Feb. 12, 2009;457(7231):854-8. doi: 10.1038/nature07730. PMID: 19212405; PMCID: PMC2745234.

Gezer U, Yörüker EE, Keskin M, Kulle CB, Dharuman Y, Holdenrieder S. Histone Methylation Marks on Circulating Nucleosomes as Novel Blood-Based Biomarker in Colorectal Cancer. Int J Mol Sci. Dec. 11, 2015;16(12):29654-62. doi: 10.3390/ijms161226180. PMID: 26690425; PMCID: PMC4691123.

Barault L, et al. Discovery of methylated circulating DNA biomarkers for comprehensive non-invasive monitoring of treatment response

(56) References Cited

OTHER PUBLICATIONS in metastatic colorectal cancer. Gut. Nov. 2018;67(11):1995-2005. doi: 10.1136/gutjnl-2016-313372. Epub Oct. 5, 2017. PMID: 28982739; PMCID: PMC5897187.

Cree IA, Uttley L, Buckley Woods H, Kikuchi H, Reiman A, Harnan S, Whiteman BL, Philips ST, Messenger M, Cox A, Teare D, Sheils O, Shaw J; UK Early Cancer Detection Consortium. The evidence base for circulating tumour DNA blood-based biomarkers for the early detection of cancer: a systematic mapping review. BMC Cancer. Oct. 23, 2017;17(1):697. doi: 10.1186/s12885-017-3693-7. PMID: 29061138; PMCID: PMC5654013.

Lokk K, Modhukur V, Rajashekar B, Martens K, Mägi R, Kolde R, Koltsina M, Nilsson TK, Vilo J, Salumets A, Tõnisson N. DNA methylome profiling of human tissues identifies global and tissue-specific methylation patterns. Genome Biol. Apr. 1, 2014;15(4):r54. doi: 10.1186/gb-2014-15-4-r54. Erratum in: Genome Biol. Nov. 1, 2016;17 (1):224. PMID: 24690455; PMCID: PMC4053947.

Ziller MJ, Gu H, Müller F, Donaghey J, Tsai LT, Kohlbacher O, De Jager PL, Rosen ED, Bennett DA, Bernstein BE, Gnirke A, Meissner A. Charting a dynamic DNA methylation landscape of the human genome. Nature. Aug. 22, 2013;500(7463):477-81. doi: 10.1038/nature12433. Epub Aug. 7, 2013. PMID: 23925113; PMCID: PMC3821869.

Cheng J, Tang Q, Cao X, Burwinkel B. Cell-Free Circulating DNA Integrity Based on Peripheral Blood as a Biomarker for Diagnosis of Cancer: A Systematic Review. Cancer Epidemiol Biomarkers Prev. Nov. 2017;26(11):1595-1602. doi: 10.1158/1055-9965.EPI-17-0502. Epub Aug. 22, 2017. PMID: 28830871.

Moss J, Magenheim J, Neiman D, Zemmour H, Loyfer N, Korach A, Samet Y, Maoz M, Druid H, Arner P, Fu KY, Kiss F, Spalding KL, Landesberg G, Zick A, Grinshpun A, Shapiro AMJ, Grompe M, Wittenberg AD, Glaser B, Shemer R, Kaplan T, Dor Y. Comprehensive human cell-type methylation atlas reveals origins of circulating cell-free DNA in health and disease. Nat Commun. Nov. 29, 2018;9(1):5068. doi: 10.1038/s41467-018-07466-6. PMID: 30498206; PMCID: PMC6265251.

International Search Report for PCT/IL2019/050281 Completed Jul. 15, 2019; dated Sep. 17, 2019 6 pages.

Written Opinion for PCT/IL2019/050281 Completed Jul. 15, 2019; dated Sep. 17, 2019 9 pages.

IPRP for PCT/IL2019/050281 Completed Jul. 15, 2019; dated Sep. 17, 2019 6 pages.

\* cited by examiner
† cited by third party

Coverage (normalized read counts / 2kb window)

H3K4me1

H3K4me3

Coverage (normalized read counts / 2kb window)

DIAGNOSTIC USE OF CELL FREE DNA CHROMATIN IMMUNOPRECIPITATION

CROSS REFERENCE TO RELATED APPLICATIONS

This application is a National Phase of PCT Patent Application No. PCT/IL2019/050281 having International filing date of Mar. 13, 2019, which claims the benefit of priority of U.S. Provisional Patent Application Nos. 62/642,158, filed Mar. 13, 2018, and 62/667,528, filed May 6, 2018, the contents of which are all incorporated herein by reference in their entirety.

FIELD OF INVENTION

The present invention is in the field of cell free DNA-protein complex analysis.

BACKGROUND OF THE INVENTION

Upon cell death (via apoptosis or necrosis) short DNA fragments are released to the blood plasma. These are often termed circulating cell-free DNA (cfDNA) or circulating tumor DNA (ctDNA, if originating from tumor cells). The presence of cfDNA has been recognized for decades, with typical length of cfDNA fragments around multiples of ~166 bp—the length of mononucleosomal DNA (~146 bp), with some additional linker DNA. The plasma of healthy people contains the equivalent of ~1000 genomes per ml, with up to 100 times more cfDNA present in many pathologies (e.g. cancer) and some physiological conditions (e.g. following exercise). These fragments are short-lived, with an estimated half-life of less than an hour, making them ideal biomarkers for monitoring physiological and pathological processes in a noninvasive manner. Use of cfDNA as a diagnostic tool has greatly expanded in recent years. For example, next-generation sequencing of fetal cfDNA in maternal blood is now used for non-invasive prenatal screening/diagnosis of chromosomal abnormalities and parental derived mutations. Because of the very low amount of cfDNA present in a blood sample, most current cfDNA diagnostic methods rely on mutations with the cfDNA to distinguish it from cfDNA from healthy tissues and blood cells. Indeed, white blood cell cfDNA is by far the greatest contributor to the total cfDNA pool and can make cfDNA diagnosis of conditions from other tissues difficult.

Most current cfDNA-based methods rely on detecting genomic alterations in cfDNA to quantify the contribution of cfDNA from cells with altered genomic sequence, such as fetus, a transplant, or mutated genes in tumors. Thus, these methods are biased towards a set of pre-selected genes and are blind to events that involve turnover and death of cells whose genome is identical to the host genome. More recent approaches leverage epigenetic information in cell free DNA. Extremely deep sequencing of total cfDNA can provide data that reflect tissue of origin and gene expression. However, it relies on detecting changes in coverage over target regions, with a signal of source tissue imposed on the background of normal cells (e.g., detection of an event causing nucleosome depletion in 10% of the cells requires 90% occupancy to be distinguished from 100% occupancy). Thus, such methods avoid sampling noise by using extremely deep sequencing coverage (100 s of million reads per sample). Even with such sequencing depth, there is a prohibitive harsh detection limit for events in rare subsets of cells. A promising alternative is assaying DNA CpG methylation along the sequence to identify cell of origin. DNA methylation serves as a stable epigenetic memory and is mostly unchanged after differentiation. As such, it is highly informative regarding cell lineage, but much less about transient changes in expression, and cells originating from a close or same lineage. Moreover, unbiased analysis of DNA methylation requires high sequencing depth since most CpGs are methylated.

A method that allows for accurately determining the origin of cfDNA, as well as providing information on the molecular events that occurred in the cell close to the time of cell death would allow not just for early diagnosis of conditions that were unknown to the doctor or patient, but also may help in tailoring a treatment to newly discovered malady.

SUMMARY OF THE INVENTION

The present invention provides methods of determining the origin of cell free DNA (cfDNA), for detecting death of a cell type or tissue, for determining a cellular state of a cell in a subject, and combinations thereof, by sequencing cfDNA isolated by extracting proteins and modified proteins bound to that cfDNA. Computer program products for doing same are also provided.

According to a first aspect, there is provided a method of determining a cellular state, tissue of origin, cell type or a combination thereof of a cell that released its DNA, comprising:
a. providing a sample, wherein the sample comprises cell free DNA (cfDNA);
b. contacting the sample with at least one reagent that binds to a DNA-associated protein;
c. isolating the reagent and any thereto bound proteins and cfDNA;
d. sequencing the isolated cfDNA; and
e. designating a cfDNA molecule comprising a DNA sequence of an informative genomic location as originating from a cell in a cellular state, originating from a tissue, originative from a cell type or a combination thereof, wherein association of the DNA-associated protein with the informative genomic location is indicative of the cellular state, tissue of origin, cell type or combination thereof in the cell that released the cfDNA;

thereby determining a cellular state, tissue of origin cell type or combination thereof of a cell that released its DNA.

According to another aspect, there is provided a computer program product for determining a cell or tissue of origin of cell free DNA (cfDNA), comprising a non-transitory computer-readable storage medium having program code embodied thereon, the program code executable by at least one hardware processor to
a. measure or access sequencing of cfDNA isolated with a reagent that binds a DNA-associated protein;
b. assign a cfDNA molecule from the cfDNA to a cell or tissue of origin by comparing a DNA sequence of the molecule to sequences associated with the DNA-associated protein in the cell type or tissue; and
c. provide an output regarding the cell or tissue of origin of cfDNA.

According to another aspect, there is provided a computer program product for determining a cellular state, tissue of origin, cell type or a combination thereof of a cell in a subject as the cell died, comprising a non-transitory computer-readable storage medium having program code embodied thereon, the program code executable by at least one hardware processor to
  a. measure or access sequencing of cfDNA from the subject isolated with a reagent that binds a DNA-associated protein;
  b. assign a cfDNA molecule from the cfDNA to a cellular state, tissue of origin, cell type or combination thereof by comparing a DNA sequence of the molecule to sequences associated with the DNA-associated protein in the cellular state, tissue, cell type or combination thereof; and
  c. provide an output regarding the cellular state, tissue of origin, cell type or combination thereof of a cell in the subject as the cell died.

According to another aspect, there is provided a solid support, comprising a capturing agent and a barcoding reagent.

According to another aspect, there is provided a method for multiplexing an assay on more than one molecule of interest in a single solution, the method comprising:
  a. capturing within the solution a first molecule of interest to a first solid support of the invention;
  b. capturing within the solution at least a second molecule of interest to a second solid support of the invention;
  c. attaching the first molecule of interest and a first barcode and at least the second molecule of interest and a second barcode;
  d. simultaneously performing the assay on the first and second molecules of interest, wherein the result of the assay on the first molecule of interest is identified by the first barcode and the result of the assay on the second molecule of interest is identified by the second barcode;
thereby multiplexing an assay on more than one molecule of interest in a single solution.

According to some embodiments, the sample is from a subject.

According to some embodiments, the cell that released its DNA is a dead cell and the method is for detecting death of at least one of:
  a. a cell type in a subject,
  b. a tissue in a subject, and
  c. a cell in a cellular state in a subject.

According to some embodiments, the cellular state is a disease state. According to some embodiments, the disease state is selected from bacteremia, cancer, pre-cancer, infection, neurodegenerative disease, tissue damage, cardiac disease, liver disease, inflammation, autoimmune disease, arthritis, liver inflammation, bowel inflammation, autoimmune disease, tissue damage from drug side effects, tissue necrosis, and diabetes. According to some embodiments, the disease state is selected from cardiac disease or damage, brain disease or damage, gastrointestinal disease or damage, cancer, bacteremia, infection and liver disease or damage.

According to some embodiments, at least 500 genomes of cfDNA are provided. According to some embodiments, the designating can be performed with as little as 0.1% of the cfDNA in the sample being from the cell type, the tissue, or the cellular state.

According to some embodiments, the reagent is selected from an antibody or antigen binding fragment thereof, a protein, or a small molecule.

According to some embodiments, the reagent is conjugated to a physical support.

According to some embodiments, the DNA-associated protein is selected from a histone, a high-mobility group (HMG) protein and a member of the transcriptional machinery. According to some embodiments, the histone is a histone variant and/or a modified histone. According to some embodiments, the histone variant is selected from Histone 3 monomethylated lysine 4 (H3K4me1), Histone 3 demethylated lysine 4 (H3K4me2), Histone 3 trimethylated lysine 36 (H3K36me3) and Histone 3 trimethylated lysine 4 (H3K4me3). According to some embodiments, the reagent is an anti-modified histone antibody or fragment thereof.

According to some embodiments, association of the DNA-associated protein with the genomic location is indicative of active transcription and the genomic location is within a tissue, cell type or cellular state specific gene or enhancer element or is at a disease-specific mutation. According to some embodiments, association of the DNA-associated protein with the genomic location is indicative of silenced transcription and the genomic location is within a repressor element, or a gene silenced in the tissue, cell-type or cellular state, or is at a disease-specific mutation.

According to some embodiments, the method of the invention further comprises performing steps a-d again using a reagent that binds to a second DNA-associated protein, and wherein the second DNA associated protein is different from the first DNA-associated protein.

According to some embodiments, the method of the invention comprises contacting the sample with at least 2 reagents, wherein each regent is bound to a physical support and the support comprises a short DNA tag unique to each reagent, wherein upon sequencing the isolated cfDNA the short DNA tag identifies the reagent that isolated the cfDNA.

According to some embodiments, the designating comprises comparing the sequenced cfDNA to at least 10 genomic locations with the greatest unique association of the DNA-associated protein in a tissue, cell type or cellular state, and wherein a cfDNA with a sequence that is the same as a DNA sequence within the at least 10 genomic locations is considered to be from the tissue, cell type or cellular state.

According to some embodiments, the DNA-associated protein is a marker of active transcription and the designating comprises comparing the sequenced cfDNA to a known transcriptional program of a tissue, cell type or cellular state, wherein a cfDNA with a sequence that is from a gene transcribed in the transcriptional program is from the tissue, cell type or cellular state.

According to some embodiments, the designating comprises comparing the sequenced cfDNA to a DNA-protein association atlas of at least 5 cell types or tissues, wherein the atlas comprises at least 10 genomic location with the greatest unique association of the DNA-associated protein in each of the 5 cell types or tissues, and wherein a cfDNA with a sequence that is the same as a DNA sequence within the at least 10 genomic locations is considered to be from the tissue or cell type.

According to some embodiments, the designating comprises comparing the sequenced cfDNA to a transcriptional program atlas of at least 5 transcriptional programs, wherein the atlas comprises at least one genomic location with the greatest unique association of the DNA-associated protein in each of the 5 transcriptional programs and wherein a cfDNA with a sequence that is the same as a DNA sequence within the at least one genomic location indicates activation of the transcriptional program.

According to some embodiments, the cellular state is selected from: hypoxia, inflammation, ER stress, mitochondrial stress, interferon response, quiescence, senescence, cycling, malignant, and calcium flux.

According to some embodiments, the informative genomic location is selected from a promoter, an enhancer element, a silencer element, a gene body and a disease-associated mutation.

According to some embodiments, the method of the invention is wherein:
a. the DNA-associated protein is a marker of active transcription and the disease associated mutation is within an oncogene or
b. the DNA-associated protein is a marker of silenced transcription and the disease associated mutation is within a tumor suppressor gene.

According to some embodiments, the method of the invention is for use in detecting a disease state in the subject.

According to some embodiments, the method of the invention is wherein the detecting a disease state comprises at least one of:
a. early detection of the disease state;
b. detection of residual metastatic disease; and
c. monitoring of disease progression with or without treatment.

According to some embodiments, the method of the invention further comprises treating the subject with a suitable treatment based on the cellular state, tissue of origin, cell type or a combination thereof of the cell that died in the subject.

According to some embodiments, the solid support is a magnetic or paramagnetic bead, or an agarose bead.

According to some embodiments, the capturing agent is a protein. According to some embodiments, the capturing protein is an antibody, or antigen binding fragment thereof.

According to some embodiments, the barcoding reagent is a short nucleic acid molecule. According to some embodiments, the nucleic acid molecule is between 5 and 30 nucleotides.

According to some embodiments, the capturing agent and barcoding reagent are conjugated to the solid support.

According to some embodiments, the molecule of interest is a protein or a nucleic acid molecule.

According to some embodiments, the assay is chromatin immunoprecipitation followed by sequencing (ChIP-Seq).

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description together with the drawings makes apparent to those skilled in the art how embodiments of the invention may be practiced.

DETAILED DESCRIPTION OF THE INVENTION

Figure 1A:
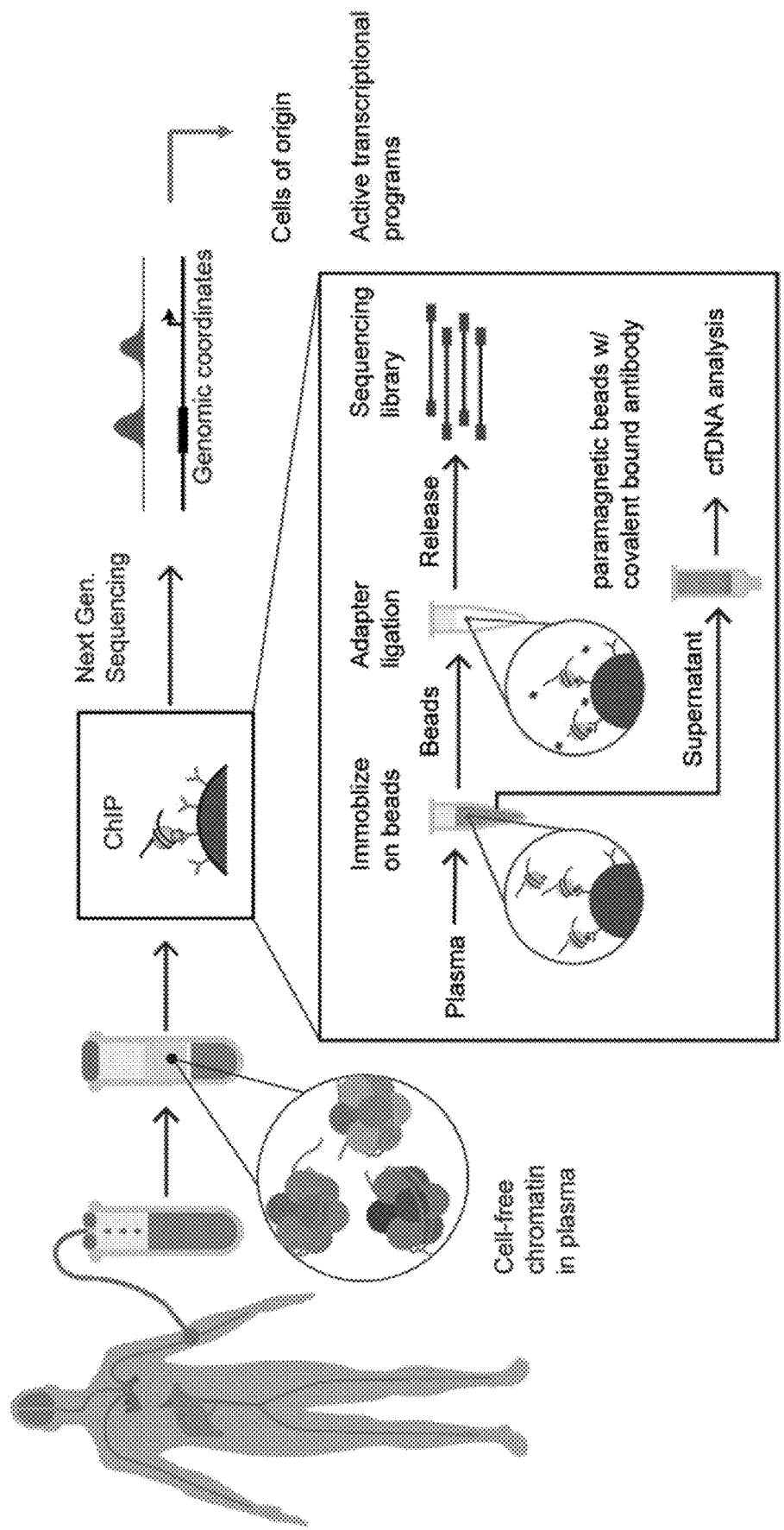
FIGS. 1A-I: (1A) Outline of the proposed method. Chromatin fragments from different cells in the body are released to the blood. These are immunoprecipitated, and sequenced. Interpretation of the resulting sequences informs of tissue-of-origin and gene activity program. Inset-cfChIP protocol, using antibody covalently bound to paramagnetic beads. Target fragments are immunoprecipitated directly from plasma. After removing the plasma, and washing the beads bound to target fragments, on-bead-ligation is used to add sequencing adapters (possibly with indexing barcodes) to the fragments and isolation of ligated DNA, and PCR amplification a sequencing-ready library is ready. (1B) Heatmaps of reads for cell type-specific H3K4me 1 and H3K4me3 sites as compiled from Roadmap Epigenomics data. Shown are the sites that are specific to a single tissue/cell-type and/or related group of cells. (1C) Aligned segment of chromosome 2, showing a cfChIP-seq signal. Top tracks are cfChIP-seq signals from four subjects identified as healthy. The lower tracks are published ChIP-seq results from human white blood cells (leukocytes) and tissues. Below is a 100-fold zoom in showing agreement in location of peaks. (1D) Histograms of meta-analysis of cfChIP signals over active promoters and enhancers. (1E) Histogram of the distribution of sizes of sequenced cfChIP fragments shows clear mono- and di-nucleosome sizes. (1F) Browser view of cfChIP-seq signal over two regions with megakaryocyte-specific genes that appear in healthy subject but not in ChIP of blood cells and solid tissues. (1G) Browser view of non-PBMC H3K4me3 signal at promoters of selected genes (similar to FIG. 1F). Upper and lower panels depict cfChIP and tissue ChIP signal, respectively. (1H) Browser view of mouse CTCF signal at known CTCF sites. The sites are confirmed by the depletion of H3K4me3 signal. (1I) Meta-analysis of mouse CTCF (upper) and H3K4me3 (lower) signals throughout the mouse genome.

The present invention provides methods of determining the origin of cell free DNA (cfDNA), detecting death of a cell type or tissue in a subject and for determining a cellular state of a cell as it died by determining DNA-protein associations from transcriptionally active or inactive chromatin in the subject. The methods of the invention are based on the surprising finding that cell free nucleosomes retain protein-DNA associations that are informative about not only the tissue/cell of origin of the nucleosome, but also the pathways that were active and inactive in the cell as it died. Further, this was surprisingly possible even though the amount of cf-nucleosomes that can be captured was very small. As little as a thousand genomes worth of cf-nucleosomes was sufficient to perform the methods of the invention.

The methods of the invention can be performed with very little input cfDNA, as little as 1000 genomes, and with very shallow sequencing, as little as 0.5M reads. The technique can be so performed because only positive associations are examined. The entire cfDNA is not sequenced, rather only cfDNA bound by a particular protein (e.g. a modified histone) is isolated and sequenced. Since only a small fraction of the cfDNA is sequenced the process is cheaper, faster and can be done with a lower depth of sequencing. Even within this smaller sample only informative genomic loci are examined; most locations are not informative about the tissue/cell of origin or the pathways active in the cell that died. By only examining informative loci, much of the noise present in the cfDNA can be ignored. Lastly, because DNA sequences that only are associated with the protein of interest in certain circumstances are investigated, only a few reads in these regions are needed to identify a positive reading in the cfDNA. For example, if binding of a protein of interest to DNA sequences that are uniquely bound in cardiac tissue is investigated, a healthy person (who has none or negligible cardiac cell death) would have only a handful of reads within these regions (See FIG. 3A-E). Healthy subjects showed a very low variance in the tissues and reads that were found, and so detection of abnormal cell death could be performed even with very few reads that were different than healthy individuals. A subject with an elevated number of reads at genomic regions unique to heart tissue would be identified as having ongoing elevated cardiac cell death. Not every read within these regions would need to be measured because negative data is not relevant, rather just a significant elevation of reads over the baseline of a healthy person would be sufficient. This can also be done to investigate the pathways, and cellular state of the dying cells. As cfDNA from a healthy subject has very few reads showing activation of genes in the hypoxia pathway, reads within in these regions would be indicative of hypoxia being the cause of increased cell death in a patient.

cfChIP has the potential to circumvent many of the limitations that exist in current analysis of cfDNA. Targeted enrichment of active marks results in reduced representation of the genome such that fewer sequencing reads (~two orders of magnitude less) are required to obtain informative signal. Since we target marks associated with active transcription, we are assaying a positive signal, where few reads are indicative to the presence of a particular cell type or expression program. This is in contrast to methods such as occupancy or DNA methylation that either measure negative signal (lack of nucleosome occupancy) or both negative and positive signals (e.g., % methylated). Moreover, the cfChIP assay leaves most of the original sample intact, enabling using the same material for multiple assays (e.g., genomic sequencing, methylation analysis, or cfChIP with additional antibodies), which is important where blood volume is a limiting factor.

Intensive research during the last two decades established the connection between specific histone marks and chromatin-templated processes including transcription, replication, and damage repair. Leveraging this rich and complex information to blood cfDNA analysis has the potential to unravel physiological processes in remote organs, such as cell proliferation, hypoxia, inflammation, metabolic changes, and cancerous transformation, in real time and with minimal invasiveness. All of these processes involve activation of large transcriptional programs, which leave unique imprint on chromatin.

A key factor in using cfDNA-based assay for detection of cfDNA from rare cells, such as in early cancer diagnosis, is low detection limit. Several features of cfChIP can dramatically improve detection limits. 1. cfChIP detects "positive" signal, thus even low signals contribute significantly. 2. cfChIP can be performed with various antibodies targeting different genomic regions and states thus generating large signatures and the range of hundreds or thousands of sites with differential signal between different tissues or transcriptional programs. 3. Since cfChIP is by nature a low representation method cfChIP is unbiased, as all the captured DNA fragments are sequenced.

Assaying modified cf-nucleosomes, either used alone or in combination with existing biomarkers, has multiple potential medical applications, such as early disease detection (e.g., detecting unknown tumors), improved diagnosis (e.g., replacing tissue biopsy with liquid biopsy), and noninvasive monitoring of disease progression and treatment efficacy.

By a first aspect, there is provided a method of determining a cell or tissue of origin of cell free DNA (cfDNA), the method comprising:
 a. providing a sample comprising cfDNA;
 b. contacting the sample with at least one reagent that binds a DNA-associated protein;
 c. isolating the reagent and any thereto bound proteins and cfDNA; and
 d. sequencing the isolated cfDNA;
wherein the isolated cfDNA comprises a DNA sequence of an informative genomic location and association of the DNA-associated protein with the informative genomic location is indicative of a cell type or tissue; thereby determining the cell or tissue of origin of cfDNA.

By another aspect, there is provided a method of determining a cellular state, tissue of origin, cell type or a combination thereof of a cell that released its DNA, comprising:
 a. providing a sample, wherein the sample comprises cell free DNA (cfDNA);
 b. contacting the sample with at least one reagent that binds to a DNA-associated protein;
 c. isolating the reagent and any thereto bound proteins and cfDNA;
 d. sequencing the isolated cfDNA; and
 e. designating a cfDNA molecule comprising a DNA sequence of an informative genomic location as originating from a cell in a cellular state, originating from a tissue, originative from a cell type or a combination thereof, wherein association of the DNA-associated protein with the informative genomic location is indicative of the cellular state, genome of origin, cell type or combination thereof in the cell that released the cfDNA;

thereby determining a cellular state, tissue of origin cell type or combination thereof of a cell that released its DNA By another aspect, there is provided a method of determining a cell or tissue of origin of cell free DNA (cfDNA), comprising:
   a. providing a sample comprising cfDNA;
   b. contacting the sample with at least one reagent that binds a DNA-associated protein;
   c. isolating the reagent and any thereto bound proteins and cfDNA;
   d. sequencing the isolated cfDNA; and
   e. designating a cfDNA molecule comprising a DNA sequence of an informative genomic location as originating in a cell type or tissue, wherein association of the DNA-associated protein with the informative genomic location is indicative of the cell type or tissue; thereby determining the cell or tissue of origin of cfDNA.

By another aspect, there is provided a method of determining a cell or tissue of origin of cell free DNA comprising sequencing cfDNA isolated by the cfDNA's binding to a DNA-associated protein; wherein the isolated cfDNA comprises a DNA sequence of an informative genomic location and association of the DNA-associated protein with the informative genomic location is indicative of a cell type or tissue; thereby determining the cell or tissue of origin of cfDNA.

By another aspect, there is provided a method of determining a cellular state of a cell in a subject, comprising:
   a. providing a sample from the subject, wherein the sample comprising cfDNA;
   b. contacting the cfDNA with at least one reagent that binds to a DNA-associated protein;
   c. isolating the reagent and any thereto bound proteins and cfDNA; and
   d. sequencing the isolated cfDNA;
wherein the isolated cfDNA comprises a DNA sequence of an informative genomic location and association of the DNA-associated protein with the informative genomic location is indicative of a cellular state; thereby determining a cellular state of a cell in a subject.

By another aspect there is provided a method of determining a cellular state of a cell in a subject, as the cell died, comprising:
   a. providing a sample from the subject, wherein the sample comprises cfDNA;
   b. contacting the sample with a reagent that binds to a DNA-associated protein;
   c. isolating the reagent and any thereto bound proteins and cfDNA;
   d. sequencing the isolated cfDNA; and
   e. designating a cfDNA molecule comprising a DNA sequence of an informative genomic location as originating from a cell in a cellular state, wherein association of the DNA-associated protein with the informative genomic location is indicative of the cellular state; thereby determining a cellular state of a cell as the cell died in a subject.

By another aspect, there is provided a method of determining a cellular state of a cell in a subject, comprising sequencing cfDNA isolated by the cfDNA's binding to a DNA-associated protein; wherein the isolated cfDNA comprises a DNA sequence of an informative genomic location and association of the DNA-associated protein with the informative genomic location is indicative of a cellular state; thereby determining a cellular state of a cell in a subject. In some embodiments, the cell is a cell that has died in the subject.

By another aspect, there is provided a method of determining a cellular state, tissue of origin or cell type of a cell in a subject, as the cell died, comprising:
   a. providing a sample from the subject, wherein the sample comprises cfDNA;
   b. contacting the sample with a reagent that binds to a DNA-associated protein;
   c. isolating the reagent and any thereto bound proteins and cfDNA; and
   d. sequencing the isolated cfDNA;
wherein the isolated cfDNA comprises a DNA sequence of a tissue or cell type-specific binding site of the DNA-associated protein indicating the cell type or tissue of origin and association of the DNA-associated protein with the tissue or cell type-specific binding site is indicative of a cellular state; thereby determining a cellular state of a cell in a subject.

By another aspect, there is provided a method of determining a cellular state, tissue of origin or cell type of a cell in a subject, as the cell died, comprising:
   a. providing a sample from the subject, wherein the sample comprises cfDNA;
   b. contacting the sample with a reagent that binds to a DNA-associated protein;
   c. isolating the reagent and any thereto bound proteins and cfDNA;
   d. sequencing the isolated cfDNA; and
   e. designating a cfDNA molecule comprising a DNA sequence of a tissue or cell type-specific binding site of the DNA-associated protein as originating from the tissue or cell type, and as originating from a cell in a cellular state, wherein association of the DNA-associated protein with the binding site is indicative of the cellular state; thereby determining a cellular state and tissue of origin or cell type of a cell as the cell died in a subject.

In some embodiments, the method is for determining a cellular state of the cell. In some embodiments, the method is for determining a tissue of origin of the cell. In some embodiments, the method is for determining the cell type of the cell. In some embodiments, the sample is from a subject and the method is for detecting death of any one of: cells of a tissue, a cell type and cells in a cellular state in the subject. In some embodiments, the sample is from a subject and the method is for detecting a disease in the subject, wherein death of cells of a tissue, of a cell type or in a cellular state are indicative so the disease. For non-limiting example, death of liver cells may be indicative of liver disease, death of GI cells may indicate GI cancer, death of cells with active interferon response may indicate an infection and death of beta cells may indicate pancreatic damage/disease.

In some embodiments, detecting a disease state comprises at least one of: early detection of the disease state, detection of residual disease and monitoring disease progression. In some embodiments, detecting a disease state comprises early detection. In some embodiments, early detection comprises detection during routine blood work. In some embodiments, early detection comprises detection before development of symptoms. In some embodiments, the residual disease is residual metastatic disease. In some embodiments, residual disease is residual cancer after surgery. In some embodiments, disease monitoring comprises monitoring before treatment. In some embodiments, disease monitoring comprises monitoring after treatment. In some embodiments, disease monitoring comprises monitoring disease relapse. In some embodiments, disease monitoring comprises monitoring treatment efficacy.

In some embodiments, the cell died. In some embodiments, the cell released its DNA. In some embodiments, a cell that released its DNA is a dead and/or dying cell or a cell that denucleated. In some embodiments, a cell that released its DNA is a dead and/or dying cell. In some embodiments, the cell death is selected from apoptotic death and necrotic death. In some embodiments, a denucleated cell is an erythrocyte. In some embodiments a cell that is losing its nucleus is an erythroblast. Erythroblasts lose their nucleus to become erythrocytes, and as such the lost nucleus may appear in cfDNA.

In some embodiments, the sample is from a subject. In some embodiments, the cfDNA is from a subject and detecting a cfDNA molecule of a cell tissue of origin or cellular state indicates detection of death of that cell type, tissue or cellular state. In some embodiments, the subject is suspected of having increased cell death. In some embodiments, the subject is not suspected of having increased cell death. In some embodiments, the subject appears healthy and/or is not known to suffer from a disease or condition.

In some embodiments, the determining is determining the cellular state of the cell as it died. In some embodiments, the methods of the invention are further for determining a cellular state of a cell in a subject as the cell died and further comprise designating a cfDNA molecule comprising a DNA sequence of an informative genomic location as originating from a cell in a cellular state, which association of the DNA-associated protein with the informative genomic location is indicative of the cellular state.

In some embodiments, the sample is a bodily fluid. In some embodiments, the bodily fluid is blood. In some embodiments, the bodily fluid is selected from at least one of: blood, serum, gastric fluid, intestinal fluid, saliva, bile, tumor fluid, cerebrospinal fluid, breast milk, semen, urine, vaginal fluid, interstitial fluid, and stool. Standard techniques for cell-free DNA extraction are known to a skilled artisan, a non-limiting example of which is the QIAamp Circulating Nucleic Acid kit (QIAGEN).

As used herein, "a reagent that binds" refers to any protein binding molecule or composition. Protein binding is well known in the art and may be assessed by any assay known in the art, including but not limited to yeast-2-hybrid, immunoprecipitation, competition assay, phage display, tandem affinity purification, and proximity ligation assay. In some embodiments, the reagent is a proteinaceous molecule. In some embodiments, the reagent is selected from an antibody or antigen binding fragment thereof, a protein and a small molecule. Small molecules that bind to specific proteins are well known in the art and may be used for pull-down experiments. Additionally, well characterized protein-protein interactions may be used for pull-downs. Indeed, any reagent that may be used for precipitation, immunoprecipitation (IP) or chromatin immunoprecipitation (ChIP), may be used as the reagent. In some embodiments, the reagent is an antibody or antigen binding fragment thereof.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')2 single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)~Fc fusions and scFv-scFv-Fc fusions.

Immunoglobulin molecules can be of any type (e.g., IgG, IgE, IgM, IgD, IgA and IgY), class (e.g., IgG1, IgG2, IgG3, IgG4, IgA1 and IgA2) or subclass.

In some embodiments, one reagent is contacted. In some embodiments, at least one reagent is contacted. In some embodiments, more than one reagent is contacted. In some embodiments, each reagent binds a different DNA-associated protein. In some embodiments, the DNA-associated protein is a sequence specific DNA-binder, and more than one reagent targeting more than one protein is contacted. Since the target sequence of binding is known, following sequencing of the isolated cfDNA the sequences can be assigned to each binding reagent based on the target motif present in the sequence. Sequences containing more than one motif can either be discarded or included as bound by multiple DNA-associated proteins.

In some embodiments, the reagent is conjugated to a physical support. As used herein, the term "physical support" refers to a solid and stable molecule that gives support to the reagent. In some embodiments, the support is a scaffold or scaffolding agent. In some embodiments, the support is a resin. In some embodiments, the support is a bead. In some embodiments, the support is a magnetic or paramagnetic bead. Magnetic beads may be purchased for examples from Dynabeads or Pierce. In some embodiments, the support is an agarose bead. In some embodiments, the support is a protein A/G bead. In some embodiments, the reagent is conjugated to the physical support before the contacting. In some embodiments, the conjugating is a covalent linkage. In some embodiments, the conjugating is by epoxy chemistry. In some embodiments, the support aids in isolation of the reagent, wherein the isolating is isolating the physical support.

As used herein, the term "DNA-associated protein" refers to any protein that can be precipitated with DNA or when precipitated brings along DNA. In some embodiments, the DNA-associated protein directly binds DNA. In some embodiments, the DNA-associated protein is a component of chromatin. In some embodiments, the DNA-associated protein binds-indirectly to DNA. In some embodiments, the DNA-associated protein binds to genomic DNA. In some embodiments, the DNA-binding protein binds in the promoter. In some embodiments, the DNA-binding protein binds in a gene body. In some embodiments, the DNA-binding protein binds to a cis or trans regulatory element.

In some embodiments, the DNA-associated protein binds DNA and is a non-sequence specific DNA binder. In some embodiments, the DNA-associated protein binds DNA is a sequence specific DNA binder or a non-sequence specific DNA binder. Examples of non-sequence specific DNA binders include histones, high-mobility group (HMG) proteins, members of the DNA damage repair machinery and members of the general transcriptional machinery. The general transcriptional machinery is well defined and includes, but is not limited to, RNA polymerases, DNA helicases, general cofactors, the splicing machinery and the polyA machinery. The DNA damage repair machinery is also well defined and includes, but is not limited to, members of the nucleotide excision repair pathway, base excision repair pathway and the mismatch repair system. In some embodiments, the DNA-associated protein is a modified protein. In some embodiments, the modification is a post-translational modification. In some embodiments, the reagent binds to the modified form of the protein. In some embodiments, the reagent binds only or predominantly to the modified form of the protein.

In some embodiments, the DNA-associated protein is a histone, modified histone or histone variant. Modifications to the histone tail are well known in the art, and include but are not limited to methylation, acetylation, sumoylation, ubiquitylation and phosphorylation. Modifications may be multiple such as tri-methylation or poly-ubiquitylation. In some embodiments, a tail may have multiple modifications such as methylation and phosphorylation. The histone may be one of the core histones, H1, H2A, H2B, H3 and H4, or it may be a histone variant such as, for non-limiting example, H2A.z, gammaH2AX, H1T, and H3.3. In some embodiments, the modified or variant histone has an activating function or a repressing function on transcription. In some embodiments, the modified or variant contributes to the formation of euchromatin or heterochromatin. In some embodiments, the modified histone is selected from Histone 3 monomethylated lysine 4 (H3K4me1), Histone 3 demethylated lysine 4 (H3K4me2), Histone 3 trimethylated lysine 36 (H3K36me3) and Histone 3 trimethylated lysine 4 (H3K4me3).

In some embodiments, the DNA-associated protein binds DNA and is a sequence specific DNA binder. Examples of sequence specific DNA binders include but are not limited to transcription factors (TFs), activators, repressors, insulators, DNA modifying enzymes and members of the general transcriptional machinery. In some embodiments, the DNA-associated protein is a transcription factor. In some embodiments, the DNA-associated protein is an insulator. In some embodiments, the transcription factor is selected from an activator, a repressor, an insulator, a DNA modifying enzyme and a member of the general transcriptional machinery. In some embodiments, the transcription factor is selected from an activator, a repressor, and an insulator. In some embodiments, the transcription factor is an insulator. In some embodiments, the transcription factor is CTCF.

As used herein, the term "transcription factor" refers to any protein that is not part of the general transcriptional machinery but controls/modulates the rate of transcription of a DNA sequence. In some embodiments, TFs are factors that bind in a promoter region. Transcription factors are well known in the art, as are reagents that bind to them. Performing ChIP with TFs is also well known.

In some embodiments, the agent binds a transcription factor that binds to tissue and/or cell type specific enhancer elements. In some embodiments, the DNA sequence in the cfDNA is the sequence located at the tissue and/or cell type specific enhancer element. Due to the tissue/cell type specificity, association of the TF with this element in the cfDNA indicates the cfDNA is from that tissue and/or cell type. Since the enhancer element enhances transcription of a particular target the target may indicate the cellular state of the cell. In this one, one association of TF to genomic locus can be informative of both the tissue/cell of origin and the cellular state. A non-limiting example of this is tissue-specific NF-kB enhancer binding. NF-kB is known to bind at specific loci only in various tissues (cardiac for example) and mediate inflammation. Thus, isolation with an anti-NF-kB agent, and then identification of the tissue-specific enhancer sequence in the cfDNA indicates not only the cellular origin of the cfDNA, but also that the cell was in an inflammatory state at the time of death. In some embodiments, the DNA-associated protein is a transcription factor (TF), and the binding site is the TF binding site.

As used herein, "activators" refer to proteins that increase transcription. In some embodiments, activators bind to enhancer elements in DNA. In some embodiments, activators bind to promoter proximal or distal elements. As used herein, "repressors" refer to proteins that decrease transcription. In some embodiments, repressors bind to repressor elements in DNA. In some embodiments, repressors bind to promoter proximal or distal elements.

As used herein, "insulators" refers to proteins that separate regions of DNA that have different chromatin architecture or transcriptional rates. In some embodiments, an insulator is an enhancer-blocker. In some embodiments, an insulator separates euchromatin and heterochromatin. Non-limiting examples of insulators in include CTCF, gypsy and BDF1. In some embodiments, insulators bind outside of the promoter and gene bodies.

DNA-modifying enzymes are well known in art, and examples include members of the base/nucleotide excision repair machinery, DNA methyltransferases and DNA demethylases.

In some embodiments, the DNA-associated protein does not bind DNA. In some embodiments, the protein modifies a protein that binds DNA. Examples of such include but are not limited to histone modifying enzymes and polycomb proteins.

In some embodiments, association of the DNA-associated protein with an informative genetic locus is tissue or cell type specific. In some embodiments, association of the DNA-associated protein with an informative genetic locus is differentiation specific. In some embodiments, association of the DNA-associated protein with an informative genetic locus is cellular state specific. In some embodiments, association of the DNA-associated protein with an informative genetic locus is indicative of transcriptional activation, active transcription, transcriptionally active chromatin or a combination thereof. In some embodiments, association of the DNA-associated protein with an informative genetic locus is indicative of transcriptional silencing, lack of transcription, transcriptionally inactive chromatin or a combination thereof. The transcription need not be at the genetic locus of binding, but may be at a near or far gene, such as is the case with activators and suppressors. As used herein, the term "genetic locus" and "genomic location" are synonymous and refer to a particular region of DNA that can be bound by a protein. In some embodiments, the genetic locus is a TF binding site, or some other short sequence of DNA.

In some embodiments, the locus is between 2 and 20, 2 and 16, 2 and 12, 2 and 10, 2 and 8, 2 and 6, 2 and 4, 4 and 20, 4 and 16, 4 and 12, 4 and 10, 4 and 8 or 4 and 6 base pairs. Each possibility represents a separate embodiment of the invention. In some embodiments, the locus is a nucleosome, or a nucleosome length of DNA (~170 bp). In some embodiments, the genetic locus is between 150 and 190, or 160 and 180 bp.

As used herein, the terms "informative genomic location" and "informative genetic locus" are used synonymously and refer to a unique DNA sequence in a particular location in the genome that when associated with a given DNA-associated protein is informative of the cell in which the association occurs. In some embodiments, it is informative of the tissue of origin or cell type of the cell in which the association occurs. In some embodiments, the location is a tissue or cell type specific binding/association site. In some embodiments, the binding/association is not specific/unique, but highly enriched in the tissue or cell type. In some embodiments, it is informative of the cellular state of the cell in which the association occurs. In some embodiments, it is informative of both the tissue of origin and/or cell type and the cellular state of the cell in which the association occurs. In some embodiments, it is informative of a disease in the cell. In some embodiments, it is informative of a transcriptional program in the cell.

As used herein, the term "transcriptional program" refers to a group of genes that act in concert transcriptionally. The genes may be actively transcribed and/or repressed, and/or inactive, and/or accessible, and/or inaccessible. In some embodiments, the genes are all transcriptional regulated together. In some embodiments, a transcriptional program is indicative of a cellular state. In some embodiments, a transcriptional program is indicative of an active signaling pathway. Signatures for tissue specific, cell type specific, cellular state specific and/or transcriptional programs can be found in, for example, the Roadmap Epigenomics Project (roadmapepigenomics.org), the Cancer Genome Atlas (cancergenome.nih.gov), the Genotype-Tissue Expression (GTEx) Project (gtexportal.org) or the Xena project (xena.ucsc.edu). Tables provided herein also provide such signatures.

In some embodiments, the reagent binds histones. In some embodiments, the reagent is an anti-histone antibody or fragment thereof. In some embodiments, the reagent binds modified or variant histones. In some embodiments, the reagent is an anti-modified histone antibody or fragment thereof. In some embodiments, the reagent is an anti-variant histone antibody or fragment thereof. In some embodiments, the reagent is selected from anti-Histone 3 monomethylated lysine 4 (H3K4me1) and anti-Histone 3 trimethylated lysine 4 (H3K4me3) antibodies.

In some embodiments, the isolating comprises isolating a physical support conjugated to the reagent. In some embodiments, the isolating comprises contacting the reagent and bound proteins and DNA with the physical support and then isolating the physical support. In some embodiments, the methods of the invention comprise ChIP. In some embodiments, the isolating comprises ChIP. In some embodiments, the isolating comprised washing steps.

In some embodiments, the sequencing comprises sequencing at least an average of 1, 2, 3, 5, or 10 million sequencing reads. Each possibility represents a separate embodiment of the invention. In some embodiments, the sequencing comprises sequencing at least 1, 2, 3, 5, or 10 million sequencing reads. Each possibility represents a separate embodiment of the invention. In some embodiments, the amplified cfDNA comprises less than 1, 2, 3, 5, or 10 million sequencing reads. Each possibility represents a separate embodiment of the invention. In some embodiments, the sequencing is at a depth of at most 1, 2, 3, 5, or 10 million sequencing reads. Each possibility represents a separate embodiment of the invention.

In some embodiments, the sequencing comprises PCR amplification of the cfDNA. In some embodiments, the amplification comprises ligation of a barcode or additional DNA sequence. In some embodiments, the amplification is performed while the cfDNA is still associated with the protein. In some embodiments, the amplification is performed while the cfDNA is still associated with the physical support. In some embodiments, the amplification is performed without disassociating the cfDNA from the reagent and/or the support.

In some embodiments, the method further comprises comparing the sequencing data to tissue/cell type specific data of DNA binding proteins, wherein binding of a protein to a sequence that is specifically bound by that protein in a tissue/cell type indicates the cfDNA is from that tissue/cell type. Tissue/cell type specific binding data can be found in sources such as the Encode consortium, the NIH Epigenome Roadmap consortium and the Gene Transcription Regulation Database to name but a few. In some embodiments, the genomic location is within a tissue or cell-type specific gene or element. In some embodiments, the protein is associated with active transcription and the genomic location is within a tissue or cell-type specific gene or enhancer element. Non-limiting examples of this include H3K4me3 located in tissue specific genes, or H3K4me1 in enhancers. Non-limiting examples of tissue specific genes include TNNI3 and MYBPC3 in heart cells, and C8a and C8b in liver cells. Tissue expression levels for specific proteins can be found on numerous websites including the Uniprot database (www.uniprot.org), and the GTEx portal (www.gtexportal.org) for example. Tissue specific gene expression and regulation can also be found in numerous locations, most notably the TiGER database (bioinfo.wilmer.jhu.edu/tiger), and the Human Protein Atlas (www.proteinatlas.org). In some embodiments, the protein is associated with silenced transcription and the genomic location is within a repressor element, or a gene specifically silenced in the tissue or cell-type. Tissue-specific protein-DNA binding is well known in the art and can be found in the resources described herein above. Any informative locus binding may be used to determine the source of the cfDNA.

In some embodiments, the sequencing data is compared to at least the top 1, 2, 5, 10, 20, 30, 40, 50, 60, 70, 80, 90 or 100 peaks of binding in a particular tissue/cell type. Each possibility represents a separate embodiment of the invention. In some embodiments, only one particular tissue/cell type is investigated. In some embodiments, binding data from at least 1, 2, 3, 5, 10, 15, 20, 25, 30, 35, 40, 45, or 50 tissues or cell/types is used to compare to the sequencing data. Each possibility represents a separate embodiment of the invention.

In some embodiments, the methods of the invention further comprise comparing the sequenced cfDNA to at least 1 genomic location with the greatest association of the DNA-associated protein in a tissue, cell type and/or cellular state, and wherein a cfDNA with a sequence that is the same as a DNA sequence within the at least 1 genomic location is considered to be from that tissue, cell type and/or cellular state. In some embodiments, the at least one genomic location has the greatest unique association of the DNA-associated protein. As used herein, the term "unique association" refers to an association that occurs only, or nearly exclusively, within a tissue or cell type, or a cell state. Thus, if the 10 most unique locations are selected for example, locations with protein binding only in a certain tissue, cell type or state should be examined, and specifically the 10 with the highest binding should be selected. Should there not be the required number of sites with completely unique binding, then the site with the most unique binding should be selected. Any determination of greatest uniqueness may be used. Examples of such include, but are not limited to, having binding in the fewest other tissues, and having the highest difference in the amount of binding between the tissue of interest and another tissue.

In some embodiments, the methods of the invention further comprise comparing the sequenced cfDNA to a DNA-protein association atlas of at least 2 cell types and/or tissues, wherein the atlas comprises at least 1 genomic location with the greatest association of the DNA-associated protein in each of the 2 tissues, cell types and/or cellular states, and wherein a cfDNA with a sequence that is the same as a DNA sequence within the at least 1 genomic location is considered to be from that t tissue, cell type and/or cellular state. In some embodiments, genomic locations have the greatest unique association of the DNA-associated protein. In some embodiments, the atlas is of at least 1, 2, 3, 5, 7, 10, 15, or 20 cell types and/or tissues. Each possibility represents a separate embodiment of the invention. In some embodiments, the atlas comprises at least 1, 2, 5, 10, 15, 20, 25, 30, 35, 40, 45, 50, 60, 70, 75, 80, 90 or 100 genomic locations per tissue, cell type and/or cellular state. Each possibility represents a separate embodiment of the invention.

Examples of genomic locations that when associated with a DNA-associated protein are indicative of a tissue or cell type can be found in Table 1. Table 1 gives exemplary locations for H3K4me3 tissue-informative locations. In some embodiments, the atlas comprises all or a portion of the location in Table 1. In some embodiments, the sequencing of cfDNA is compared to Table 1.

TABLE 1

H3K4me3 tissue-specific locations

| Signature | Gene | Genomic Location |
|---|---|---|
| Thymus | RAG1 | chr11: 36579801-36602400 |
| Thymus | RAG1 | chr11: 36582401-36604800 |
| Thymus | RAG2 | chr11: 36608001-36630200 |
| Thymus | CD1E | chr1: 158316001-158338000 |
| Thymus | CD1B | chr1: 158287601-158309400 |
| Thymus | OR10R3P | chr1: 158449201-158471600 |
| Thymus | CD1E | chr1: 158314001-158335200 |
| Thymus | CCR9 | chr3: 45919001-45940200 |
| Thymus | . | chr17: 74980401-75001800 |
| Thymus | AK057554 | chr1: 158451801-158474200 |
| Thymus | . | chr1: 158322001-158345000 |
| Thymus | . | chr15: 58058601-58080800 |
| Thymus | . | chr12: 123546401-123567800 |
| Thymus | CTB-26E19.1 | chr5: 177857801-177880400 |
| Thymus | CD1B | chr1: 158291401-158313200 |
| Thymus | CD1B | chr1: 158290401-158311200 |
| Thymus | RP11-35J23.1 | chr10: 98057201-98079800 |
| Thymus | CD1E | chr1: 158315201-158336000 |
| Thymus | AC005780.1 | chr19: 28863601-28886000 |
| Thymus | CD1B | chr1: 158289401-158310200 |
| Thymus | PTCRA | chr6: 42873201-42894800 |
| Thymus | ARL5C | chr17: 37315801-37338400 |
| Thymus | . | chr2: 57914401-57936600 |
| Thymus | ARPP21-AS1 | chr3: 35681801-35704200 |
| Brain | DLX1 | chr2: 172935201-172957800 |
| Brain | LINC00461 | chr5: 87956401-87978400 |

TABLE 1-continued

H3K4me3 tissue-specific locations

| Signature | Gene | Genomic Location |
|---|---|---|
| Brain | SRRM4 | chr12: 119409601-119432400 |
| Brain | MIR9-3; LINC00925 | chr15: 89896801-89919000 |
| Brain | SLC32A1 | chr20: 37341401-37363400 |
| Brain | NCAN | chr19: 19312401-19334400 |
| Brain | C14orf23 | chr14: 29228001-29250400 |
| Brain | . | chr7: 96629601-96652200 |
| Brain | MIR9-3; LINC00925 | chr15: 89894601-89916800 |
| Brain | NRXN3 | chr14: 78627201-78649200 |
| Brain | TMEM161B-AS1 | chr5: 87680201-87703000 |
| Brain | AKAP6 | chr14: 32788401-32811000 |
| Brain | C14orf23 | chr14: 29230401-29252800 |
| Brain | . | chr14: 23945401-23966600 |
| Brain | GPR56 | chr16: 57663601-57685200 |
| Brain | BC034423 | chr14: 29233801-29256400 |
| Brain | SOX2-OT | chr3: 181410201-181432400 |
| Brain | . | chr2: 172944801-172966800 |
| Brain | TIAM2 | chr6: 155527601-155549800 |
| Brain | . | chr20: 37344401-37365600 |
| Brain | MBP | chr18: 74716401-74738600 |
| Brain | . | chr2: 172946801-172968600 |
| Brain | NRXN3 | chr14: 78629201-78651200 |
| Brain | TMEM161B-AS1 | chr5: 87677201-87700200 |
| Brain | SRXN1; SCRT2 | chr20: 642601-665400 |
| Brain | AK055364 | chr16: 72448601-72471600 |
| Brain | . | chr20: 37343401-37364400 |
| Brain | LOC100130155 | chr8: 65276601-65298200 |
| Brain | . | chr7: 96628601-96649600 |
| Brain | C10orf90 | chr10: 128347801-128370000 |
| Brain | POU3F2 | chr6: 99279201-99301800 |
| Brain | ERMN | chr2: 158169201-158191600 |
| Brain | HAPLN2 | chr1: 156578601-156601600 |
| Brain | MIR9-1 | chr1: 156378001-156399600 |
| Brain | RAPGEF5 | chr7: 22219201-22242000 |
| Brain | LOC100130155 | chr8: 65275001-65296600 |
| Brain | CNTN2 | chr1: 205002801-205024000 |
| Brain | PRKCZ | chr1: 1995601-2017000 |
| Brain | SOX1 | chr13: 112713201-112734400 |
| Brain | ROBO1 | chr3: 78707201-78730200 |
| Brain | MBP | chr18: 74713601-74735600 |
| Brain | SLC32A1 | chr20: 37338801-37361000 |
| Brain | PREX1 | chr20: 47261001-47283600 |
| Brain | CLVS2 | chr6: 123308001-123329400 |
| Brain | MYT1 | chr20: 62781201-62803600 |
| Brain | DLX1 | chr2: 172943201-172964400 |
| Brain | BC034423 | chr14: 29236401-29258800 |
| Brain | ERMN | chr2: 158166801-158189200 |
| Brain | ST18 | chr8: 53310401-53332800 |
| Brain | CNDP1 | chr18: 72191201-72214200 |
| Brain | DOHH | chr19: 3482401-3504800 |
| Brain | SOX2-OT | chr3: 181412401-181434600 |
| Brain | NCAN | chr19: 19314401-19336200 |
| Brain | NAT16 | chr7: 100812801-100833800 |
| Brain | FOXG1 | chr14: 29221801-29244200 |
| Brain | C10orf90 | chr10: 128346001-128367800 |
| Brain | CRB1 | chr1: 197227601-197250000 |
| Brain | CACNG3 | chr16: 24257201-24279800 |
| Brain | HPN-AS1 | chr19: 35585601-35608400 |
| Brain | MIR3065; MIR338 | chr17: 79091201-79112600 |
| Brain | FOXG1 | chr14: 29224801-29245600 |
| Brain | LOC150622 | chr2: 6064001-6086000 |
| Brain | . | chr13: 112702401-112723200 |
| Brain | BCAS1 | chr20: 52634401-52656200 |
| Brain | ELAVL3 | chr19: 11580201-11601200 |
| Brain | CAPN3 | chr15: 42686401-42708600 |
| Brain | EPHA10 | chr1: 38220601-38242000 |
| Brain | . | chr2: 172932801-172954800 |
| Brain | SLC24A2 | chr9: 19776001-19798400 |
| Brain | FOXG1 | chr14: 29227001-29247600 |
| Brain | ABR | chr17: 971001-991800 |
| Brain | SCRT1 | chr8: 145547601-145568800 |
| Brain | SLCO1A2 | chr12: 21466001-21488600 |
| Brain | DLX6-AS1 | chr7: 96633201-96655200 |
| Brain | C14orf23 | chr14: 29232801-29253800 |
| Brain | MSRA | chr8: 9942801-9965800 |
| Brain | TTBK1 | chr6: 43200801-43222200 |
| Brain | ANK3 | chr10: 62136401-62158600 |

TABLE 1-continued

H3K4me3 tissue-specific locations

| Signature | Gene | Genomic Location |
|---|---|---|
| Brain | SOX1 | chr13: 112716001-112737600 |
| Brain | DLEU7 | chr13: 51407201-51428000 |
| Brain | CACNG2 | chr22: 37085801-37108800 |
| Brain | SRRM4 | chr12: 119408401-119429600 |
| Brain | SOX1 | chr13: 112714401-112736000 |
| Brain | . | chr20: 37345601-37366600 |
| Brain | OMG | chr17: 29613001-29634400 |
| Brain | LINC00461 | chr5: 87895401-87917800 |
| Brain | BCAS1 | chr20: 52632401-52654400 |
| Brain | CNTNAP4 | chr16: 76301601-76323600 |
| Brain | SLC24A2 | chr9: 19773601-19796000 |
| Brain | BX537900 | chr8: 65279001-65299800 |
| Brain | NR2E1 | chr6: 108476201-108497000 |
| Brain | AMER2 | chr13: 25730601-25752600 |
| Brain | . | chr13: 112700801-112721600 |
| Brain | AL832737 | chr6: 168084401-168107400 |
| Brain | MIR9-1 | chr1: 156376401-156398000 |
| Brain | . | chr13: 112699401-112720800 |
| Brain | . | chr7: 96632201-96653200 |
| Brain | NTM; NTM-AS1 | chr11: 131522401-131544200 |
| Brain | TMTC4 | chr13: 101277001-101299200 |
| Brain | . | chr11: 2601801-2623200 |
| Brain | AC017053.1 | chr2: 6452401-6475400 |
| Brain | MTUS1 | chr8: 17568601-17590400 |
| Brain | MOBP | chr3: 39501201-39523800 |
| Brain | LRRC4C | chr11: 41469601-41491600 |
| Brain | LPPR1 | chr9: 104021401-104043200 |
| Brain | ANO4 | chr12: 101178401-101199200 |
| Brain | ANLN | chr7: 36436801-36458800 |
| Brain | LINC00634 | chr22: 42337401-42358800 |
| Brain | TMEM161B-AS1 | chr5: 87674201-87697200 |
| Brain | ST18 | chr8: 53306801-53329800 |
| Brain | LOC400940 | chr2: 6113001-6135200 |
| Brain | SOX2-OT | chr3: 181318401-181341000 |
| Brain | BC040833 | chr10: 91091601-91112600 |
| Brain | CTD-2049O4.1 | chr16: 27717401-27739600 |
| Brain | . | chr17: 40112801-40134400 |
| Sk. Muscle | MYLK2 | chr20: 30397401-30420200 |
| Sk. Muscle | MYOG | chr1: 203043801-203066400 |
| Sk. Muscle | . | chr20: 3275401-3298400 |
| Sk. Muscle | ANKRD23 | chr2: 97498401-97520800 |
| Sk. Muscle | . | chr6: 51990401-52013000 |
| Sk. Muscle | MYF6 | chr12: 81089601-81111800 |
| Sk. Muscle | AC005616.2 | chr19: 28989401-29011400 |
| Sk. Muscle | NEB | chr2: 152579201-152602000 |
| Sk. Muscle | MYOT | chr5: 137193801-137216200 |
| Sk. Muscle | CLCN1 | chr7: 143002801-143025600 |
| Sk. Muscle | . | chr6: 51993001-52015400 |
| Sk. Muscle | ART1 | chr11: 3655401-3678000 |
| Sk. Muscle | PCNT | chr21: 47758201-47780400 |
| Sk. Muscle | STAC3 | chr12: 57633601-57656200 |
| Sk. Muscle | . | chr20: 23119201-23141200 |
| Sk. Muscle | KLHL40 | chr3: 42718001-42738800 |
| Sk. Muscle | FEZ2 | chr2: 36808801-36831800 |
| Sk. Muscle | NEB | chr2: 152576401-152599200 |
| Sk. Muscle | IDI2 | chr10: 1059801-1082600 |
| Sk. Muscle | TPM3 | chr1: 154153401-154174400 |
| Sk. Muscle | PTPN3 | chr9: 112172401-112193800 |
| Sk. Muscle | CASQ1 | chr1: 160151201-160172500 |
| Sk. Muscle | MYADML2 | chr17: 79888401-79909400 |
| Sk. Muscle | C8orf22 | chr8: 49974801-49996400 |
| Sk. Muscle | MYOZ1 | chr10: 75390401-75411400 |
| Sk. Muscle | . | chr8: 6620801-6641800 |
| Sk. Muscle | RP11-18B3.3 | chr9: 108461201-108483200 |
| Sk. Muscle | . | chr5: 137196601-137218200 |
| Sk. Muscle | . | chr4: 23383601-23405400 |
| Sk. Muscle | ASB5 | chr4: 177177801-177200400 |
| Sk. Muscle | MSS51 | chr10: 75180601-75203600 |
| Sk. Muscle | . | chr10: 908001-929200 |
| Sk. Muscle | ASB18 | chr2: 237138601-237160200 |
| Sk. Muscle | MYL1 | chr2: 211156201-211179000 |
| Sk. Muscle | RP11-6I2.4 | chr8: 75004601-75027600 |
| Sk. Muscle | . | chr10: 53877601-53900200 |
| Sk. Muscle | ASB5 | chr4: 177177201-177198800 |
| Sk. Muscle | . | chr13: 21393201-21416000 |
| Sk. Muscle | MYL1 | chr2: 211166001-211188600 |
| Sk. Muscle | VGLL2 | chr6: 117578001-117599800 |
| Sk. Muscle | . | chr13: 21384801-21407400 |
| Sk. Muscle | LSMEM1 | chr7: 112110201-112133000 |
| Sk. Muscle | . | chr4: 23381601-23403600 |
| Sk. Muscle | . | chr15: 93507801-93529600 |
| Sk. Muscle | LOC100507537 | chr3: 154998801-155020800 |
| Sk. Muscle | TNNT1 | chr19: 55650601-55672600 |
| Sk. Muscle | MYBPC1 | chr12: 101951201-101973800 |
| Sk. Muscle | PKIA | chr8: 79494401-79516600 |
| Sk. Muscle | . | chr3: 16869601-16891000 |
| Sk. Muscle | PICK1 | chr22: 38454201-38475400 |
| Sk. Muscle | MYLPF | chr16: 30375801-30397600 |
| Sk. Muscle | . | chr3: 69157401-69179000 |
| Sk. Muscle | . | chr12: 117865601-117887200 |
| Sk. Muscle | . | chr2: 97495801-97517400 |
| Sk. Muscle | . | chr8: 42125001-42146200 |
| Sk. Muscle | . | chr10: 76822201-76844000 |
| Sk. Muscle | . | chr3: 15996801-16019400 |
| Sk. Muscle | . | chr10: 75389201-75410400 |
| Sk. Muscle | CASQ1 | chr1: 160150601-160171200 |
| Sk. Muscle | MYF6 | chr12: 81093001-81115000 |
| Heart | TNNT2 | chr1: 201335801-201356800 |
| Heart | TENM2 | chr5: 167352201-167374400 |
| Heart | NEBL | chr10: 21173801-21196600 |
| Heart | RBMS3 | chr3: 29956401-29978800 |
| Heart | . | chr1: 231971401-231993600 |
| Heart | MYL4 | chr17: 45276001-45298400 |
| Heart | TNNI3 | chr19: 55658201-55679800 |
| Heart | NEBL | chr10: 21171001-21193800 |
| Heart | PRDM6 | chr5: 122423401-122444400 |
| Heart | . | chr10: 15745201-15767200 |
| Heart | . | chr3: 24220001-24242400 |
| Heart | RP11-405A12.2 | chr12: 19918801-19940600 |
| Heart | SLC5A1 | chr22: 32445001-32467200 |
| Heart | . | chr17: 8516601-8539000 |
| Heart | . | chr10: 92715801-92738400 |
| GI Sm. Muscle | TACR2 | chr10: 71165401-71187200 |
| GI Sm. Muscle | TACR2 | chr10: 71163401-71185200 |
| GI Sm. Muscle | . | chr19: 7409601-7432600 |
| GI Sm. Muscle | AC007392.3 | chr2: 66909201-66931200 |
| GI Sm. Muscle | . | chr15: 98548401-98570200 |
| GI Sm. Muscle | . | chr1: 225636601-225658800 |
| GI Sm. Muscle | SIPA1L2 | chr1: 232638201-232660600 |
| Stomach | CLDN18 | chr3: 137707601-137730000 |
| Stomach | CTSE | chr1: 206306801-206329000 |
| Stomach | TFF1 | chr21: 43774801-43797000 |
| Stomach | . | chr8: 124945601-124968400 |
| Stomach | CLDN18 | chr3: 137710001-137732400 |
| Stomach | MUC5B | chr11: 1141601-1163800 |
| Stomach | CAPN8 | chr1: 223840401-223862200 |
| Stomach | AX747250 | chr6: 1069601-1091400 |
| Stomach | C5orf66-AS1 | chr5: 134363801-134384600 |
| Stomach | . | chr17: 71941801-71963800 |
| Stomach | FAM177B | chr1: 222900601-222922400 |
| Stomach | ANXA10 | chr4: 169003801-169026000 |
| Stomach | C5orf66-AS1 | chr5: 134364601-134385000 |
| Stomach | PAX9 | chr14: 37122201-37142600 |
| Stomach | . | chr14: 37125401-37146400 |
| GI Mucosa | BTNL3 | chr5: 180405801-180428000 |
| GI Mucosa | . | chr1: 233830001-233852800 |
| GI Mucosa | RBP2 | chr3: 139183201-139205400 |
| GI Mucosa | . | chr17: 46794401-46815600 |
| GI Mucosa | FRYL | chr4: 48671401-48693200 |
| GI Mucosa | UBE2V2P1 | chr10: 19327801-19350700 |
| GI Mucosa | . | chr17: 71941801-71963800 |
| GI Mucosa | FAM177B | chr1: 222900601-222922400 |
| GI Mucosa | REP15 | chr12: 27840801-27862600 |
| GI Mucosa | . | chr7: 12830601-12853600 |
| GI Mucosa | ANXA10 | chr4: 169003801-169026000 |
| GI Mucosa | FABP2 | chr4: 120231801-120253400 |
| GI Mucosa | . | chr10: 3017801-3039200 |
| GI Mucosa | NXPE4 | chr11: 114454001-114475600 |
| GI Mucosa | . | chr16: 68407201-68429400 |
| GI Mucosa | LOC93432 | chr7: 141801601-141823000 |
| GI Mucosa | . | chr11: 76775401-76797200 |
| GI Mucosa | SLC5A1 | chr22: 32429201-32450000 |

TABLE 1-continued

H3K4me3 tissue-specific locations

| Signature | Gene | Genomic Location |
|---|---|---|
| Digestive | CLDN18 | chr3: 137707601-137730000 |
| Digestive | CTSE | chr1: 206306801-206329000 |
| Digestive | TFF1 | chr21: 43774801-43797000 |
| Digestive | . | chr8: 124945601-124968400 |
| Digestive | CLDN18 | chr3: 137710001-137732400 |
| Digestive | MUC5B | chr11: 1141601-1163800 |
| Digestive | BTNL3 | chr5: 180405801-180428000 |
| Digestive | . | chr1: 233830001-233852800 |
| Digestive | SPDEF | chr6: 34512401-34534000 |
| Digestive | CAPN8 | chr1: 223840401-223862200 |
| Digestive | RBP2 | chr3: 139183201-139205400 |
| Digestive | . | chr17: 46794401-46815600 |
| Digestive | FRYL | chr4: 48671401-48693200 |
| Digestive | . | chr11: 119767401-119789600 |
| Digestive | UBE2V2P1 | chr10: 19327801-19350000 |
| Digestive | AX747250 | chr6: 1069601-1091400 |
| Digestive | . | chr11: 119765201-119787400 |
| Digestive | C5orf66-AS1 | chr5: 134363801-134384600 |
| Digestive | TMC5 | chr16: 19419201-19440600 |
| Digestive | TRIM31 | chr6: 30068401-30090000 |
| Digestive | . | chr17: 71941801-71963800 |
| Digestive | FAM177B | chr1: 222900601-222922400 |
| Digestive | REP15 | chr12: 27840801-27862600 |
| Digestive | . | chr7: 12830601-12853600 |
| Digestive | ANXA10 | chr4: 169003801-169026000 |
| Digestive | FABP2 | chr4: 120231801-120253400 |
| Digestive | . | chr10: 3017801-3039200 |
| Digestive | BCAR3 | chr1: 94037801-94059200 |
| Digestive | . | chr4: 149590201-149612200 |
| Digestive | ERN2 | chr16: 23713001-23734400 |
| Digestive | C5orf66-AS1 | chr5: 134364601-134385000 |
| Digestive | NXPE4 | chr11: 114454001-114475600 |
| Digestive | PAX9 | chr14: 37122201-37142600 |
| Digestive | . | chr16: 68407201-68429400 |
| Digestive | LOC93432 | chr7: 141801601-141823000 |
| Digestive | . | chr14: 37125401-37146400 |
| Digestive | . | chr11: 76775401-76797200 |
| Digestive | VSIG2 | chr11: 124610401-124631800 |
| Digestive | SLC5A1 | chr22: 32429201-32450000 |
| Pancreas Islet | SLC30A8 | chr8: 118138601-118161400 |
| Pancreas Islet | SLC30A8 | chr8: 118135801-118158600 |
| Pancreas Islet | PAM | chr5: 102134201-102156200 |
| Pancreas Islet | G6PC2 | chr2: 169747201-169769400 |
| Pancreas Islet | G6PC2 | chr2: 169749401-169771600 |
| Pancreas Islet | KCNMB2-IT1; KCNMB2 | chr3: 178127201-178149200 |
| Pancreas Islet | IAPP | chr12: 21515201-21537400 |
| Pancreas Islet | GCK | chr7: 44216201-44239000 |
| Pancreas Islet | . | chr2: 77425801-77448600 |
| Pancreas Islet | ELAVL4 | chr1: 50561401-50583000 |
| Pancreas Islet | . | chr4: 43755001-43777000 |
| Pancreas Islet | GNAS | chr20: 57405601-57427400 |
| Pancreas Islet | . | chr14: 62341201-62363800 |
| Pancreas Islet | CNTN4 | chr3: 2544801-2567400 |
| Pancreas Islet | LINC01099 | chr4: 178815401-178837400 |
| Pancreas Islet | IAPP | chr12: 21517401-21539400 |
| Pancreas | SLC30A8 | chr8: 118138601-118161400 |
| Pancreas | SLC30A8 | chr8: 118135801-118158600 |
| Pancreas | PRSS1 | chr7: 142447001-142468600 |
| Pancreas | TPST2 | chr22: 26950201-26971200 |
| Pancreas | CTRB2 | chr16: 75230001-75251200 |
| Pancreas | PAM | chr5: 102134201-102156200 |
| Pancreas | CELA3A | chr1: 22318401-22340600 |
| Pancreas | G6PC2 | chr2: 169747201-169769400 |
| Pancreas | SYCN | chr19: 39684001-39705600 |
| Pancreas | PNLIPRP1 | chr10: 118341201-118364200 |
| Pancreas | LOC644838 | chr2: 67431001-67452200 |
| Pancreas | G6PC2 | chr2: 169749401-169771600 |
| Pancreas | PTF1A | chr10: 23469201-23491000 |
| Pancreas | KCNMB2-IT1; KCNMB2 | chr3: 178127201-178149200 |
| Pancreas | RBPJL; MATN4 | chr20: 43925001-43946800 |
| Pancreas | . | chr1: 236428801-236451600 |
| Pancreas | . | chr10: 23477601-23500000 |
| Pancreas | IAPP | chr12: 21515201-21537400 |
| Pancreas | CELA3A | chr1: 22320601-22343200 |
| Pancreas | CTRC | chr1: 15754801-15776800 |
| Pancreas | SYCN | chr19: 39682401-39704200 |
| Pancreas | GCK | chr7: 44216201-44239000 |
| Pancreas | PTF1A | chr10: 23471601-23492400 |
| Pancreas | CELA3B | chr1: 22292601-22315000 |
| Pancreas | AC011298.2 | chr2: 241616201-241638400 |
| Pancreas | PRSS1 | chr7: 142448601-142470200 |
| Pancreas | . | chr2: 77425801-77448600 |
| Pancreas | ELAVL4 | chr1: 50561401-50583000 |
| Pancreas | AQP8 | chr16: 25218201-25239400 |
| Pancreas | . | chr4: 43755001-43777000 |
| Pancreas | NPHS1 | chr19: 36331601-36354200 |
| Pancreas | RP11-20120.2 | chr4: 1117401-1139800 |
| Pancreas | GNAS | chr20: 57405601-57427400 |
| Pancreas | . | chr14: 62341201-62363800 |
| Pancreas | CNTN4 | chr3: 2544801-2567400 |
| Pancreas | LINC01099 | chr4: 178815401-178837400 |
| Pancreas | IAPP | chr12: 21517401-21539400 |
| Placenta | . | chr19: 9108001-9130600 |
| Placenta | LOC100506655 | chr16: 25148801-25170400 |
| Placenta | DLG5 | chr10: 79605601-79627600 |
| Placenta | . | chr6: 140458801-140481400 |
| Placenta | . | chr6: 168803001-168825200 |
| Placenta | STRA6; HP11097 | chr15: 74483601-74505400 |
| Placenta | ZFAT | chr8: 135697001-135719600 |
| Placenta | . | chr3: 72495001-72517800 |
| Placenta | BCAR4 | chr16: 11909801-11932800 |
| Placenta | ZFP42 | chr4: 188906601-188928400 |
| Placenta | ERVW-1 | chr7: 92095801-92117400 |
| Placenta | . | chr11: 2147001-2168000 |
| Placenta | HSD3B1 | chr1: 120039801-120060800 |
| Placenta | . | chr19: 6204401-6225800 |
| Placenta | TRIM60 | chr4: 165942401-165964000 |
| Placenta | NAA11 | chr4: 80236000-80257600 |
| Placenta | . | chr4: 133255401-133277000 |
| Placenta | RNU6-964P | chr2: 230792601-230815000 |
| Placenta | GCM1 | chr6: 53002201-53024000 |
| Placenta | CCBP2 | chr3: 42840801-42862800 |
| Placenta | . | chr11: 2152001-2173800 |
| Placenta | . | chr5: 86536801-86559200 |
| Placenta | PSG1 | chr19: 43371001-43394000 |
| Placenta | . | chr1: 245057601-245078800 |
| Placenta | LGALS13 | chr19: 40083201-40104800 |
| Placenta | RPS20P15 | chr3: 27494401-27516800 |
| Placenta | . | chr1: 120040801-120061800 |
| Placenta | GRAMD3 | chr5: 125685801-125707800 |
| Placenta | AK127846 | chr19: 53500801-53522400 |
| Placenta | PSG6 | chr19: 43410601-43432000 |
| Placenta | BRWD1 | chr21: 40682201-40703600 |
| Placenta | . | chr7: 114530401-114552000 |
| Placenta | CGA | chr6: 87793201-87814800 |
| Placenta | ARID3A | chr19: 949401-970800 |
| Placenta | LINC00577 | chr6: 105374201-105396800 |
| Placenta | BC031304 | chr2: 46645601-46667600 |
| Placenta | . | chr20: 39599401-39621800 |
| Placenta | . | chr11: 105376001-105397200 |
| Placenta | . | chr1: 204272601-204293400 |
| Placenta | PSG3; PSG7 | chr19: 43428601-43451600 |
| Placenta | RP3-407E4.4 | chr6: 64141401-64162200 |
| Placenta | . | chr19: 54140601-54162200 |
| Placenta | FAM13A | chr4: 89845601-89867800 |
| Liver | . | chr4: 155518001-155542600 |
| Liver | CPS1 | chr2: 211411001-211433600 |
| Liver | APOH | chr17: 64212601-64235600 |
| Liver | BAAT | chr9: 104134601-104157400 |
| Liver | C8B | chr1: 57418401-57441000 |
| Liver | TAT | chr16: 71599001-71621400 |
| Liver | CCL16 | chr17: 34296601-34319200 |
| Liver | . | chr17: 44000401-44023000 |
| Liver | UGT2B4 | chr4: 70349201-70372200 |
| Liver | C4BPA | chr1: 207267801-207290000 |
| Liver | APCS | chr1: 159546801-159569000 |
| Liver | GYS2 | chr12: 21745401-21767800 |
| Liver | CCND2P1 | chr11: 62998801-63021000 |
| Liver | SULT2A1 | chr19: 48378401-48399600 |
| Liver | RDH16 | chr12: 57339401-57361000 |

TABLE 1-continued

H3K4me3 tissue-specific locations

| Signature | Gene | Genomic Location |
|---|---|---|
| Liver | SERPINC1 | chr1: 173874401-173896000 |
| Liver | . | chr7: 45719401-45741600 |
| Liver | CCND2P1 | chr11: 63001001-63023000 |
| Liver | . | chr17: 41530801-41553400 |
| Liver | . | chr6: 132157001-132179400 |
| Liver | C5orf27 | chr5: 95178201-95200400 |
| Liver | CYP2B6 | chr19: 41487401-41509600 |
| Liver | SERPINA10 | chr14: 94747001-94768800 |
| Liver | SLC22A1 | chr6: 160533601-160556200 |
| Liver | SEPP1 | chr5: 42813801-42836200 |
| Liver | CPN1 | chr10: 101829401-101852000 |
| Liver | CPB2 | chr13: 46666201-46688000 |
| Liver | C9 | chr5: 39353401-39375000 |
| Liver | KCTD21-AS1 | chr11: 77870601-77892200 |
| Liver | AHSG | chr3: 186320401-186342200 |
| Liver | CPB2 | chr13: 46668001-46689600 |
| Liver | SPP2 | chr2: 234949401-234971600 |
| Liver | . | chr12: 111502801-111524800 |
| Liver | ADCY10 | chr1: 167871201-167893400 |
| Liver | JB175316 | chr12: 9269801-9291800 |
| Liver | AOC4; AF047486 | chr17: 41009601-41031800 |
| Liver | TTC39C | chr18: 21683801-21706400 |
| Liver | C19orf80 | chr19: 11340201-11362000 |
| Liver | TFR2 | chr7: 100227801-100249800 |
| Liver | APOC3 | chr11: 116690001-116712000 |
| Liver | ALB | chr4: 74262801-74285400 |
| Liver | AKR1C4 | chr10: 5229201-5252200 |
| Liver | ITIH2 | chr10: 7734201-7756400 |
| Liver | . | chr4: 77221201-77243600 |
| Liver | C8A | chr1: 57310801-57332800 |
| Liver | MIR122 | chr18: 56102601-56124400 |
| Liver | NCOR1 | chr17: 15930001-15952600 |
| Liver | APOA2 | chr1: 161182601-161204000 |
| Liver | CYP2C8 | chr10: 96818001-96840200 |
| Liver | . | chr3: 16363001-16385400 |
| Liver | ABCB11 | chr2: 169876201-169898000 |
| Liver | C9 | chr5: 39351601-39373400 |
| Liver | HAO1 | chr20: 7909801-7931600 |
| Liver | CYP2C9 | chr10: 96689201-96710800 |
| Liver | FGL1 | chr8: 17740801-17763200 |
| Liver | C8B | chr1: 57421001-57443600 |
| Liver | PON1 | chr7: 94942001-94963600 |
| Liver | CPS1 | chr2: 211413601-211436000 |
| Liver | LEAP2 | chr5: 132199401-132220400 |
| Liver | . | chr3: 148924401-148946600 |
| Liver | C5 | chr9: 123801201-123822600 |
| Liver | AKR1D1 | chr7: 137750801-137773000 |
| Liver | . | chr5: 68030601-68052600 |
| Liver | SLC22A10 | chr11: 63046601-63068800 |
| Liver | C5 | chr9: 123799401-123821200 |
| Liver | GBP7 | chr1: 89629801-89651800 |
| Liver | . | chr16: 76555001-76577000 |
| Liver | APCS | chr1: 159549001-159571200 |
| Liver | AOC4; AF047486 | chr17: 41007601-41029600 |
| Liver | MASP2 | chr1: 11095801-11117400 |
| Liver | U91324.1 | chr2: 8269401-8292000 |
| Liver | . | chr5: 115064401-115086800 |
| Liver | GPLD1 | chr6: 24477801-24500400 |
| Liver | . | chr10: 113975801-113997400 |
| Liver | PZP | chr12: 9349001-9371000 |
| Liver | . | chr2: 138689001-138711400 |
| Liver | HAO1 | chr20: 7907801-7929800 |
| Liver | . | chr10: 96817201-96838000 |
| Liver | APOC3 | chr11: 116692001-116714000 |
| Liver | SERPINA11 | chr14: 94907801-94929400 |
| Liver | . | chr2: 31923201-31945400 |
| Liver | ITIH2 | chr10: 7736401-7758600 |
| Liver | . | chr12: 24178601-24201400 |
| Liver | SERPINA10 | chr14: 94748801-94769600 |
| Liver | RCL1 | chr9: 4829201-4850800 |
| Liver | NR1I3 | chr1: 161196001-161218400 |
| Liver | SLC17A2 | chr6: 25919801-25942200 |
| Liver | RTP3 | chr3: 46530201-46552000 |
| Liver | CFHR5 | chr1: 196937001-196960000 |
| Liver | SLC17A2 | chr6: 25917401-25939800 |
| Liver | HRG | chr3: 186373201-186395000 |
| Liver | CYP2A6 | chr19: 41345001-41366400 |
| Liver | GLYATL1 | chr11: 58696801-58718800 |
| Liver | ADH1A | chr4: 100199201-100221200 |
| Liver | . | chr16: 51074401-51096600 |
| Liver | . | chr12: 7635801-7658000 |
| Liver | . | chr2: 151010601-151033400 |
| Liver | BDH1 | chr3: 197289201-197311000 |
| Liver | SLC22A10 | chr11: 63048801-63071000 |
| Liver | A1BG | chr19: 58853801-58875400 |
| Liver | CFHR4 | chr1: 196847601-196869600 |
| Liver | RTP3 | chr3: 46528401-46550200 |
| Liver | CYP4A22 | chr1: 47593001-47615200 |
| Liver | . | chr8: 63909801-63931800 |
| Liver | C4BPA | chr1: 207270001-207292200 |
| Liver | EPHX1 | chr1: 226004401-226025800 |
| Liver | . | chr6: 132154601-132177000 |
| Liver | LDHD | chr16: 75143001-75165600 |
| Liver | INHBC | chr12: 57818401-57839600 |
| Liver | F12 | chr5: 176825201-176846600 |
| Liver | LPAL2 | chr6: 160921201-160943000 |
| Liver | FETUB | chr3: 186349001-186371200 |
| Liver | SLC6A13 | chr12: 336001-357400 |
| Liver | SLC22A1 | chr6: 160530801-160553600 |
| Liver | ANXA10 | chr4: 169075401-169098400 |
| Liver | . | chr22: 43860201-43881800 |
| Liver | IGFBP1 | chr7: 45919601-45941800 |
| Liver | SLC22A9 | chr11: 63126601-63148200 |
| Liver | . | chr2: 21306401-21328800 |
| Liver | APOC4-APOC2 | chr19: 45435401-45457000 |
| Liver | CSAD | chr12: 53552001-53574400 |
| Liver | . | chr1: 84222001-84244800 |
| Liver | HABP2 | chr10: 115304201-115326000 |
| Liver | INHBA | chr7: 41737001-41758800 |
| Liver | AKR1CL1 | chr10: 5215201-5236800 |
| Liver | ALB | chr4: 74260001-74281200 |
| Liver | CLDN14 | chr21: 37842201-37864600 |
| Liver | AC004862.6 | chr7: 79991801-80014200 |
| Liver | HRG | chr3: 186375201-186396800 |
| Liver | . | chr6: 136139401-136161600 |
| Liver | SAA4 | chr11: 18247401-18269200 |
| Liver | SERPINC1 | chr1: 173876001-173897600 |
| Liver | . | chr2: 21308801-21331000 |
| Liver | ADH1A | chr4: 100201201-100223200 |
| Liver | . | chr16: 28526401-28548400 |
| Liver | CFHR5 | chr1: 196934001-196957000 |
| Liver | . | chr13: 74729801-74752200 |
| Liver | . | chr1: 119912601-119935400 |
| Liver | LINC01485 | chr5: 173206601-173228000 |
| Liver | SLC22A9 | chr11: 63128201-63149800 |
| Liver | . | chr6: 8896801-8919400 |
| Liver | . | chr4: 155495201-155517000 |
| Liver | ITIH3 | chr3: 52818201-52839800 |
| Liver | . | chr9: 4604001-4626000 |
| Liver | . | chr5: 133740201-133762400 |
| Liver | EVA1A | chr2: 75734201-75756200 |
| Liver | DQ590166; HSD17B6 | chr12: 57148201-57170200 |
| Liver | RDH16 | chr12: 57341001-57362600 |
| Liver | CRP | chr1: 159670801-159693400 |
| Liver | FAM214A | chr15: 52988401-53010800 |
| Liver | SERPIND1 | chr22: 21117801-21139600 |
| Liver | . | chr10: 77781001-77803200 |
| Liver | RP11-328K4.1 | chr4: 104335601-104357400 |
| Liver | . | chr16: 76552801-76575000 |
| Liver | GAS2 | chr11: 22687201-22710200 |
| Liver | . | chr1: 161182001-161202600 |
| Liver | CFHR3; CFHR1 | chr1: 196733201-196756000 |
| Liver | SMUG1P1 | chr18: 47166801-47189200 |
| Liver | CP | chr3: 148926601-148947800 |
| Liver | GYS2 | chr12: 21742801-21765400 |
| Liver | CPN2 | chr3: 194061201-194082800 |
| Liver | ABCG5; ABCG8 | chr2: 44058201-44080900 |
| Liver | RNA5SP288 | chr9: 97895001-97916600 |
| Liver | . | chr8: 85387401-85410200 |
| Liver | ATP11B | chr3: 182602601-182624400 |
| Liver | LEAP2 | chr5: 132200401-132222200 |
| Liver | HABP2 | chr10: 115301601-115323400 |

TABLE 1-continued

H3K4me3 tissue-specific locations

| Signature | Gene | Genomic Location |
|---|---|---|
| Liver | F13B | chr1: 197023001-197045200 |
| Liver | LOC157273 | chr8: 9173001-9195800 |
| Liver | MIR122 | chr18: 56100601-56122600 |
| Liver | . | chr4: 155522601-155543600 |
| Liver | . | chr10: 72073201-72093 800 |
| Liver | . | chr12: 92884601-92906800 |
| Liver | SLCO1B3 | chr12: 20953001-20975200 |
| Liver | . | chr5: 56936401-56957600 |
| Liver | MIR122 | chr18: 56104601-56125200 |
| Liver | SDS | chr12: 113830001-113851400 |
| Liver | . | chr3: 125326001-125348200 |
| Liver | F13B | chr1: 197025201-197047400 |
| Liver | . | chr6: 23572401-23595000 |
| Liver | UGT2B15 | chr4: 69523801-69546000 |
| Liver | . | chr10: 93857601-93880200 |
| Vasculary | AC073130.3 | chr12: 105852801-105875400 |
| Vasculary | AC073130.3 | chr7: 115956001-115977800 |
| Vasculary | PTPRE | chr10: 129774601-129797600 |
| Vasculary | . | chr12: 96820801-96843600 |
| Vasculary | CTD-2337A12.1 | chr5: 95910001-95932000 |
| Vasculary | ESM1 | chr5: 54269201-54289800 |
| Vasculary | VEPH1 | chr3: 157240001-157261000 |
| Vasculary | RP11-322E11.5 | chr18: 33034401-33055800 |
| Vasculary | . | chr2: 216702601-216724000 |
| Vasculary | LOC729987 | chr1: 98666201-98687400 |
| Vasculary | . | chr6: 12284601-12306200 |
| Vasculary | . | chr1: 98542601-98565600 |
| Vasculary | . | chr4: 85779401-85801400 |
| Vasculary | RP3-390M24.1 | chr6: 79303001-79325000 |
| Vasculary | RP11-679B17.2 | chr6: 11598201-11619800 |
| Vasculary | RP11-115J23.1 | chr11: 28714401-28736800 |
| Vasculary | ESM1 | chr5: 54269801-54290400 |
| Vasculary | VEPH1 | chr3: 157237601-157260000 |
| Vasculary | . | chr2: 56133801-56155600 |
| Vasculary | CTD-2337A12.1 | chr5: 95912001-95933800 |
| Vasculary | TNFSF18 | chr1: 173008201-173030600 |
| Vasculary | RP3-390M24.1 | chr6: 79305001-79325600 |
| Vasculary | . | chr5: 28145601-28167600 |
| Vasculary | PCAT19 | chr19: 41974401-41995000 |
| Vasculary | MIR216A | chr2: 56204201-56227000 |
| Vasculary | LOC100507254 | chr6: 132445801-132466600 |
| Vasculary | . | chr8: 78257401-78280400 |
| T-Helper-Cells | . | chr21: 26927401-26948400 |
| T-Helper-Cells | . | chr5: 156641201-156666200 |
| T-Helper-Cells | CCL20 | chr2: 228666201-228688600 |
| T-Helper-Cells | . | chr21: 26931801-26953600 |
| T-Helper-Cells | MAP3K4 | chr6: 161491601-161513200 |
| T-Helper-Cells | . | chr12: 94157201-94179600 |
| T-Helper-Cells | . | chr8: 128992001-129013600 |
| T-Helper-Cells | . | chr9: 123675001-123695800 |
| T-Helper-Cells | . | chr2: 228661001-228683200 |
| T-Helper-Cells | . | chr21: 26929001-26949600 |
| T-Helper-Cells | . | chr17: 80269601-80291000 |
| T-Helper-Cells | BC045668; IL21 | chr4: 123529201-123551000 |
| T-Helper-Cells | . | chr1: 206746601-206768000 |
| T-Helper-Cells | . | chr7: 130631401-130652200 |
| T-Helper-Cells | . | chr6: 161493201-161514800 |
| T-Helper-Cells | . | chr6: 16427801-16449400 |
| T-Helper-Cells | . | chr22: 47061801-47083200 |
| T-Helper-Cells | . | chr8: 128993601-129014600 |
| T-Helper-Cells | . | chr14: 103262801-103285200 |
| T-Helper-Cells | . | chr15: 60982201-61004600 |
| T-Helper-Cells | . | chr2: 228663201-228685200 |
| T-Helper-Cells | . | chr18: 9079201-9101400 |
| T-Helper-Cells | . | chr2: 228703401-228725600 |
| T-Helper-Cells | . | chr5: 156640201-156661200 |
| T-Helper-Cells | . | chr21: 26928401-26949000 |
| T-Helper-Cells | . | chr2: 157174801-157195600 |
| T-Cells | . | chr6: 112176801-112199600 |
| T-Cells | RNU6-933P | chr11: 60740601-60763400 |
| T-Cells | . | chr21: 26927401-26948400 |
| T-Cells | . | chr10: 6087801-6110800 |
| T-Cells | . | chr5: 156641201-156666200 |
| T-Cells | RP11-61O1.1 | chr14: 98658001-98680400 |
| T-Cells | . | chr10: 6090801-6111800 |
| T-Cells | ARHGAP15 | chr2: 143995201-144017000 |

| Signature | Gene | Genomic Location |
|---|---|---|
| T-Cells | CCL20 | chr2: 228666201-228688600 |
| T-Cells | . | chr21: 26931801-26953600 |
| T-Cells | CTLA4 | chr2: 204722601-204743400 |
| T-Cells | . | chr2: 204707801-204730400 |
| T-Cells | MAP3K4 | chr6: 161491601-161513200 |
| T-Cells | ICOS | chr2: 204788401-204810600 |
| T-Cells | RNU6-933P | chr11: 60744201-60765800 |
| T-Cells | AX747844 | chr12: 47593001-47614600 |
| T-Cells | TNIP3 | chr4: 122135801-122158200 |
| T-Cells | . | chr12: 94157201-94179600 |
| T-Cells | . | chr15: 60853601-60876400 |
| T-Cells | . | chr8: 128992001-129013600 |
| T-Cells | . | chr9: 123672801-123693800 |
| T-Cells | . | chr9: 123675001-123695800 |
| T-Cells | . | chr8: 134065601-134087400 |
| T-Cells | TLDC1 | chr16: 84575801-84597200 |
| T-Cells | . | chr2: 228661001-228683200 |
| T-Cells | . | chr21: 26929001-26949600 |
| T-Cells | . | chr3: 16333201-16354200 |
| T-Cells | CDC14A | chr1: 100875801-100898600 |
| T-Cells | . | chr4: 90199801-90222200 |
| T-Cells | CYTIP | chr2: 158293001-158314600 |
| T-Cells | . | chr2: 204796001-204817800 |
| T-Cells | . | chr22: 37605601-37626400 |
| T-Cells | . | chr17: 80269601-80291000 |
| T-Cells | . | chr21: 26933601-26955200 |
| T-Cells | RP11-291B21.2 | chr12: 10695601-10716800 |
| T-Cells | CTLA4 | chr2: 204724801-204745600 |
| T-Cells | . | chr15: 60863601-60886200 |
| T-Cells | RTKN2 | chr10: 63983001-64005400 |
| T-Cells | RP11-799D4.2 | chr17: 33505001-33527400 |
| T-Cells | ETS1 | chr11: 128324001-128346600 |
| T-Cells | . | chr1: 160518401-160540200 |
| T-Cells | BC045668; IL21 | chr4: 123529201-123551000 |
| T-Cells | RP11-61O1.1 | chr14: 98655401-98678000 |
| T-Cells | . | chr6: 128289201-128312200 |
| T-Cells | . | chr4: 143305601-143328400 |
| T-Cells | . | chr12: 9938801-9960200 |
| T-Cells | . | chr14: 61791401-61814000 |
| T-Cells | . | chr1: 206746601-206768000 |
| T-Cells | . | chr2: 204566201-204588800 |
| T-Cells | . | chr1: 90062201-90084400 |
| T-Cells | . | chr7: 130631401-130652200 |
| T-Cells | . | chr22: 40294801-40317200 |
| T-Cells | . | chr6: 161493201-161514800 |
| T-Cells | . | chr16: 27409001-27431000 |
| T-Cells | . | chr1: 117292801-117314600 |
| T-Cells | . | chr6: 16427801-16449400 |
| T-Cells | . | chr6: 33302001-33323400 |
| T-Cells | . | chr4: 143308401-143331200 |
| T-Cells | . | chr22: 47061801-47083200 |
| T-Cells | CTLA4 | chr2: 204723801-204744400 |
| T-Cells | . | chr4: 143287401-143310000 |
| T-Cells | . | chr8: 128993601-129014600 |
| T-Cells | . | chr21: 36404601-36426800 |
| T-Cells | . | chr14: 103262801-103285200 |
| T-Cells | . | chr3: 108542801-108564600 |
| T-Cells | . | chr15: 60982201-61004600 |
| T-Cells | . | chr2: 228663201-228685200 |
| T-Cells | BC062769 | chr2: 197115801-197137400 |
| T-Cells | . | chr1: 90066401-90088800 |
| T-Cells | USP44 | chr12: 95934801-95957200 |
| T-Cells | . | chr3: 59982801-60005400 |
| T-Cells | FANK1 | chr10: 127674201-127696600 |
| T-Cells | . | chr2: 106344201-106367000 |
| T-Cells | ANK3 | chr10: 62475401-62498200 |
| T-Cells | . | chr19: 9963401-9985000 |
| T-Cells | . | chr8: 121733601-121754600 |
| T-Cells | . | chr17: 38758401-38780400 |
| T-Cells | . | chr18: 9079201-9101400 |
| T-Cells | . | chr2: 228703401-228725600 |
| T-Cells | . | chr5: 156640201-156661200 |
| T-Cells | . | chr14: 98640001-98662400 |
| T-Cells | . | chr3: 42669401-42691200 |
| T-Cells | . | chr8: 129539401-129562400 |
| T-Cells | . | chr7: 50411401-50433000 |

TABLE 1-continued

H3K4me3 tissue-specific locations

| Signature | Gene | Genomic Location |
|---|---|---|
| T-Cells | . | chr15: 60856401-60879200 |
| T-Cells | . | chr2: 181994801-182017400 |
| T-Cells | TRABD2A | chr2: 85056801-85079600 |
| T-Cells | RN7SL328P | chr9: 134593001-134614600 |
| T-Cells | TIGIT | chr3: 114003001-114024400 |
| T-Cells | . | chr16: 27407801-27428600 |
| T-Cells | GIMAP4 | chr7: 150250801-150272800 |
| T-Cells | . | chr5: 156608401-156630800 |
| T-Cells | . | chr21: 26928401-26949000 |
| T-Cells | . | chr2: 157174801-157195600 |
| T-Cells | CLEC2D | chr12: 9818401-9840200 |
| T-Cells | . | chr1: 12560601-12581600 |
| T-Cells | RP11-61O1A | chr14: 98660401-98681600 |
| T-Cells | . | chr14: 102271201-102293000 |
| T-Cells | . | chr6: 154541401-154564200 |
| T-Cells | . | chr1: 214803401-214825800 |
| T-Cells | . | chr2: 143999001-144021000 |
| T-Cells | RP1-281H8.3 | chr6: 149806001-149828200 |
| NK | TARP | chr7: 38304201-38325800 |
| NK | . | chr2: 8411201-8432600 |
| NK | KLRF1 | chr12: 9970201-9991600 |
| NK | . | chr17: 66206801-66229600 |
| NK | CMC1 | chr3: 28323201-28344800 |
| NK | KLRD1 | chr12: 10451601-10472400 |
| NK | TRDC | chr14: 22910401-22932800 |
| NK | AK096766 | chr7: 38333401-38355000 |
| NK | KLRD1 | chr12: 10452401-10473400 |
| NK | CMC1 | chr3: 28324801-28346400 |
| NK | SH2D1B | chr1: 162369401-162391200 |
| NK | TCRDV2 | chr14: 22916401-2293 8600 |
| NK | KLRD1 | chr12: 10448001-10470000 |
| Lymphocytes | . | chr6: 112176801-112199600 |
| Lymphocytes | RNU6-933P | chr11: 60740601-60763400 |
| Lymphocytes | . | chr21: 26927401-26948400 |
| Lymphocytes | HLA-DOB | chr6: 32774001-32794800 |
| Lymphocytes | . | chr10: 6087801-6110800 |
| Lymphocytes | . | chr5: 156641201-156666200 |
| Lymphocytes | TARP | chr7: 38304201-38325800 |
| Lymphocytes | RP11-61O1.1 | chr14: 98658001-98680400 |
| Lymphocytes | . | chr10: 6090801-6111800 |
| Lymphocytes | AK128525 | chr2: 89147801-89169600 |
| Lymphocytes | . | chr2: 8411201-8432600 |
| Lymphocytes | KLRF1 | chr12: 9970201-9991600 |
| Lymphocytes | ARHGAP15 | chr2: 143995201-144017000 |
| Lymphocytes | . | chr3: 40655601-40676800 |
| Lymphocytes | CCL20 | chr2: 228666201-228688600 |
| Lymphocytes | . | chr21: 26931801-26953600 |
| Lymphocytes | CTLA4 | chr2: 204722601-204743400 |
| Lymphocytes | . | chr2: 204707801-204730400 |
| Lymphocytes | . | chr17: 66206801-66229600 |
| Lymphocytes | MAP3K4 | chr6: 161491601-161513600 |
| Lymphocytes | ICOS | chr2: 204788401-204810600 |
| Lymphocytes | RNU6-933P | chr11: 60744201-60765800 |
| Lymphocytes | CMC1 | chr3: 28323201-28344800 |
| Lymphocytes | AX747844 | chr12: 47593001-47614600 |
| Lymphocytes | TNIP3 | chr4: 122135801-122158200 |
| Lymphocytes | . | chr12: 94157201-94179600 |
| Lymphocytes | . | chr15: 60853601-60876400 |
| Lymphocytes | . | chr8: 128992001-129013600 |
| Lymphocytes | . | chr9: 123672801-123693800 |
| Lymphocytes | . | chr9: 123675001-123695800 |
| Lymphocytes | KLRD1 | chr12: 10451601-10472400 |
| Lymphocytes | . | chr8: 134065601-134087400 |
| Lymphocytes | TLDC1 | chr16: 84575801-84597200 |
| Lymphocytes | . | chr2: 228661001-228683200 |
| Lymphocytes | FYN | chr6: 112103401-112125600 |
| Lymphocytes | LILRB1 | chr19: 55118401-55140200 |
| Lymphocytes | . | chr21: 26929001-26949600 |
| Lymphocytes | . | chr3: 16333201-16354200 |
| Lymphocytes | CDC14A | chr1: 100875801-100898600 |
| Lymphocytes | . | chr4: 90199801-90222200 |
| Lymphocytes | CYTIP | chr2: 158293001-158314600 |
| Lymphocytes | . | chr2: 204796001-204817800 |
| Lymphocytes | TRDC | chr14: 22910401-22932800 |
| Lymphocytes | . | chr22: 37605601-37626400 |
| Lymphocytes | . | chr17: 80269601-80291000 |
| Lymphocytes | SAMD3 | chr6: 130525801-130546600 |
| Lymphocytes | . | chr21: 26933601-26955200 |
| Lymphocytes | AK096766 | chr7: 38333401-38355000 |
| Lymphocytes | RP11-291B21.2 | chr12: 10695601-10716800 |
| Lymphocytes | CTLA4 | chr2: 204724801-204745600 |
| Lymphocytes | . | chr15: 60863601-60886200 |
| Lymphocytes | FCRL3 | chr1: 157659001-157680800 |
| Lymphocytes | RTKN2 | chr10: 63983001-64005400 |
| Lymphocytes | RP11-799D4.2 | chr17: 33505001-33527400 |
| Lymphocytes | ETS1 | chr11: 128324001-128346600 |
| Lymphocytes | . | chr1: 160518401-160540200 |
| Lymphocytes | BC045668; IL21 | chr4: 123529201-123551000 |
| Lymphocytes | RP11-61O1.1 | chr14: 98655401-98678000 |
| Lymphocytes | . | chr6: 128289201-128312200 |
| Lymphocytes | . | chr4: 143305601-143328400 |
| Lymphocytes | . | chr12: 9938801-9960200 |
| Lymphocytes | . | chr14: 61791401-61814000 |
| Lymphocytes | . | chr1: 206746601-206768000 |
| Lymphocytes | KLRD1 | chr12: 10452401-10473400 |
| Lymphocytes | . | chr2: 204566201-204588800 |
| Lymphocytes | . | chr1: 90062201-90084400 |
| Lymphocytes | . | chr7: 130631401-130652200 |
| Lymphocytes | . | chr22: 40294801-40317200 |
| Lymphocytes | . | chr6: 161493201-161514800 |
| Lymphocytes | . | chr16: 27409001-27431000 |
| Lymphocytes | . | chr1: 117292801-117314600 |
| Lymphocytes | . | chr6: 16427801-16449400 |
| Lymphocytes | . | chr6: 33302001-33323400 |
| Lymphocytes | . | chr4: 143308401-143331200 |
| Lymphocytes | CCL5 | chr17: 34196201-34217200 |
| Lymphocytes | . | chr22: 47061801-47083200 |
| Lymphocytes | CTLA4 | chr2: 204723801-204744400 |
| Lymphocytes | . | chr4: 143287401-143310000 |
| Lymphocytes | . | chr8: 128993601-129014600 |
| Lymphocytes | . | chr21: 36404601-36426800 |
| Lymphocytes | . | chr14: 103262801-103285200 |
| Lymphocytes | . | chr3: 108542801-108564600 |
| Lymphocytes | . | chr15: 60982201-61004600 |
| Lymphocytes | . | chr2: 228663201-228685200 |
| Lymphocytes | CMC1 | chr3: 28324801-28346400 |
| Lymphocytes | CYB561A3 | chr11: 61112201-61134000 |
| Lymphocytes | BC062769 | chr2: 197115801-197137400 |
| Lymphocytes | . | chr1: 90066401-90088800 |
| Lymphocytes | USP44 | chr12: 95934801-95957200 |
| Lymphocytes | SH2D1B | chr1: 162369401-162391200 |
| Lymphocytes | . | chr3: 59982801-60004400 |
| Lymphocytes | FANK1 | chr10: 127674201-127696600 |
| Lymphocytes | . | chr2: 106344201-106367000 |
| Lymphocytes | ANK3 | chr10: 62475401-62498200 |
| Lymphocytes | . | chr19: 9963401-9985900 |
| Lymphocytes | . | chr1: 25241001-25262600 |
| Lymphocytes | . | chr8: 121733601-121754600 |
| Lymphocytes | . | chr17: 38758401-38780400 |
| Lymphocytes | . | chr18: 9079201-9101400 |
| Lymphocytes | . | chr2: 228703401-228725600 |
| Lymphocytes | . | chr5: 156640201-156661200 |
| Lymphocytes | . | chr14: 98640001-98662400 |
| Lymphocytes | . | chr3: 42669401-42691200 |
| Lymphocytes | . | chr8: 12953 9401-129562400 |
| Lymphocytes | . | chr17: 61995401-62017200 |
| Lymphocytes | AC002480.5 | chr7: 22689001-22711600 |
| Lymphocytes | . | chr7: 50411401-50433000 |
| Lymphocytes | CCL5 | chr17: 34192801-34214800 |
| Lymphocytes | GTF3C1 | chr16: 27464001-27486600 |
| Lymphocytes | . | chr15: 60856401-60879200 |
| Lymphocytes | . | chr2: 181994801-182017400 |
| Lymphocytes | AK128525 | chr2: 89149801-89170400 |
| Lymphocytes | TRABD2A | chr2: 85056801-85079600 |
| Lymphocytes | RN7SL328P | chr9: 134593001-134614600 |
| Lymphocytes | TIGIT | chr3: 114003001-114024400 |
| Lymphocytes | TCL1A; BX247990 | chr14: 96170201-96192800 |
| Lymphocytes | TCRDV2 | chr14: 22916401-22938600 |
| Lymphocytes | . | chr16: 27407801-27428600 |
| Lymphocytes | GIMAP4 | chr7: 150250801-150272800 |
| Lymphocytes | . | chr5: 156608401-156630800 |
| Lymphocytes | . | chr21: 26928401-26949000 |

TABLE 1-continued

H3K4me3 tissue-specific locations

| Signature | Gene | Genomic Location |
|---|---|---|
| Lymphocytes | . | chr2: 157174801-157195600 |
| Lymphocytes | KLRD1 | chr12: 10448001-10470000 |
| Lymphocytes | CLEC2D | chr12: 9818401-9840200 |
| Lymphocytes | . | chr1: 12560601-12581600 |
| Lymphocytes | RP11-61O1.1 | chr14: 98660401-98681600 |
| Lymphocytes | . | chr14: 102271201-102293000 |
| Lymphocytes | . | chr6: 154541401-154564200 |
| Lymphocytes | . | chr1: 214803401-214825800 |
| Lymphocytes | . | chr2: 143999001-144021000 |
| Lymphocytes | RP11-428G5.5 | chr12: 32029401-32050200 |
| Lymphocytes | RP1-281H8.3 | chr6: 149806001-149828200 |
| Neutrophils | SIGLEC5 | chr19: 52120201-52141600 |
| Neutrophils | MMP9 | chr20: 44627401-44649000 |
| Neutrophils | CMTM2 | chr16: 66611001-66632200 |
| Neutrophils | RP1-229K20.5 | chr6: 41228801-41249800 |
| Neutrophils | PGLYRP1 | chr19: 46515801-46536800 |
| Neutrophils | . | chr3: 128940401-128961200 |
| Neutrophils | . | chr16: 84800001-84821600 |
| Neutrophils | HCAR3 | chr12: 123188801-123210200 |
| Neutrophils | RP1-229K20.5 | chr6: 41227401-41248800 |
| Neutrophils | IL1R2 | chr2: 102599401-102620000 |
| Neutrophils | . | chr16: 1978001-1999200 |
| Neutrophils | FFAR2 | chr19: 35931001-35951800 |
| Neutrophils | APOBEC3A | chr22: 39338601-39359200 |
| Neutrophils | 8-Mar | chr10: 45948801-45969800 |
| Neutrophils | FFAR2 | chr19: 35930201-35950800 |
| Neutrophils | . | chr1: 180091001-180111800 |
| Neutrophils | BTNL8 | chr5: 180326601-180347800 |
| Neutrophils | . | chr16: 84798801-84819400 |
| Neutrophils | . | chr17: 76402401-76423000 |
| Neutrophils | . | chr16: 84799401-84820000 |
| Neutrophils | . | chr17: 79113601-79134400 |
| Neutrophils | . | chr16: 3090401-3111200 |
| Neutrophils | PAM16 | chr16: 4385601-4406600 |
| Neutrophils | . | chr19: 52121601-52142200 |
| Neutrophils | PGLYRP1 | chr19: 46515201-46535800 |
| Neutrophils | AC002511.3 | chr19: 35911201-35933000 |
| Neutrophils | ARRB2 | chr17: 4610401-4631400 |
| Neutrophils | BC016366 | chr4: 185765601-185787000 |
| Monocytes | RPL7AP64 | chr17: 7029801-7052600 |
| Monocytes | E02193 | chr12: 69735601-69758600 |
| Monocytes | CD300E | chr17: 72608201-72629400 |
| Monocytes | CD300E | chr17: 72606001-72628200 |
| Monocytes | CD300LB | chr17: 72516401-72537400 |
| Monocytes | CD300C | chr17: 72531201-72552200 |
| Monocytes | CD300E | chr17: 72609401-72631000 |
| Monocytes | . | chr7: 36746601-36769200 |
| Monocytes | CLEC12A | chr12: 10115801-10136600 |
| Monocytes | SPIDR | chr8: 48262801-48285200 |
| Monocytes | CLEC12A | chr12: 10115201-10135800 |
| Monocytes | . | chr3: 196407201-196427800 |
| Monocytes | CTSS | chr1: 150724601-150745200 |
| Monocytes | CLEC12A | chr12: 10114601-10135200 |
| Leukocytes | GNLY | chr2: 85913801-85933900 |
| Leukocytes | . | chr6: 112176801-112199600 |
| Leukocytes | PRKCQ-AS1 | chr10: 6616201-6637800 |
| Leukocytes | PRF1 | chr10: 72351601-72372600 |
| Leukocytes | RPL7AP64 | chr17: 7029801-7052600 |
| Leukocytes | SEMA4A | chr1: 156114401-156135400 |
| Leukocytes | RNU6-933P | chr11: 60740601-60763400 |
| Leukocytes | . | chr21: 26927401-26948400 |
| Leukocytes | HLA-DOB | chr6: 32774001-32794800 |
| Leukocytes | . | chr10: 6087801-6110800 |
| Leukocytes | KLRK1 | chr12: 10531401-10552400 |
| Leukocytes | NUP214 | chr9: 134093401-134114400 |
| Leukocytes | KLRK1 | chr12: 10529601-10551400 |
| Leukocytes | . | chr5: 156641201-156666200 |
| Leukocytes | SIGLEC5 | chr19: 52120201-52141600 |
| Leukocytes | TARP | chr7: 38304201-38325800 |
| Leukocytes | FASLG | chr1: 172618601-172640600 |
| Leukocytes | RP4-576H24.4; SIRPB1 | chr20: 1557601-1579000 |
| Leukocytes | RP11-61O1.1 | chr14: 98658001-98680400 |
| Leukocytes | . | chr10: 6090801-6111800 |
| Leukocytes | SYNE1 | chr6: 152495001-152516800 |
| Leukocytes | AK128525 | chr2: 89147801-89169600 |
| Leukocytes | . | chr1: 206729201-206751200 |
| Leukocytes | KLRC4-KLRK1 | chr12: 10549001-10571400 |
| Leukocytes | CD226 | chr18: 67613201-67634600 |
| Leukocytes | MMP9 | chr20: 44627401-44649000 |
| Leukocytes | . | chr8: 128978201-128999200 |
| Leukocytes | . | chr2: 8411201-8432600 |
| Leukocytes | KLRK1 | chr12: 10527001-10549600 |
| Leukocytes | KLRF1 | chr12: 9970201-9991600 |
| Leukocytes | CD86 | chr3: 121764201-121785400 |
| Leukocytes | ARHGAP15 | chr2: 143995201-144017000 |
| Leukocytes | ARRB2 | chr17: 4607201-4628800 |
| Leukocytes | . | chr8: 126949201-126969800 |
| Leukocytes | . | chr3: 40655601-40676800 |
| Leukocytes | LINC01259 | chr4: 38501601-38522800 |
| Leukocytes | . | chr20: 24922601-24943800 |
| Leukocytes | MORC2 | chr22: 31325201-31347800 |
| Leukocytes | E02193 | chr12: 69735601-69758600 |
| Leukocytes | CMTM2 | chr16: 66611001-66632200 |
| Leukocytes | CD33 | chr19: 51718401-51739400 |
| Leukocytes | CCL20 | chr2: 228666201-228688600 |
| Leukocytes | . | chr21: 26931801-26953200 |
| Leukocytes | CTLA4 | chr2: 204722601-204743400 |
| Leukocytes | RP1-229K20.5 | chr6: 41228801-41249800 |
| Leukocytes | RGS3 | chr9: 116269601-116290600 |
| Leukocytes | . | chr8: 126942201-126967800 |
| Leukocytes | . | chr6: 90778601-90800000 |
| Leukocytes | . | chr2: 204707801-204730400 |
| Leukocytes | . | chr20: 57724601-57745800 |
| Leukocytes | SAMD3 | chr6: 130522801-130544800 |
| Leukocytes | CLEC2D | chr12: 9815001-9836600 |
| Leukocytes | . | chr17: 66206801-66229600 |
| Leukocytes | CD300E | chr17: 72608201-72629400 |
| Leukocytes | MAP3K4 | chr6: 161491601-161513200 |
| Leukocytes | LIM2 | chr19: 51880401-51901800 |
| Leukocytes | ICOS | chr2: 204788401-204810600 |
| Leukocytes | NLRC5 | chr16: 57064001-57085400 |
| Leukocytes | RNU6-933P | chr11: 60744201-60765800 |
| Leukocytes | . | chr6: 90780001-90801200 |
| Leukocytes | SPATA13-AS1 | chr13: 24817401-24838800 |
| Leukocytes | CMC1 | chr3: 28323201-28344800 |
| Leukocytes | AX747844 | chr12: 47593001-47614400 |
| Leukocytes | TNIP3 | chr4: 122135801-122158200 |
| Leukocytes | . | chr12: 94157201-94179600 |
| Leukocytes | FPR1 | chr19: 52241201-52262600 |
| Leukocytes | PGLYRP1 | chr19: 46515801-46536800 |
| Leukocytes | . | chr17: 8846601-8868800 |
| Leukocytes | . | chr15: 60853601-60876400 |
| Leukocytes | . | chr8: 128992001-129013600 |
| Leukocytes | . | chr9: 123672801-123693800 |
| Leukocytes | CD300E | chr17: 72606001-72628200 |
| Leukocytes | RBPJ | chr4: 26264601-26286000 |
| Leukocytes | . | chr9: 123675001-123695800 |
| Leukocytes | CD300LB | chr17: 72516401-72537400 |
| Leukocytes | LTB4R | chr14: 24773201-24794600 |
| Leukocytes | KLRD1 | chr12: 10451601-10472400 |
| Leukocytes | . | chr3: 128940401-128961200 |
| Leukocytes | . | chr20: 54993801-55015400 |
| Leukocytes | AK291611 | chr7: 38364201-38386000 |
| Leukocytes | . | chr8: 134065601-134087400 |
| Leukocytes | CD300C | chr17: 72531201-72552200 |
| Leukocytes | TLDC1 | chr16: 84575801-84597200 |
| Leukocytes | . | chr2: 228661001-228683200 |
| Leukocytes | FYN | chr6: 112103401-112125600 |
| Leukocytes | PADI4 | chr1: 17624801-17646200 |
| Leukocytes | CD300E | chr17: 72609401-72631000 |
| Leukocytes | LILRB1 | chr19: 55118401-55140200 |
| Leukocytes | ARHGEF11 | chr1: 156922801-156943800 |
| Leukocytes | . | chr21: 26929001-26950400 |
| Leukocytes | . | chr3: 16333201-16354200 |
| Leukocytes | . | chr10: 71842201-71863600 |
| Leukocytes | PTPN4 | chr2: 120677201-120698400 |
| Leukocytes | . | chr16: 84800001-84821600 |
| Leukocytes | CDC14A | chr1: 100875801-100898600 |
| Leukocytes | . | chr4: 90199801-90222200 |
| Leukocytes | . | chr17: 76902001-76923000 |
| Leukocytes | CYTIP | chr2: 158293001-158314600 |
| Leukocytes | . | chr2: 204796001-204817800 |

TABLE 1-continued

H3K4me3 tissue-specific locations

| Signature | Gene | Genomic Location |
|---|---|---|
| Leukocytes | TRDC | chr14: 22910401-22932800 |
| Leukocytes | . | chr22: 37605601-37626400 |
| Leukocytes | . | chr17: 80269601-80291000 |
| Leukocytes | SAMD3 | chr6: 130525801-130546600 |
| Leukocytes | HCAR3 | chr12: 123188801-123210200 |
| Leukocytes | . | chr21: 26933601-26955200 |
| Leukocytes | . | chr1: 206726201-206747200 |
| Leukocytes | . | chr3: 58329201-58350200 |
| Leukocytes | AK096766 | chr7: 38333401-38355000 |
| Leukocytes | . | chr14: 99492001-99513200 |
| Leukocytes | . | chr13: 40952601-40973800 |
| Leukocytes | RP11-291B21.2 | chr12: 10695601-10716800 |
| Leukocytes | CTLA4 | chr2: 204724801-204745600 |
| Leukocytes | RP1-229K20.5 | chr6: 41227401-41248800 |
| Leukocytes | IL1R2 | chr2: 102599401-102620000 |
| Leukocytes | PRAM1 | chr19: 8556201-8577200 |
| Leukocytes | . | chr1: 150575601-150597000 |
| Leukocytes | SIRPG | chr20: 1626801-1647400 |
| Leukocytes | . | chr15: 60863601-60886200 |
| Leukocytes | . | chr1: 206728001-206749200 |
| Leukocytes | . | chr1: 28442001-28463200 |
| Leukocytes | FCRL3 | chr1: 157659001-157680800 |
| Leukocytes | RTKN2 | chr10: 63983001-64005400 |
| Leukocytes | RP11-799D4.2 | chr17: 33505001-33527400 |
| Leukocytes | PIK3R1 | chr5: 67566601-67587600 |
| Leukocytes | ETS1 | chr11: 128324001-128346600 |
| Leukocytes | . | chr19: 18494001-18515200 |
| Leukocytes | . | chr16: 1978001-1999200 |
| Leukocytes | . | chr1: 160518401-160540200 |
| Leukocytes | . | chr2: 235388801-235410200 |
| Leukocytes | BC045668; IL21 | chr4: 123529201-123551000 |
| Leukocytes | RP11-61O1.1 | chr14: 98655401-98678000 |
| Leukocytes | . | chr6: 128289201-128312200 |
| Leukocytes | . | chr4: 143305601-143328400 |
| Leukocytes | FFAR2 | chr19: 35931001-35951800 |
| Leukocytes | AK056689 | chr13: 74795201-74816400 |
| Leukocytes | . | chr12: 9938801-9960200 |
| Leukocytes | . | chr14: 61791401-61814900 |
| Leukocytes | FPR2 | chr19: 52256801-52278200 |
| Leukocytes | . | chr1: 206746601-206768000 |
| Leukocytes | APOBEC3A | chr22: 39338601-39359200 |
| Leukocytes | . | chr2: 69394401-69415600 |
| Leukocytes | . | chr19: 8623801-8644800 |
| Leukocytes | KLRD1 | chr12: 10452401-10473400 |
| Leukocytes | 8-Mar | chr10: 45948801-45969800 |
| Leukocytes | FFAR2 | chr19: 35930201-35950800 |
| Leukocytes | CXCR2 | chr2: 218984401-219005400 |
| Leukocytes | . | chr20: 47366601-47388000 |
| Leukocytes | LILRA5 | chr19: 54813801-54834600 |
| Leukocytes | . | chr2: 204566201-204588800 |
| Leukocytes | . | chr1: 90062201-90084400 |
| Leukocytes | . | chr17: 75419601-75440800 |
| Leukocytes | . | chr20: 57728401-57749600 |
| Leukocytes | SIRPG | chr20: 1625401-1646800 |
| Leukocytes | . | chr7: 130631401-130652200 |
| Leukocytes | . | chr22: 40294801-40317200 |
| Leukocytes | . | chr6: 161493201-161514800 |
| Leukocytes | . | chr16: 27409001-27431000 |
| Leukocytes | . | chr1: 180091001-180111800 |
| Leukocytes | . | chr1: 117292801-117314600 |
| Leukocytes | . | chr6: 16427801-16449400 |
| Leukocytes | . | chr5: 156604801-156626600 |
| Leukocytes | . | chr6: 33302001-33323400 |
| Leukocytes | . | chr4: 143308401-143331200 |
| Leukocytes | BTNL8 | chr5: 180326601-180347800 |
| Leukocytes | CCL5 | chr17: 34196201-34217200 |
| Leukocytes | PIK3R1 | chr5: 67567801-67588800 |
| Leukocytes | PILRB | chr7: 99939201-99961000 |
| Leukocytes | RP11-326C3.13; RP11-326C3.12; IFITM3 | chr11: 316201-337800 |
| Leukocytes | 9-Sep | chr17: 75443201-75464400 |
| Leukocytes | CARS2 | chr13: 111307601-111329000 |
| Leukocytes | . | chr7: 36746601-36769200 |
| Leukocytes | . | chr1: 111754201-111775600 |
| Leukocytes | . | chr22: 47061801-47083200 |
| Leukocytes | PRKCQ-AS1 | chr10: 6615601-6636200 |
| Leukocytes | CTLA4 | chr2: 204723801-204744400 |
| Leukocytes | . | chr8: 142234601-142255800 |
| Leukocytes | . | chr4: 143287401-143310000 |
| Leukocytes | . | chr2: 20614001-20635000 |
| Leukocytes | . | chr8: 128993601-129014600 |
| Leukocytes | . | chr21: 36404601-36426800 |
| Leukocytes | GZMM | chr19: 534001-554800 |
| Leukocytes | . | chr14: 103262801-103285200 |
| Leukocytes | . | chr17: 74238001-74259600 |
| Leukocytes | AC092580.4 | chr2: 7857401-7879200 |
| Leukocytes | . | chr19: 4079001-4100000 |
| Leukocytes | IL23A | chr12: 56722601-56743600 |
| Leukocytes | . | chr16: 84798801-84819400 |
| Leukocytes | . | chr3: 108542801-108564600 |
| Leukocytes | . | chr15: 60982201-61004600 |
| Leukocytes | . | chr2: 228663201-228685200 |
| Leukocytes | CMC1 | chr3: 28324801-28346400 |
| Leukocytes | . | chr17: 76402401-76423400 |
| Leukocytes | CYB561A3 | chr11: 61112201-61134000 |
| Leukocytes | SIRPG | chr20: 1627801-1648400 |
| Leukocytes | . | chr13: 110373601-110394600 |
| Leukocytes | . | chr16: 84799401-84820000 |
| Leukocytes | BC062769 | chr2: 197115801-197137400 |
| Leukocytes | . | chr1: 90066401-90088800 |
| Leukocytes | USP44 | chr12: 95934801-95957200 |
| Leukocytes | SH2D1B | chr1: 162369401-162391200 |
| Leukocytes | . | chr3: 59982801-60005400 |
| Leukocytes | RP11-14I17.3 | chr8: 26287801-26309200 |
| Leukocytes | DCTN4 | chr5: 150103601-150124800 |
| Leukocytes | . | chr17: 79113601-79134400 |
| Leukocytes | AC018816.3 | chr3: 4862201-4883600 |
| Leukocytes | FANK1 | chr10: 127674201-127696600 |
| Leukocytes | C19orf38 | chr19: 10949001-10969800 |
| Leukocytes | CLEC12A | chr12: 10115801-10136600 |
| Leukocytes | LDLRAP1 | chr1: 25880601-25901400 |
| Leukocytes | . | chr2: 106344201-106367000 |
| Leukocytes | ANK3 | chr10: 62475401-62498200 |
| Leukocytes | LINC01259 | chr4: 38503001-38525400 |
| Leukocytes | . | chr16: 3090401-3111200 |
| Leukocytes | . | chr19: 9963401-9985000 |
| Leukocytes | . | chr1: 25241001-25262600 |
| Leukocytes | . | chr8: 121733601-121754600 |
| Leukocytes | . | chr17: 38758401-38780400 |
| Leukocytes | . | chr18: 9079201-9101400 |
| Leukocytes | . | chr2: 228703401-228725600 |
| Leukocytes | PAM16 | chr16: 4385601-4406600 |
| Leukocytes | . | chr5: 156640201-156661200 |
| Leukocytes | . | chr14: 98640001-98662400 |
| Leukocytes | FPR2 | chr19: 52254001-52275000 |
| Leukocytes | . | chr8: 126947801-126968800 |
| Leukocytes | . | chr3: 42669401-42691200 |
| Leukocytes | . | chr8: 129539401-129562400 |
| Leukocytes | SPIDR | chr8: 48262801-48285200 |
| Leukocytes | CLEC12A | chr12: 10115201-10135600 |
| Leukocytes | . | chr17: 61995401-62017200 |
| Leukocytes | AC002480.5 | chr7: 22689001-22711600 |
| Leukocytes | . | chr12: 105066001-105087000 |
| Leukocytes | AK057187 | chr2: 38044801-38066400 |
| Leukocytes | . | chr7: 50411401-50433300 |
| Leukocytes | CCL5 | chr17: 34192801-34214800 |
| Leukocytes | GTF3C1 | chr16: 27464001-27486000 |
| Leukocytes | THEMIS | chr6: 128228601-128249600 |
| Leukocytes | NLRC5 | chr16: 57063001-57084000 |
| Leukocytes | . | chr7: 142614001-142635600 |
| Leukocytes | . | chr19: 52121601-52142200 |
| Leukocytes | . | chr15: 60856401-60879200 |
| Leukocytes | . | chr5: 66478801-66499800 |
| Leukocytes | RP11-127L20.3 | chr10: 106073401-106094600 |
| Leukocytes | . | chr2: 181994801-182017400 |
| Leukocytes | AK128525 | chr2: 89149801-89170400 |
| Leukocytes | TRABD2A | chr2: 85056801-85079600 |
| Leukocytes | RN7SL328P | chr9: 134593001-134614600 |
| Leukocytes | PRKCQ-AS1 | chr10: 6617801-6639400 |
| Leukocytes | C5AR2 | chr19: 47830001-47851000 |
| Leukocytes | TIGIT | chr3: 114003001-114024400 |
| Leukocytes | TCL1A; BX247990 | chr14: 96170201-96192800 |

TABLE 1-continued

H3K4me3 tissue-specific locations

| Signature | Gene | Genomic Location |
|---|---|---|
| Leukocytes | TCRDV2 | chr14: 22916401-22938600 |
| Leukocytes | . | chr1: 42194201-42215600 |
| Leukocytes | IRF4 | chr6: 384001-404600 |
| Leukocytes | . | chr16: 27407801-27428600 |
| Leukocytes | GIMAP4 | chr7: 150250801-150272800 |
| Leukocytes | . | chr5: 156608401-156630800 |
| Leukocytes | . | chr17: 76903801-76924800 |
| Leukocytes | . | chr16: 84621001-84642000 |
| Leukocytes | . | chr8: 142120401-142141800 |
| Leukocytes | DNAJC19P3 | chr19: 42134001-42155800 |
| Leukocytes | PGLYRP1 | chr19: 46515201-46535800 |
| Leukocytes | . | chr21: 26928401-26949000 |
| Leukocytes | . | chr2: 157174801-157195600 |
| Leukocytes | KLRD1 | chr12: 10448001-10470000 |
| Leukocytes | CLEC2D | chr12: 9818401-9840200 |
| Leukocytes | . | chr3: 71818801-71839800 |
| Leukocytes | . | chr1: 12560601-12581600 |
| Leukocytes | AC002511.3 | chr19: 35911201-35933000 |
| Leukocytes | . | chr5: 118665601-118687000 |
| Leukocytes | . | chr3: 196407201-196427800 |
| Leukocytes | ARRB2 | chr17: 4610401-4631400 |
| Leukocytes | RP11-61O1.1 | chr14: 98660401-98681600 |
| Leukocytes | . | chr1: 244377801-244398600 |
| Leukocytes | . | chr14: 102271201-102293000 |
| Leukocytes | . | chr6: 154541401-154564200 |
| Leukocytes | . | chr1: 214803401-214825800 |
| Leukocytes | . | chr2: 143999001-144021000 |
| Leukocytes | . | chr6: 24917801-24939400 |
| Leukocytes | CTSS | chr1: 150724601-150745200 |
| Leukocytes | RP11-428G5.5 | chr12: 32029401-32050200 |
| Leukocytes | OSCAR | chr19: 54593601-54614200 |
| Leukocytes | CLEC12A | chr12: 10114601-10135200 |
| Leukocytes | BC016366 | chr4: 185765601-185787000 |
| Leukocytes | RP1-281H8.3 | chr6: 149806001-149828200 |
| HSC | . | chr2: 124658401-124680600 |
| HSC | MLLT3 | chr9: 20370801-20392400 |
| HSC | ATP8B4 | chr15: 50397801-50420200 |
| HSC | MLLT3 | chr9: 20369001-20390400 |
| HSC | BC016361 | chr4: 75184201-75206000 |
| HSC | AP001171.1 | chr21: 21618801-21640600 |
| HSC | . | chr6: 142691401-142714400 |
| HSC | . | chr2: 124656201-124678400 |
| HSC | GFI1B | chr9: 135844201-135865200 |
| HSC | RP11-598F7.3 | chr12: 207601-230400 |
| HSC | RP13-786C16.1 | chr11: 33891201-33913400 |
| HSC | . | chr2: 16648401-16670400 |
| HSC | . | chr21: 16803001-16825200 |
| HSC | HEMGN | chr9: 100687801-100710000 |
| HSC | . | chr6: 142694401-142717400 |
| Kidney | CLDN10 | chr13: 96074201-96097200 |
| Kidney | . | chr17: 26939601-26964600 |
| Kidney | . | chr4: 22705601-22730600 |
| Kidney | SLC22A8 | chr11: 62771001-62793000 |
| Kidney | . | chr10: 17154801-17179000 |
| Kidney | SLC13A3 | chr20: 45268401-45289600 |
| Kidney | . | chr2: 209398201-209419000 |
| Kidney | . | chr11: 128724001-128745800 |
| Skin | . | chr6: 106932801-106955800 |
| Skin | . | chr6: 143644001-143666400 |
| Skin | . | chr2: 239753801-239774600 |
| Skin | . | chr7: 19131001-19153200 |
| Skin | . | chr11: 71852001-71874000 |
| Skin | AC003986.6 | chr7: 19138401-19160400 |
| Skin | . | chr2: 239754601-239776200 |
| Skin | GSDMC | chr8: 130787001-130808400 |

In some embodiments, the sequencing data from a subject is deconvoluted by comparison to the DNA-protein association atlas. In this way the percent contribution of different tissues, cell types and/or ppppcellular states to the total cfnucleosomes in a sample can be determined. In some embodiments, the deconvolution gives the percent contribution of only informative cfnucleosomes.

In some embodiments, the cfDNA and cf-nucleosomes are not analyzed by comparison to healthy tissue data but rather are analyzed by machine learning. Machine learning is well known in the art, and by performing the methods of the invention of patients with known conditions the machine learning algorithm can learn to recognize specific disease states and conditions in the cfDNA sequences provided when specific DNA-associated proteins are isolated. In some embodiments, at least 1, 2, 3, 4, 5, 6, 7, 8, 9, 10, 15, or 20 subjects with a specific condition are analyzed before the algorithm can identify that condition in a new subject.

As used herein, the term "cellular state" refers to a condition or cellular response or pathway that is active in a cell. In some embodiments, the cellular state is the cellular condition that led to and/or caused cell death. In some embodiments, the cellular state was the state of the cell just before it died but is not directly the cause of that death. In some embodiments, the cellular state is a pathway that was active or inactive in the cell when it died. In some embodiments, the cellular state is a cellular response that was active or inactive in the cell when it died. In some embodiments, the cellular state comprises expression of at least one gene informative of the cause of cell death. In some embodiments, the cellular state is a disease state. In some embodiments, the cellular state comprises expression of at least one gene informative of an active pathway in the cell when it died. In some embodiments, at least 1, 2, 3, 4, or 5 genes from a pathway is indicative of an active pathway. Each possibility represents a separate embodiment of the invention. Signaling pathways are well known in the art and online resources for determining the members of various pathways can be found by examining Gene Ontology or Thermo Fisher Scientific for example.

In some embodiments, determining a cellular state comprises determining a cellular pathway active in the cell. In some embodiments, determining a cellular state comprises determining a transcriptional program active in the cell. In some embodiments, determining a cellular state comprises determining active transcription of at least one gene informative of an active pathway. In some embodiments, at least 1, 2, 3, 4, or 5 genes from a pathway are determined. Each possibility represents a separate embodiment of the invention. In some embodiments, determining a cellular state comprises determining association of the DNA-associated protein to at least 1 genomic region that regulates a gene of the pathway. In some embodiments, the cellular state is any one of hypoxia, inflammation, ER stress, mitochondrial stress, quiescence, senescence, interferon response, cycling, malignant, and calcium flux. Any cellular state which can be defined by the expression of a gene or set of genes can be investigated by the methods of the invention.

In some embodiments, the methods of the invention further comprise comparing the sequenced cfDNA to at least 1 genomic location with the greatest association of the DNA-associated protein during activation of a cellular pathway, and wherein a cfDNA with a sequence that is the same as a DNA sequence within the at least 1 genomic location indicates activation of the cellular pathway. In some embodiments, the genomic locations with the greatest unique association are compared.

In some embodiments, the methods of the invention further comprise comparing the sequenced cfDNA to a pathway atlas of at least 2 cellular pathways, wherein the atlas comprises at least 1 genomic location with the greatest association of the DNA-associated protein in each of the 2 cellular pathways, and wherein a cfDNA with a sequence that is the same as a DNA sequence within the at least 1 genomic location indicates activation of that cellular pathway.

In some embodiments, the sequenced cfDNA is compared to at least 1, 2, 3, 5, 10, 15, 20, 25, 30, 35, 40, 45, 50, 60, 70, 80, 90 or 100 genomic locations. Each possibility represents a separate embodiment of the invention. In some embodiments, the sequenced cfDNA is compared to at least 10 genomic locations. In some embodiments, the sequenced cfDNA is compared to at least 25 genomic locations. In some embodiments the designating comprises comparing the sequenced DNA to a given number of genomic locations.

In some embodiments, the atlas is of at least 1, 2, 3, 5, 10, 10, 15, 20, 25, 30, 35, 40, 45 or 50 cell types and/or tissues. Each possibility represents a separate embodiment of the invention. In some embodiments, the atlas is of at least 1, 2, 3, 5, 10, 10, 15, 20, 25, 30, 35, 40, 45 or 50 cellular pathways. Each possibility represents a separate embodiment of the invention. In some embodiments, the atlas comprises at least 1, 2, 3, 5, 10, 15, 20, 25, 30, 35, 40, 45, 50, 60, 70, 80, 90, or 100 genomic locations. Each possibility represents a separate embodiment of the invention. In some embodiments, the atlas comprises at least 2 genomic locations. In some embodiments, the atlas comprises at least 10 genomic locations. In some embodiments, the atlas comprises at least 25 genomic locations.

In some embodiments, association of the DNA-associated protein with the genomic location is indicative of active transcription and the genomic location is within a tissue, cell type or cellular state specific gene, enhancer element or is at a disease specific mutation. In some embodiments, association of the DNA-associated protein with the genomic location is indicative of active transcription and the genomic location is within a tissue, cell type or cellular state specific gene, enhancer element. In some embodiments, association of the DNA-associated protein with the genomic location is indicative of active transcription and the genomic location is at a disease-specific mutation. In some embodiments, the DNA-associated protein is a marker of active transcription and association of the DNA-associated protein with the disease associated mutation is indicative of the disease state. In some embodiments, association of the DNA-associated protein with the genomic location is indicative of active transcription and the disease-associated mutation is within an oncogene. In some embodiments, association of the DNA-associated protein with the genomic location is indicative of silenced transcription and the genomic location is within a repressor element or a gene silenced in the tissue, cell type or cellular state or is at a disease specific mutation. In some embodiments, association of the DNA-associated protein with the genomic location is indicative of silenced transcription and the genomic location is within a repressor element or a gene silenced in the tissue, cell type or cellular state. In some embodiments, association of the DNA-associated protein with the genomic location is indicative of silenced transcription and the genomic location is at a disease-specific mutation. In some embodiments, association of the DNA-associated protein with the genomic location is indicative of silenced transcription and the disease-associated mutation is within a tumor suppressor gene. Oncogenes and tumor suppressor genes are well known in the art. Examples of oncogenes include, but are not limited to, WNT, RAS, MYC and ERK. Examples of tumor suppressor genes include, but are not limited to, p53, PTCH, NF1, p27Kip1, and APC.

As used herein, "cfDNA" refers to any DNA obtained from an organism which existed in the organism outside of a cell. As used herein, "cfnucleosome" refers to cfDNA and any proteins bound and/or associated with the cfDNA. In some embodiments, cfnucleosomes comprises cfDNA and cfhistones. In some embodiments, the cfDNA is associated with DNA-associated protein. In some embodiments, the cfDNA is not naked. In some embodiments, the cfDNA is in the sample as cfnucleosomes. In some embodiments, the cfDNA is not crosslinked. In some embodiments, the methods of the invention further comprise crosslinking the cfDNA and DNA-associated proteins prior to the contacting. In some embodiments, the methods do not comprise crosslinking the cfDNA and DNA-associated proteins prior to the contacting.

In some embodiments, the cfDNA is DNA obtained from an organism and existed in the organism outside of any vesicle. Cell-free DNA is well known in the art, and generally refers to DNA that is free floating within a bodily fluid. This DNA is generally not enclosed in a vesicle and thus DNA in transport, such as by exosomes or other vesicular transporters, in not considered cfDNA. In some embodiments, cfDNA is DNA from a dying and/or dead cell. When a cell dies the DNA is generally fragmented and released from the cell as it lyses. This DNA however, is not all immediately removed or cleaned up and thus persists in the organism. Frequently the DNA from the dead cell enters the bloodstream. In some embodiments, vesicular chromatin that is lysed is also included in the cfDNA.

In some embodiments, the cfDNA is mammalian cfDNA. In some embodiments, the cfDNA is human cfDNA. In some embodiments, the cfDNA is from a mammalian or human genome. In some embodiments, the cfDNA is fetal DNA. In some embodiments, the DNA is viral DNA. In some embodiments, the DNA is bacterial DNA. In some embodiments, the DNA is fungal DNA. In some embodiments, the DNA parasitic DNA. In some embodiments, the DNA if from a pathogen. In some embodiments, the DNA is from an organism that lives in a healthy subject. In some embodiments, the cfDNA is extracted from bodily fluid. In some embodiments, the providing comprises providing a bodily fluid and isolating the cfDNA from the bodily fluid. In some embodiments, the providing comprises providing a bodily fluid comprising cfDNA and performing the contacting in the bodily fluid. In some embodiments, the methods of the invention are performed on as little as 0.00001, 0.00005, 0.0001, 0.0005, 0.001, 0.005, 0.01, 0.05, 0.1, 0.5, 1, 1.5, 2, 2.5 or 3 ml of bodily fluid. In some embodiments, the methods of the invention are performed on as little as 2 ml of bodily fluid. Each possibility represents a separate embodiment of the invention. In some embodiments, the methods of the invention are performed with less than 0.00001, 0.00005, 0.0001, 0.0005, 0.001, 0.005, 0.01, 0.05, 0.1, 0.5, 1, 1.5, 2, 2.5, 3, 3.5, 4, 4.5, or 5 ml of bodily fluid. Each possibility represents a separate embodiment of the invention. In some embodiments, the bodily fluid is blood.

In some embodiments, the cfDNA is fetal cell free DNA (cffDNA). In some embodiments, the method is for non-invasive fetal monitoring. In some embodiments, the subject is the mother of the fetus. In some embodiments, the method is for determining a cellular state of a cell in a fetus. In some embodiments, the method is for determining a disease in a fetus. In some embodiments, the method is for determining a genetic abnormality in a fetus. In some embodiments, the method is for determining the origin of cell death in a fetus.

Since cfDNA has a short half-life in an organism, it provides a snapshot of the cell death occurring in the organism at that moment. In some embodiments, the methods of the invention detect cell death that has occurred within the last 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour 2 hours, 3 hours, 6 hours, 12 hours, 18 hours, 1 day, 2 days, 3 days, 4 days, 5 days, 6 days, 1 week 2 weeks, 3 weeks or a month from the time the sample was taken from the subject. Each possibility represents a separate embodiment of the invention. In some embodiments, the methods of the invention detect cell death that occurred immediately before taking the sample from the subject. In some embodiments, the methods of the invention further comprise extracting a sample from the subject before the providing, wherein the sample comprises cfDNA. In some embodiments, the methods of the invention further comprise freezing or keeping at about 4 degrees the sample after it is taken from the subject and before it is contacted. By freezing or keeping the sample cold the methods of the invention can still detect the cell death that occurred just before the sample was taken from the subject.

In some embodiments, at least 0.00001, 0.00005, 0.0001, 0.0005, 0.001, 0.005, 0.01, 0.05, 0.1, 0.5, 1, 2, 3, 4, 5, 6, 7, 8, 9, 10, 20, 30, 40, 50, 60, 70, 80, 90 or 100 ng of cfDNA are provided. Each possibility represents a separate embodiment of the invention. In some embodiments, as little as 0.00001, 0.00005, 0.0001, 0.0005, 0.001, 0.005, 0.01, 0.05, 0.1, 0.5, 1, 2, 3, 4, 5, 6, 7, 8, 9, 10, 20, 30, 40, 50, 60, 70, 80, 90 or 100 ng of cfDNA are provided. Each possibility represents a separate embodiment of the invention. In some embodiments, at least 50 ng are provided. In some embodiments, as little as 50 ng are provided. In some embodiments, at least 7 ng are provided. In some embodiments, as little as 7 ng are provided. In some embodiments, at least 0.5 ng are provided. In some embodiments, as little as 0.5 ng are provided. In some embodiments, the provided cfDNA is between 0.1 and 1000, 0.1 and 900, 0.1 and 800, 0.1 and 700, 0.1 and 600, 0.1 and 500, 0.1 and 400, 0.1 and 300, 0.1 and 250, 0.1 and 200, 0.1 and 150, 0.1 and 100, 0.1. and 90, 0.1 and 80, 0.1 and 70, 0.1 and 60, 0.1 and 50, 0.1 and 40, 0.1 and 30 or 0.1 and 20 ng, 0.1 and 10 ng, 0.1 and 5ng, 0.1 and 1 ng, 0.5 and 1000, 0.5 and 900, 0.5 and 800, 0.5 and 700, 0.5 and 600, 0.5 and 500, 0.5 and 400, 0.5 and 300, 0.5 and 250, 05 and 200, 0.5 and 150, 0.5 and 100, 0.5. and 90, 0.5 and 80, 0.5 and 70, 0.5 and 60, 0.5 and 50, 0.5 and 40, 0.5 and 30 or 0.5 and 20 ng, 0.1 and 10 ng, 0.5 and 5 ng, 0.5 and 1 ng, 1 and 1000, 1 and 900, 1 and 800, 1 and 700, 1 and 600, 1 and 500, 1 and 400, 1 and 300, 1 and 250, 1 and 200, 1 and 150, 1 and 100, 1 and 90, 1 and 80, 1 and 70, 1 and 60, 1 and 50, 1 and 40, 1 and 30 or 1 and 20 ng, 10 and 1000, 10 and 900, 10 and 800, 10 and 700, 10 and 600, 10 and 500, 10 and 400, 10 and 300, 10 and 250, 10 and 200, 10 and 150, 10 and 100, 10 and 90, 10 and 80, 10 and 70, 10 and 60, 10 and 50, 10 and 40, 10 and 30 or 10 and 20 ng. Each possibility represents a separate embodiment of the invention. In some embodiments, at most 0.00001, 0.00005, 0.0001, 0.0005, 0.001, 0.005, 0.01, 0.05, 0.1, 0.5, 1, 5, 10, 20, 30, 40, 50, 60, 70, 80, 90, 100, 150, 200, 250, 300, 400, 500, 600, 700, 800, 900 or 1000 ng of cfDNA are provided. Each possibility represents a separate embodiment of the invention. 1000 genomes are roughly equivalent to 6.6 ng of cfDNA.

In some embodiments, the cfDNA comprises at least 0.00001, 0.00005, 0.0001, 0.0005, 0.001, 0.005, 0.01, 0.05, 0.1, 0.5, 1, 2, 5, 10, 50, 100, 200, 300, 500, 700, 800, 1000, 2000, 3000, 4000, 5000, 6000, 7000, 8000, 9000 or 10000 genomes. Each possibility represents a separate embodiment of the invention. In some embodiments, the cfDNA comprises as little as 0.00001, 0.00005, 0.0001, 0.0005, 0.001, 0.005, 0.01, 0.05, 0.1, 0.5, 1, 2, 5, 10, 50, 100, 200, 300, 500, 700, 800, 1000, 2000, 3000, 4000, 5000, 6000, 7000, 8000, 9000 or 10000 genomes. Each possibility represents a separate embodiment of the invention. In some embodiments, the cfDNA comprises between 0.1 and 10000, 0.1 and 9000, 0.1 and 8000, 0.1 and 7000, 0.1 and 6000, 0.1 and 5000, 0.1 and 4000, 0.1 and 3000, 0.1 and 2000, 0.1 and 1000, 1 and 10000, 1 and 9000, 1 and 8000, 1 and 7000, 1 and 6000, 1 and 5000, 1 and 4000, 1 and 3000, 1 and 2000, 1 and 1000, 5 and 10000, 5 and 9000, 5 and 8000, 5 and 7000, 5 and 6000, 5 and 5000, 5 and 4000, 5 and 3000, 5 and 2000, 5 and 1000, 10 and 10000, 10 and 9000, 10 and 8000, 10 and 7000, 10 and 6000, 10 and 5000, 10 and 4000, 10 and 3000, 10 and 2000, 10 and 1000, 100 and 10000, 100 and 9000, 100 and 8000, 100 and 7000, 100 and 6000, 100 and 5000, 100 and 4000, 100 and 3000, 100 and 2000, 100 and 1000, 500 and 10000, 500 and 9000, 500 and 8000, 500 and 7000, 500 and 6000, 500 and 5000, 500 and 4000, 500 and 3000, 500 and 2000, 500 and 1000, 1000 and 10000, 1000 and 9000, 1000 and 8000, 1000 and 7000, 1000 and 6000, 1000 and 5000, 1000 and 4000, 1000 and 3000, 1000 and 2000 genomes. Each possibility represents a separate embodiment of the invention.

In some embodiments, as little as 0.00001, 0.00005, 0.0001, 0.0005, 0.001, 0.005, 0.01, 0.05, 0.1, 0.2, 0.3, 0.5, 1, 2, 3, 4, 5, or 10% of the cfDNA is from the cell type, tissue or cell in the cellular state. Each possibility represents a separate embodiment of the invention. In some embodiments, as little as 0.1% of the cfDNA is from the cell type, tissue or cell in the cellular state. In some embodiments, as little as 1% of the cfDNA is from the cell type, tissue or cell in the cellular state. In some embodiments, the limit of detection of the method is 0.1% of the cfDNA in the sample being from the cell type, the tissue, or the cellular state. In some embodiments, the limit of detection of the method is 1% of the cfDNA in the sample being from the cell type, the tissue, or the cellular state. In some embodiments, as little as 0.1% of the cfDNA is from the cell type, the tissue, or the cellular state and at least 45 peaks corresponding to the cell type, tissue or cellular state are detected. In some embodiments, as little as 0.1% of the cfDNA is from the cell type, the tissue, or the cellular state and at least 45-200 peaks corresponding to the cell type, tissue or cellular state are detected. In some embodiments, as little as 1% of the cfDNA is from the cell type, the tissue, or the cellular state and at least 25 peaks corresponding to the cell type, tissue or cellular state are detected. In some embodiments, analyzing at least 25 peaks provides a limit of detection of 1% of the cfDNA being from the cell type, the tissue, or the cellular state. In some embodiments, analyzing at least 45 peaks provides a limit of detection of 0.1% of the cfDNA being from the cell type, the tissue, or the cellular state. In some embodiments, analyzing a number of peaks comprises detecting cfDNA from at least that number of peaks. In some embodiments, the cfDNA comprises between 0.001-10, 0.001-5, 0.001-3, 0.001-2, 0.001-1.5, 0.001-1, 0.01-10, 0.01-5, 0.01-3, 0.01-2, 0.01-1.5, 0.01-1, 0.1-10, 0.1-5, 0.1-3, 0.1-2, 0.1-1.5, 0.1-1, 0.5-10, 0.5-5, 0.5-3, 0.5-2, 0.5-1.5 0.5-1, 1-10, 1-5, 1-3, or 1-2% cfDNA from the cell type, the tissue, or the cellular state. Each possibility represents a separate embodiment of the invention. In some embodiments, the cfDNA comprises between 0.1-1% cfDNA from the cell type, the tissue, or the cellular state. In some embodiments, the cfDNA comprises between 0.1-3% cfDNA from the cell type, the tissue, or the cellular state.

In some embodiments, the sequencing is at a low depth. In some embodiments, the sequencing is at a depth of less than 1 billion, 750 million, 500 million, 400 million, 300 million, 200 million, 100 million, 90 million, 80 million, 70 million, 60 million, 50 million, 40 million, 30 million, 20 million, 10 million, 9 million, 8 million, 7 million, 6 million, 5 million, 4 million, 3 million, 2 million, 1 million, 0.5 million, 0.1 million, 0.05 million, 0.01 million, 0.005 million or 0.001 million reads. Each possibility represents a separate embodiment of the invention. In some embodiments, the sequencing is at a depth of less than 10 million reads. In some embodiments, the sequencing is at a depth of less than 1 million reads. It will be understood by a skilled artisan that as the amount of information increases the limit of detection goes down. Further, as the amount of input data is increased (increasing the number of reagents, i.e. antibodies used for ChIP, increasing the number of informative loci for a given cell type/issue/state, increasing the amount of cfDNA from the cell type/issue/state) so too the required sequencing depth is decreased, and the limit of detection is decreased.

In some embodiments, the providing comprises providing a bodily fluid comprising the cfDNA. In some embodiments, the contacting occurs in the bodily fluid. In some embodiments, the contacting comprises providing a bodily fluid and isolating the cfDNA from the bodily fluid. In some embodiments, the bodily fluid is selected from: blood, serum, gastric fluid, intestinal fluid, saliva, bile, tumor fluid, interstitial fluid, breast milk, cerebrospinal fluid, urine, semen, vaginal fluid, and stool. In some embodiments, the bodily fluid is any bodily fluid that contains cfDNA. In some embodiments, the bodily fluid is blood. In some embodiments, the bodily fluid is any one of whole blood, partially lysed whole blood, plasma, or partially processed whole blood.

The sample of blood can be obtained by standard techniques, such as using a needle and syringe. In another embodiment, the blood sample is a peripheral blood sample. Alternatively, the blood sample can be a fractionated portion of peripheral blood, such as a plasma sample. In another embodiment, once the blood sample is obtained, total DNA can be extracted from the sample using standard techniques known to one skilled in the art. In some embodiments, intact cells are removed before DNA extraction, so that only free-floating DNA is extracted. Intact cells can be removed by any method known in the art, such as for non-limiting example by centrifugation or by gradient separation, such as by Ficol gradient separation. A non-limiting example for DNA extraction is the FlexiGene DNA kit (QIAGEN). Standard techniques for receiving cell-free DNA extraction are known to a skilled artisan, a non-limiting example of which is the QIAamp Circulating Nucleic Acid kit (QIAGEN).

In some embodiments, the sequencing is next generation sequencing. Next generation sequencing, also known as high-throughput sequencing or massively parallel sequencing, is any sequencing method that allows for rapid high-throughput sequencing of base pairs from DNA or RNA samples. In some embodiments, the sequencing is high-throughput sequencing. In some embodiments, the sequencing is massively parallel sequencing. Such sequencing is well known in the art and can include the use of Illumina arrays, pore and nanopore sequencers and ion torrent as non-limiting examples. Sequencing machines such as the Illumina Nextseq 500 machine may be used, and processing may be performed using the Illumina 500/550 V2 kit, for non-limiting example. In some embodiments, the sequencing is whole genome sequencing. In some embodiments, only a portion of the genome is sequenced. In some embodiments, a chip or array pertaining to only a portion of the genome is used for next generation sequencing.

In some embodiments, the sequencing is methylation sensitive sequencing. In some embodiments, the methods of the invention further comprise bisulfate conversion before sequencing. In performing sequencing, the methylation status of the DNA can also be discerned, in this way the protein-DNA association data can also be combined with DNA methylation data. This can provide further information about the activity of genes in the cell as it died, which can provide insight into the cell or tissue of origin or the cellular state of the cell.

In some embodiments the methods of the invention can be used to determine the origin of cfDNA even when the cfDNA from one tissue/cell types is a very small percentage of the whole cfDNA. In some embodiments, the cfDNA of a tissue and/or cell type comprises as little 0.0001%, 0.0005%, 0.001%, 0.005%, 0.01%, 0.05%, 0.1% 0.5%, 1%, 1.5%, 2%, 3%, 4%, 5%, 6%, 7%, 8%, 9% or 10% of all of the cfDNA. Each possibility represents a separate embodiment of the invention. In some embodiments, the cfDNA of a tissue and/or cell type comprises more than 0.0001%, 0.0005%, 0.001%, 0.005%, 0.01%, 0.05%, 0.1% 0.5%, 1%, 1.5%, 2%, 3%, 4%, 5%, 6%, 7%, 8%, 9% or 10% of all of the cfDNA. Each possibility represents a separate embodiment of the invention. In some embodiments, the cfDNA of a tissue and/or cell type comprises less than 0.0001%, 0.0005%, 0.001%, 0.005%, 0.01%, 0.05%, 0.1%, 0.5%, 1%, 1.5%, 2%, 3%, 4%, 5%, 6%, 7%, 8%, 9% or 10% of all of the cfDNA. Each possibility represents a separate embodiment of the invention. In some embodiments, the cfDNA of a tissue and/or cell type comprises between 0.0001%-10%, 0.001%-10%, 0.01%-10%, 0.1%-10%, 0.5%-10%, 1%-10%, 1.5%-10%, 2%-10%, 0.0001%-9%, 0.001%-9%, 0.01%-9%, 0.1%-9%, 0.5%-9%, 1%-9%, 1.5%-9%, 2%-9%, 0.0001%-8%, 0.001%-8%, 0.01%-8%, 0.1%-8%, 0.5%-8%, 1%-8%, 1.5%-8%, 2%-8%, 0.0001%-7%, 0.001%-7%, 0.01%-7%, 0.1%-7%, 0.5%-7%, 1%-7%, 1.5%-7%, 2%-7%, 0.0001%-6%, 0.001%-6%, 0.01%-6%, 0.1%-6%, 0.5%-6%, 1%-6%, 1.5%-6%, 2%-6%, 0.0001%-5%, 0.001%-5%, 0.01%-5%, 0.1%-5%, 0.5%-5%, 1%-5%, 1.5%-5%, 2%-5%, 0.0001%-4%, 0.001%-4%, 0.01%-4%, 0.1%-4%, 0.5%-4%, 1%-4%, 1.5%-4%, 2%-4%, 0.0001%-3%, 0.001%-3%, 0.01%-3%, 0.1%-3%, 0.5%-3%, 1%-3%, 1.5%-3%, 2%-3%, 0.0001%-2%, 0.001%-2%, 0.01%-2%, 0.1%-2%, 0.5%-2%, 1%-2%, 1.5%-2%, 0.0001%-1%, 0.001%-1%, 0.01%-1%, 0.1%-1.5%, 0.5%-1.5%, 0.1%-1%, 0.5%-1%, 0.0001%-0.1%, 0.001%-0.1%, or 0.0001%-0.001% of all of the cfDNA. Each possibility represents a separate embodiment of the invention.

In some embodiments, the contacting is incubating the reagent in the bodily fluid comprising the cfDNA. In some embodiments, the contacting is incubating the reagent in blood comprising the cfDNA. In some embodiments, the contacting is incubating the reagent and cfDNA in a binding/incubating solution. Buffers for performing ChIP, and specifically incubating buffers are well known in the art. Such buffers may be purchased from companies such as Abcam and Cell Signaling Technology who cell ChIP kits.

In some embodiments, the contacting is performed with constant mixing. In some embodiments, the contacting is done with constant rotation. In some embodiments, the contacting is done at room temperature or at 4 degrees. In some embodiments, the contacting is done on ice. In some embodiments, the contacting is for at least 1, 2, 3, 4, 5, 6, 12, 18, or 24 hours. Each possibility represents a separate embodiment of the invention. In some embodiments, the contacting is for a time sufficient for the reagent to bind to the DNA-associated protein. In some embodiments, the contacting is for a time sufficient for the reagent to bind at least 10%, 20%, 30%, 40%, 50%, 60%, 70%, 80%, 90%, 95%, 97%, or 99% of the DNA-associated protein provided. Each possibility represents a separate embodiment of the invention.

In some embodiments, the methods of the invention are for use in detecting a disease state or condition in a subject in need thereof and wherein the cfDNA is from the subject. In some embodiments, the methods of the invention are for diagnosing a disease, and/or condition in a subject in need thereof and wherein the cfDNA is from the subject. In some embodiments, the methods of the invention are for diagnosing an increased risk of a disease or condition. A skilled artisan will recognize that many if not all disease states induce cell death in the tissue or cells in which the disease is manifest. As such knowledge of the origin of cell death be a surrogate for the disease. In some embodiments, the disease state or condition is selected from cardiac disease or damage and liver disease or damage. In some embodiments, the disease state or condition is selected from cardiac disease or damage, liver disease or damage, and cancer. In some embodiments, the disease state is cancer. In some embodiments, the disease state is a pre-cancerous state. In some embodiments, the disease state is cancer or a pre-cancerous state. In some embodiments, the disease state or condition is selected from cardiac arrest and liver shock. In some embodiments, the disease state is brain damage. In some embodiments, the disease state is bacteremia. In some embodiments, the disease state is an infection. In some embodiments, the disease state or condition is selected from cancer, neurodegenerative disease, infection, tissue damage, inflammation, autoimmune disease, arthritis, liver inflammation, bowel inflammation, autoimmune disease, bacteremia, tissue damage from drug side effects, tissue necrosis, and diabetes. In some embodiments, the neurodegenerative disease is Parkinson's disease or Alzheimer's disease. In some embodiments, the autoimmune disease is lupus or multiple sclerosis. In some embodiments, the disease is cancer and the methods of the invention determine the cell or tissue of origin of the cancer. It will be well understood by a person of skill in the art, that association of proteins that indicate active transcription and sequences of cfDNA from oncogenes is indicative of a cancerous or pre-cancerous state. Further, association of proteins that indicate transcriptional silencing and sequences of cfDNA from tumor suppressors is also indicative of a cancerous or pre-cancerous state. Similarly, activation or repression of enhancer regions for oncogenes and tumor suppressors respectively is also indicative of a cancerous or pre-cancerous state.

In some embodiments, the methods of the invention further comprise performing steps a-d again using a reagent that binds to a second DNA-associated protein, and wherein the second DNA-associated protein is a different protein than the DNA associated protein already used. In some embodiments, the second DNA-associated protein is different than the first DNA-associated protein. In some embodiments, the methods of the invention can be repeated at least 2, 3, 4, 5, 6, 7, 8, 9, or 10 times wherein each time a different DNA-associated protein is bound. Each possibility represents a separate embodiment of the invention.

In some embodiments, the methods of the invention comprise contacting the sample with at least 2 reagents, wherein each reagent is bound to a physical support and the support comprises a short DNA tag unique to each reagent, wherein upon sequencing the isolated cfDNA the short DNA tag identifies the reagent that isolated the cfDNA. In some embodiments, the DNA tag is ligated to a cfDNA molecule before sequencing. In some embodiments, the support is a bead conjugated to a single reagent and a short DNA tag that is unique to the reagent. In some embodiments, the reagent is an antibody and the short DNA tag is a DNA barcode. This can, for example be paramagnetic beads covalently bound to a ChIP antibody such as H3K4me1 and bound to a barcode for identifying H3K4me1 associated DNA, and other paramagnetic beads covalently bound to a ChIP antibody such as H3K4me3 and bound to a barcode identifying H3K4me3 associated DNA which are added to the sample simultaneously, ligated to cfDNA simultaneously and sequenced simultaneously.

In some embodiments, the method further comprises treating the subject. In some embodiments, the treatment is for the detected disease. In some embodiments, the treatment is a suitable treatment based on the cellular state, tissue of origin, cell type of a combination thereof of the cell that died in the subject. It will be understood by a skilled artisan that if for example a cancer is found in a particular organ that therapy can be tailored to that type of cancer. Similarly, in a particular pathway is active in a cancer or disease, then one treatment modality may be more suitable than another. For example, detection of active transcription of the long noncoding RNA EGFR-AS1 that mediates cancer addiction to EGFR and when highly expressed can render tumors insensitive to EGFR inhibition by anti EGFR antibody treatment, would indicate that EGFR inhibitory treatments should be avoided.p Disease Detection By another aspect, there is provided a method of detecting a disease state in a subject, the method comprising:
  a. providing a sample from the subject, wherein the sample comprises cfDNA;
  b. contacting the sample with at least one reagent that binds to a DNA-associated protein;
  c. isolating the reagent and any thereto bound proteins and cfDNA;
  d. sequencing the isolated cfDNA; and
  e. designating a cfDNA molecule comprising a disease-associated mutation as originating from a cell in the disease state;

thereby detecting a disease state in a subject.

By another aspect, there is provided a method for improving disease detection in cfDNA from a subject, the method comprising performing chromatin immunoprecipitation on the cfDNA from the subject before performing the disease detection in the immunoprecipitated cfDNA.

In some embodiments, the chromatin immunoprecipitation comprises:
  a. contacting the cfDNA from the subject with at least one reagent that binds to a DNA-associated protein; and
  b. isolating the reagent and any thereto bound proteins and cfDNA.

In some embodiments, disease detection comprises sequencing of the cfDNA. In some embodiments, disease detection comprises sequencing of the cfDNA from the subject. In some embodiments, disease detection comprises sequencing of the immunoprecipitated cfDNA. In some embodiments, disease detection and/or sequencing comprises amplification of the cfDNA. In some embodiments, disease detection and/or sequencing does not comprise amplification of the cfDNA. In some embodiments, disease detection in cfDNA from the subject comprises amplification of the cfDNA. In some embodiments, non-improved disease detection comprises amplification of the cfDNA. In some embodiments, disease detection in the immunoprecipitated cfDNA does not comprise amplification of the immunoprecipitated cfDNA. In some embodiments, improved disease detection does not comprise amplification of the immunoprecipitated cfDNA. In some embodiments, the amplification is PCR amplification. In some embodiments, the amplification is non-specific amplification. In some embodiments, the amplification is amplification of a disease-associated sequence.

As used herein, "disease-associated mutation" refers to a DNA mutation that is known to cause or increase the risk of developing the disease. Disease-associated mutations are well known, and include for example, deletion of 1522A, 1523T and 1524C (deletion of F508) of CFTR in cystic fibrosis, 1226A to G (N370S) in the GBA locus in Gaucher disease, mutations in SERPINA1 in alpha1-antitrypsin deficiency, mutations in HBB in Beta-thalassemia, and mutations in PSEN1 in Alzheimer's disease. Many disease-associated mutations are known in cancer, some are common to many types of cancer and some are specific to specific cancers. Mutations in p53, MYC, BREF, BRCA, to name but a few, are well known in the art. Panels of disease associated mutations can also be investigated. In some embodiments, at least 1, 2, 3, 5, 7, 10, 12, 15, 17, or 10 mutations are investigated. Each possibility represents a separate embodiment of the invention. In some embodiments, instead of sequencing, PCR with mutation specific-primers is employed. Any method of detecting DNA mutations may be employed in place of sequencing; however, sequencing provides the advantage of checking multiple mutations simultaneously, including a panel of mutations.

In some embodiments, association of the DNA-associated protein with the disease-associated mutation is indicative of the disease state. It will be well understood by a person of skill in the art, that association of proteins that indicate active transcription mutations in the coding region of a gene would indicate the mutant gene is being transcribed and would be indicative of a cancerous or pre-cancerous state. Similarly, mutations in a regulatory region would be associated with a protein that is indicative of that regulatory region and thus would also be indicative of a cancerous or pre-cancerous state.

In some embodiments, the disease-associated mutation is in a coding region of a gene and association of the DNA-associated protein with DNA is indicative of active transcription. In some embodiments, the gene is an oncogene or a tumor suppressor gene. In some embodiments, the disease-associated mutation is in a regulatory region, and association of the DNA-associated protein with DNA is indicative of the regulatory region.

In some embodiments, the method of the invention further comprises performing steps b-e again using a reagent that binds to a second DNA-associated protein, and wherein the second DNA-associated protein is different from the first DNA-associated protein. If multiple mutations are to be investigated and they are located in different genomic regions (gene body and an enhancer for instance), the ChIP can be repeated for a different DNA-associated protein.

Immunoprecipitation of only a portion of the cfDNA (such as enrichment for gene body sequences of actively transcribed genes by H3K36me3 immunoprecipitation) greatly enhances the concentration of informative DNA. As a result, sequencing can be performed much more cheaply and using fewer reagents. Further, this methodology allows detection of mutations associated with specific genomic annotations (active gene, active promoter, active enhancer etc.) without predefining a limited set of genomic locations (such as a set of cancer risk genes) and designing specific reagents to amplify and/or detect those predefined sequences. By first reducing the effective size of the sequenced portion of the genome (to only what is immunoprecipitated) sequencing cost is dramatically reduced. Additionally, because there are fewer repeat sequences and uninformative sequences there is less background and fewer false positive results. Lastly, sequencing at a given depth provides more reads over the sequences that are informative.

In some embodiments, the improving comprises at least one of: decreasing signal to noise ratio, increasing confidence in positive detection of the disease, decreasing false detection of the disease and accurately detecting the disease with less cfDNA from the subject. In some embodiments, the increasing is at least a 10, 20, 30, 40, 50, 60, 70, 80, 90, 100, 200, 300, 400, 500 or 1000% increase. Each possibility represents a separate embodiment of the invention. In some embodiments, the decreasing is at least a 10, 20, 30, 40, 50, 60, 70, 80, 90, 85, 97, 99 or 100% decrease. Each possibility represents a separate embodiment of the invention.

In some embodiments, the less cfDNA from the subject is less than 1000, 900, 800, 700, 600, 500, 400, 300, 200, 100, 90, 80, 70, 60, or 50 ng of cfDNA. Each possibility represents a separate embodiment of the invention. In some embodiments, the same accuracy can be achieved with the less cfDNA as compared to a larger amount of cfDNA. In some embodiments, the same sequencing coverage at the mutation can be achieved with the less cfDNA as compared to the coverage achieved with a larger amount of cfDNA.

Computer Program Products

By another aspect, there is provided a computer program product for determining a cell or tissue of origin of cell free DNA (cfDNA), comprising a non-transitory computer-readable storage medium having program code embodied thereon, the program code executable by at least one hardware processor to:
  a. sequence or access sequencing of cfDNA isolated with a reagent that binds a DNA-associated protein;
  b. assign a cfDNA molecule from the cfDNA to a cell or tissue of origin by comparing a DNA sequence of the molecule to sequences associated with the DNA-associated protein in the cell type or tissue; and
  c. provide an output regarding the cell or tissue of origin of cfDNA.

By another aspect, there is provided a computer program product for determining a cellular state of a cell in a subject as the cell died, comprising a non-transitory computer-readable storage medium having program code embodied thereon, the program code executable by at least one hardware processor to:
  a. sequence or access sequencing of cfDNA from the subject isolated with a reagent that binds a DNA-associated protein;
  b. assign a cfDNA molecule from the cfDNA to a cellular state by comparing a DNA sequence of the molecule to sequences associated with the DNA-associated protein in the cellular state; and
  c. provide an output regarding the cellular state of a cell in the subject as the cell died.

By another aspect, there is provided a system for determining the cell or tissue of origin of cfDNA, comprising:
  a. one or more devices for sequencing cfDNA isolated with a reagent that binds a DNA-associated protein;
  b. a processor; and
  c. storage medium comprising a computer application that, when executed by the processor, is configured to:

i. sequence or access sequencing of cfDNA isolated with a reagent that binds a DNA-associated protein;
ii. assign a cfDNA molecule from the cfDNA to a cell or tissue of origin by comparing a DNA sequence of the molecule to sequences associated with the DNA-associated protein in the cell type or tissue; and
iii. output from the processor the cell or tissue of origin of cfDNA.

By another aspect, there is provided a system for determining a cellular state of a cell in a subject as the cell died, comprising:
a. one or more devices for sequencing cfDNA isolated with a reagent that binds a DNA-associated protein;
b. a processor; and
c. storage medium comprising a computer application that, when executed by the processor, is configured to:
i. sequence or access sequencing of cfDNA isolated with a reagent that binds a DNA-associated protein;
ii. assign a cfDNA molecule from the cfDNA to a cellular state by comparing a DNA sequence of the molecule to sequences associated with the DNA-associated protein in the cellular state; and
iii. output from the processor the cell or tissue of origin of cfDNA.

By another aspect, there is provided a computer program product for detecting a disease state in a subject, comprising a non-transitory computer-readable storage medium having program code embodied thereon, the program code executable by at least one hardware processor to
a. assign a cfDNA molecule from the cfDNA to a disease state by comparing a DNA sequence of the molecule to mutant sequences associated with the disease state;
b. provide an output regarding the disease state in a subject.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

Embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the embodiments should not be construed as limited to any one set of computer program instructions. Further, a skilled programmer would be able to write such a computer program to implement one or more of the disclosed embodiments described herein. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act.

By device for sequencing it is meant a combination of components that allows the sequence of a piece of DNA to be determined. In some embodiments, the testing device allows for the high-throughput sequencing of DNA. In some embodiments, the testing device allows for massively parallel sequencing of DNA. The components may include any of those described above with respect to the methods for sequencing.

In certain embodiments the system or test kit further comprises a display for the output from the processor.

Multiplexing

By another aspect, there is provided a solid support, comprising a capturing agent and a barcoding reagent.

As used herein, the term "capturing agent" refers to a molecule that binds to a protein and can thus capture and retain the protein to the solid support. In some embodiments, the capturing agent is a small molecule. In some embodiments, the capturing agent is a protein. In some embodiments, the capturing protein captures a second protein by protein-protein interaction. In some embodiments, the capture protein is an antibody or antigen binding fragment thereof. The capturing agent can be any molecule that specifically binds chromatin or nucleic acids.

As used herein, the term "barcoding reagent" refers to any substrate that comprises a unique molecule or moiety that can be used as a barcode for identifying a molecule of interest. Barcodes are well known in the art and any molecule or moiety that is unique enough to identify a molecule of interest can be used as a barcode. In some embodiments, the barcoding reagent is the barcode itself. In some embodiments, the barcode is a protein barcode. In some embodiments, the barcode is a protein tag. In some embodiments, the barcode is a fluorescent protein.

In some embodiments, the barcode is a nucleic acid barcode. In some embodiments, the nucleic acid molecule is a short nucleic acid molecule. In some embodiments, it is less than 3, 5, 7, 10, 12, 15, 17, 20 or 25 nucleotides long. Each possibility represents a separate embodiment of the invention. In some embodiments, the nucleic acid molecule is between 3 and 10, 3 and 15, 3 and 20, 3 and 25, 3 and 30, 3 and 35, 3 and 40, 4 and 45, 3 and 50, 5 and 10, 5 and 15, 5 and 20, 5 and 25, 5 and 30, 5 and 35, 5 and 40, 5 and 45, or 5 and 50 nucleotides long. Each possibility represents a separate embodiment of the invention. In some embodiments, the barcoding reagent is an enzyme for joining the barcode to a molecule of interest. In some embodiments, the barcoding reagent is a ligase. In some embodiments, the barcoding reagent is the barcode and the solid support further comprises an enzyme for joining the barcode to a molecule of interest.

In some embodiments, the molecule of interest is a protein. In some embodiments, the molecule of interest is a nucleic acid molecule. In some embodiments, the molecule of interest in a DNA or RNA. In some embodiments, the capturing agent captures a protein associated with the molecule of interest. In some embodiments, the capturing agent captures a DNA-associated protein and the molecule of interest is DNA. In some embodiments, the DNA is cfDNA. In some embodiments, the molecule of interest is in complex with the protein captured by the capturing agent.

The solid support may be any polymer, or inorganic material to which biological macromolecules can be attached. The attachment can be direct or indirect. In some embodiments, the solid support is made from material used to assemble microfluidic devices. In some embodiments, the solid support is a bead. In some embodiments, the bead is an agarose bead. In some embodiments, the solid support is a magnetic or paramagnetic bead. In some embodiments, the solid support is an agarose or magnetic or paramagnetic bead. In some embodiments, the support is conjugated to the capturing agent. In some embodiments, the support is conjugated to a ChIP antibody. In some embodiments, the support is conjugated to the barcoding reagent. In some embodiments, the support is conjugated to capturing agent and the barcoding reagent. Conjugation can be performed by any method known in the art including, but not limited to covalent bonding, charge-based bonding, and hydrophobic interactions. In some embodiments, the conjugation is biotin to avidin conjugation. In some embodiments, the conjugation is by amine binding technologies. In some embodiments, the amine binding technology is epoxy. In some embodiments, the conjugation is by carboxyl group capturing.

By another aspect, there is provided a method for multiplexing an assay on more than one molecule of interest in a single solution, the method comprising:
  a. capturing within the solution a first molecule of interest to a first solid support of the invention;
  b. capturing within said solution at least a second molecule of interest to a second solid support on the invention;
  c. attaching the first molecule of interest and a first barcode and at least the second molecule of interest and a second barcode;
  d. simultaneously performing the assay on the first and second molecules of interest, wherein the result of the assay on the first molecule of interest is identified by the first barcode and the result of the assay on the second molecule of interest is identified by the second barcode; thereby multiplexing an assay on more than one molecule of interest in a single solution.

Figure 5A:
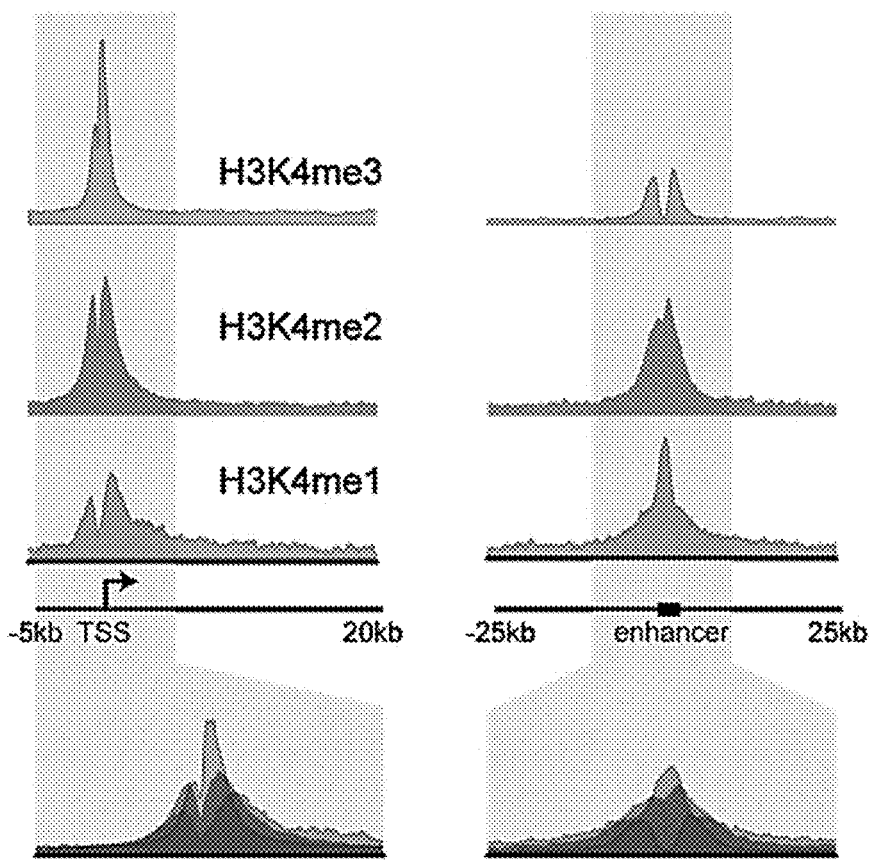
FIGS. 5A-M: (5A) Histograms of meta-analysis of cfChIP signal over active promoters and enhancers. (5B-C) Browser view of tracks of cfChIP of H3K4me3, H3K4me2, and H3K4me13 from a healthy subject. (5B) Shown is a region of highly expressed genes. We can see di-methylation and mono-methylationextending out from the tri-methylation signal. (5C) Shown is the locus surrounding IFNB1. ChromHMM tracks show prediction of promoters and enhancers according to combination of histone modification and chromatin accessibility assays. Arrows mark regions with enriched di- and mono-methylation. (5D-E) Scatter plots showing (5D) correlation of H3K4me2 and H3K4me3 at promoters in two samples, a healthy subject and a cancer patient and (5E) agreement between H3K4me2 of healthy subjects, and between H3K4me2 of two samples taken months apart from a cancer patient. Notable differences between healthy and cancer samples. (5F-H) Browser view of tracks comparing H3K4 methylation marks between healthy sample and a cancer sample (C002.2) for (5F) TCF3, (5G) CDX1 and (5H) CEACAM5 and CEACAM6. (5I) Histogram of meta-analysis of cfChIP for H3K36me3 signal over gene bodies with 5 kb flanking the transcription start site (TSS) and transcription end site (TES). Genes length is scaled. (5J) Scatter plot of correlation of H3K36me3 between Leukocytes and healthy sample (5K) Box plot of H3K36me3 marks active genes—healthy sample H3K36me3 counts (normalized by gene length) broken by quantiles of RNA levels of Leukocytes. (5L) Scatter plot of the raw Hf3K36me3 counts at gene bodies. Each dot represents a gene. x-axis: healthy samples. y-axis: colorectal adenocarcinoma sample. Color dots represent genes that are overexpressed in colorectal adenocarcinoma (COAD-red) or glioblastoma multiforme (GBM-green). (5M) Browser view of H3K4me3 and H3K36me3 signals at genes that show differential levels of these marks between healthy subject and colorectal adenocarcinoma patient. VIL1 gene shows differential signal for the two marks while CTDSP1 shows similar levels of H3K4me3 but marked increase in H3K36me3 in the sample from the colorectal adenocarcinoma patient.
Figure 5B:
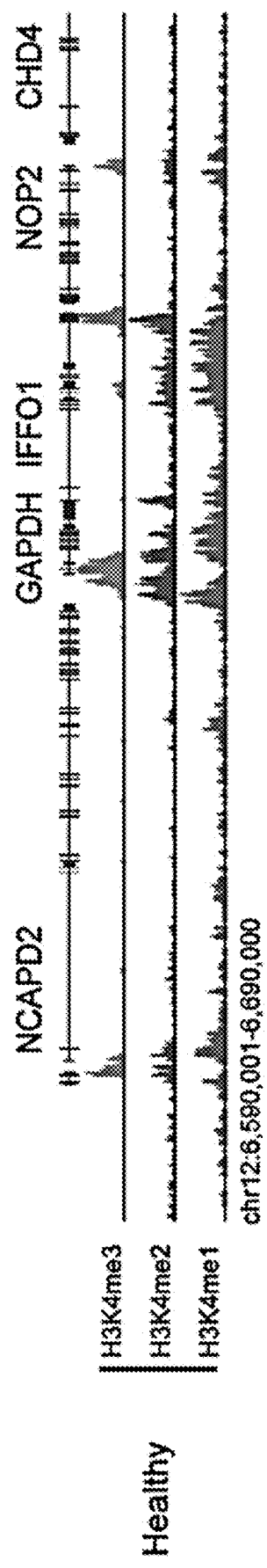

As used herein, "multiplexing an assay" refers to performing one assay on multiple samples simultaneously. Multiplexing is useful when samples are limited, the assay is costly in terms of time, money, reagents or sample input. By multiplexing using the method of the invention assays can be performed from start to finish simultaneously so that variation between samples is reduced (FIG. 5B). For example, in a multiplex chromatin immunoprecipitation followed by next generation sequencing (ChIP-Seq) assay using the method of the invention, the protein capture for all antibodies used is performed in one tube and at one time. The ligation of the barcode all occurs at once as well and washing and sequencing is all also performed as one. This greatly limits any inter-sample variability in assay performance. In some embodiments, the assay is any one of ChIP, ChIP-Seq, cfChIP, cfChIP-Seq, protein quantification, and a protein-protein interaction assay. Protein quantification can be achieved by adding a generic DNA adapter/sequence to the protein and then ligating the barcode. In some embodiments, the methods of the invention further comprise attaching an adapter to the protein of interest. In some embodiments, the assay is chromatin immunoprecipitation followed by sequencing (ChIP-Seq).

In some embodiments, the molecule of interest is a protein. In some embodiments, the molecule of interest is a nucleic acid molecule. In some embodiments, the molecule of interest is a protein and/or a nucleic acid molecule.

In some embodiments, the identifying by the barcode comprises quantification of the amount and/or number of the molecules of interest. In some embodiments, the amount and/or number of barcodes is equal to the amount and/or number of molecules of interest. In some embodiments, the amount and/or number of barcodes is proportional to the amount and/or number of molecules of interest. In some embodiments, the amount and/or number of barcodes is equal or proportional to the amount and/or number of molecules of interest.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Patients

All clinical studies were approved by the relevant local ethics committees. The study was approved by the Ethics Committees of the Hebrew University-Hadassah Medical Center of Jerusalem. Informed consent was obtained from all subjects or from their legal guardians before blood sampling.

Sample Collection

Blood samples were collected in VACUETTE® K3 EDTA tubes, transferred immediately to ice and 1× protease inhibitor cocktail (Roche) and 10 mM EDTA were added. The blood was centrifuged (10 minutes, 1500×g, 4° C.), the supernatant was transferred to fresh 14 ml tubes, centrifuged again (10 minutes, 3000×g, 4° C.), and the supernatant was used as plasma for ChIP experiments. The plasma was used fresh or flash frozen and stored at −80° C. for long storage.

Bead Preparation

50 μg of antibody were conjugated to 5 mg of epoxy M270 Dynabeads (Invitrogen) according to manufacturer instructions. The antibody-beads complexes were kept at 4° C. in PBS, 0.02% azide solution.

Immunoprecipitation, NGS Library Preparation, and Sequencing 0.2 mg of conjugated beads (~2 μg of antibody) were used per cfChIP sample. The antibody-beads complexes were added directly into the plasma (1-2 ml of plasma) and allowed to bind to cf-nucleosomes by rotating overnight at 4° C. The beads were magnetized and washed 6 times with blood wash buffer (BWB 50 mM Tris-HCl, 150 mM NaCl, 1% Triton X-100, 0.1% Sodium DeoxyCholate, 2 mM EDTA, 1× protease inhibitors cocktail), twice with BWB-500 (same as BWB only with 500 mM NaCl), and three times with 10 mM Tris pH 7.4. All washes were done with 150 ul buffer on ice by shifting the beads from side to side on a magnet. Vacuum was not used to remove supernatant during washes in buffers that do not contain detergents. Following removal of the beads, the plasma was stored as it was suitable for further rounds of cfChIP.

On-beads chromatin barcoding and library amplification was done to overcome the issue of low input material. This procedure supports preparation of cfChIP from as little as 1000 cells. The following steps were all performed on the beads so as to reduce loss of cfDNA that might occur during freeing of the cfDNA and tube transfers. DNA ends were repaired by T4 DNA polymerase and T4 polynucleotide kinase. Following a wash Klenow exo minus was employed to add an adenine base to the repaired end of the DNA. Following another wash DNA adapters were ligated on; in this case Illumina adapters with DNA barcode sequences were used. For the DNA elution and cleanup steps the beads were incubated for 1 hour at 55° C. in 50 µl of chromatin elution buffer (10 mM Tris pH 8.0, 5 mM EDTA, 300 mM NaCl, 0.6% SDS) supplemented with 50 units of proteinase K (Epicenter), and the DNA was purified by 1.2× SPRI cleanup (Ampure xp, agencourt). The purified DNA is eluted in 25 µl EB (10 mM tris pH 8.0) and 23 µl of the eluted DNA were used for PCR amplification with Kapa hotstart polymerase (16 cycles). The amplified DNA was purified by 1.2×SPRI cleanup and eluted in 12 µl EB. The eluted DNA concentration was measured by Qubit and the fragments size was analysed by tapestation visualization. Note: If adapter dimers were still visible by tapestation post library amplification, samples that are not identically barcoded can be pooled, separated on a 4% agarose gel (E-Gel® EX Agarose Gels, 4%, Invitrogen), and fragments larger than adapter dimers (>200 bp) are gel purified. Alternatively, gel purification can be avoided by performing an additional X 0.8 SPRI cleanup post sample pooling, which remove most of the adapter dimers. DNA libraries were paired end sequenced by Illumina NextSeq 500.

Sequence Analysis

Reads were aligned to the human genome (hg19) using bowtie2 with 'no-mixed' and 'no-discordant' flags. We discarded reads with low alignment scores and duplicate fragments.

Roadmap Epigenome Atlas

We downloaded consolidated aligned data from the Roadmap Epigenome Consortium database (egg2.wustl.edu/roadmap/data/byFileType/alignments/consolidated/). To these we added Kidney samples (egg2.wustl.edu/roadmap/data/byFileType/alignments/unconsolidated/H3K4me3/BI.Adult Kidney.H3 K4me3.27.filt.tagAlign.gz and egg2.wustl.edu/roadmap/data/byFileType/alignments/unconsolidated/H3K4me3/BI.Adult Kidney.H3 K4me3.153.filt.tagAlign.gz). For our analysis we discarded pre-natal, ESC, and cell-line samples, resulting with 71 tissues and cell types.

Tumor-Type Gene Signatures

We downloaded RNA-seq data from the TCGA and GTEx projects as analyzed by the Xena project (Toil enables reproducible, open source, big biomedical data analyses, Vivian J, et al., Nat. Biotechnol., 2017, and Toil RNAseq Recompute database, tcga-data.nci.nih.gov). We defined the set of genes that are over-expressed in a tumor type to satisfy three requirements: 1) Significantly higher expression in tumor samples compared to the corresponding tissue samples (t-test, q<0.001 after FDR correction); 2) Significantly higher expression compared to all healthy samples (t-test, q<0.001 after FDR correction); and 3) Median expression in the tumor is higher than median expression in each of the healthy samples.

TSS Location Catalogue

We downloaded the Roadmap Epigenome Consortium ChromHMM annotation of all consolidated tissues (egg2.wustl.edu/roadmap/data/byFileType/chromhmmSegmentations/ChmmModels/coreMarks/jointM odel/final/all.mnemonics.bedFiles.tgz). Using these annotations, we constructed a catalogue of potential TSS sites. We extended the catalogue to include 3 kb regions centered on TSS of annotated transcripts in the UCSC gene database and ENSEMBL transcript database (UCSC known genes: Bioconductor AnnotationHub AH5036; ENSEMBL transcripts Bioconductor AnnotationHub AH5046; Genomic annotations: Bioconductor AnnotationHub AH5040). We used the combined catalogue to define regions along the genome, which are either TSS or "background" (most likely not TSS). The later regions were tiled by 5 kb sized windows.

We quantified the number of reads covering each region in the catalogue in each of our samples and atlas samples. We estimated locally adaptive model of non-specific reads along the genome for each of the samples and extracted counts that represent specific ChIP signal in the catalogue for each sample (see below). These were then normalized (Supplemental Text) and scaled to 1M reads in the reference healthy samples.

Tissue/Process Signatures

To define tissue specific signatures of a specific modification, we examined binned representation of the atlas. For each tissue we defined a signature of unique windows with signal in one of the samples of the target tissue and without coverage in all others (see below).

To define process signature, we converted gene specific annotations (e.g., GO) to genomic windows by including all windows that overlap with promoters of genes in the annotation.

Statistical Analysis

We consider two different statistical tests. For both tests we need to estimate the background coverage, that is reads from non-specific pulldown (see below).

The first test is whether a signature is present. Formally, we examined whether we can reject the null hypothesis that the number of reads in signature windows will be Poisson distribution according to background rate (see below). We compute p-value of the actual number of observed reads in signature windows as the probability of having this number or higher according to the null hypothesis. Rejection of the null hypothesis for a specific signature is an indication that some of the windows in the signature carry the modification in question in a subpopulation of cells contributing to the cf-nucleosome pool.

The second test is whether a signature is over-represented than expected in healthy baseline subjects. To define the latter expected we use average signal from 5 healthy samples to define the average number of reads (per million) in each window. We then estimate two sample-specific parameters—first a background rate (discussed above) and second a scaling factor that rescales average expectations to the sequencing depth of the specific sample (see below) Together, these define the expected coverage in each window under the null-hypothesis that the subject is from the healthy population. We compute p-value of the actual number of observed reads in signature windows as the probability of having this number or higher according to the null hypothesis. Rejection of the null hypothesis for a specific signature is an indication that some of the windows in the signature have higher signal than we expected in healthy subjects. The interpretation is that these are abnormal processes active in the cells contributing to the subject's cf-nucleosome pool.

TSS Location Catalogue

We constructed a TSS catalogue through the following steps. All steps were carried on human genome version "hg19":

1. We downloaded ChromHMM calls for 111 tissues and cell types throughout the human genome from Roadmap Epigenomics website (egg2.wustl.edu/roadmap/data/byDataType/rna/expression/57epigenomes.RPKM.pc.gz). UCSC Browser known gene annotations and ENSEMBL transcript annotations were downloaded (UCSC known genes: Bioconductor AnnotationHub AH5036; ENSEMBL transcripts Bioconductor AnnotationHub AH5046; Genomic annotations: Bioconductor AnnotationHub AH5040).
2. We filtered all genomic ranges that were marked with states "1_TssA" or "2_TssAFlnk" and merged adjacent ranges that were marked as either state in exactly the same set of tissues. We call these "ChromHMM TSS windows". We found 476,931 such windows. Each ChromHMM TSS window was assigned gene name(s) through the following steps.
   a. If it was within 2.5 Kb of one or more TSSs in UCSC known gene annotation, it was assigned the name of these genes.
   b. If not, we searched for an ENSEMBL transcript start within 2.5 Kb. Again, if such were found the TSS window received the gene name associated with the transcript.
   c. All other TSS windows remained without a name
3. To include transcripts that are not represented in the TSS catalogue, we examined all genes in the UCSC Known Gene database and all transcripts in the ENSEMBL database. For each we defined a TSS window of size 3 Kb centered on the TSS. We discarded all such windows that overlapped with a TSS window from step 2. In total this step added 14,857 and 41,376 TSS windows from UCSC Known genes and ENSEMBL transcripts, respectively.
4. We created windows that tile the remaining genomic regions between TSS windows. For each TSS window without an adjacent TSS window, we created "flanking" regions of size 1 Kb (or less). This resulted in 370,332 flanking windows (as some of the TSS windows are adjacent to each other, depending on ChromHMM calls in different tissues). The remaining uncovered regions were tiled with "background" regions of size 5 Kb (or less). In total there were 502,263 such windows.

The resulting catalogue was saved as BED file (TSS.bed).

Processing of Sequencing Files

Base calling was performed with bcl2fastq (2.18). Paired-end reads were mapped to the human genomes (hg19) using bowtie2 with "no-mixed" and "no-discordant" flags descarding reads with quality 0. BEDPE files (start and end of every fragment) were obtained using BEDtools "bamtobed" with "bedpe" flag, discarding duplicate fragments. BEDPE files were converted to coverage counts over windows in the catalogue using BEDtools "intersect" command and also using BioConductor "GenomicRanges" countOverlaps( ) function. Both methods count for each window the number of sequenced fragments that overlap with the window.

Estimating Background Signal

Every ChIP procedure has non-specific background signal. In the case of cfChIP the background is due to some forms of non-specific binding of DNA and chromatin fragments to the beads-antibody complex. Our experience showed that the background levels varied between samples and batches of bead-antibody ligation. Moreover, the sequencing depth varied between samples, and in a deeply sequenced sample the number of background reads increase. Thus, it was important to estimate background signal levels to be able to contrast them with actual signal.

We initially applied a simple-minded procedure for removing background in H3K4me3 signal. We reasoned that virtually all of the specific signal in H3K4me3 is at TSS and gene 5' regions. Thus, reads in other locations represent background. To account for TSSs that are not annotated in our TSS catalogue, we reasoned that some small fraction of background windows might contain real signal, and thus we removed the ones with the highest values.

In more detail we did the following. We created a vector with the coverage of all "background" windows of size>=4 Kb (421,465 out of 549,385). And applied the following procedure:

$estimateBackground(X)$ $T \leftarrow \text{quantile}(95, X)$  // find the 95th quantile of $X$ $X \leftarrow X[X \leq T]$  // restrict ourselves to values below $T$ $\hat{\lambda} = \arg\max_{\lambda} \prod_{i=1}^{|X|} P_\lambda(x_i \mid x_i \leq T)$  // maximum likelihood of truncated poisson Return $\hat{\lambda}/5$  // convert to reads/$Kb$ This procedure was relatively robust to the choice of quantile for removing outlier windows.

However, in some samples the Poisson distribution was not a good fit for background values. Further examination revealed that much of this discrepancy was due to local background effects. One local effect is the sex chromosomes that appear in 50% levels in males, and 100% (X) and 0% (Y) in female. These were not the only local effects—some regions showed higher levels of background. This could be due to segmental duplication (regions close to centromeres and telomeres) or accessibility issues. Moreover, in cancer samples there were clear aberrations that were patient specific.

To overcome these issues, we devised a localized background rate estimate. We used the above estimation procedure, but in successive levels of resolution.
1. Genome-wide background level.
2. Chromosome-specific background.
3. Tiles of 10 Mb covering each chromosome at offsets of 2.5 Mb.

4. Tiles of 5 Mb covering each chromosome at offset of 1.25 Mb.

The estimate at each level used the estimate of the previous level as a prior (using pseudo-counts of 1000 windows in levels 2 and 3, and 500 windows in level 4).

Figure 6A:
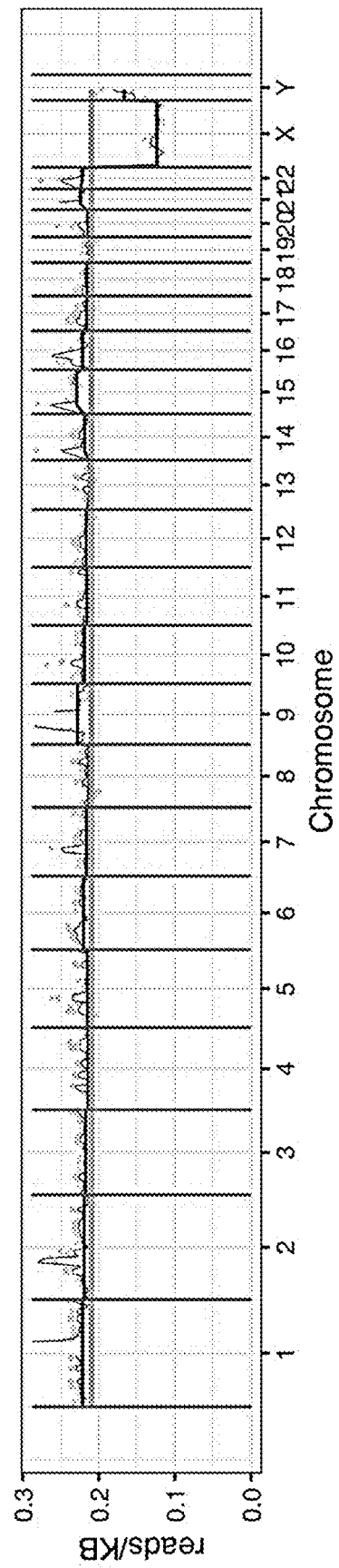
FIGS. 6A-C: (6A-C) Line graph examples of the background estimate for (6A) a healthy male sample, (6B) a healthy female sample and (6C) a cancer patient.
Figure 6B:
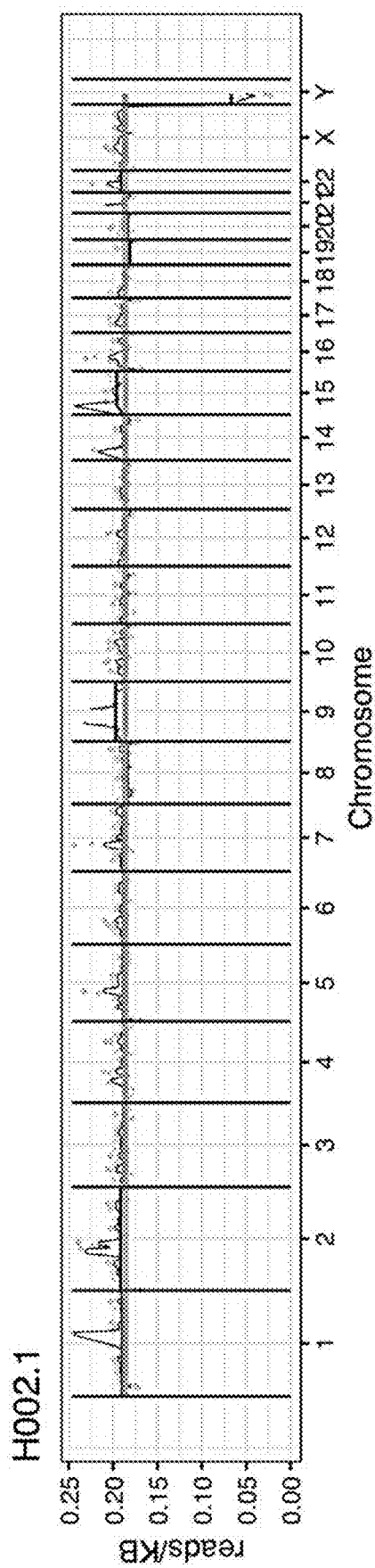
Figure 6C:
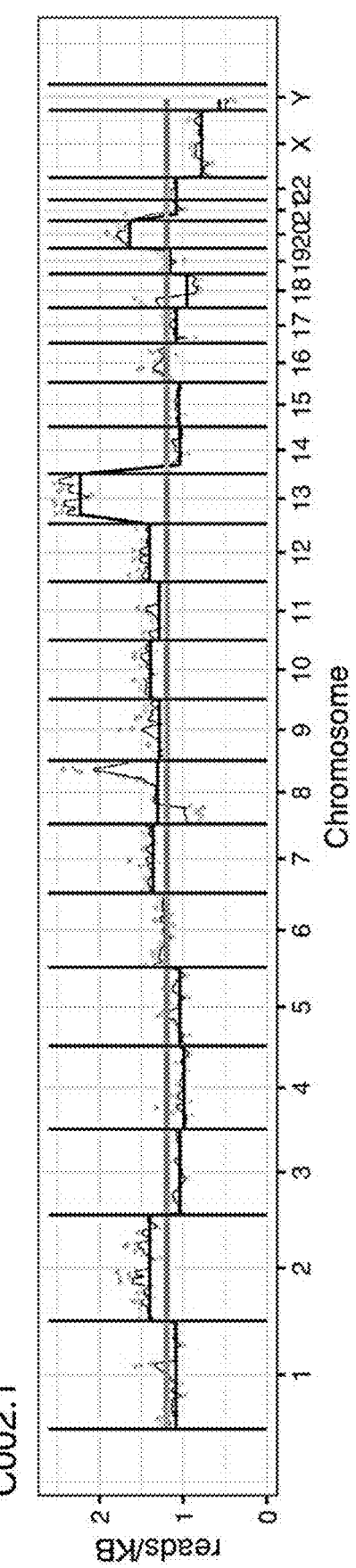

The result is an estimate of background coverage rate at overlapping tiles of 5 Mb. To get a single estimate, for each location we take the maximum of the estimate of the tiles covering it (typically 4 tiles). We choose the maximum as we reasoned that over-estimate of background might reduce the estimated signal but would reduce the number of background artifact. FIG. 6A shows the background estimate for a healthy male sample. FIG. 6B shows a healthy female sample, wherein the chrX background is lower than autosomal chromosomes (slightly more than half) and chrY background is a bit lower. Many locations in chrY are orthologous to ones in chrX leading to skewed estimates. Other deviations occur close to centromeres where we find the background level to be higher in some chromosomes (e.g., chr1, chr9). When a patient with cancer is examined, the background estimate is much more variable, presumably reflecting chromosomal aberrations in the tumor (FIG. 6C).

Gene-Level Signal and Normalization

For each gene we assigned a set of TSS windows that are annotated with the gene name. For each sample we computed the actual total coverage over the windows assigned to the gene and the expected mean of background reads over these windows (using possibly different local rate at each window and the window size).

More precisely, $$C[g, s] = \sum_{w \in W_g} C[w, s]$$

$$B[g, s] = \sum_{w \in W_g} \hat{\lambda}[w, s] * \text{width}(w)$$

Where $W_g$ is the set of windows assigned to gene g, $C[w,s]$ the coverage of window w in sample s, and $\hat{\lambda}[w, s]$ the estimated background rate of window w in sample s.

The null assumption is that the coverage $C_g$ is distributed as a Poisson with parameter $G_b$. Thus, we argued that values much larger than expected are signal. We define the raw signal at gene g as:

$S[g,s] = C[g,s] - B[g,s]$ if $C[g,s] \geq B[g,s] + 2\sqrt{B[g,s]}$ and 0 otherwise Thus, we consider $C[g,s,]$ to be a real signal if it is larger than two standard deviations from the mean of the background level for the gene.

Applying this procedure for each sample generates a matrix of counts for each gene in each sample. We also include in this matrix the samples from Roadmap Epigenomics data of H3K4me3 ChIP which were processed in the same manner.

To normalize the effect of different coverage, we reasoned that the signal at promoters of "housekeeping" autosomal genes should be similar in different samples. We defined these genes as ones with highly significant signal in a set of reference healthy samples. The precise choice of significance level did not change the normalization.

On the matrix of raw signal samples X housekeeping genes we applied quantile normalization (Bioconductor normalize.quantiles). This resulted in normalized values for housekeeping genes in each sample. However, it does not assign values for all other genes. We thus, estimate a multiplicative normalization factor for each sample to best match quantile-normalized values to raw values. For most samples the relation between the two was linear.

The scaling factors were rescaled so that the total normalized signal (below) at the set of reference healthy samples will be a million on average.

Using these normalization factors, levels v [s] we computed for each sample the normalized gene levels:

$N[g,s] = v[s] * S[g,s]$

Using the same normalization procedure, we also normalized the coverage at each window in each sample:

$N[w,s] = v[s] * \max(C[w,s] - B[w,s], 0)$

Defining Tissue-Specific Signature

Using the Roadmap Epigenomics metadata table we defined sets of Roadmap samples that belonged to a tissue or group of tissues. These definitions included some redundancies. For example, the group Lymphocytes included B-Cells, T-Cells, and NK samples, and thus subsumed each of these groups.

We then defined for each group the set of specific windows, as windows w passing the following criteria:
1. The window w is on an autosomal chromosome
2. In at least one of the atlas samples in the group, $N[w, s] \geq 35$
3. In all atlas samples outside the group, $N[w, s] < 15$
4. n all windows w' within 1 Kb of w, $N[w, s] < 15$ The last condition is added as we noticed that often when a gene is expressed there is "spill over" to neighboring windows.

Figure 7:
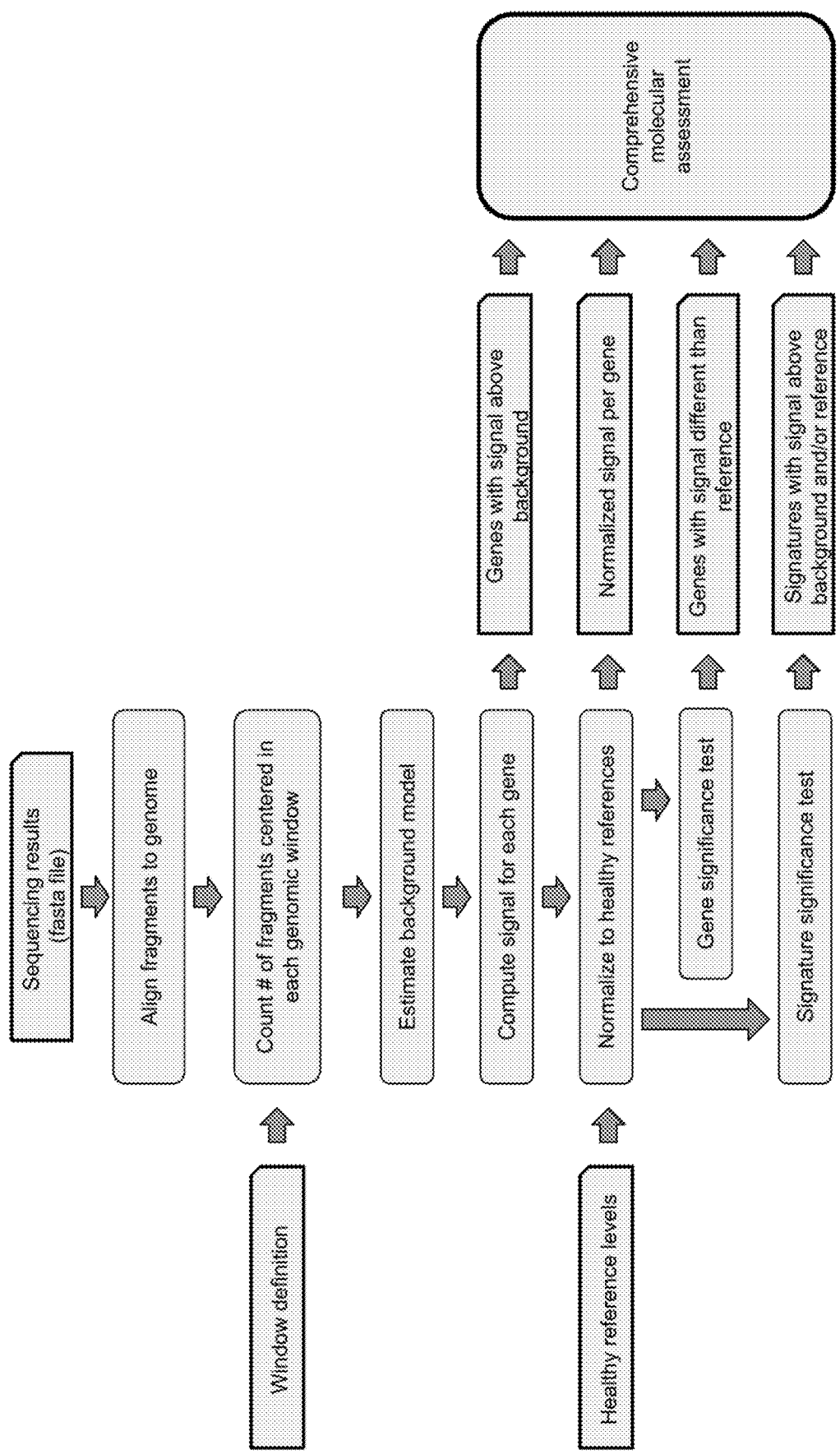
FIG. 7: Work flow of processing and analysis of cf-ChIP.

Groups for which we found less than 4 specific windows were considered to be without signature. For all other groups, we define the signature as the set of specific windows (see Table 1). The workflow of cfChIP processing and analysis is provided in FIG. 7.

Statistical Tests

We use two main tests herein:

Detection test. To test whether a gene or a signature is present above background in a sample, we used a Poisson distribution. More specifically:

computeDetectionPValue (W,s)

$$\lambda \leftarrow \sum_{w \in W} B[w, s]$$

$$x \leftarrow \sum_{w \in W} C[w, s]$$

Return $P_\lambda(X \geq x)$   // Poisson p-value

Here W is a set of windows, it can be the windows associated with a gene or tissue-specific signature as above.

Over-expression test. To test whether the observed signal of a set of genes is higher than expected in healthy samples, we used a reference of healthy subjects to define the expected normalized signal of the gene H [g] as the average of N [g, s] in the reference samples.

We then used the following procedure:

computeOverExpressionPValue(G, s)

$$\lambda \leftarrow \sum_{g \in G} B[g, s] + \frac{1}{v[s]} * \sum_{g \in G} H[g]$$

$$x \leftarrow \sum_{g \in G} C[g, s]$$

Return $P_\lambda(X \geq x)$ // Poisson $p$-value

The main difference from the previous test is that we included the contribution of healthy samples after we transform from normalized units to the units of the specific sample. The second difference is that we work at the level of genes.

Results

Example 1

Chromatin Immunoprecipitation of cf-Nucleosomes From Plasma

Figure 1B:
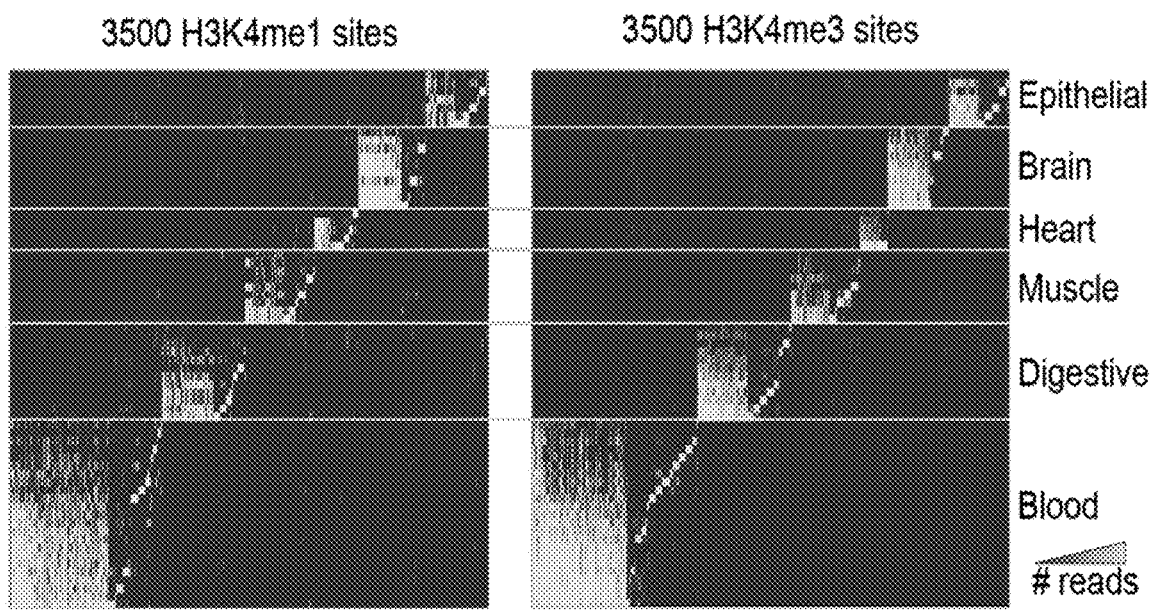

Most plasma cfDNA is likely in the form of nucleosomal DNA (cf-nucleosomes) with intact histone modifications. Whether extracting and sequencing DNA from cf-nucleosomes carrying specific histone marks could be used to determine information about the cell of origin of the cfDNA was investigated (FIG. 1A). This is approach is attractive for several reasons. First, ChIP experiments by design sequence only the positive signal reducing the number of reads required for a positive signal and thus lower the costs and work associated with the assay. Second, positive targets are relatively rare; promoter marks, such as H3K4me3, appear in ~50,000 locations in the genome (<1% of the genome). Enhancer marks (e.g., H3K4me1) can appear in many regions (~10% of the genome) but are limited in each cell. Third, histone marks are mostly tissue-specific. In particular, most enhancers are tissue-specific and thus provide strong H3K4me1/3 tissue specificity (FIG. 1B). Fourth, histone modifications reflect transcriptional activity and respond to changes in cell state. Thus, they create an opportunity to detect changes in activity in cells as they die.

Figure 1C:
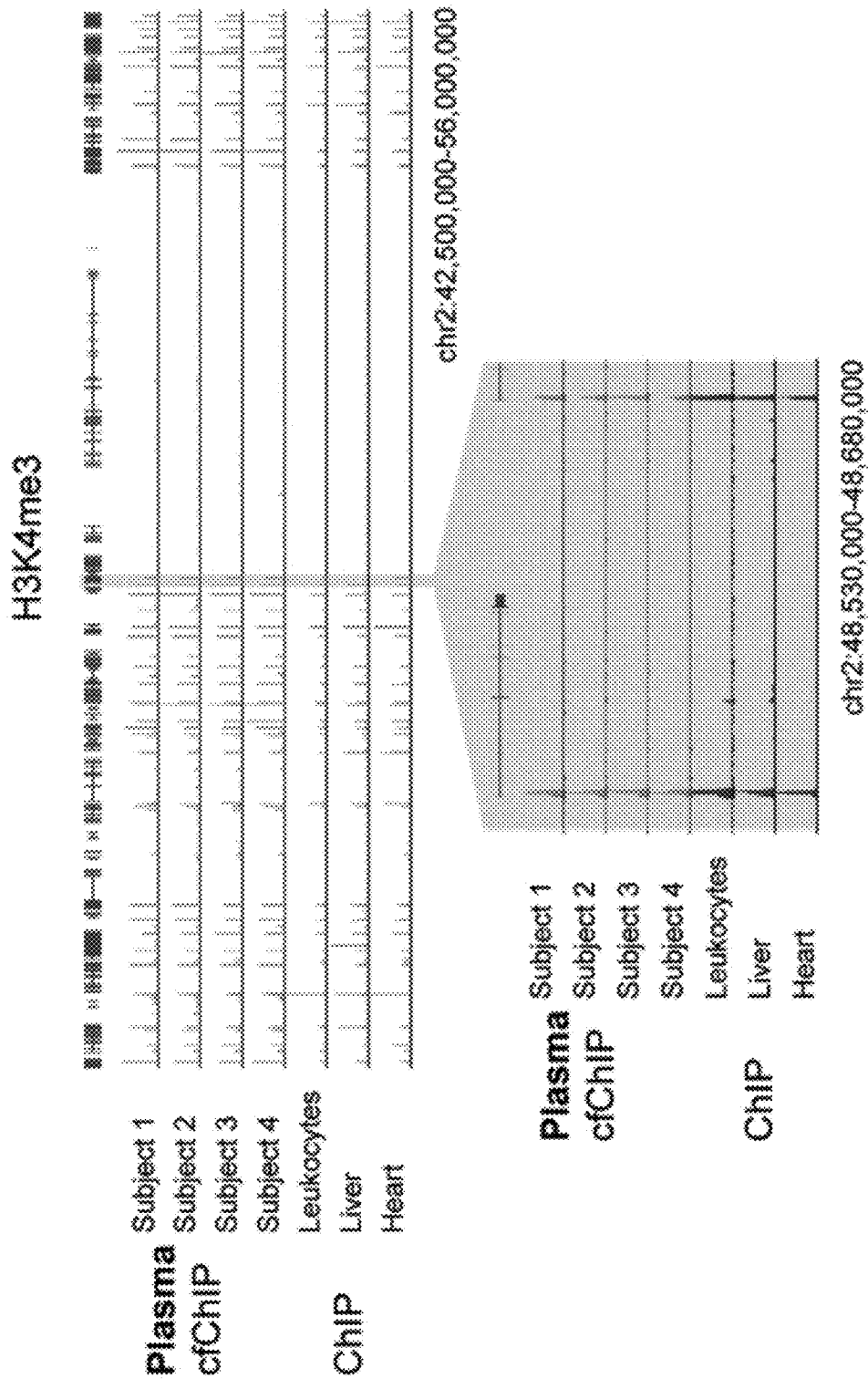
Figure 1C:
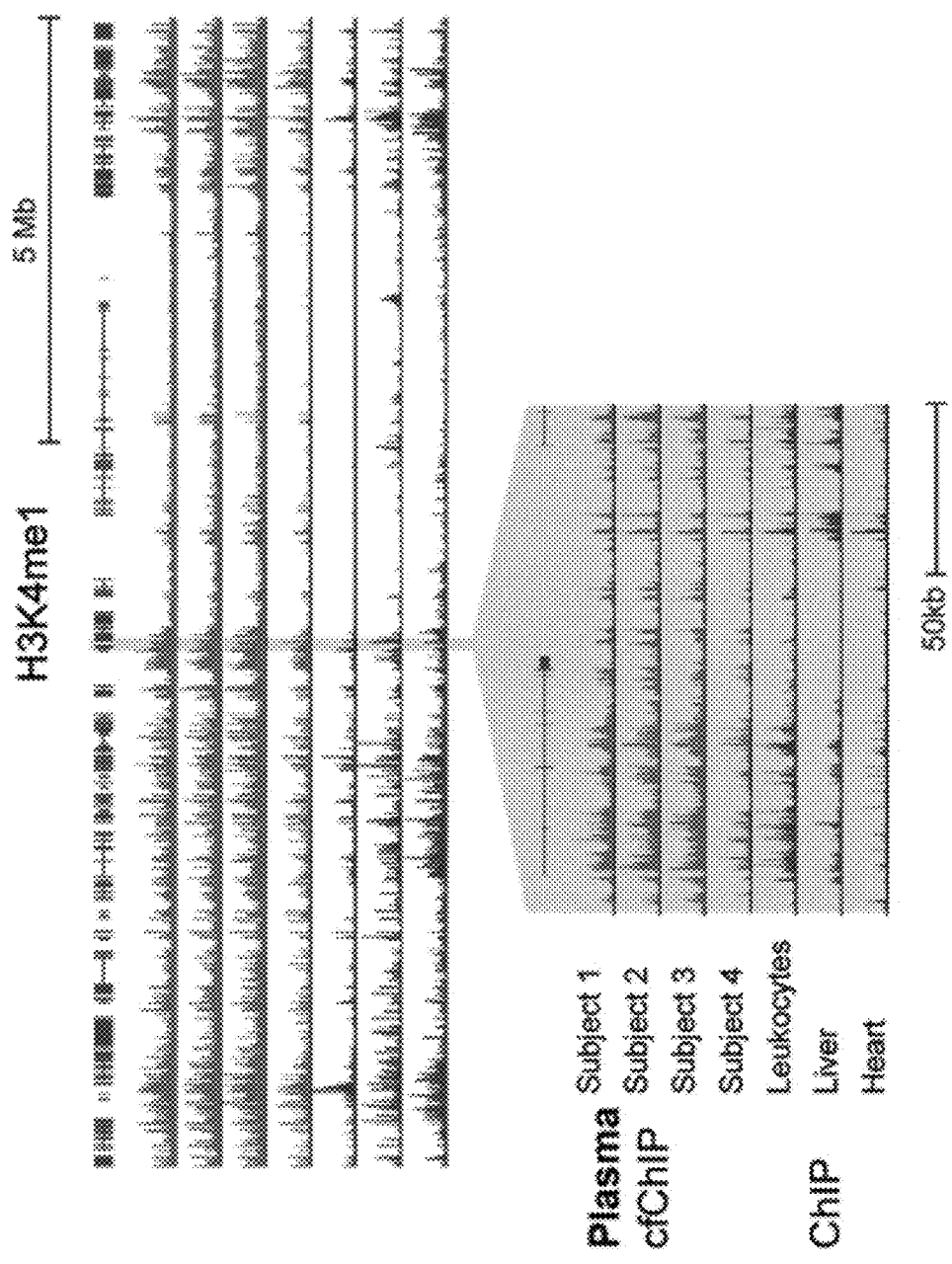
Figure 1D:
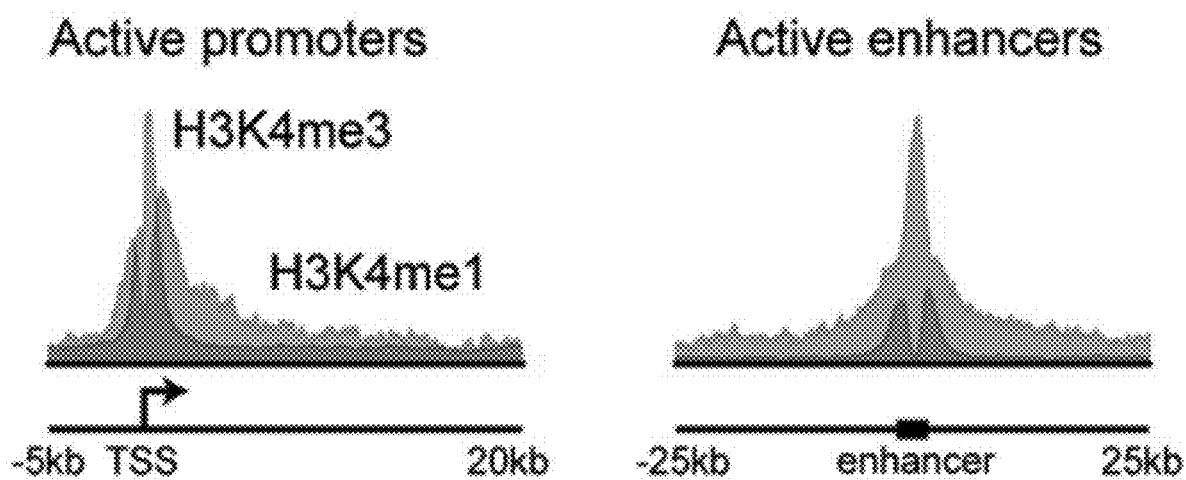

We devised a simple protocol for cf-nucleosome ChIP-seq (cfChIP) from as little as 1-2 ml of plasma (FIG. 1A inset, 1C). cfChIP and paired-end sequencing on plasma samples from 11 healthy individuals produced 0.3-1.7 and 0.9-25 million unique reads per sample for H3K4me3, and H3K4me1 respectively, suggesting that ~1-2% of nucleosomes in the plasma with the respective mark (e.g., H3K4me3) were captured, adapter ligated, and sequenced (see Materials and Methods). Importantly, the cfChIP signal surrounding ubiquitously-expressed genes shows high correlation with reference ChIP-seq from tissues (NIH Epigenome Roadmap consortium) (FIG. 1C). Globally, meta-analysis of the cfChIP signal for H3K4me1 and H3K4me3 yields the expected typical distribution for these marks around enhancers and promoters (FIG. 1D).

Figure 1E:
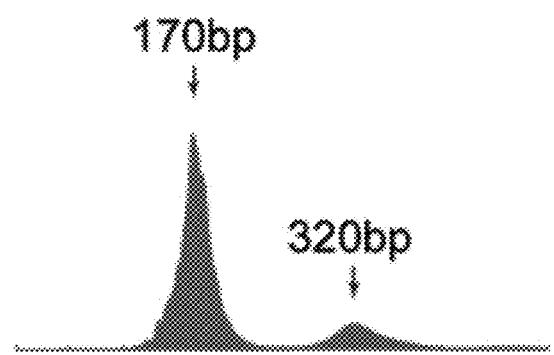
Figure 1F:
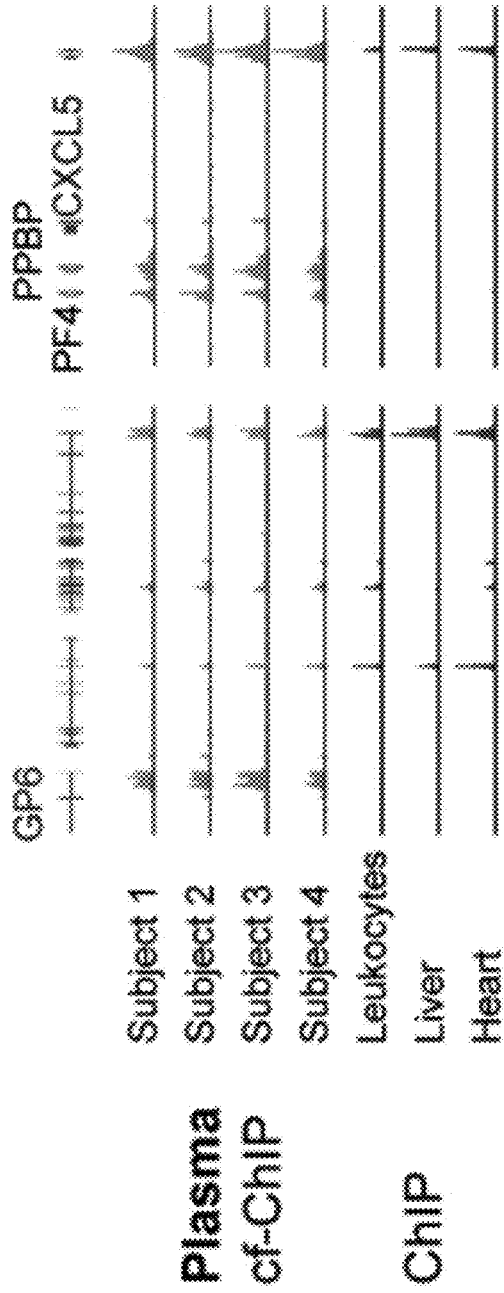
Figure 1G:
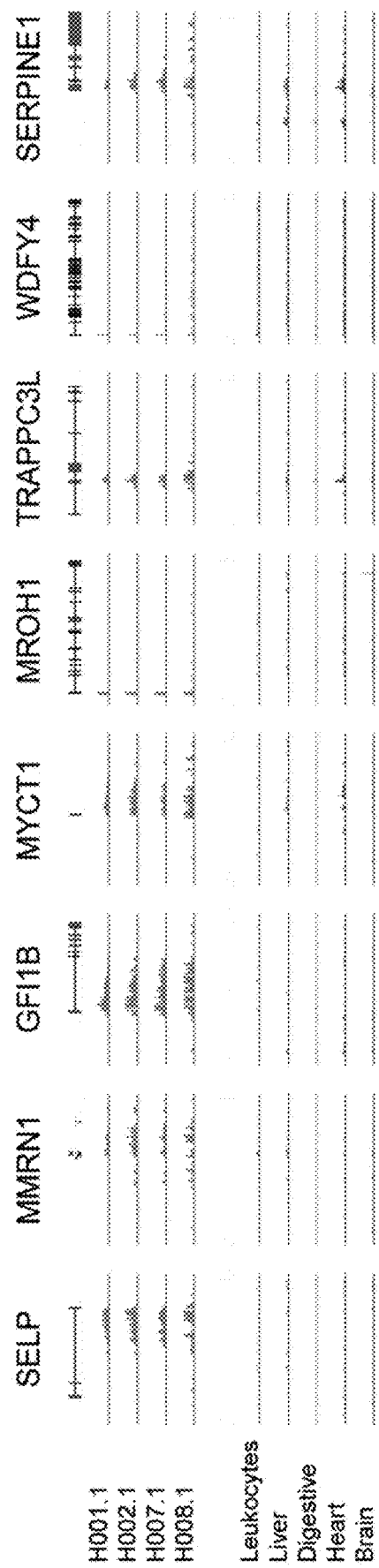

A potential concern is contamination by chromatin released from the lysis of white blood cells during blood draw. Several lines of evidence argue that this is highly unlikely. (a) Fragment size distributions of cfChIP libraries show two peaks at ~170 and ~320 bp corresponding to DNA wrapped around mono- and di-nucleosomes (FIG. 1E), consistent with apoptotic and in some cases necrotic cell death, but not cell lysis, which results in fragments at the range of 10 kb or larger. (b) We identified thousands of enhancers carrying H3K4me1 and tens of promoters carrying H3K4me3 that are absent in ChIP-seq from leukocytes that constitute the largest portion of nucleated blood cells (peripheral blood mononuclear cells; FIG. 1F-1G). Analysis of the promoters that are marked by H3K4me3 in cfChIP but not in leukocytes identifies strong signal from megakaryocytes that reside in the bone marrow. (c) We are able to detect disease-related chromatin from remote tissues from patients (see below).

Figure 1H:
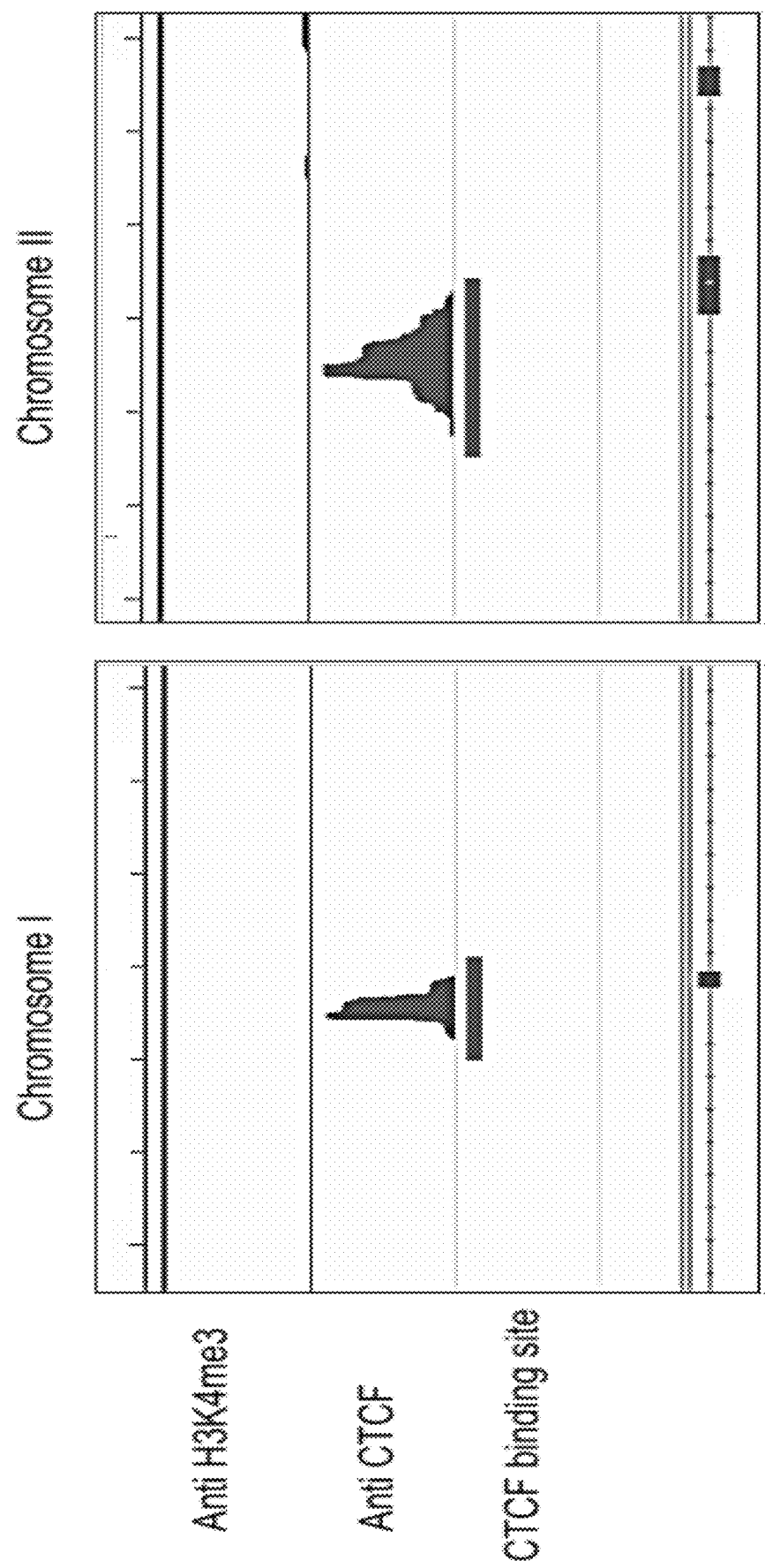
Figure 1I:
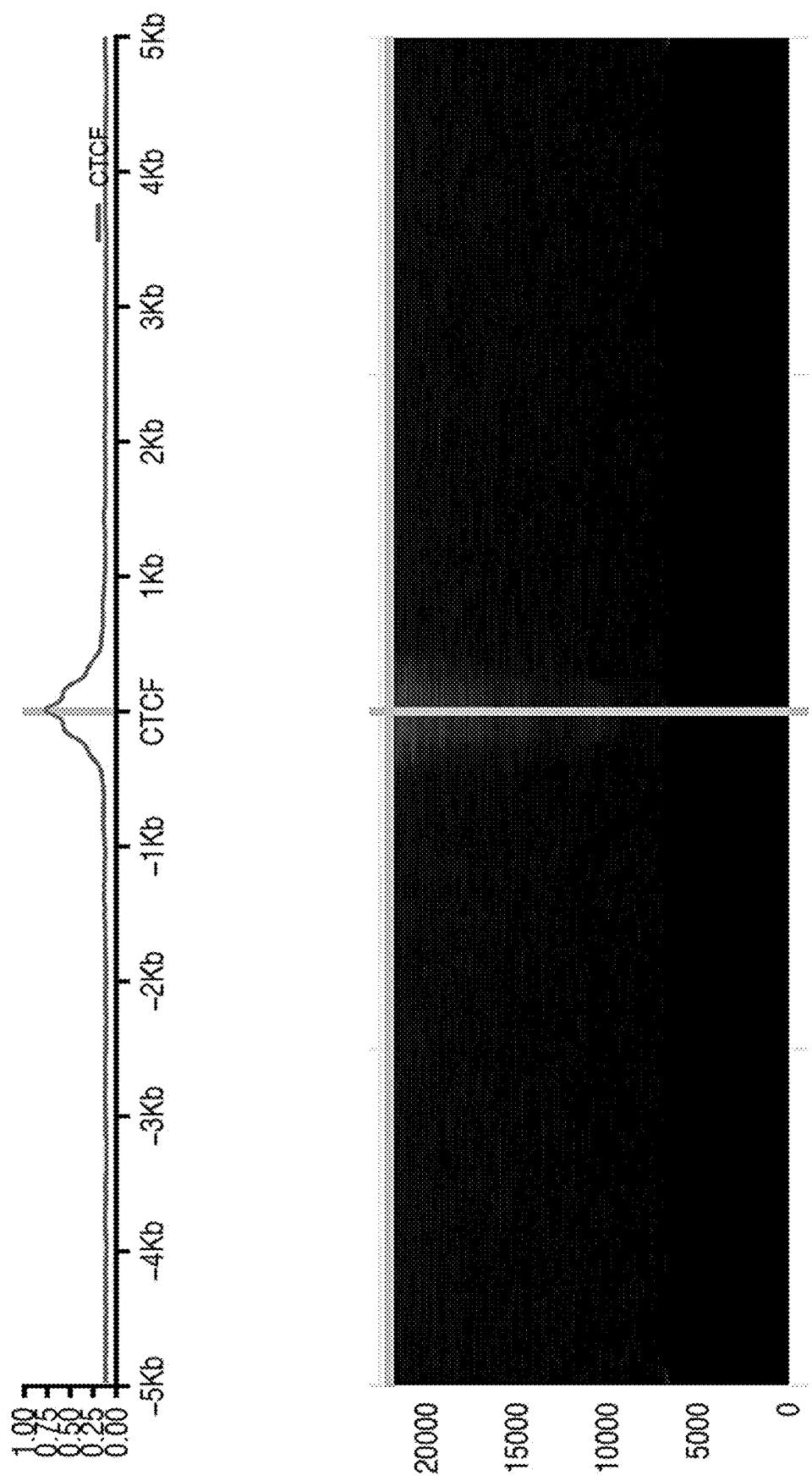
Figure 1I:
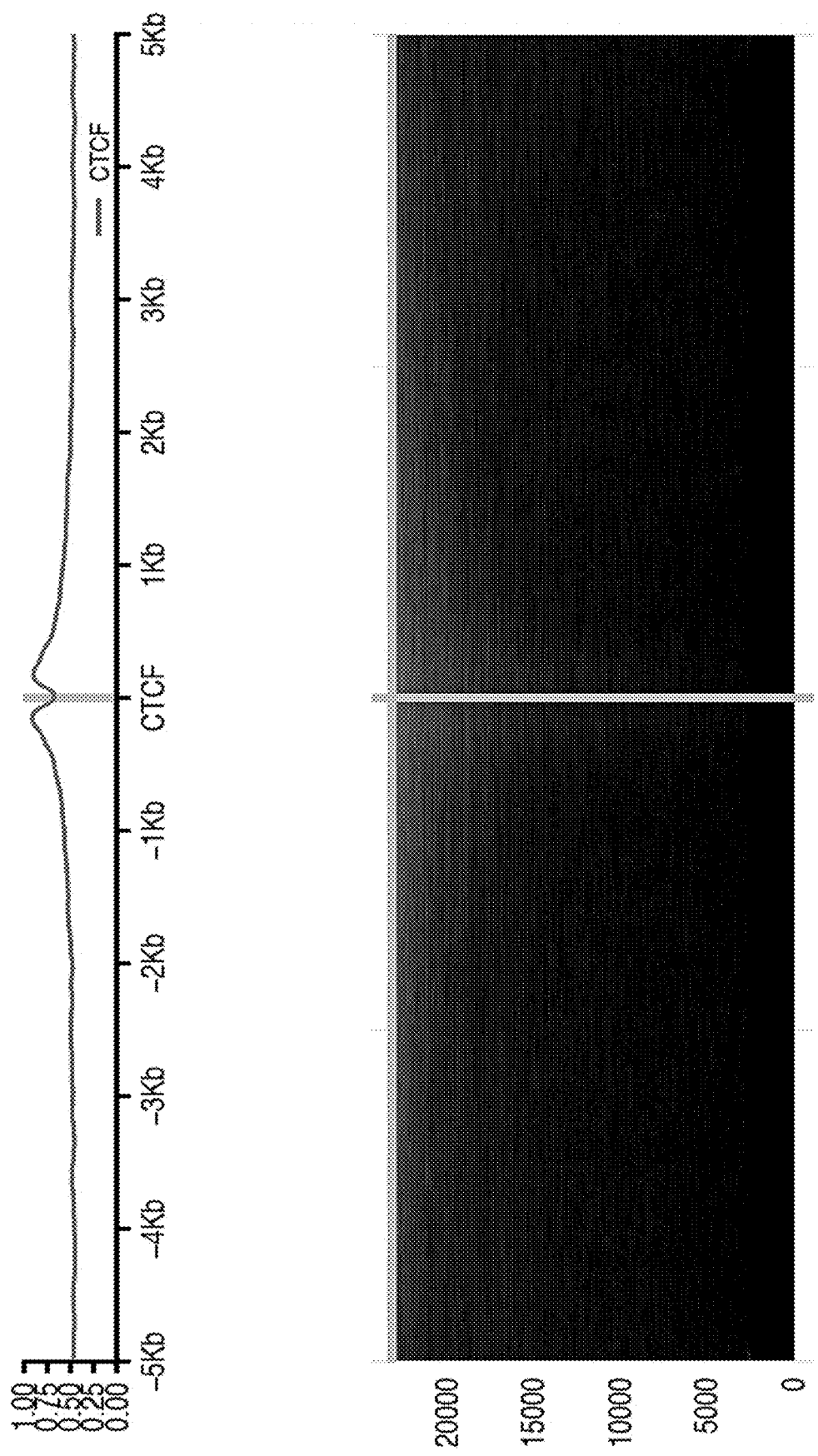

Non-histone DNA associated proteins can also be used for cf-ChIP. We spiked human plasma with 90 ng of chromatin prepared by native MNase treatment of DNA from mouse embryonic stem cells and performed cfChIP with anti-CTCF antibody. Sequencing reads from the cf-ChIP were aligned to the mouse genome, and clear sharp peaks that overlapped with peaks obtained from ChIP-Seq for CTCF from mouse cells were observed (FIG. 1H). Meta-analysis of the data shows a clear signal at CTCF sites throughout the genome, and similar analysis of cfChIP with anti-H3K4me3 antibody showed depletion of the histone mark at the same sites (FIG. 1I). CTCF binding and H3K4 trimethylation are generally mutually exclusive, so this result helps to confirm that the CTCF signal is genuine.

Together, these results strongly suggest that cf-nucleosomes preserve well established endogenous patterns of active histone marks and transcription factor binding. We focus our analysis on H3K4me3 at this point since it is relatively straightforward to assign H3K4me3 peaks to specific genes.

Figure 2A:
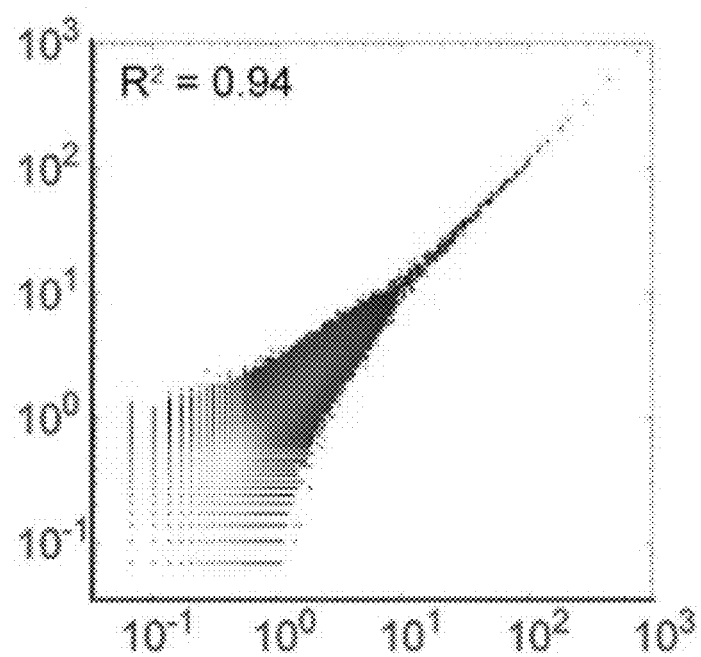
FIGS. 2A-M: (2A-2B) Scatter plots comparing cfChIP with anti-H3K4me1 and anti-H3K4me3 antibodies of (2A) technical replicates and (2B) 1 male and 1 female healthy individual. Each point is a 2 kb window in the genome, the x and y axises are the number of reads (in log(x+1) scale) mapped to the window in the two samples. Color code reflects density of points. (2C) Histograms of the correlations between H3K4me3 cfChIP samples of healthy subjects. (left) Correlations of counts in 2 kb windows (as FIG. 2A-B) and (right) Correlation in counts at gene promoters. We see that samples from the same subject (red histograms) tend to be slightly more correlated to each other than samples of different subjects (blue histograms). (2D) Browser examples of gender-specific peaks. Male and female plasma samples were mixed in known proportions, and cfChIP of H3K4me3 performed. (2E) Bar chart of detection of male-specific chrY signature in samples shown in 2D. FDR adjusted q-values for background signal are shown. (2F) Chart showing H3K4me3 male signal is linear with the fraction. Compared are read counts in simulations based on the 100% male sample and Poisson samples vs observed numbers. (2G) Line graph estimation of the probability of detecting a specific location with different number of reads. The probability of detection was estimated by down-sampling from the actual result. Bars represent 95% confidence interval for the estimate. (2H) Line graph extrapolation of spike-in for larger signatures size. Shown are the probability of detecting 0.1% male for two sample sizes. (2I) Bar chart of the size of tissue highly specific signatures (see Table 1). (2J) Scatter plots of the correlations between H3K4me3 at promoters of constitutively expressed genes and RNA levels. (top) ChIP-seq of PBMC (leukocytes) vs RNA-seq of PBMC. (bottom) cfChIP of healthy subjects vs RNA-seq of PBMC. (2K) Scatter plot comparison of H3K4me3 cfChIP-seq and expression levels. Each dot is a gene. x-axis: number of H3K4me3 reads (after normalization; Methods) in the gene promoter. y-axis: Leukocytes RNA-seq counts of the gene. (2L) Dot plot of tissue specific signatures detected in cfChIP of healthy subjects. Shown are the signature counts for cells whose cfDNA is expected to be represented in cfDNA: neutrophils, 35% cfDNA; monocytes, 25% cfDNA; and hepatocytes, 1% and for negative control (heart). The points in each column are the counts for specific individuals. (2M) A dot plot showing the significance of the signatures from FIG. 2L.
Figure 2A:
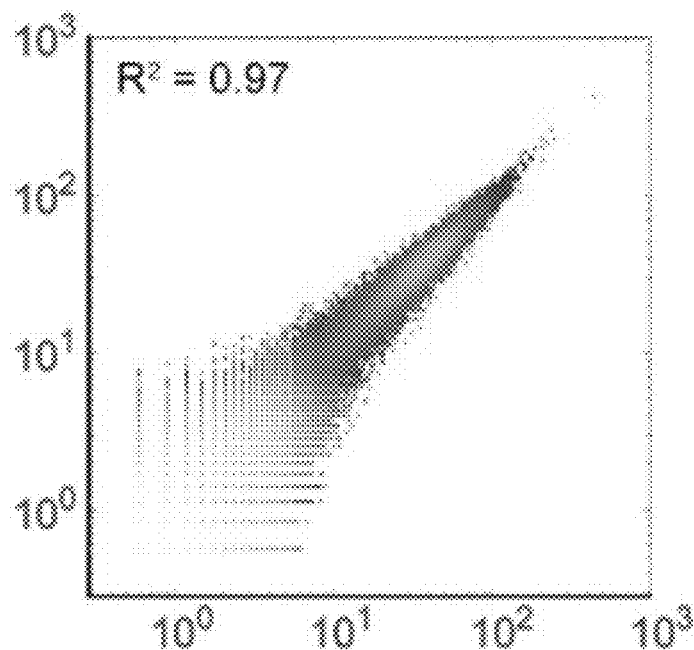
Figure 2B:
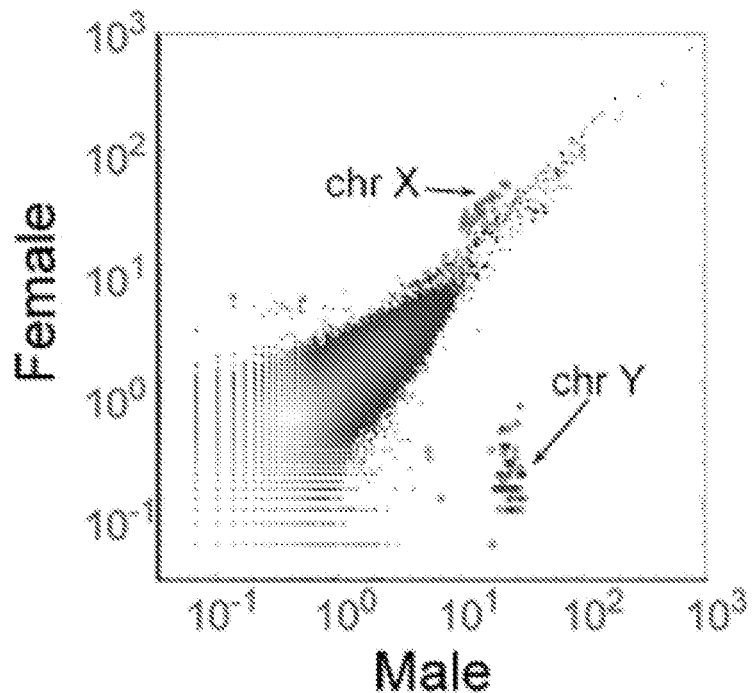
Figure 2B:
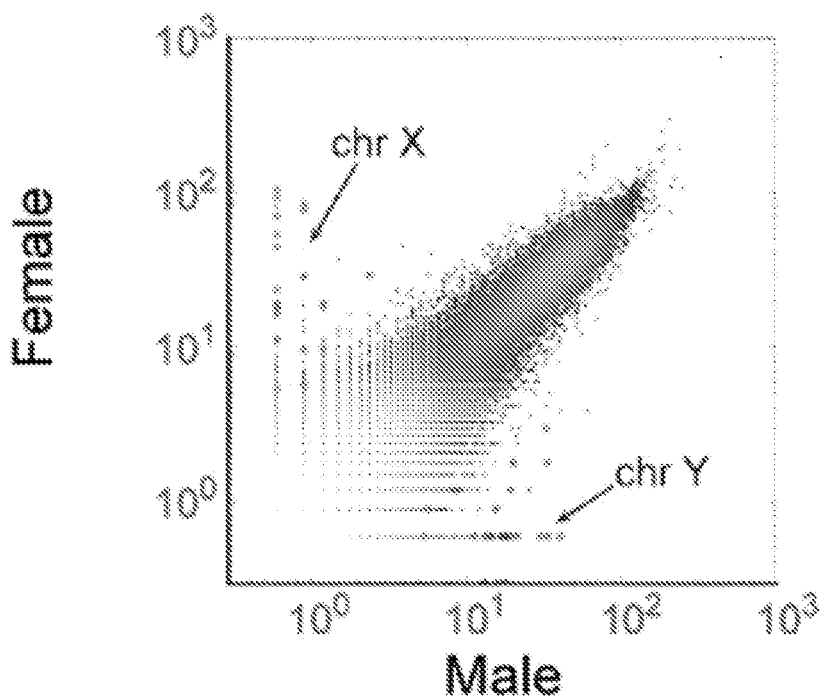
Figure 2C:
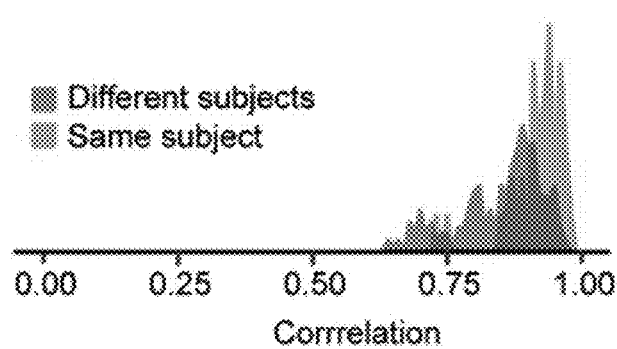
Figure 2C:
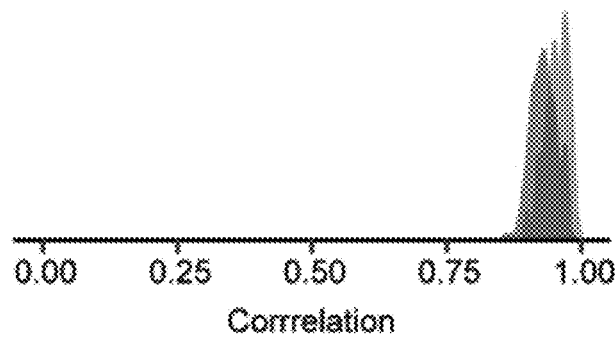

To assess the reproducibility of cfChIP, we performed technical and biological replicates from several subjects. Replicates from the same individual and between healthy individuals show correlations of 0.94-0.97 and 0.92-0.94, respectively (FIG. 2A-C). Peaks with low reproducibility between subjects are enriched for X or Y-chromosome specific genes and are indeed not apparent when comparing two individuals of the same sex (FIG. 2B).

Figure 2D:
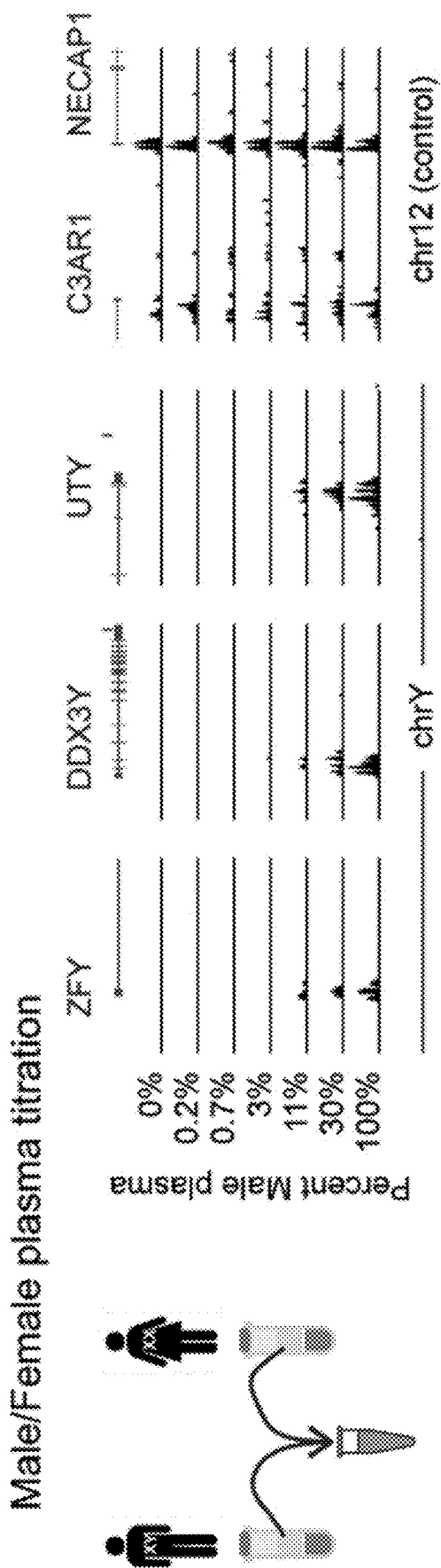
Figure 2E:
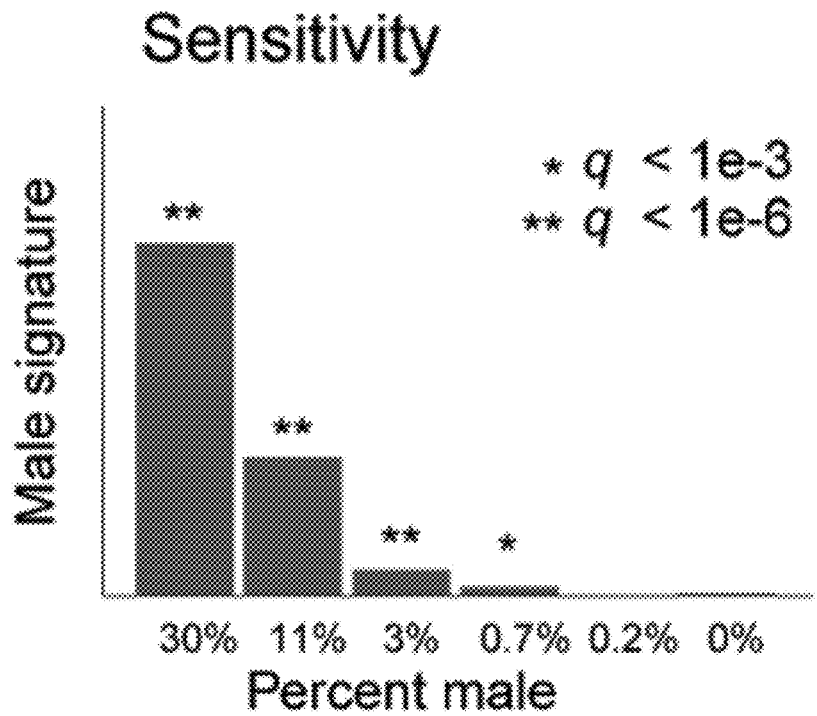
Figure 2F:
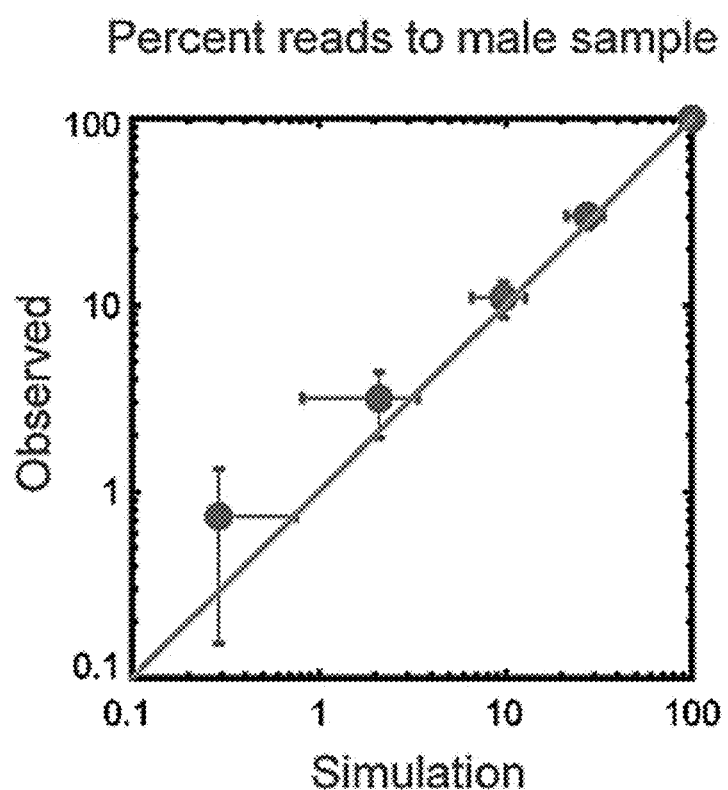
Figure 2G:
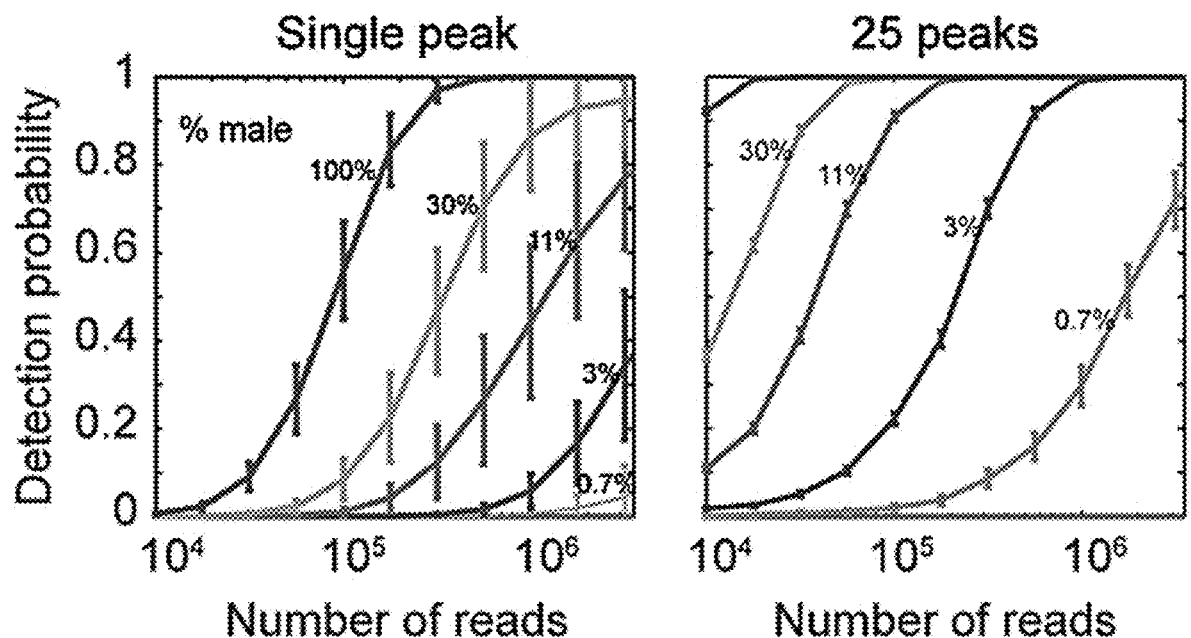
Figure 2H:
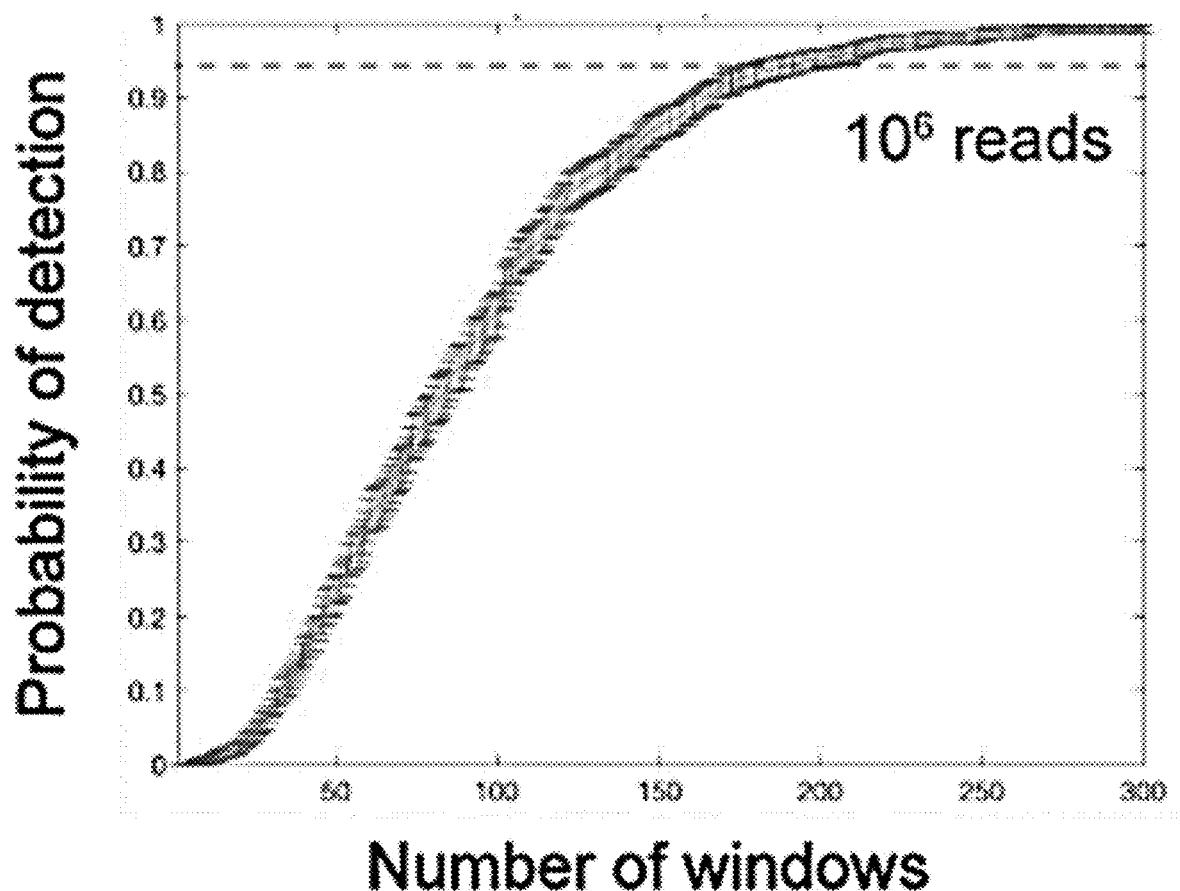
Figure 2H:
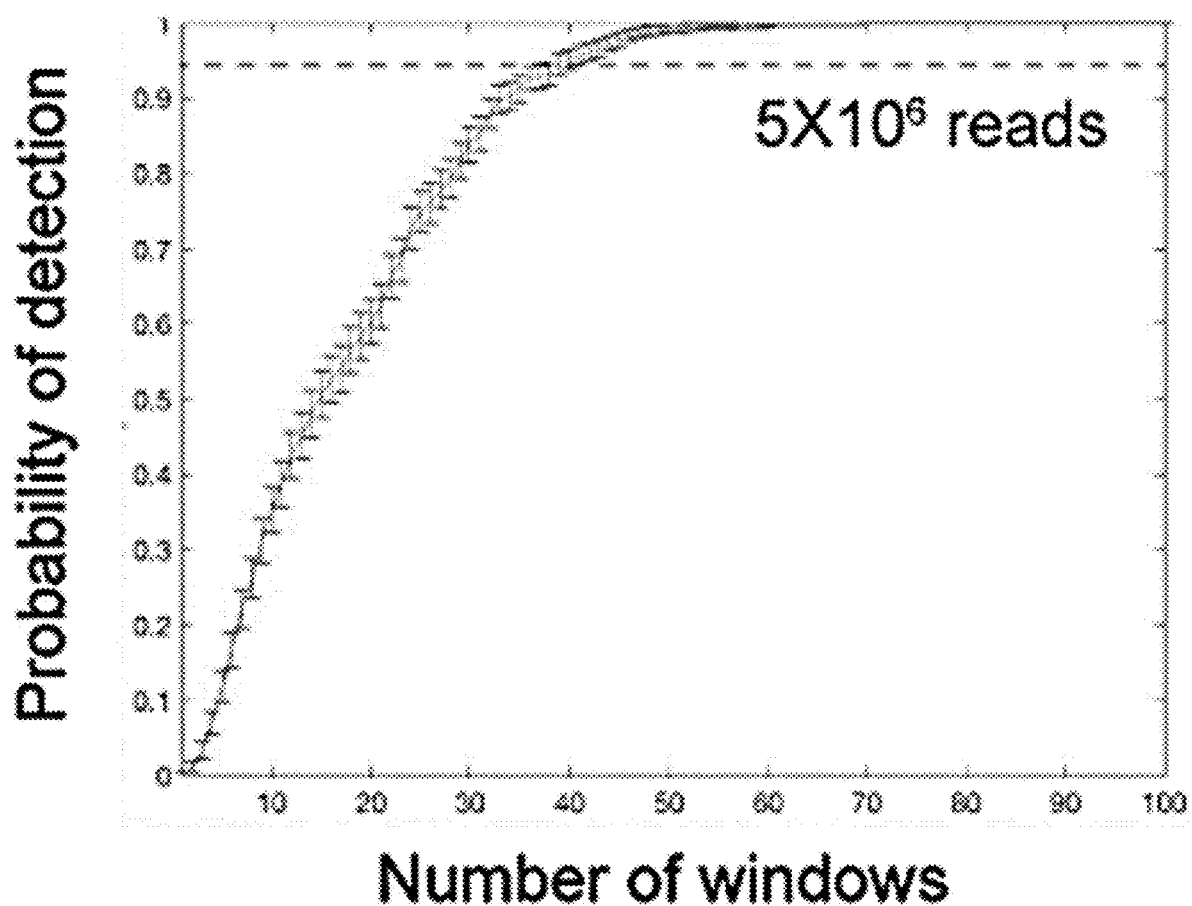
Figure 2I:
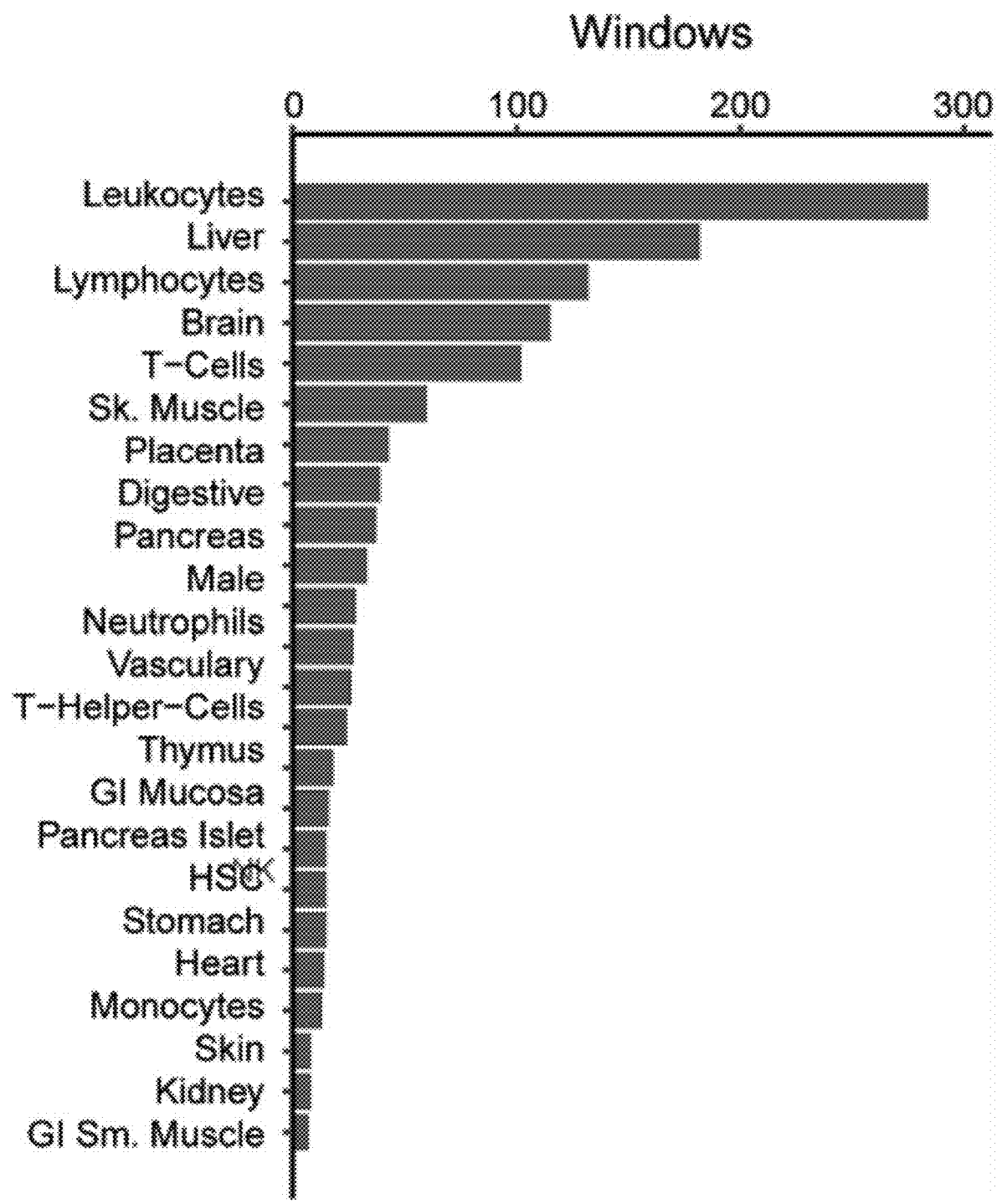

To test the detection limit of cfChIP we took advantage of sequences unique to the Y chromosome and titrated male-derived plasma into female-derived plasma. We evaluated the sensitivity for a particular genomic location as well as for a genomic signature—an ensemble of differentially represented genomic locations that can define a certain cell type or a certain transcriptional program. The H3K4me3 cfChIP signal at male-specific peaks on the Y chromosome (FIG. 2D) shows that we can reliably identify single male-specific peaks even when male plasma accounted for less than 10% of the total plasma (FIG. 2D). Moreover, the contribution at male specific peaks increases linearly with the fraction of male plasma mixed (FIG. 2E-F), demonstrating that cfChIP sensitivity is linearly related to the fraction and size of the signature locations and sequencing depth. Indeed, combining signal from 25 male-specific peaks improves the detection sensitivity to 1% (FIG. 2E, 2G). This is likely an underestimate since there is a single Y chromosome in a diploid genome. Extrapolating from our male spike-in experiments, we estimate that modest signature sizes of 45 to 200 peaks can detect cfDNA from cells that constitute 0.1% of the cfDNA pool with high probability (0.95 or higher) at low sequencing depths (FIG. 2H). Signatures of this size can be identified for specific cell types or transcriptional programs (FIG. 2I).

Figure 2J:
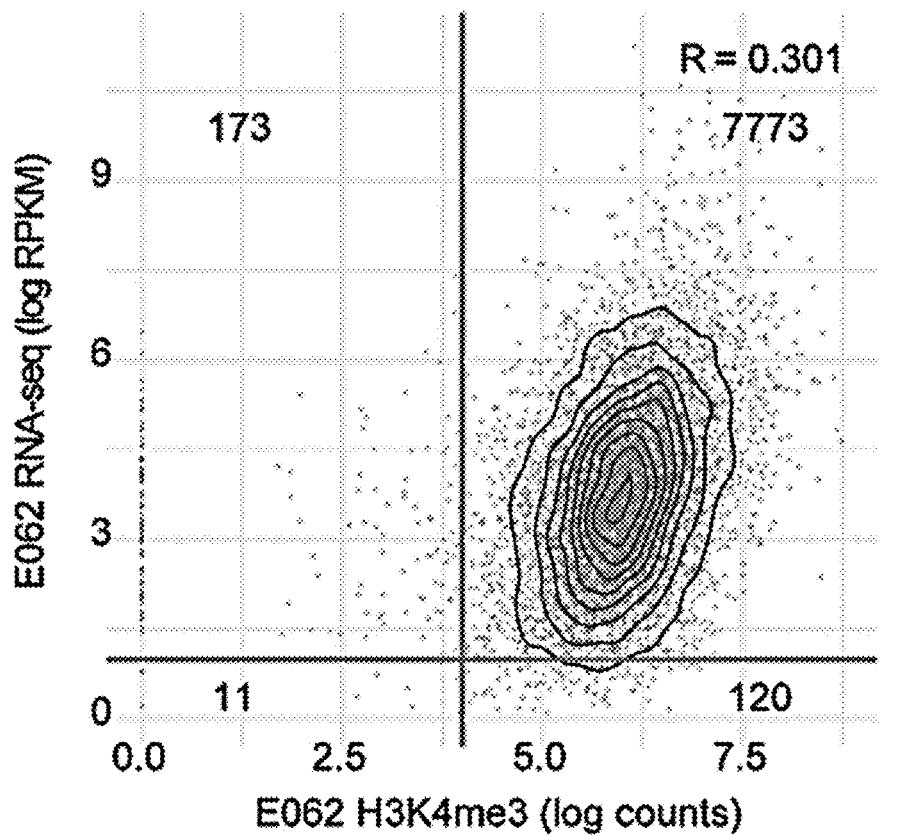
Figure 2J:
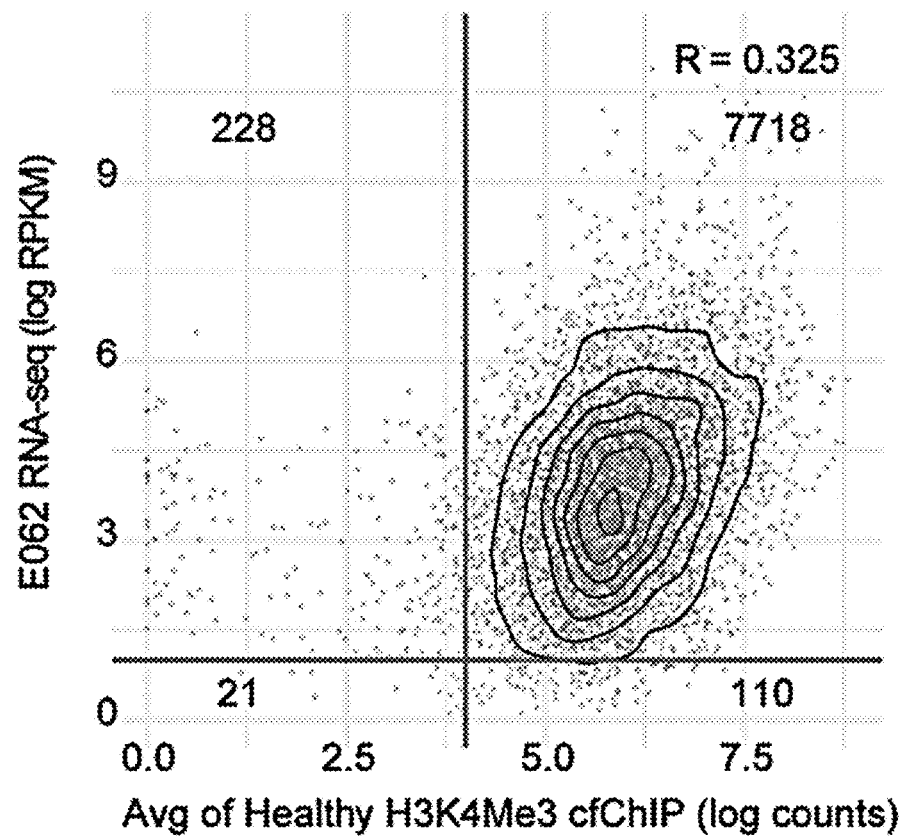
Figure 2K:
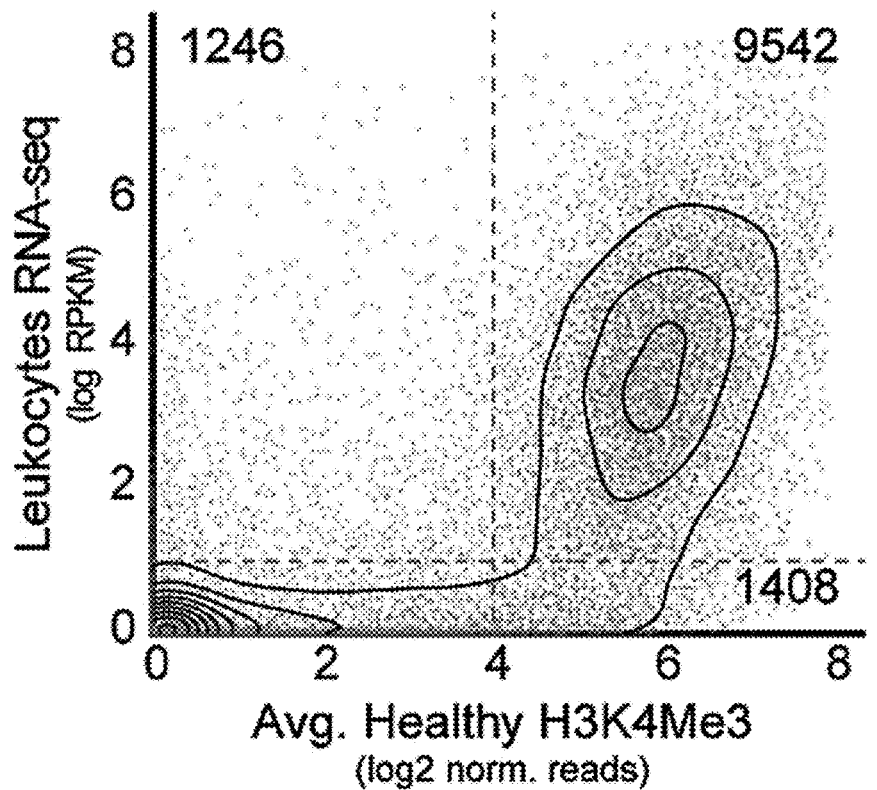

The level of H3K4me3 at promoters from tissue samples correlates with the level of transcription and is strongly predictive of gene expression levels. We find that the cfChIP H3K4me3 correlates with leukocytes RNA-seq at constitutive genes (based on Roadmap Epigenomics Consortium and GTEx Consortium 2015) and this correlation is similar to that of ChIP-seq from leukocytes (FIG. 2J). Similarly, we find high correlation with leukocyte expressed genes in agreement with their major contribution to the cfDNA pool in healthy individuals (FIG. 2K). These results strongly suggest that cfChIP of transcription-related histone modifications can provide insights into the gene expression patterns at the cfDNA's cells of origin.

Figure 2L:
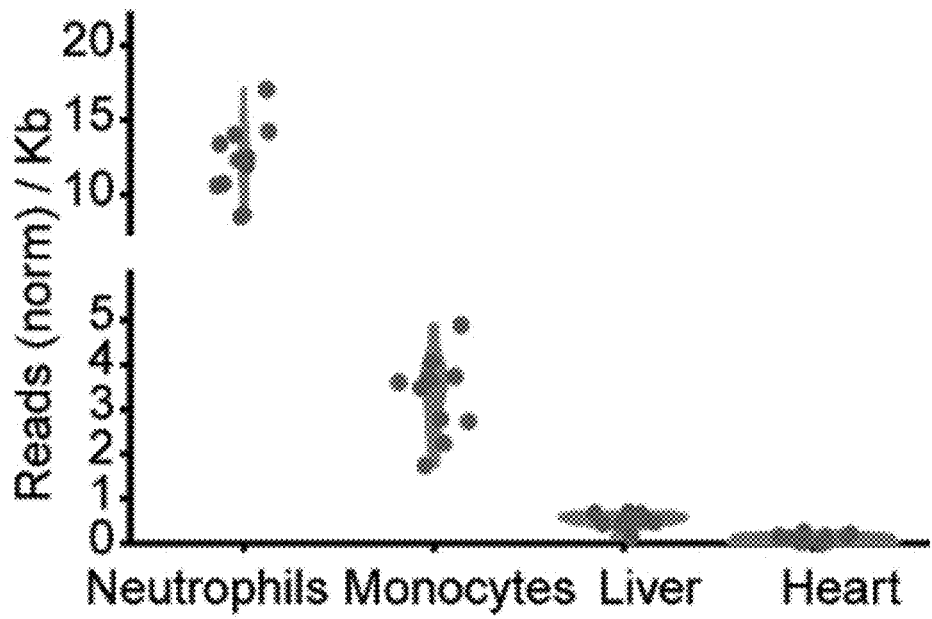
Figure 2M:
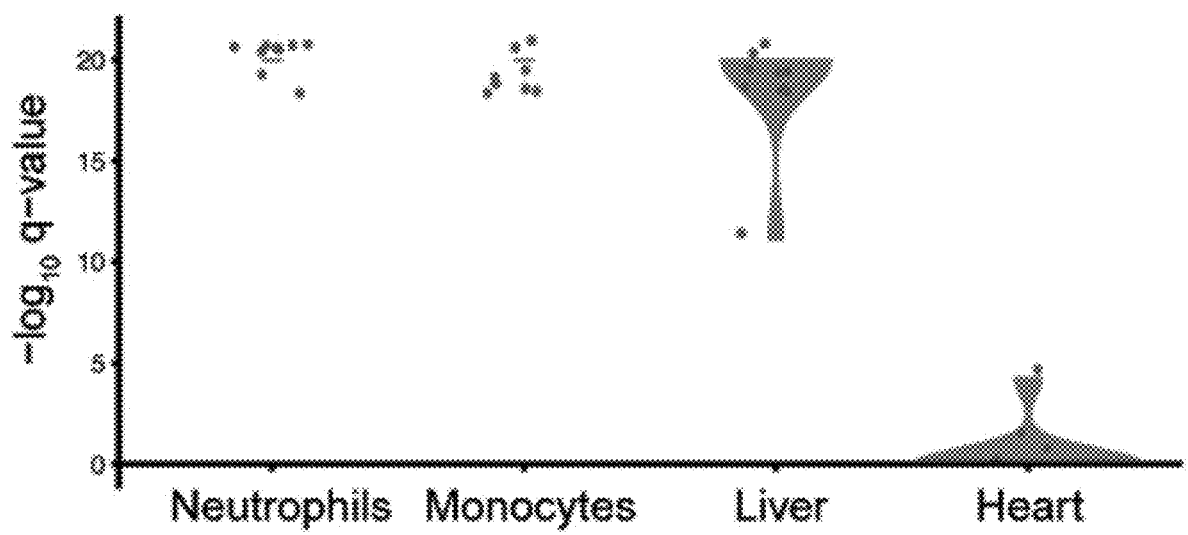

With these findings in mind, we set out to test the ability to detect tissue-specific signatures in samples from healthy subjects. A previous study on cfDNA CpG methylation estimated that ~55% of cfDNA emanates from leukocytes, and ~1% from the liver, with minimal or no contribution of cfDNA from the heart and brain. Using the Roadmap Epigenomics dataset of H3K4me3 ChIP-seq on multiple healthy tissues as a reference, we defined tissue-specific signatures in an unbiased manner (see Materials and Methods, Table 1). We then evaluated the normalized number of reads for each signature in each subject and the statistical significance of these counts (FIG. 2L-M; Materials and Methods). As expected, the presence of leukocytes can be detected when using a few specific peaks or even a single one. Using a larger signature, the presence of liver cfDNA is also clearly and significantly detected in contrast to brain and heart signatures that are absent in blood, as expected. These signals are specific with high statistical confidence ($q<10-20$, see Materials and Methods), and they demonstrate the ability of cfChIP to detect cf-nucleosomes from rare populations of cells.

Example 2 cfChIP Detects Pathology Related Cell Death

The ability of cfChIP to identify signatures of cells from remote tissues suggested the exciting possibility for this tool to detect cf-nucleosomes originating from disease-related pathologic cell death. To test this hypothesis, we collected samples from patients diagnosed with acute myocardial infarction (AMI), a process that results in extensive cardiomyocyte cell death. We collected samples from patients admitted to the emergency room, with samples obtained both prior to, immediately after, and ~12 hours following urgent percutaneous coronary intervention (PCI) to restore blood flow. We expect to observe cfChIP signal from myocardial cell death only in AMI patients but not in healthy subjects, particularly in samples following PCI.

Figure 3A:
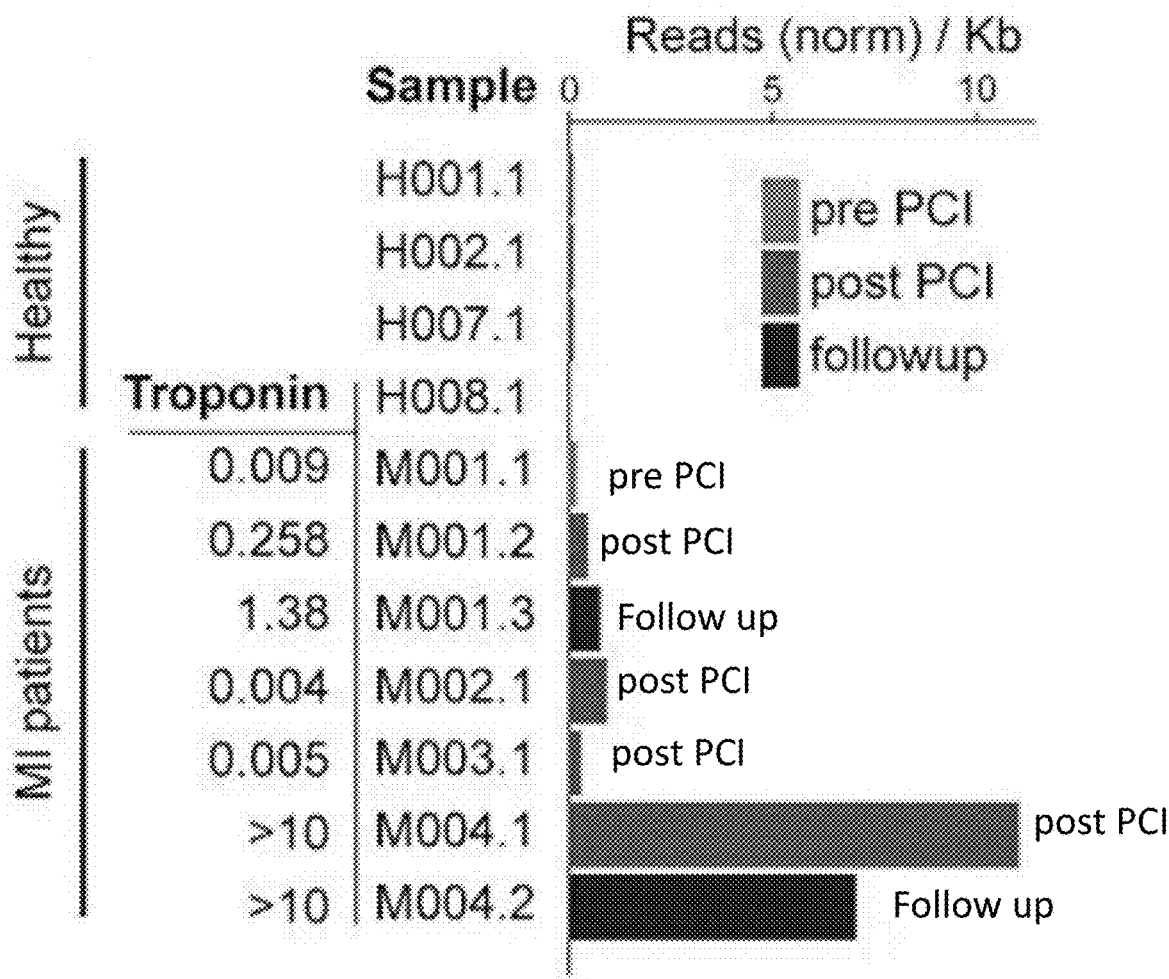
FIGS. 3A-J: (3A) A bar chart of H3K4me3 cfChIP-seq signal in heart-specific windows in four healthy subjects and samples from myocardial infarction (MI) patients. Inset, measured troponin levels at the time the blood samples were drawn. (3B) Examples of browser views of signals at heart-specific windows. Each browser section displays 20 kb region around windows (marked with gray background). Tracks are all normalized and shown to the same scale. Top tracks show cfChIP samples and bottom ChIP-seq of tissue samples (bottom) from Roadmap Epigenomics Atlas. (3C) Dot plot comparisons to external indications of cardiomyocyte death. x-axis: measured Troponin levels (top panel) cardiomyocyte fraction as measured using DNA methylation markers (bottom panel). y-axis: strength of Heart-specific signature (relative to healthy subjects). (3D) Heatmap showing the level (Brown scale), and significance (Blue scale) of selected cell-type signatures in healthy subjects and myocardial infarction patients. Each cell in the map is divided in half, the top left half represents statistical significance (FDR corrected q-value) and the bottom half density of reads in the signature (normalized reads per kb). (3E) Heatmap of the tissue signatures for all samples; and extension of 3D and 3I. (3F) Examples of browser view of Liver-specific windows that are part of evaluated signature (see FIG. 3B). (3G) Line graph of the change in signature strength in a myocardial infarction patient before/after PCI. Signatures strength are normalized to healthy subjects. The variability among healthy subjects is shown on the left. We can see initially high level of liver cells and elevated levels of heart cells. Following PCI liver cell decline and heart cells increase. (3H) Dot plot comparisons to external indications of cancer patients and liver signature. Presented as in FIG. 3C. (3I) Heatmap showing cell-type signatures in cancer patients (see FIGS. 3D and 3E). (3J) Combined line graph and bar graph of changes in liver signature (bars) and ALT levels (liver damage biomarker, black line) from blood samples of a patient undergoing hepatectomy.
Figure 3B:
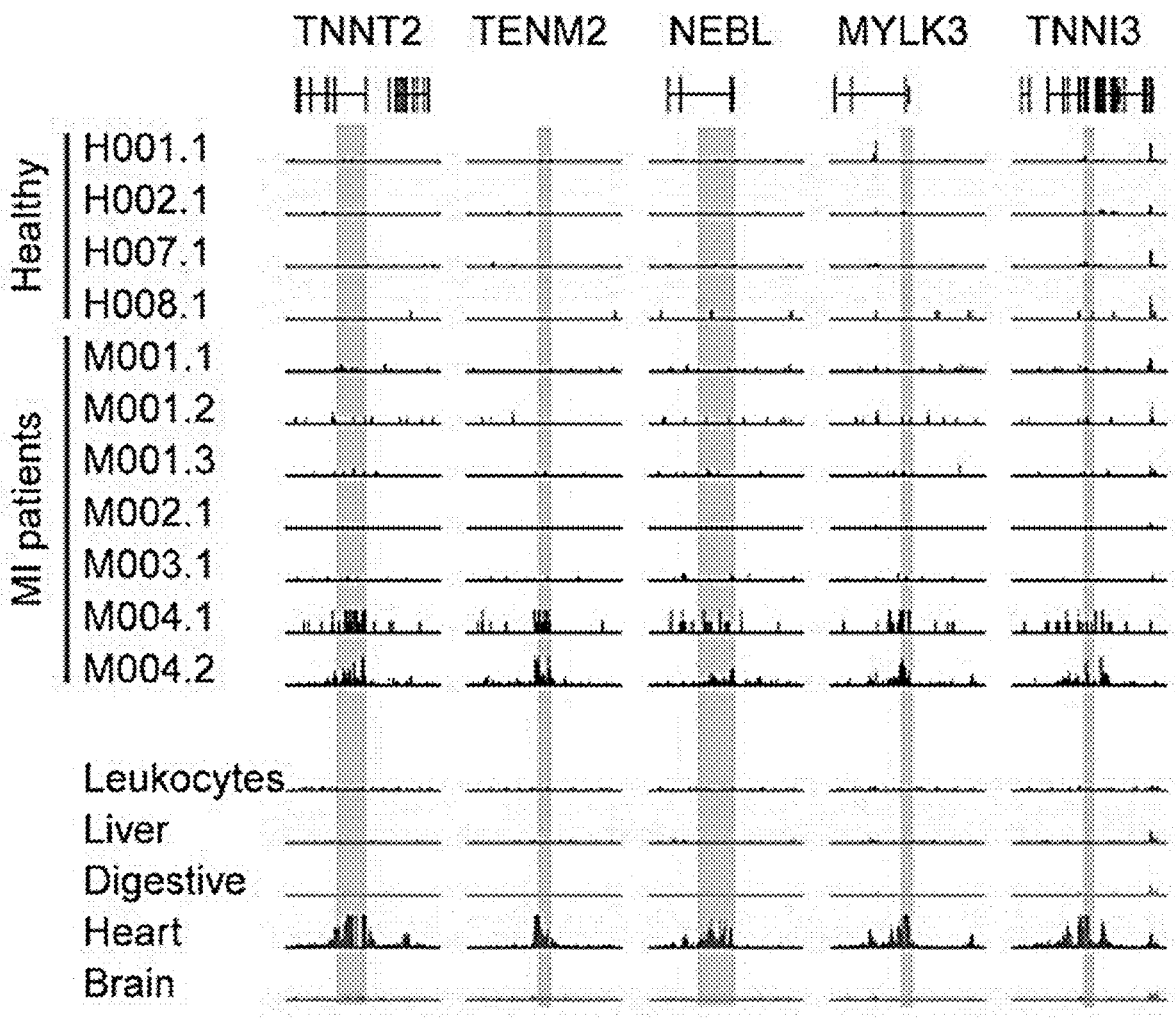
Figure 3C:
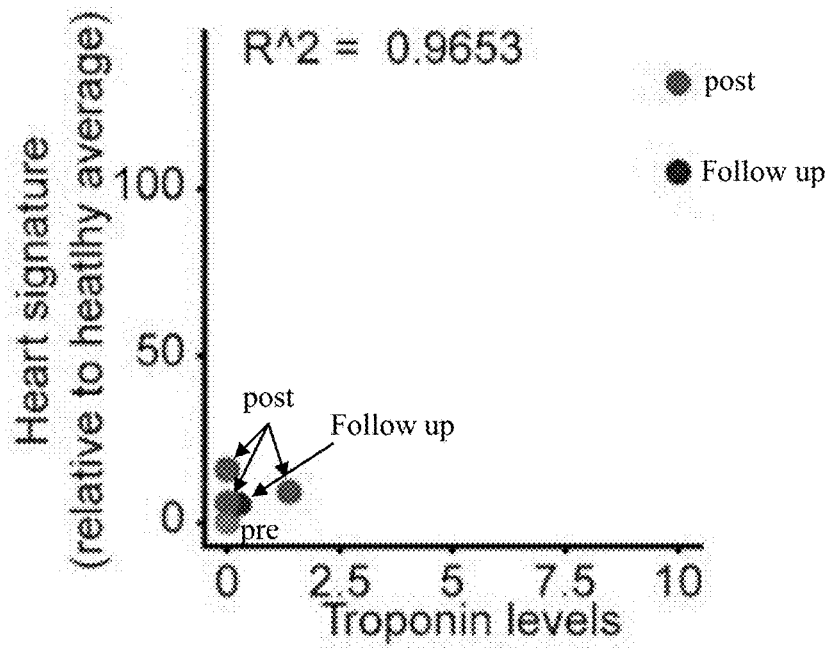
Figure 3C:
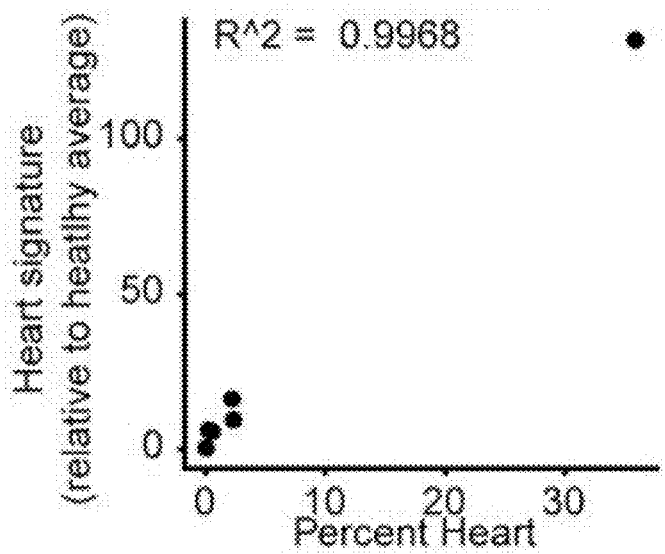

As predicted, heart-specific H3K4me3 peaks were strongly and significantly detected in post-PCI patient samples, but not in samples from healthy individuals or from pre-PCI patients (FIG. 3A). The heart signal includes clear peaks in promoters of heart-specific genes. For example, TNNT2 and TNNI3 that encode for the heart-specific Troponin T2 and I3 are clearly active and observed only in these samples. These two genes encode canonical protein markers for myocardial damage (FIG. 3B). Indeed, we see good correlation between the strength of the cfChIP heart signature, the levels of troponin measured in the blood, and the estimate of heart cfDNA based on heart-specific differentially methylated CpGs (FIG. 3C).

Figure 3D:
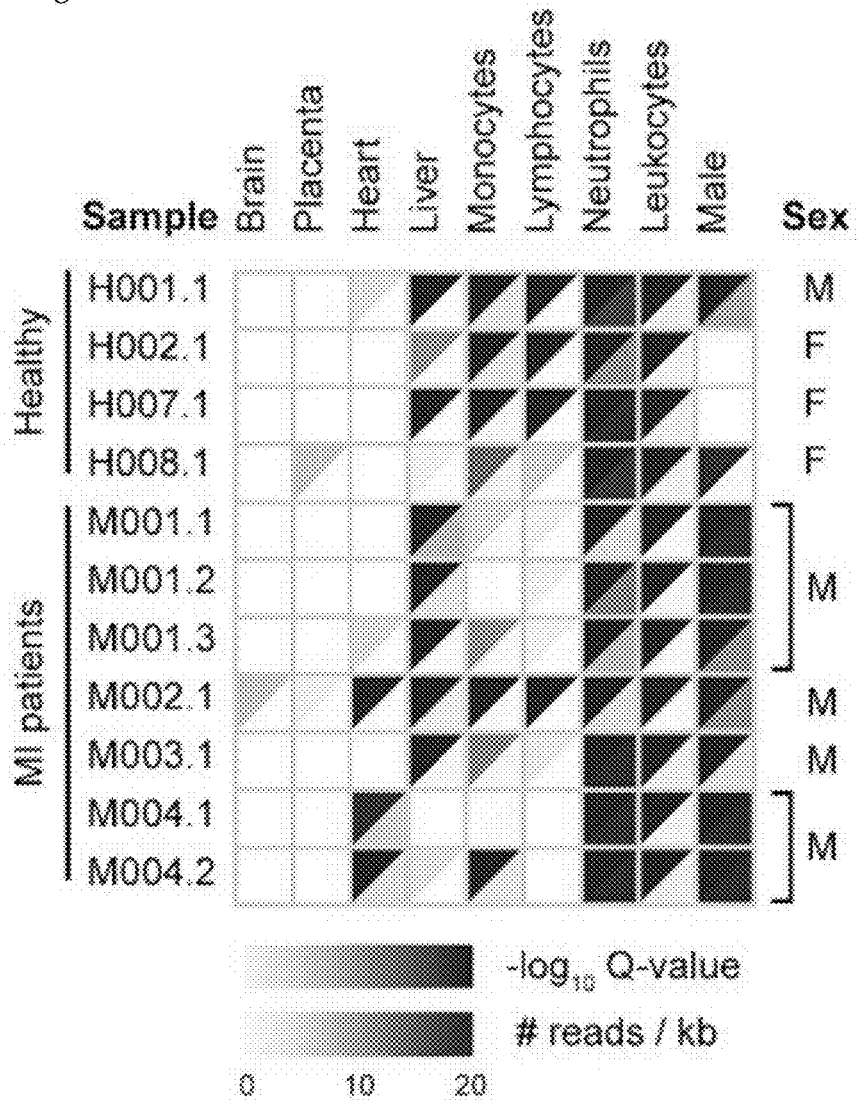
Figure 3E:
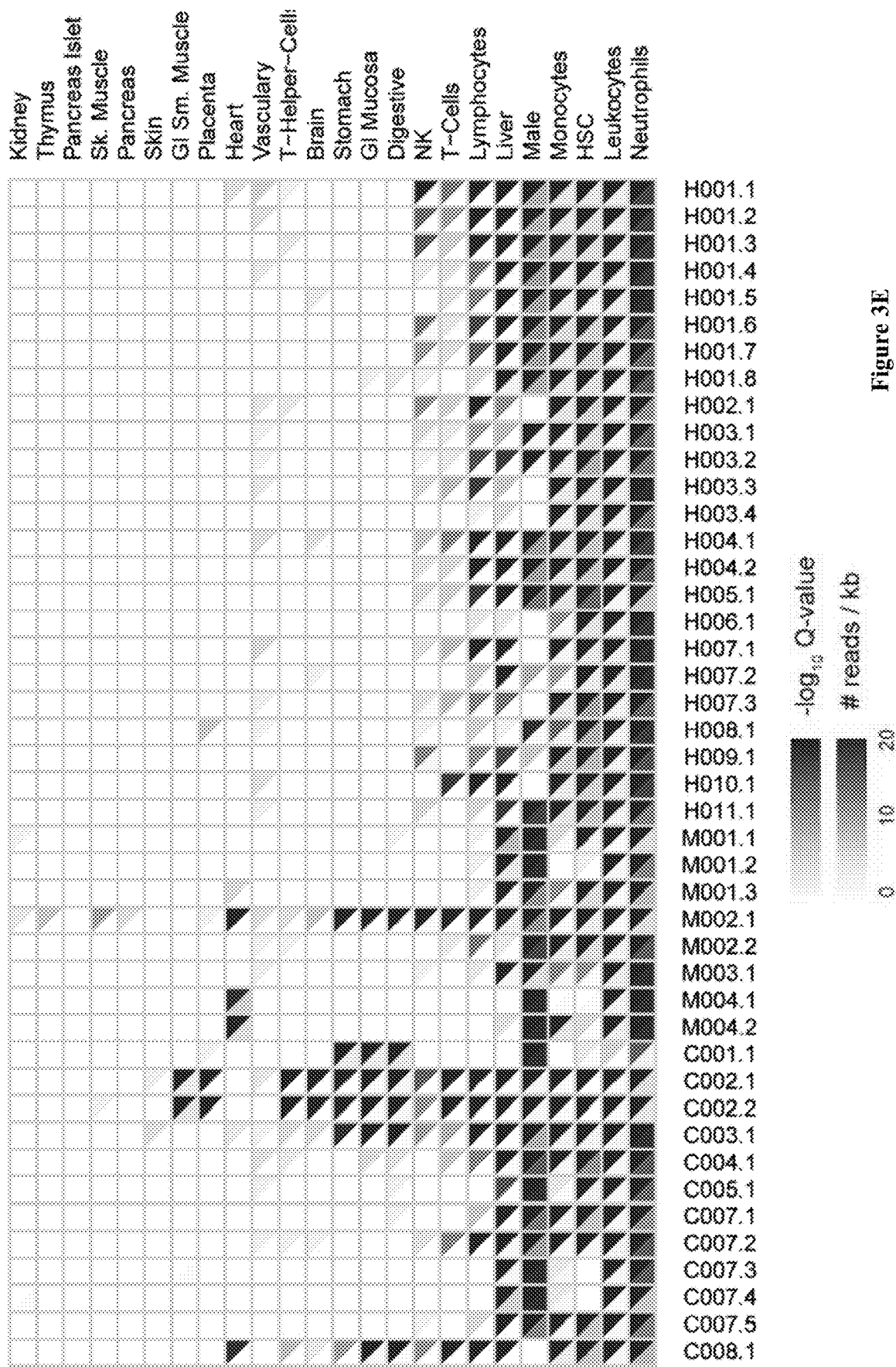

For an unbiased view of our ability to describe tissue-of-origin, we evaluated a panel of cell-type specific signatures across cfChIP samples (FIG. 3D-E). This analysis shows that in all samples we can detect signatures of a range of cell types from the blood (e.g., monocytes and neutrophils), and organs (e.g., liver). One of our subjects (H008) was four months pregnant carrying a male fetus and her sample exhibited a significant placenta signature. Indeed, we were able to detect low but significant Y-chromosome signal in her plasma as well (FIG. 3D).

Figure 3F:
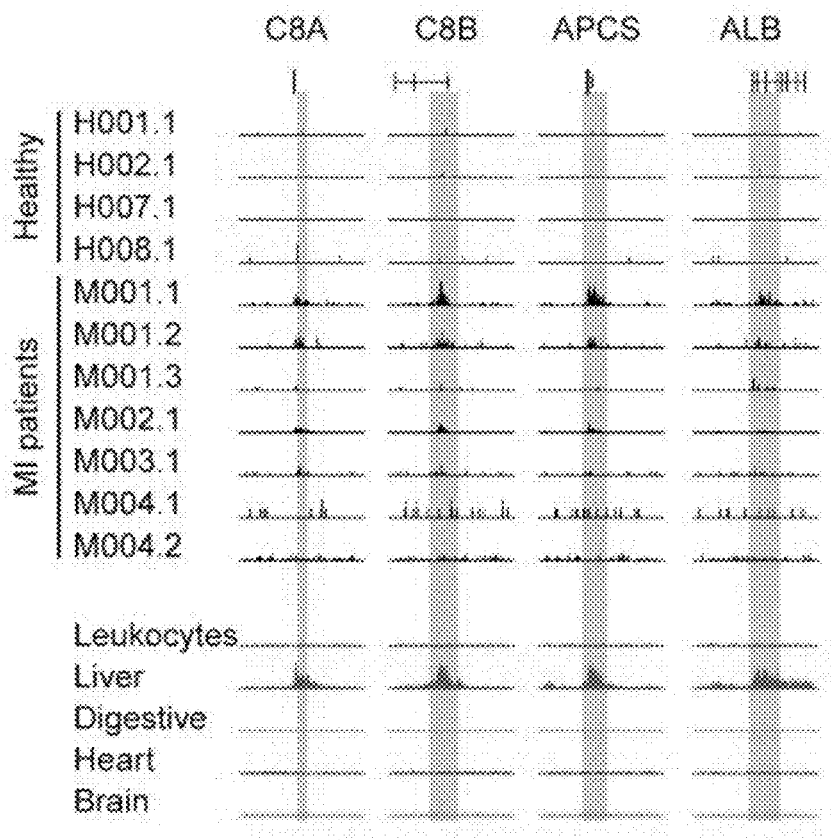
Figure 3G:
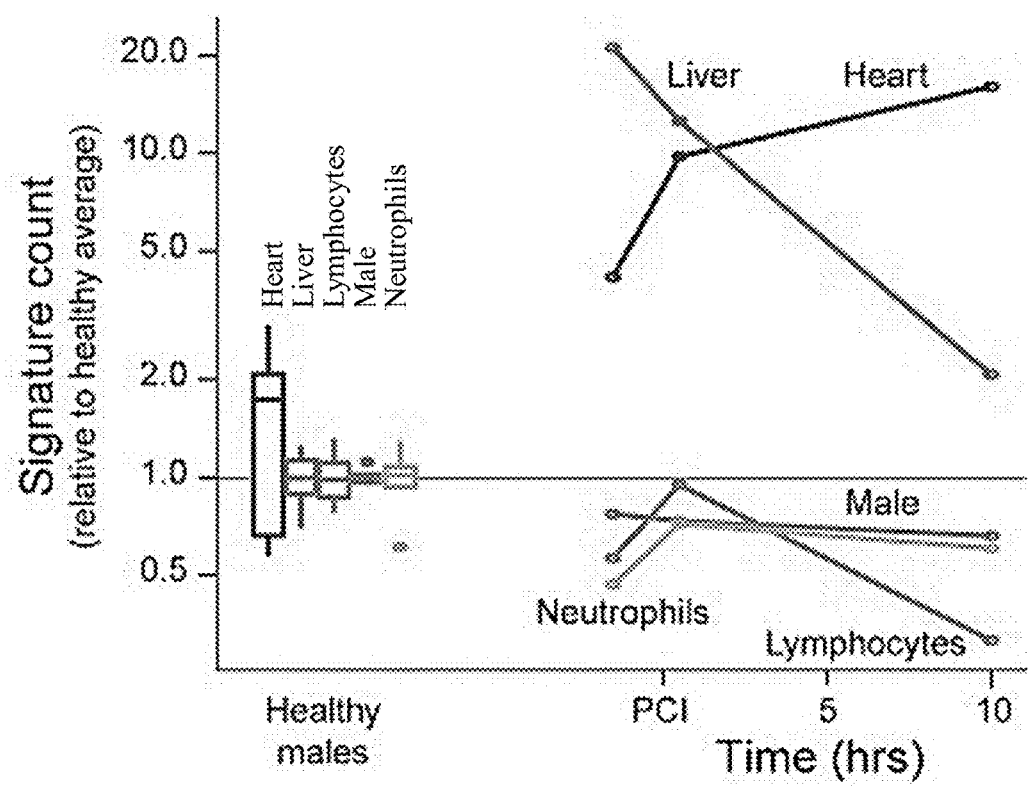
Figure 3H:
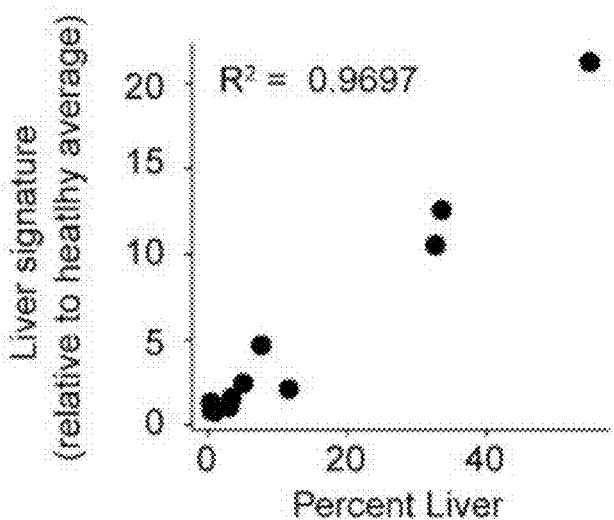

In AMI patient samples the picture is more complex. As discussed above, AMI patients sampled several hours post PCI show a clear cardiomyocyte signature (FIG. 3A, 3D). In addition, however, in AMI patients both before and shortly after PCI, we observed a significant increase in hepatocyte signature. This signature includes clear signal at liver-specific genes, such as Albumin and complement genes (FIG. 3F). This unanticipated observation is presumably a result of the well-known phenomenon of liver injury in AMI patients secondary to low organ perfusion and liver hypoxia. One of these AMI patients (M002) also exhibited increased levels of active chromatin from erythroblast-associated genes, including the hemoglobin locus (see below), and the erythropoietin locus (EPO), most likely from hepatocytes due to liver response to hypoxia. Together this data suggests a systemic response to oxygen shortage. The liver and erythroblasts signals were likely due to transient damage caused by reduced systemic perfusion associated with AMI. Indeed, a follow up cfChIP-seq on this patient 11 months later appeared normal. In a second AMI patient (M001), we observe a gradual decrease in liver signature within hours following PCI, suggesting a prompt relief of the liver oxygen shortage (FIG. 3G). To confirm our cfChIP observations we analyzed the cfDNA methylation status for liver-specific genes for which the DNA methylation status is indicative of liver cell death. Indeed, we observe good agreement between liver cfChIP signature levels and liver cfDNA estimates ($R2=0.97$, FIG. 3H).

Figure 3I:
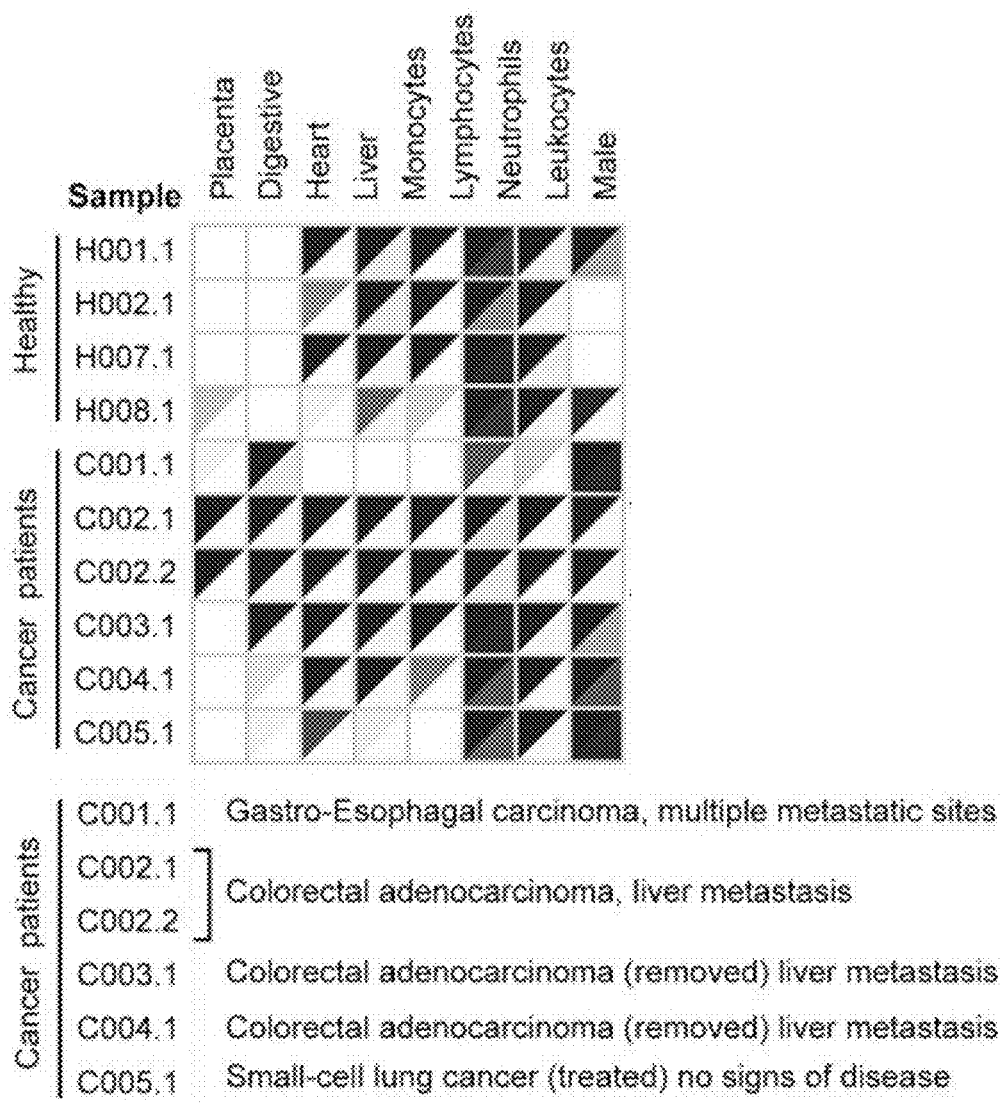

An important potential application of cfChIP is identification of cancer tissue of origin. Advanced stage cancer is often accompanied by higher cfDNA content in the plasma, much of it from tumor cells (ctDNA). We collected plasma samples from patients with gastrointestinal (GI) tract tumors and analyzed their cf-nucleosomes tissue of origin (FIG. 3I, 3E). In general, plasma from cancer patients contains signal from tissues that are not observed in healthy subjects. Most evidently, we observe signal originating from gastrointestinal (GI) tissue and from GI smooth muscle, which is in agreement with the primary locations of the tumors. A weaker but significant GI signature was evident even when the primary tumor was removed by surgery and only residual metastatic disease was evident (patients C004 and C005). We also observe low but significant signal from additional tissues, such as the brain signal observed in C001. These signals can be due to treatment (C001 underwent brain radiotherapy) or due to collateral damage to normal (non-malignant) tissue.

Figure 3J:
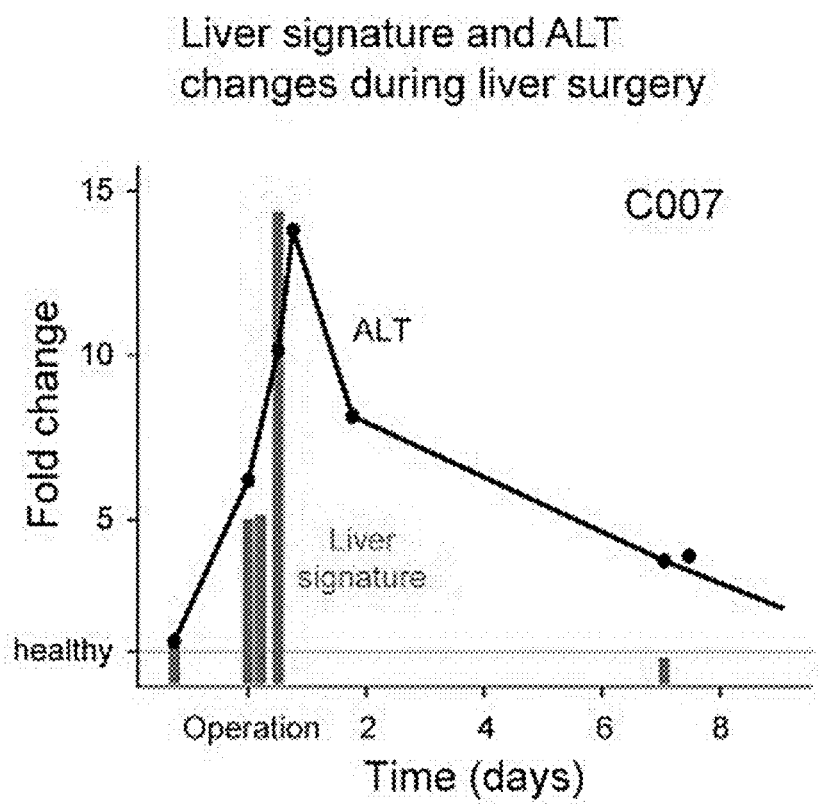

We also examined a patient with localized hepatocellular carcinoma (HCC) that underwent partial hepatectomy (PHx). We collected blood samples before, during, and at different time points post operation, and analyzed both circulating cf-nucleosomes using cfChIP along with measurements of the classic marker for liver damage, the enzyme ALT (FIG. 3J). Surprisingly, ALT levels were normal prior to operation despite the fact that the patient had active cirrhosis in addition to the HCC. The levels of ALT increased during the first day following PHx and gradually decreased during the following days. cfChIP analysis of liver signature strongly agrees with the ALT test, suggesting again that cfChIP detects dynamic processes at remote tissues. One difference is that the cfChIP liver signature dropped back to normal levels about 2 days earlier than ALT. This difference is likely due to the shorter half-life of cfDNA (<2 hours) compared to ALT (~47 hours) in the circulation.

Together, these results demonstrate that there are pronounced differences in cfChIP signal of healthy subjects compared to patients with ongoing pathological processes.

These differences correspond to the tissue where these processes take place, such as heart, liver, and gastrointestinal tissue.

Example 3

Plasma Chromatin Reflects Gene Activity Patterns

A major challenge for cfDNA analysis is the inference of gene expression in the tissue of origin. The major approach proposed to this problem so far relied on under-representation of specific promoter elements in cfDNA as an indication of gene expression; however, this approach requires extremely deep sequencing and is limited to situations where cfDNA from the tissue of interest comprises a majority population in blood. We tested to what extent cfChIP can report on non-constitutive gene expression programs that took place in the cells of origin.

Figure 4A:
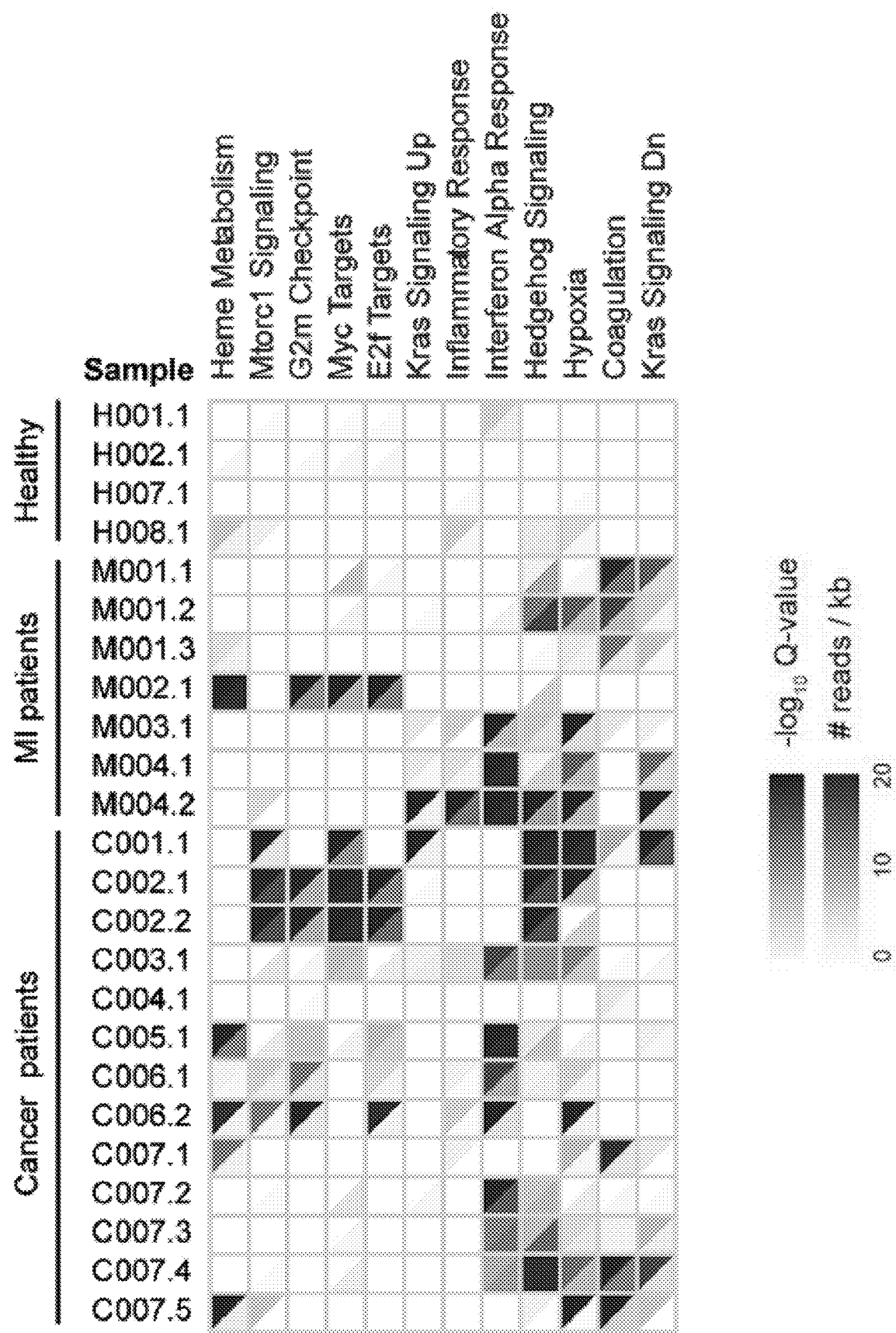
FIGS. 4A-H: (4A) Heatmap (as in FIG. 3D) showing processes Hallmark genes that are over-represented in subjects (compared to healthy baseline). See FIG. 4C for full table with all hallmarks and subjects. (4B) Examples of browser view of genes with higher than expected signal in these expression signatures (see FIG. 3B). (4C) Heatmap of hallmarks signatures for all samples and signatures. Extends FIG. 4A. (4D) Browser view of H3K4me3 cfChIP and tissue ChIP signals at promoters of selected glycolytic genes (see FIG. 4B). (4E) Exemplary scatter plots of method for defining genes with elevated signal at a specific sample. Scatter plot of the normalized H3K4me3 counts at promoters of each gene. x-axis: average of reference healthy samples. y-axis: counts in the sample in question. Color dots represent genes in cancer signatures. Larger dots are significantly over-represented. (4F) Heatmap showing enrichment of tumor-specific signatures in the over-expressed genes. Each cell is divided in half, the top left half represents statistical significance (FDR corrected q-value) and the bottom half overlap with the signature (% number of genes in signature). See FIG. 4G for full table with all tumors and subjects. (4G) Heatmap of cancer signatures for all samples. (4H) Examples of browser view of cancer-associated genes and their signal in different samples.
Figure 4B:
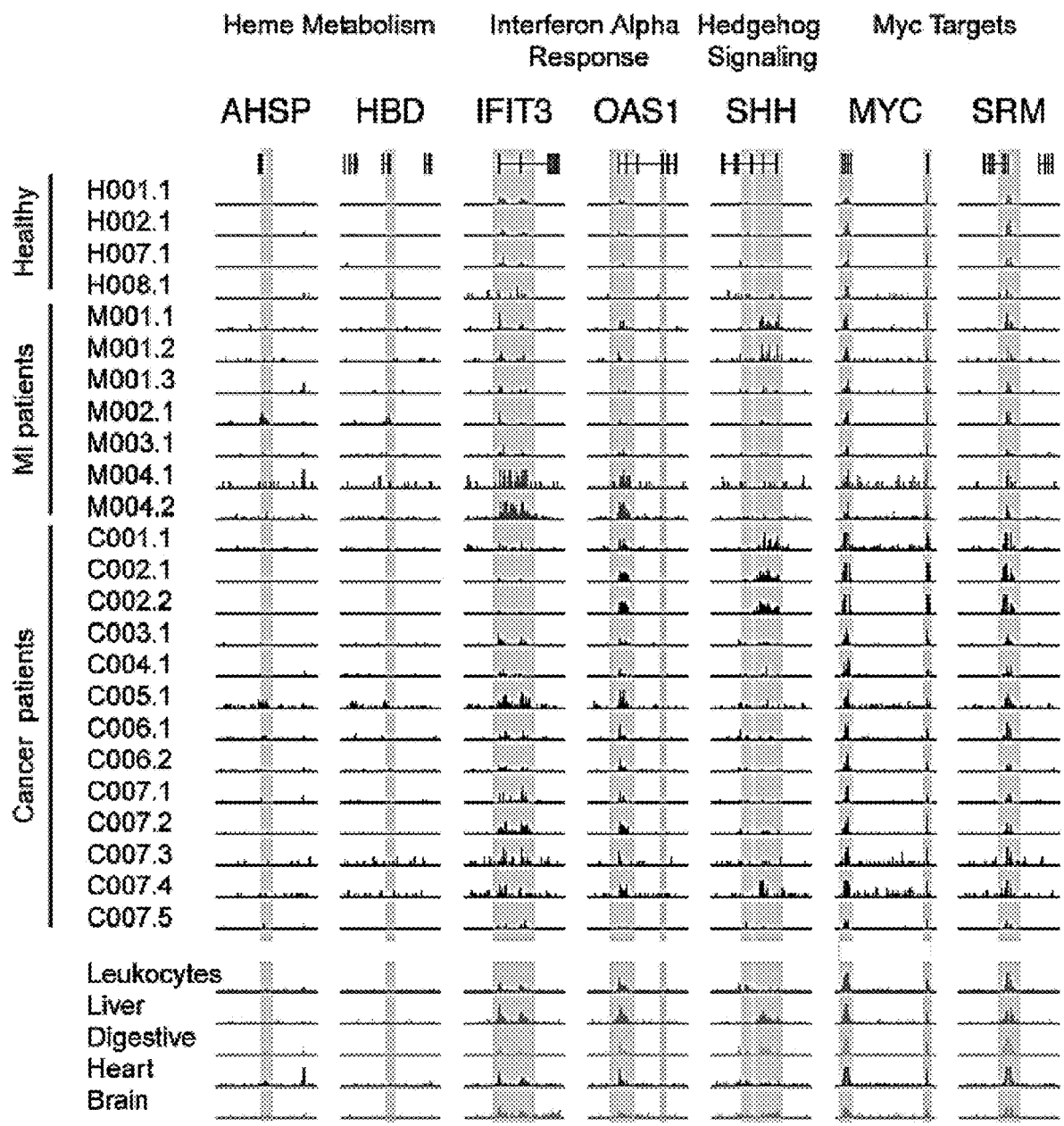
Figure 4C:
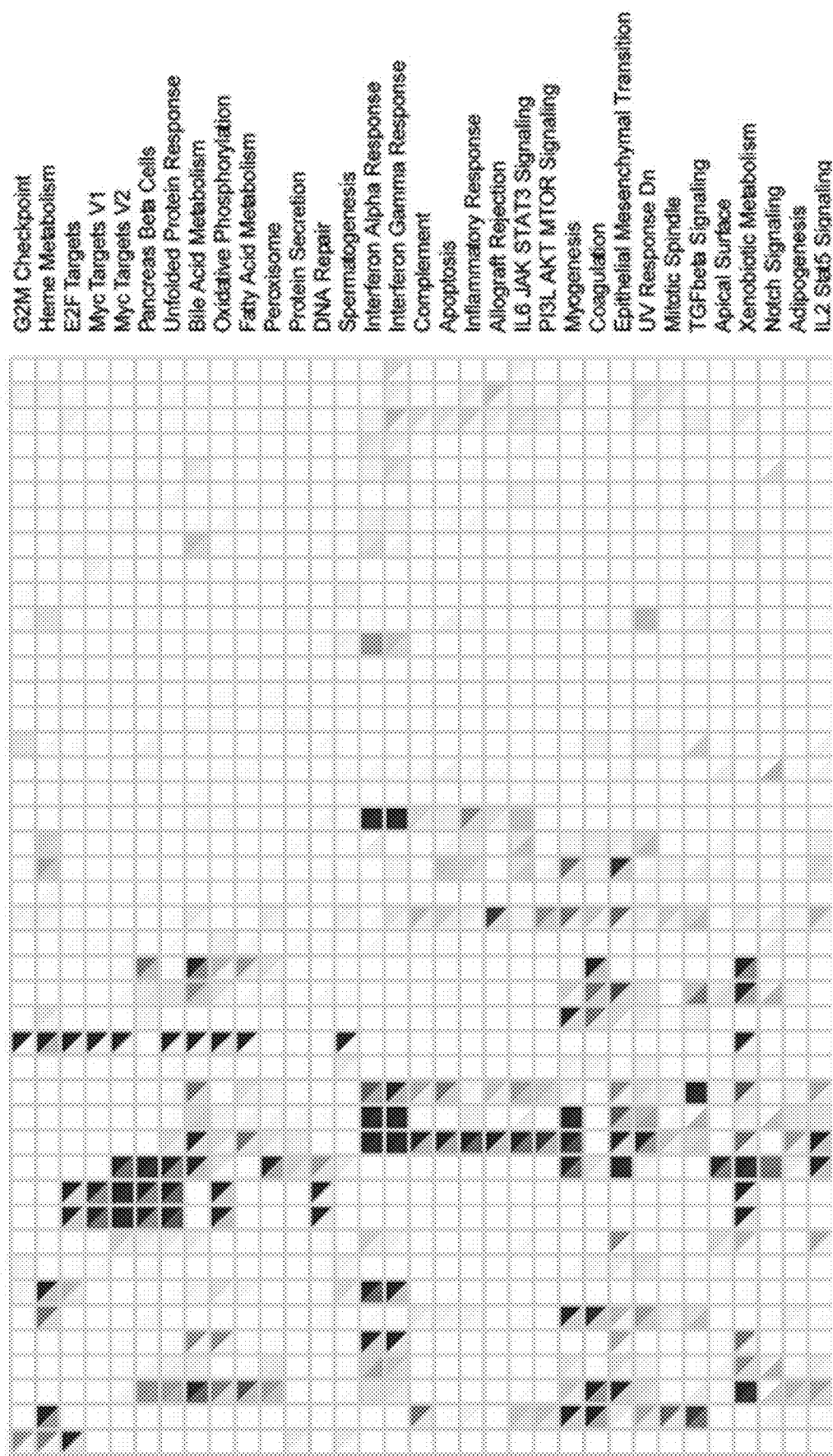
Figure 4C:
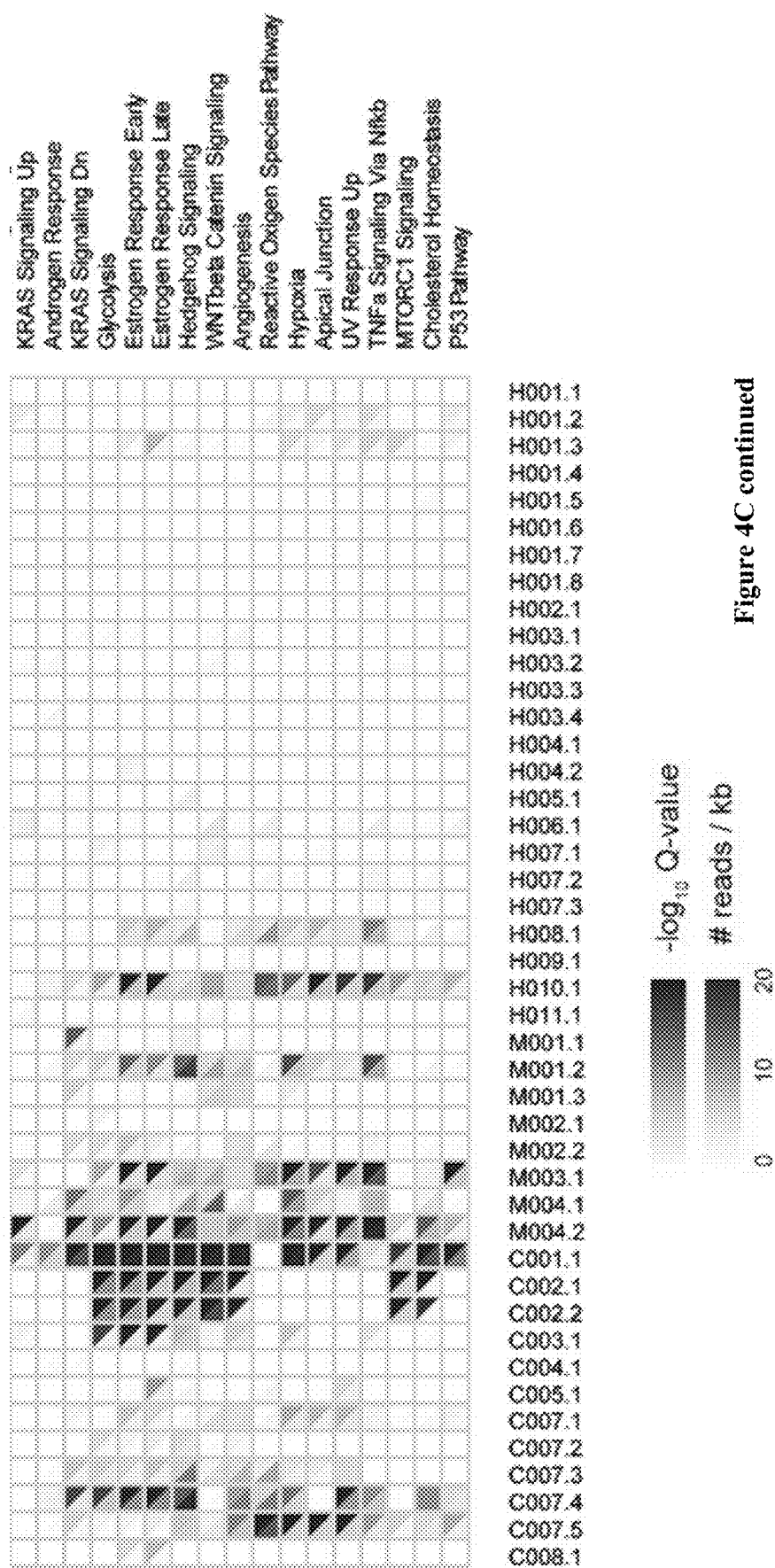

H3K4me3 is closely associated with transcriptional activity and dynamically changes in response to changes in transcriptional programs, raising the exciting possibility that cfChIP might be able to detect more dynamic transcriptional programs beyond the information on tissue of origin. To test this hypothesis, we compared the H3K4me3 cfChIP signal from patients with AMI or cancer to a collection of hallmark gene expression signatures representing different cellular processes and responses (FIG. 4A-C).

This analysis uncovered multiple signatures that have higher than expected signal—that is, the amount of cf-nucleosomes captured for the signature is significantly higher than what we see in healthy subjects. For example, we see a strong signature of Heme Metabolism in M002 and C005, patients who suffered from hypoxia and bacteremia, respectively. The blood count of C005 indeed shows high red cell distribution width (RDW) and low red blood cell count (RBC) and hemoglobin (HGB) indicating high production of red blood cells due to anemia. This signal could be from enhanced cell death of erythrocytes progenitors or closely related cells, or due to nuclear loss in erythroblasts undergoing maturation into erythrocytes. Thus, this signature is indicative of a specific hematopoietic cellular differentiation process.

Figure 4D:
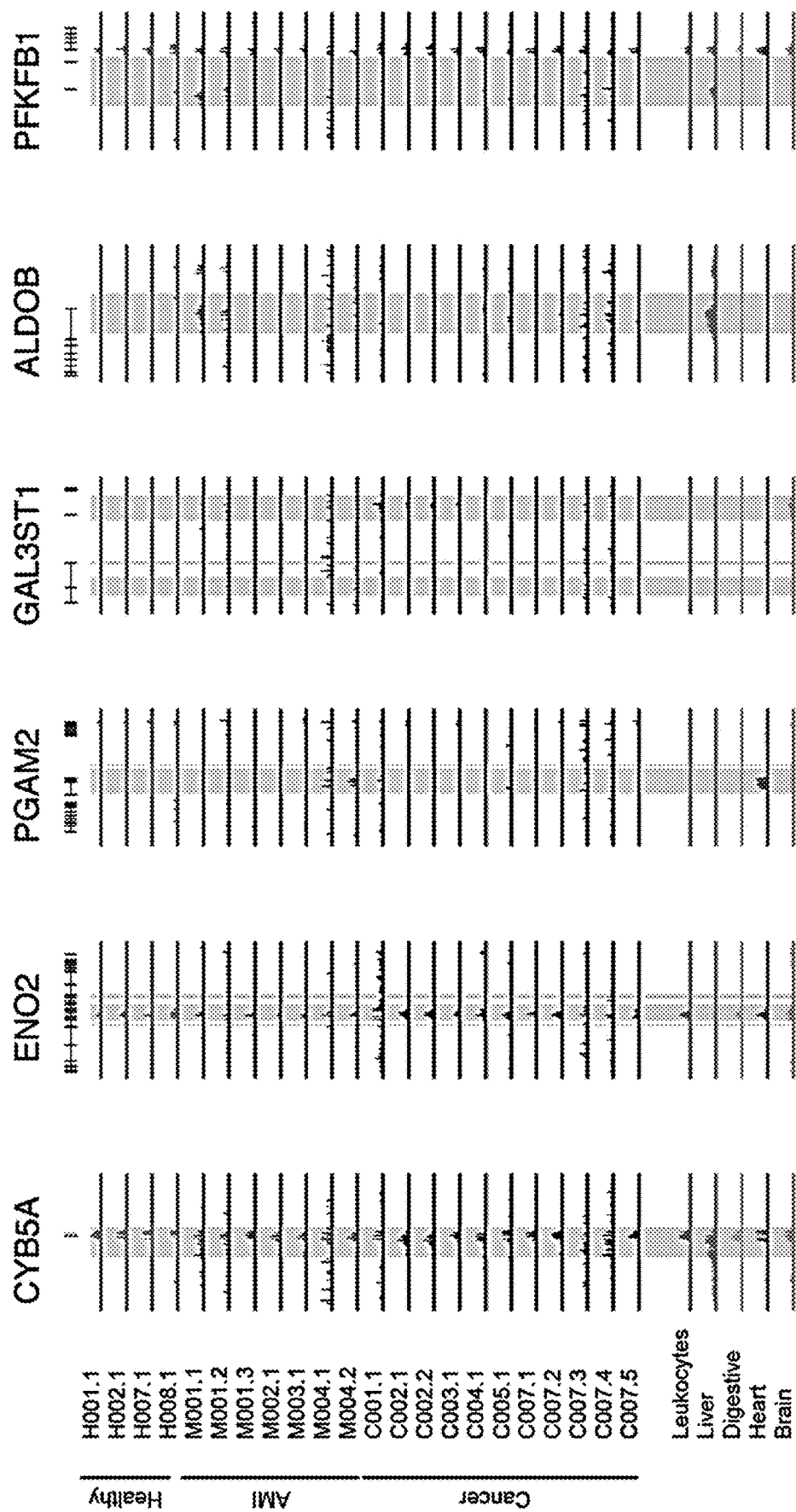

Other signatures, such as glycolysis or interferon-alpha response reflect processes that can take place in multiple cell types. We observe higher glycolysis signatures in cancer patients, in agreement with the metabolic reprogramming, known as the Warburg effect, that is considered a hallmark of advanced cancers (FIG. 4D). We also see a clear increase in glycolysis signature in M002, who suffers from extensive liver damage. Interestingly, in M002, we also see an increased signal of several liver-specific glycolysis genes such as ALDOB and PFKFB1 while in cancer patients the enhanced glycolysis signature does not include signal from these genes. These results suggest that cfChIP can detect cell-specific transcriptional programs with relevance to an underlying pathophysiological state. As expected, in plasma from cancer patients we also observe increases in several proliferation associated signatures (Kras, Myc targets, E2F targets, G2M checkpoint), and the mTORC1 pathway that coordinates metabolism and cell growth. Interestingly, parts of these signatures are also observed in AMI patients that experience liver damage and may reflect liver recovery from ischemic damage following PCI.

Another example of detectable transcriptional programs is Interferon-alpha response that is normally induced due to the presence of pathogens such as viruses and bacteria. We observe dramatic increase in interferon signature in M004 and C005. In the latter this is likely due to severe bacteremia for which he was hospitalized. M004, whose samples show high interferon and inflammation signatures, seems to have experienced more severe heart damage as compared to other AMI patients in terms of troponin levels and cfChIP heart markers (FIG. 3A, 3C). This could be due to induction of IRF3/interferon I response in M004 which was recently shown to promote a fatal response to AMI.

Together, these observations demonstrate that cf-nucleosomes not only report on death of specific cell types but can also reflect detailed changes in gene expression programs in a broad range of cell types.

Plasma Chromatin Allows Dissection of Patient-Specific Molecular Phenotypes

Figure 4E:
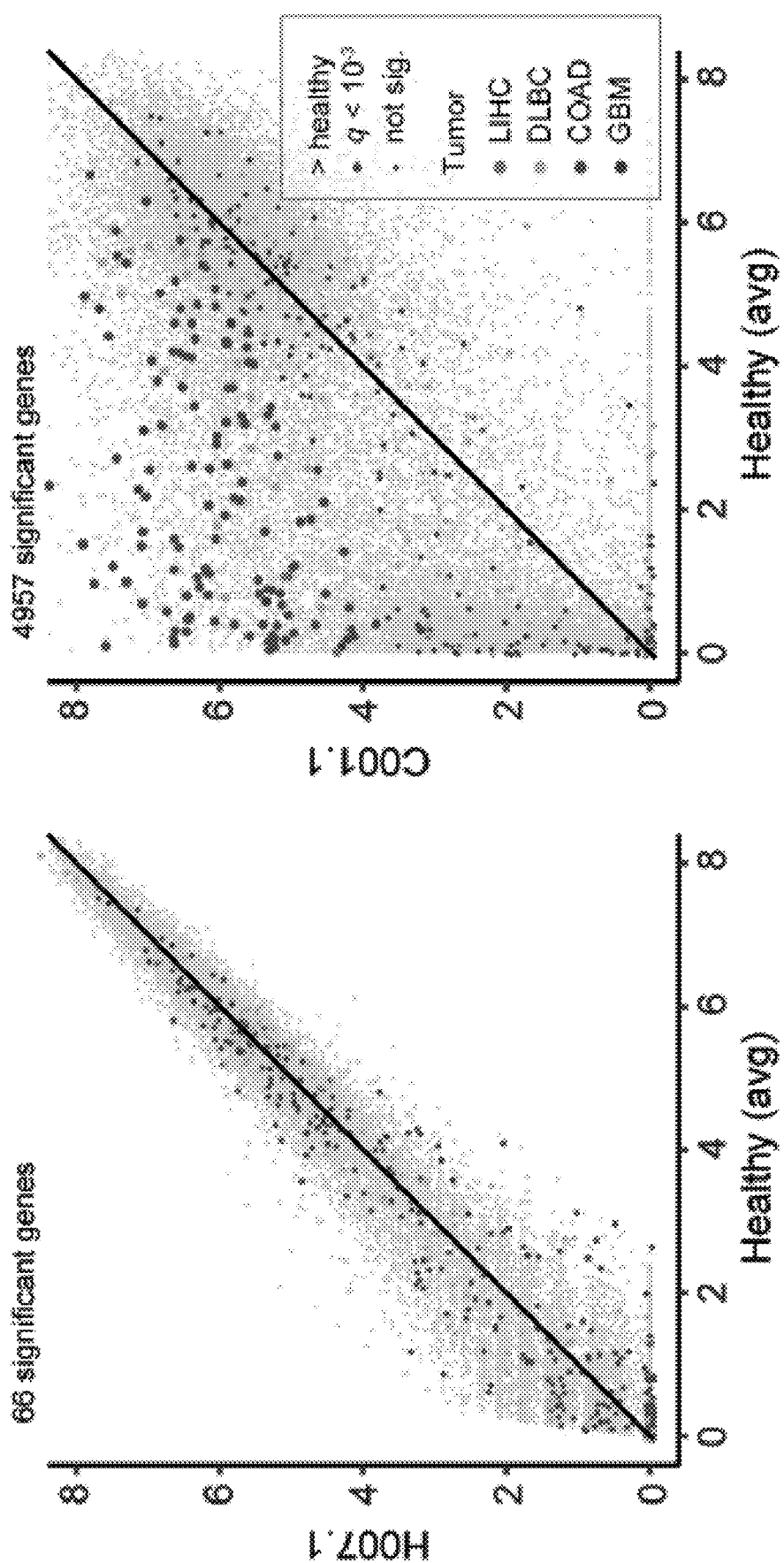

A hallmark of cancer cells is genetic alterations that lead to dysregulated gene expression programs. Identification of such cancer-specific transcriptional programs can assist diagnosis and treatment choice. For each sample, we tested for genes whose signal was elevated compared to five "reference" healthy samples. As a control, unrelated healthy samples outside the reference set were in high correlation with healthy reference, with few genes (usually less than 50) showing significantly elevated signal (FIG. 4E). In contrast, samples from patients revealed hundreds to thousands of genes with significantly elevated signal (FIG. 4E). Examining these genes for enrichment in annotated gene lists recapitulated some of the results discussed above. For example, genes in C001 were enriched for gene sets of GI tract and Brain consistent with the pathology of this patient.

Figure 4F:
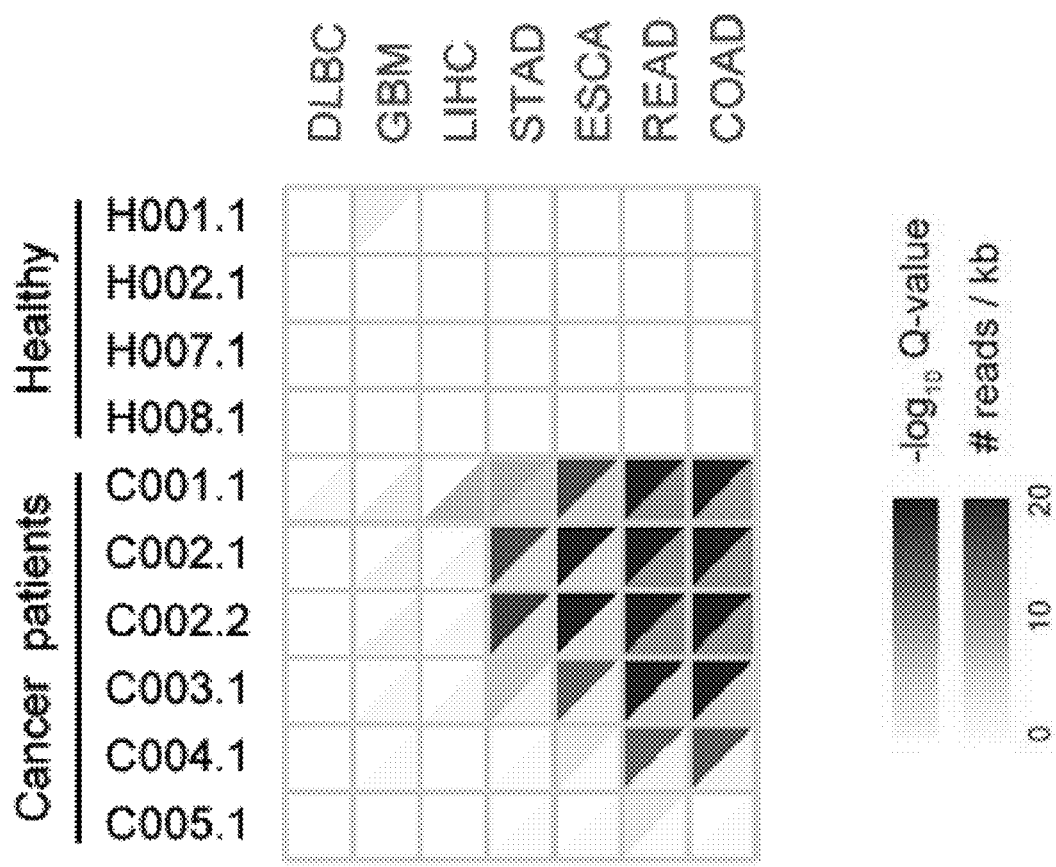
Figure 4G:
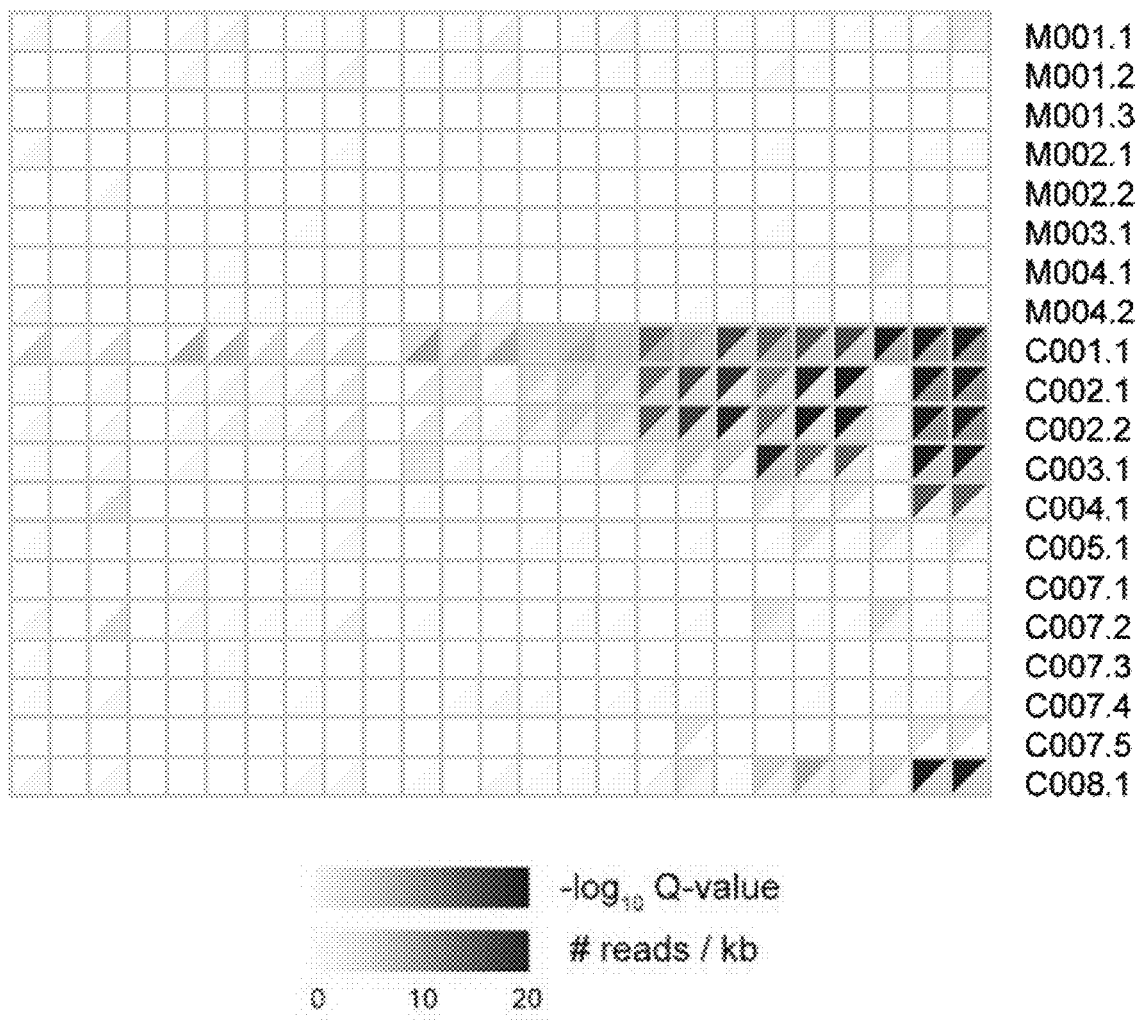
Figure 4G:
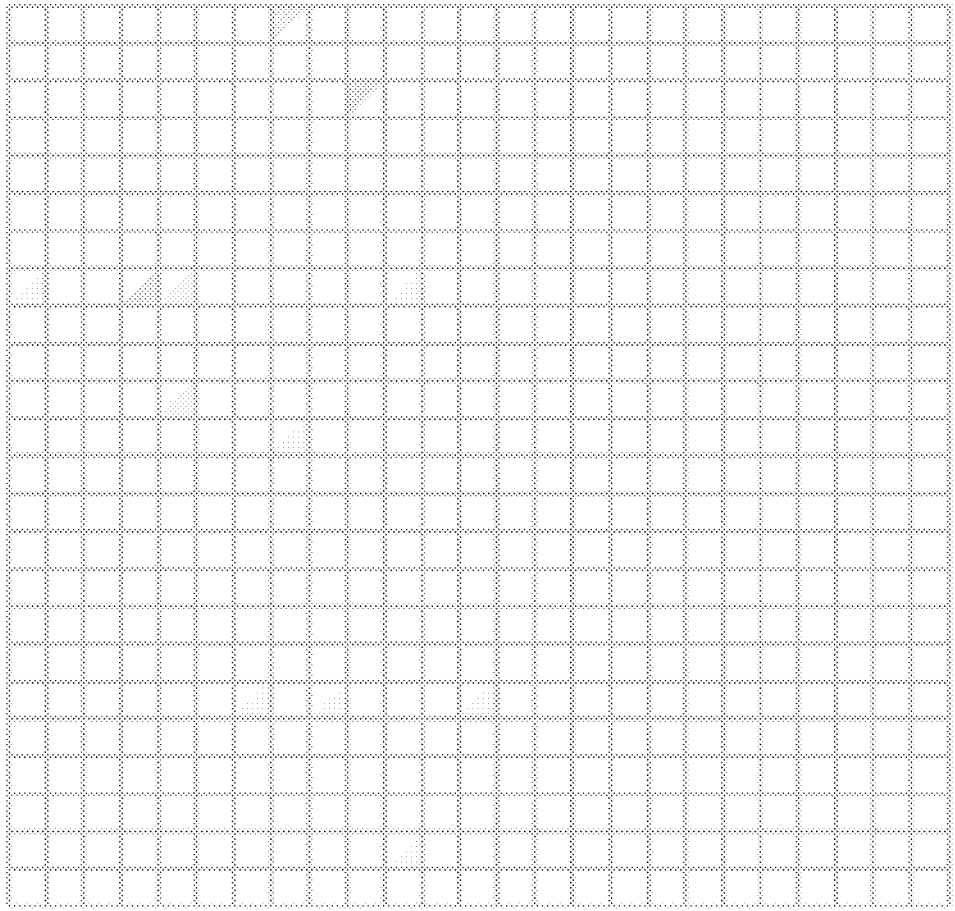
Figure 4H:
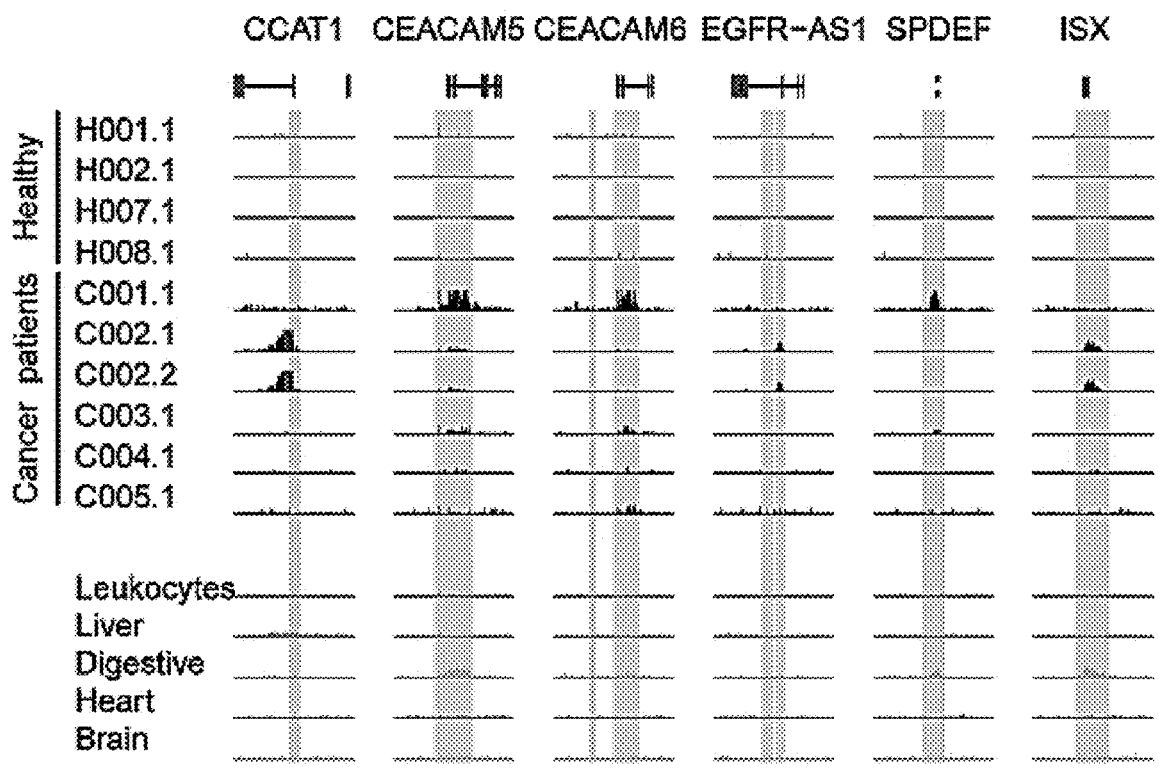

We next looked for cancer-specific signatures in the H3K4me3 cfChIP signal. We analyzed expression profiles from The Cancer Genome Atlas and GTEx projects to identify for each tumor type a set of genes that are significantly higher in the tumor compared to normal tissues (see Materials and Methods, Table 2). We then tested for significant overlaps between the set of genes with higher H3K4me3 signal in a sample and the set of genes overexpressed in a tumor type (see Materials and Methods). For example, C002 has significant overlap (q<10-60) with GI-tract adenocarcinoma genes (FIG. 4E). The analysis of all samples against all tumor types (FIG. 4F-G) shows that only samples from cancer patients have significant enrichment of tumor related gene expression, while healthy and MI patients do not. Importantly, the enrichment is for cancers of the GI tract in line with the diagnosed pathology.

Focusing on specific genes that are known to be upregulated in gastric and colorectal cancers we observe a clear increase of the H3K4me3 cfChIP signal in these patients compared to healthy reference (FIG. 411). Among these genes we find the carcinoma markers CEACAM5 and CEACAM6. The protein products of these genes are used in an antibody-based assay for clinical cancer diagnosis. A second colorectal cancer marker, the long non-coding RNA CCAT1 (colorectal cancer associated transcript 1) shows strong signal in one of the cancer patients but not in healthy subjects. Another example is the long non-coding RNA EGFR-AS1 that mediates cancer addiction to EGFR and when highly expressed can render tumors insensitive to EGFR inhibition. While cfChIP signal for EGFR is detected in all cancers, EGFR-AS1 is only detected in C002 but not in other patients. This finding, which would not be detected by cfDNA mutation analysis, raises the exciting possibility that cfChIP can be informative for treatment choice beyond genomic mutations

TABLE 2

Cancer signatures

Acute Myeloid Leukemia: ITGA4, RP11-1094M14.7, ITPK1-AS1, ABCE1, RP13-786C16.1, RP11-680G24.4, RPL23AP23, RP11-863H1.1, AC005757.6, GCNT6, RP1-308E4.1, SETP5, VPS13C, KRR1, RP11-252K23.2, RP11-447H19.3, BRIP1, TTC24, RP11-306G20.1, ODCP, RP11-513G19.1, KB-1836B5.1, FTH1P4, RP11-182J1.5, ADAM1A, RP11-415J8.7, RP11-638I2.2, RP11-759F5.1, LDLRAD4-AS1, RPL13AP6, SPIN2A, CDC42-IT1, CCNA2, SKA3, RP11-330L19.2, MPHOSPH9, MGA, XRCC2, KCNA6, GAPDHP39, GUSBP3, GUSBP9, NEMP1, RP11-932O9.10, BIVM-ERCC5, KB-1507C5.3, RP11-662B19.2, EAF2, RP11-766H1.1, TCTEX1D1, CAP2P1, RP11-177C12.4, WDR12, RP11-434H14.1, SLC25A36, HNRNPA1P68, RP11-20L24.1, RP11-983P16.2, RP11-475E11.2, KIAA1524, CTC-260E6.6, AC002454.1, C5orf42, RP11-9E13.4, RP11-728K20.2, AC002543.2, PPAT, B3GALNT1P1, VN1R82P, KRT18P63, FAM196B, AC114730.2, RP4-633O19_A.1, EEF1A1P19, RIF1, SREK1, SMARCAD1, ERG, MTRNR2L3, STARD4-AS1, FCER1A, RP11-49O14.2, FANCB, IGLL1, HOXA9, TYMS, AC007919.19, RP3-431A14.4, UBE2D3P2, CTD-2349P21.5, CPXM1, ATP5L2, RPAP2, RP11-207C16.4, AC104634.3, RPL3P1, ZNF519, TAS2R12, AC002400.1, HSPA8P3, FBXL19-AS1, TUBG1P, RP11-392O18.2, RP11-474L11.5, RPSAP51, GS1-259H13.7, LYST-AS1, RP11-142C4.4, RP11-169K17.2, RP11-491H9.3, BEND3P3, RP11-165F24.3, NRBF2P5, GLTSCR1-AS1, RN7SKP80, TICRR, KNTC1, MOB1B, LA16c-361A3.3, SUMO2P8, NEIL3, PHBP2, IRGM, RP11-139E19.2, MYCBP2, FAM111B, RP11-118F19.1, C3orf80, SUGT1P3, CDCA7, HNRNPH1P1, PTH2R, RPL29P23, RP4-603I14.3, RP11-215A21.2, PSMA2P1, MAD2L1, RP1-168P16.2, RP1-168P16.1, BIRC6-AS1, RP11-231I16.1, RP11-615I2.1, RP11-731C17.2, SNORD17, RP3-472M2.2, SAMD11P1, RP11-430C7.2, AC010886.2, SACS, RAB40AL, HSPA8P15, RP13-46H24.1, GUCY1A3, RPS16P5, RN7SL505P, RP11-421E14.2, NRIP1, CLSPN, SNORA71B, SMG1P3, SMG1P1, ZNF33BP1, ZDHHC21, ZNF141, DNTT, BCOR, PFN1P2, RP11-253I19.3, RP11-288K12.1, RP11-540B6.2, RP11-666F17.2, FOXN3-AS2, C8orfl7, BAHCC1, SNRPCP4, RP11-697N18.2, GMDS-AS1, ZFP14, RP11-443B20.1, SUCNR1, SNORD97, CCDC26, RP5-837J1.4, DISC1-IT1, GLUD1P3, NREP, RPS5P2, CBX5, CASP8AP2, RP11-180P8.3, HTR1F, CPA3, AC006116.22, RN7SL502P, RP11-493E3.1, HIST1H4C, ATAD5, ATAD2, GAPDHP2, RP11-16E23.4, RP11-184I16.3, RP11-1007J8.1, MTND5P25, RP11-497H17.1, BRD7P4, RP11-319G9.3, RP11-319G9.5, MTND5P28, KCNQ1OT1, ZNF625, ZNF621, RP11-750H9.7, RPL21P65, CTD-3037G24.3, RAD51AP1P1, RP11-792A8.3, WDR49, ANKRD26, RP11-381E24.1, RPL23AP18, RPL23AP11, LRRC37A4P, AC114776.1, SND1-IT1, TAS2R50, RP11-649E7.5, RP11-332O19.2, RP5-1099D15.1, RP11-336A10.2, SCML2, RP11-393I2.2, CTB-50L17.5, RPS20P4, RP11-58K22.4, RP11-91A18.4, ZNF788, RP11-430L17.1, AC002550.5, NAA25, ZBED4, ANKRD63, RN7SL334P, RP11-18F14.4, PSMD10P1, ASB9P1, RP6-159A1.3, RPL21P123, RP11-252I14.1, DSCC1, CTB-26E19.1, RP11-177A2.5, RP11-318K15.2, RPS20P33, DNA2, SNORD3B-1, RP3-340B19.5, RAD51AP1, PPP1R26P1, RP11-124D2.7, EBLN2, RP11-511H9.3, AMIGO3, ZNF891, CERS6, CTC-265F19.2, ARGFXP2, VANGL1, ZNF708, DENND4C, GUSBP2, RFX8, RFX7, TGIF2P1, SATB1-AS1, SCOCP1, RNVU1-14, ZNF138, PPAN-P2RY11, RP11-720N19.2, RPL18AP2, RN7SL449P, H2AFZP1, AC013474.4, HSP90AB4P, ZNF367, RN7SL328P, RP11-489G11.3, RP11-477E3.2, UHRF1, WDHD1, RXFP2, ZHX1, DYTN, RN7SKP78, MANEA, EPHA1-AS1, RPL36AP15, RPL36AP13, RP11-574F11.3, IQCH-AS1, RN7SL778P, CHRFAM7A, AC108004.3, RP11-386I23.1, SNORD3B-2, B4GALT6, SOGA1, RP11-16P6.1, RP11-182I10.2, FOSB, WARS2-IT1, IL12A, ZNF675, ZNF678, RP3-497J21.1, PRSS57, KIF4A, RP11-453E17.4, EGOT, TPM3P1, RP11-493P1.2, LA16c-390H2.4, NDC1, TRIM24, RP11-527J8.1, RP11-343B5.1, ZSCAN5D, C5orf66, C8orf44-SGK3, ACTG1P20, RP11-90L20.2, TARBP1, RP11-685N10.1, RPL9P2, ANKRD36, AC007679.4, AE000661.50, SLC24A1, ANKRD36C, ANKRD36B, LPAR4, HNRNPCP7, CTD-2012K14.6, RP6-91H8.3, NUTM2G, CTB-134F13.1, RPS23P6, RBM12B-AS1, RP11-571F15.2, CTD-2017C7.3, RP5-867C24.4, RP5-867C24.5, HMGB1P10, HMGB1P14, RP11-69L16.4, CTD-2528A14.5, NADK2-AS1, RP11-124N14.3, AC008440.5, RPL23AP64, UHRF1BP1, QSER1, LA16c-385E7.1, CTD-2026D20.2, ZNF736, ZNF737, AC007787.2, SCARNA7, RP11-452H21.4, RP11-452H21.2, SNHG4, AP001432.14, RP11-648O15.1, ZNF69, ZNF66, AC096921.2, ZBED3, ZBED6, KB-1958F4.1, RFC3, RP11-383J24.2, RP3-522J7.5, RP5-997D24.3, RNASEH2B-AS1, CTC-325H20.7, MYCN, PARPBP, CTC-379B2.4, RPS7P11, RP3-323N1.2, AP000936.1, RPL9P3, IFNK, GLMN, RP13-93L13.2, SPNS3, KRBA2, KIF18B, ERCC6L, LL22NC03-2H8.4, TWISTNB, RP11-709A23.1, MTND6P4, TTF2, PUS7, STAG3L3, STAG3L2, TAS2R41, TAS2R46, RP11-271C24.3, KCNK17, RP11-665C16.1, ALG10, ALG11, RP11-184B22.2, AC073283.7, AC109631.1, CKAP2L, YBX1P3, DUTP1, SNORA12, GCSAML, RP11-484L8.1, DAPK1-IT1, GPR174, SNX25P1, RP1-315G1.1, PNPT1P1, RP11-466F5.3, WRN, AC007365.3, RP11-677N16.1, SPIN4, RP11-173A16.1, RP11-10L12.2, KIF14, KIF11, RP11-295B17.6, TAS2R43, TAS2R42, RP11-69H7.4, VPREB1, MMS22L, KIF4CP, ATP5G2P3, CSNK1G2P1, MDN1, TET1, CD38, ZNF321P, RP11-166B2.5, MTBP, SMC4, RN7SL413P, FAM179B, RN7SL182P, TAS2R62P, DLEU2L, SEC13P1, RN7SL614P, SNORA71B, ATP5HP4, RP11-815J21.4, RP11-815J21.1, ST8SIA6, RPL23AP30, POLE2, RPL7P7, ZNF566, FAM60BP, NDUFA3P2, MRPL37P1, SIAH2-AS1, RP13-580F15.2, RP11-710F7.3, RP11-497G19.1, RP5-894A10.6, RP11-383G10.3, RP11-45M22.3, CENPK, CENPI, CENPF, CENPE, CENPQ, MYCBP2-AS1, RP11-552C15.1, RAVER2, CTD-2291D10.4, PDXDC2P, FUT10, RP11-333E13.4, RPL21P4, RPL21P1, RPS20P15, ZNF491, NPM1P29, PPP5D1, FAM35CP, ZNF260, UQCRBP1, HNRNPA1P34, INTS2, RP11-214J9.1, SCAI, RP11-968A15.8, AC005682.5, PTTG3P, LUZP1, ZNF878, SPN, HMGB3P4, AC100830.4, RPS4XP14, RP11-431N15.2, RP1-180M12.1, CEP128, SETP11, CHD9, MPO, MPL, ACOT11, YPEL5P2, TAS2R10, TAS2R13, SGK494, SPECC1L-ADORA2A, FAM72D, RP11-253I19.4, RP11-616K22.1, GJA1P1, SERPINH1P1, BRI3BP, URB2, TMEM14E, PGAM1P7, BRCA1, BRCA2, FAM208B, FLT3, RP11-697N18.3, CTC-45812.2, POLQ, RP11-307L3.4, ATP8B4, LY75-CD302, RN7SL128P, ANKRD44-IT1, AC114763.1, CTB-181H17.1, RP11-83A16.1, VDAC1P1, AC002306.1, RP11-557C18.3, RP11-411G7.2, CCNE2, CYTL1, AC008746.3, AC008746.5, RP11-403A21.3, SRGAP2-AS1, YEATS2-AS1, SGOL1, RP11-345I18.4, GAPDHP70, OGFOD1P1, AC124914.3, PPIAL4G, RPL7P49, ADPGK-AS1, RPL7AP2, AC007036.4, HERC2P10, BANF1P3, TMEM75, ZNF618, SMCR5, RP3-340H11.2, RP11-64K12.9, SSBP3-AS1, RN7SL698P, KANTR, KIF20B, MKI67, ZNF551, PDHA1P1, RP11-53B2.1, RP11-53B2.2, RP11-53B2.4, AC093732.1, AP000487.4, RP11-90O23.1, BNIP3P42, BNIP3P41, GABPB1-AS1, RCC2P6, ARF1P2, RP11-302M6.5, AC074286.1, RP11-95J11.1, RP11-214K3.20, RP11-553K8.5, RP11-377G16.2, RP11-172F4.2, RP11-158M2.2, RP11-133K1.7, MARK2P8, ISPD, FXNP2, RGS17P1, YWHAZP4, RP11-193I22.2, RP11-252K23.1, ARHGAP11A, ARHGAP11B, TIFAB, QRSL1P3, ASPM, CTC-425O23.2, RP11-197K3.1, CTC-527H23.1, AC004383.3, POU5F1P4, RPL17P40, RP11-384C4.6, RP11-473O4.4, MORF4L1P4, CTD-2587H24.10, ATP5F1P1, C1orf86, IPPKP1, KMT2A, CLEC11A, CRYM-AS1, ZNF718, ZNF714, ZNF717, PTPN2P1, SIGLEC6, CTA-339C12.1, ZNF43, TAS2R19, TAS2R14, FKTN, RP5-1154L15.1, MRPL53P1, RP11-18B3.3, XPO4, SLC15A2, RP11-16C1.3, ZNF100, RP11I11.8, RP11-474I11.7, FAM53B-AS1, AOX2P, RP11-40C6.2, DCUN1D2-AS, DDX11-AS1, TEC, LRRC58, HMGN2P20, FNBP1P1, CTD-2381F24.1, RP11-876N24.2, RP11-77K12.3, ZNF805, AE000661.37, ZNF37A, RP13-487P22.1, MCM4, MCM2, AC007041.2, RP11-201O14.1, RP11-96D1.9, PTPRJ-AS1, KRR1P1, AC003104.1, ZNF101P2, AC079922.2, RP11-525G13.2, TAS2R60, RP11-440L14.4, RP11-293A21.2, CTC-451P13.1, CATIP-AS2, RP4-635A23.4, OSTCP1, CTD-2542L18.1, ASS1P1, ZNF888, SEPT7P1, SOX12, FTX, RP11-158G18.1, GPR151, CICP13, RP11-306O13.1, MBLAC2, KIAA0101, TMTC4, ZNF660, RP11-550A5.2, RPL31P58, RP11-1379J22.5, TABLE 2-continued Cancer signatures HPDL, AP001171.1, KLF4P1, RP11-632K20.8, RP11-480C16.1, RN7SL118P, BNIP3P10, RP11-438N5.2, RP11-476B13.2, RP1-5O6.4, RPS6P16, OFD1P17, AC010522.1, NDUFAF4P4, ANKRD28, SLC35E1P1, RP11-75C10.7, PTX4, RP11-754B17.1, N4BP2, HEATR1, RN7SL262P, EXO1, FIGNL1, AC017104.2, ZNF415P1, RPS3AP47, RHOQP2, RC3H1-IT1, CCDC88A, RXFP4, EEF1A1P24, HMGB1P23, TRH, RP11-216N14.7, KIAA1586, CDC42P1, GPR52, SRSF10P1, RAI1-AS1, PAICS, PUS7L, RP11-678G14.2, ATP6V0CP1, FDPSP4, POLA1, EIF5AP3, KIAA1919, SCARNA9, RP4-591N18.2, SLC7A5P1, TRGV1, AC011933.2, RP11-35J23.1, DTL, RP11-702F3.1, CYB5RL, AURKAPS1, SOX4, RP6-99M1.3, RPS12P26, ZNF283, RP11-1023L17.1, ZRSR1, AC003989.4, FLJ42393, RP11-981G7.1, RP11-46A10.8, RP11-276H1.3, RP11-276H1.2, MCM10, GPR75, GJA9, RP11-56B16.1, RP5-916O11.3, ZNF852, ZNF850, ZNF326, RPS2P45, RYKP1, LPPR3, RP11-305O6.3, HELLS, TCEB3C, TGIF2-C20orf24, AKAP9, RP11-426C22.4, CTD-3060P21.1, TAS2R4, TAS2R3, CCDC144B, P2RY4, HOXB-AS2, ANGPT1, ZNF91, ZNF92, SPICE1, TAS2R30, TAS2R31, AC136289.1, RIMKLBP1, ZRANB3, HNRNPA1P37, DNMT3B, RP11-480I12.5, E2F8, RP11-212F11.1, RP11-290D2.3, ZZZ3, ZNF439, COQ10BP2, RPS12P27, RP11-69M1.4, PAPD7, LRBA, RP1-168P16.3, RPS15AP10, RPS15AP16, RP11-874G11.1, RP11-417O11.5, RP11-312J18.3, LYRM7, RPL21P10, ARL5C, RP11-420A6.2, RP11-797H7.1, RPS17P13, SNRPCP19, CCDC14, CCDC18, RABGAP1L-IT1, HIGD1AP16, ZNF280D, RP11-69M1.3, RBL1, KIT, BNIP3P25, RP1-91J24.3, FAM124B, POU5F1P6, SHMT1P1, RPL7AP3, RP11-157K17.5, UTP20, IGF2BP2-AS1, RP11-565F19.4, RP6-109B7.4, RP11-384B12.3, RP11-264L1.4, ULK4P1, ZNF221, RP11-17G12.2, RP11-402L5.1, MIB1, AC019097.1, GS1-184P14.2, CTB-102L5.7, RN7SKP180, RN7SKP185, MKRN5P, HTATSF1P2, STXBP4, ERVFRD-1, CCNJP2, CDK1, CDK6, PIN4P1, ZNF573, STIL, NTAN1P2, RPS15AP6, PI4K2B, GSE1, RP13-1056D16.2, TFEC, RN7SKP237, RP11-198M15.1, RP11-544A12.5, RN7SL743P, EEF1B2P1, SSBP2, KNOP1P4, RP11-496H15.2, SH3GL1P2, ZNF772, RP11-347P5.1, CTD-2331H12.7, BMI1, RP1-56K13.2, RLIMP1, ZNF26, ZNF28, SLC9A7, RP11-43D4.2, CTD-2530N21.5, BDP1, ERMP1, AP001625.6, C1QL3, NPM1P19, ZNF253, RP11-2J18.1, RPL5P11, AC010240.2, RP11-265B8.5, PRR11, BMS1P1, WDPCP, AC066692.3, CHCHD4P5, RP11-576N17.3, CTD-2184D3.7, MIS18BP1, RP1-256G22.2, CLDN20, SNRPGP18, RP11-10N23.2, ORC1, PGAM1P11, TCEB1P33, RP11-477J21.6, RP4-591B8.2, PPIAP16, C20orf197, ATP6V0E1P1, RBM41, AC005546.2, RP11-307P22.1, CHEK1, PLD4, ALG10B, RP11-556E13.1, ZNF460, NUCB2, SRP72P2, TAS2R63P, SEC14L1P1, TDGF1P6, TDGF1P5, RP11-798K23.5, RP11-274B21.1, ZNF124, ZNF121, TRBVB, ACAP2-IT1, RP11-16C1.2, RP11-539G18.1, PIGFP2, RP11-631M6.3, RP11-1250I15.3, MSH2, PM20D2, DBIL5P2, ZC3HAV1L, BTF3P12, ANKRD36BP1, RP11-540O11.4, RP11-540O11.6, RP11-102M11.1, ZNF681, TUBB8P1, RP4-614O4.11, SMC2, MPRIP-AS1, RP11-75C10.9, IQGAP3, RP11-12A2.1, RP1-209B5.2, MFSD1P1, UHRF2P1, RP11-356M20.1, CHML, MYB, SPC25, RP11-117N2.2, AC006042.8, RP11-384B12.2, SLC25A6P5, RP1-29C18.9, RP11-343C2.9, SHPRH, FASTKD1, VPS26BP1, CTC-435M10.10, GAPDHP62, KAT6B, RP11-519P18.1, RPL7P52, OCLM, AC005264.2, RP11-488L18.3, RP11-584P21.4, CTB-193M12.1, RP11-96D1.5, SLC2A3P2, RP11-571I18.5, KIAA0125, RP1-224A6.8, RP11-346C16.1, EIF4BP5, ZNF724P, GAS5-AS1, FCF1P5, FCF1P7, ZRANB2-AS1, RP11-15F12.1, AP001469.5, USP41, RP11-118E18.4, RP11-797A18.6, RP11-830F9.7, RN7SL174P, RP1-278E11.3, PROX2, CTC-244M17.1, ZMYM1, RP11-603K19.1, RP4-534N18.2, TYRO3P, KRT18P57, PDC, THRA1/BTR, TSEN2, ESCO2, DCAF13P3, AC010642.2, TRPC5, PHF14, LATS2-AS1, COL24A1, ALG1L2, AC004893.10, DLEU1, RP11-342M21.2, BCL11A, DPY19L4, RP4-752I6.1, RBMS2P1, RP11-674I16.1, TATDN1P1, ZNF726, AK3P5, ZNF70, E2F3-IT1, RP11-697N18.4, BTBD8, DIAPH2-AS1.

Adrenocortical Cancer: EBP, FAM64A, C1orf53, EPB41L1, TSPAN12, RP5-940J5.9, CTSA, NR5A1, GSTA3, TNFRSF12A, PPIF, ZNF275, RP11-215A21.2, NANOGP1, MINOS1-NBL1, SERPINA5, RP11-649E7.5, FAM222A, PLBD2, SRRM3, LDLR, AGRP, FAM19A4, LONP1, GRTP1-AS1, DBP, HSPE1, RP11-688G15.3, NPTX2, KLHDC8B, TECRP1, SPINK13, C1orf233, MGARP, RP11-320G24.1, BST2, UBE2C, RP11-40C6.2, FAM131C, FDXR, SCARB1, PRDX2, HMGCR, SLC26A2, NETO2, C19orf48, RP1-241P17.4, RP11-159K7.2, QPRT, MAMSTR, TMEM229B, PTPRH, AC009784.3, FAM43B, ESM1, AMHR2, ULBP2, RPS2P55, NHLRC4, CTC-518P12.6, MSMO1, TBX3, DHCR7, NR0B1, CYB5B, POR, DLK1, SRXN1, ANO4, FAM195A.

Brain Lower Grade Glioma: RP11-229P13.23, RP5-940J5.9, FERMT1, TAAR3, RP11-215A21.2, RP11-64K12.4, NUDT4P1, RP11-698N11.2, UHRF1, RP4-791C19.1, RP11-565P22.6, AC000089.3, VIPR2, BTBD17, MDFI, NMB, BMP2, RP5-1177M21.1, SHD, DLL3, CX3CR1, MAGED4, NES, BCHE, RPE65, RP11-231C18.1, SOX2OT_exon3, PAX1, RP11-40C6.2, FREM3, GSX1, SOX11, HES6, PCDHB9, NDST4, TREM2, RP1-241P17.4, SOX4, KLRC2, SMOC1, PIGY, PAPD7, RPS2P55, HAPLN1, BCAN, GPR34, MEX3A, MKRN3-AS1.

Breast Invasive Carcinoma: FAM64A, NKAIN1, RP11-229P13.23, IL20, CRABP2, NAT1, RP5-940J5.9, HMGB3, RRM2, RIPPLY3, MXRA5, LRRC15, FAM111B, CHRNA6, COL1A1, RP11-649E7.5, AC005255.3, CST2, CST1, UHRF1, EPYC, KRT18, COL11A1, KIF4A, AGR3, HIST1H3G, PAFAH1B3, KIF26B, UBD, TK1, ERCC6L, ANXA9, MMP10, MMP11, MMP13, GALNT6, RP11-400N13.3, CENPF, GRP, UBE2MP1, MKI67, POSTN, CXCL9, UBE2C, RET, YWHAZP4, HLA-DPB2, ERVMER34-1, RP11-40C6.2, TPD52, RP11-10G12.1, FOXA1, KIAA0101, LDHAP7, TREM2, SRMS, INHBA, MAL2, NUSAP1, PIGY, TGIF2-C20orf24, RP11-579D7.2, COL10A1, PAPD7, CXCL11, CDK1, CENPA, PI4K2B, TLR7, CTC-518P12.6, ESR1, PRR11, CCR8, CACNG4, ESRP1, SPC25, RP11-5P18.5, RP11-379F12.4, ABCC11, CXCL10, SAPCD2, MEX3A.

Colon Adenocarcinoma: ITGA2, POU5F1B, GCNT1, RP11-357H14.17, FAM64A, CHMP4C, RP11-229P13.23, SKA3, LAMB3, RP5-940J5.9, LY6G6D, RBBP8NL, HMGB3, SEL1L3, CKMT1A, BCL2L15, CEP55, ATP10B, TRABD2A, TDGF1, FERMT1, CDH17, HTR1D, RRM2, KRT8P45, NEIL3, MAP7, FAM111B, RP11-93K22.13, ILDR1, CDCA7, RP11-215A21.2, MAD2L1, CEMIP, EPCAM, ANKS4B, AC012363.4, PPP1R14D, VWA2, MUC13, KRTCAP3, HKDC1, F2RL1, AP000439.3, AC007099.1, NOX1, AC005255.3, CLRN3, PRSS8, RAD51AP1, CDT1, CST1, ATP2C2, PHLDA2, EREG, RHPN2, C15orf48, CCL20, LLGL2, GAL3ST2, KRT8, HMGN2P17, UHRF1, EPYC, AURKB, MET, KRT18, ABHD17C, LY75, FAM83H, FAM84A, GMDS, LSR, KIF4A, AGR2, PRR15L, AP1S3, FUT3, MMP1, UBD, CASC9, TLCD1, NOS2, KIFC1, PARPBP, TMEM45B, TK1, LRRC31, CCNF, AC000089.3, KIF18B, ERCC6L, RP11-150O12.3, RP11-150O12.6, MMP10, MMP11, MMP12, GGH, GALNT4, GALNT5, GALNT6, GALNT3, KIF11, ASCL2, HMGA1, C6orf222, C6orf223, PLS1, AREG, GRM8, HOXB8, HOXB9, MARVELD2, KRTAP4-1, RP11-400N13.3, ENC1, CENPF, MACC1, STAP2, EPHB2, MELK, GPA33, CASC21, ETV4, LGALS4, CTB-191K22.5, C10orf91, GRIN2D, KRT8P48, B3GNT3, SLC44A3, SLC44A4, TPX2, MISP, BRI3BP, LY75-CD302, VIL1, TMEM211, TJP3, MKI67, GUCY2C, CXCL3, CXCL9, UBE2C, UBE2T, CCAT1, YWHAZP4, ARHGAP11A, TNFSF11, CBLC, AP003774.1, RPL36A-HNRNPH2, EPHX4, DSG2, RP11-40C6.2, RNF43, AP1M2, PRR15, MCM4, MCM2, VDR, FAM105A, SGPP2, PPP1R1B, RP11-187E13.1, CCNB1, LAMC2, RP11-10G12.1, NOXO1, RAB19, KIAA0101, DACH1, CRB3, HPDL, TRIM15, LDHAP7, AL163953.2, FXYD3, EXO1, RXFP4, TOR4A, RP11-284F21.7, CDH1, RP11-22L13.1, ECT2, ST14, NFE2L3, SRMS, SOX9, MAL2, NUSAP1, PLEKHG6, MCM10, MYBL2, PIGY, TGIF2-C20orf24, RP11-579D7.2, USH1C, RP11-480I12.5, COL10A1, E2F8, PYCR1, GPR160, CDX1, CDX2, CDC6, CLDN2, CLDN3, CLDN4, CLDN7, BIK, EDAR, AC123023.1, TMEM238, CXCL11, RPS2P55, CDK1, CENPM, CENPA, ANLN, RP11-44F14.2, C17orf77, PRR11, SLC12A2, CCR8, ESRP1, GINS2, CYP2S1, PLEK2, TRIM31-AS1, FOXP4-AS1, TABLE 2-continued Cancer signatures AC021218.2, TOX3, IQGAP3, MYB, SPC25, RP5-881L22.5, IHH, TSPAN8, BBOX1-AS1, MYEOV, ACSL5, TRIM31, TFF3, TMPRSS4, CEACAM1, CEACAM5, CEACAM6, ARHGEF35, STX19, CXCL10, SATB2, GPR35, GPX2, FEZF1-AS1, CDCP1, SAPCD2, MYO5B, DDC.

Diffuse Large B-Cell Lymphoma: CKS1B, DLGAP5, MZB1, C16orf59, PLA2G7, RMI2, PCNA, DNPH1, CCNA2, SKA1, SKA3, WNT10A, PLA2G2D, ZWINT, AC023590.1, EAF2, PARP1, SNRPD2, SNRPD1, MND1, EEF1A1P19, LSM3, CEP55, TYMS, HSPA8P1, FCRLA, PDCD1LG2, KBTBD8, RRM2, RRM1, NEIL3, HLA-DOA, HLA-DRB6, HLA-DQA1, FAM111B, CDCA7, CDCA5, RP11-215A21.2, MAD2L1, MRPL13, MRPL14, MRPL17, MS4A1, CCL18, RASGRP3, RPS21, POU2AF1, RFC4, RP11-815N9.2, FEN1, RP4-706A16.3, IL21R, CXCR5, RP11-16K12.1, DSCC1, RAD51AP1, CDT1, RGS13, GTSE1, RPL13AP20, RP11-627K11.1, HMGN2P17, CCDC58, UHRF1, WDHD1, AURKB, KIF4A, WDR76, KB-1980E6.3, MRTO4, C12orf45, UBD, NCAPG, BCAS4, CD80, CD83, RFC3, KIFC1, PARPBP, TK1, CCDC167, RPS7P11, CCNF, AC000089.3, TOMM5, KIF18B, ERCC6L, CDC20, MMP12, CLECL1, KIF14, KIF11, METTL1, AC007381.3, DBI, RPL17-C18orf32, PRDX1, TRAF4, RPS3AP26, ELL3, FAM72B, FAM72A, EBI3, POLE2, MIXL1, C12orf77, CENPN, CENPK, CENPI, MELK, RP11-151F5.2, RP11-203B7.2, SPC24, BFSP2, TIMM8A, FAM72D, TPX2, BRI3BP, MCOLN2, SGOL1, SHCBP1, AC020743.2, RP11-624L12.1, MKI67, RPL39, SNRNP25, CXCL9, UBE2C, UBE2T, BIRC5, HAUS1, RFTN1, MTHFD1L, ARHGAP11A, TIFAB, ASPM, EEF1B2, HLA-DPB2, C1orf186, PAX5, RP11-40C6.2, RP11-360L9.7, NME1, NME2, MCM4, MCM2, HSPB11, MREG, AC079922.2, CCNB1, CTC-451P13.1, RP11-10G12.1, KIAA0101, SNRPEP2, AC079767.4, CD19, FUCA1, EXO1, RPS3AP47, RPL35P1, NPM3, BYSL, PAICS, RPL41, C19orf48, NAPSB, RPL22L1, IL4I1, MCM10, GGCT, MYBL2, TGIF2-C20orf24, FPR3, RPL36A, SNRPF, SNRPG, SNRPE, E2F8, RAB42, CDC6, CD40, CD79B, CD79A, IDO1, TMA16, CXCL11, RPS2P55, CDK1, CDK4, RPL17, CENPM, CENPA, SLAMF8, DTYMK, NOP16, CHEK1, GINS2, GINS3, BLNK, SPC25, CD70, CD72, CCL19, GCSAM, HJURP, CTD-2342N23.3, NDC80, RPS7, RPL26, RP1-278E11.3, DEPDC1B, SHFM1, ESCO2, HTRA4, SPIB, CXCL10, TUBBP1, BCL11A, BRIX1, RP11-253E3.1.

Esophageal Carcinoma: ITGA2, ITGA6, DLGAP5, RP11-357H14.17, FAM64A, SKA3, LAMB3, RP11-397A16.1, BIVM-ERCC5, SIPA1L3, RNU1-28P, RAB27B, AC002543.2, HIST1H1B, CKMT1A, CEP55, FERMT1, RPSAP52, PI3, RRM2, RIPPLY3, MXRA5, NEIL3, PMAIP1, SAMD9, FAM111B, RP11-93K22.13, FOXM1, ILDR1, MUC4, KLK6, MAD2L1, PRDM1, SNORD17, COL1A1, CEMIP, AC012363.4, RP11-421E14.2, CLSPN, WNT7B, ENTPD7, HEPHL1, RSC1A1, POU6F2, CKAP2, HIST1H4C, CTD-2555C10.3, SERINC2, F2RL1, KLF5, SND1-IT1, NRARP, RNU1-27P, AC002550.5, RP4-594A5.1, RAD51AP1, CDT1, CST2, CST1, RP4-669H2.1, TGFA, PHLDA2, RHPN2, RNVU1-18, KCNK1, CCL20, CCL22, GAL3ST2, RIPK4, HSP90AB4P, TMEM189-UBE2V1, UHRF1, WDHD1, AURKB, AC073046.25, MET, RMRP, KRT17, KRT19, ABHD17C, RP11-108M12.3, LY75, KPNA7, FAM83H, LSR, KIF4A, CTD-2357A8.3, RP11-757F18.3, TMEM30B, LPAR5, HIST1H3G, ABCA13, SLC7A5, RP5-867C24.5, AP1S3, MMP1, KIF26B, JUP, UBD, CASC9, TLCD1, SCARNA7, RAET1E-AS1, PTBP3, SQLE, ZNF296, FOXP3, PARPBP, RP11-16I16.2, CELSR1, CCNF, KIF18B, ERCC6L, RP11-709A23.1, AC011288.2, MMP10, MMP11, MMP12, MMP13, ALG1L, CKAP2L, RP1-315G1.1, EPPK1, GALNT6, GALNT3, KIF14, KIF11, IGF2BP3, IGF2BP2, NRG1, SPINT1, HMGA1, HMGA2, DSPP, FAM72B, RP11-8L2.1, FAM83H-AS1, MARVELD2, KRTAP4-1, POLE2, TOP2A, MRPL37P1, CENPK, CENPI, CENPF, CENPE, MACC1, RP4-694A7.2, EPHB2, MELK, MDFI, SLC10A7A, NCEH1, CORO2A, ETV4, ETV7, AC005537.2, MYO10, C10orf91, GRIN2D, B3GNT5, RP11-510J16.5, FAM72D, SLC44A5, TPX2, RP11-429J17.7, RP11-616K22.1, S100A7, BRI3BP, ZNF695, PGAM1P7, IFI6, BRCA2, KIF23, POLQ, LY75-CD302, CTB-181H17.1, RP11-69L16.6, SGOL1, ARNTL2, RPPH1, C2orf48, FSCN1, RP11-1103G16.1, KIF20B, KIF20A, MKI67, RP11-90O23.1, CXCL9, UBE2C, UBE2T, CCAT1, MARK2P8, TNIP3, ARHGAP11A, ASPM, POU5F1P4, CBLC, ERVMER34-1, DDR1, DSG2, RNF43, AP1M2, RP5-884M6.1, MCM4, MCM2, SGPP2, RP11-201O14.1, BLM, TNFSF15, CCNB1, LAMC2, CTD-2542L18.1, RAB19, KIAA0101, AC010761.10, RP11-550A5.2, HPDL, CTD-3051D23.4, CTHRC1, FXYD3, IL22RA2, EXO1, E2F7, RP11-216N14.7, TTYH3, FAM83B, RP11-284F21.7, CDH1, NETO2, ECT2, ST14, NFE2L3, SRMS, SOX9, SOX4, MAL2, NUSAP1, PLEKHG6, FU42393, MCM10, MYBL2, HELLS, HIST1H2AM, RP11-626H12.2, COL10A1, E2F8, CXADR, PAPD7, OAS3, OAS2, CDC6, CLDN4, RP11-499F3.2, BIK, EDAR, FOSL1, LAD1, RP11-157K17.5, PRRG4, RP11-27M24.1, ULBP2, ULBP3, F11R, TMEM238, KDELR3, CXCL11, GS1-184P14.2, CTB-102L5.7, DEPDC1, CDK1, STIL, CENPA, ANLN, RN7SL4P, RP11-44F14.2, CTC-480C2.1, AC010240.2, PRR11, PRR7, GJD3, CSRP, GSE, CDS1, ESRP1, RBM47, GINS4, CYP2S1, ZNF460, RNU1-1, SAMD12, RP11-16C1.2, PLEK2, FRK, FOXP4-AS1, CSF2, IQGAP3, GYLTL1B, SPC25, C1orf106, OCLN, BBOX1-AS1, DDIAS, MYEOV, TMPRSS4, DEPDC1B, APOBEC3B, TYRO3P, CEACAM5, ARHGEF35, ESCO2, CXCL10, GPX2, FEZF1-AS1, CDCP1, SAPCD2, MYO5B, ZNRF2P1, SLC7A11, GNGT1.

Glioblastoma Multiforme: FAM64A, OTP, MSMP, TUBA1C, TNFRSF12A, RRM2, NEIL3, TAAR3, DMRTA2, FAM111B, CHRNA9, CRISPLD1, CHI3L1, RP11-351I24.3, HIST1H4J, SPINK8, HSPE1-MOB4, RP11-134N1.2, ADORA3, IGFBP2, GAL3ST4, TMEM189-UBE2V1, RP11-698N11.2, UHRF1, WARS2-IT1, KIF4A, F2R, TK1, RP11-565P22.2, TMSB15A, MEST, AC092675.3, RP11-84A19.3, TP53, CENPI, MDFI, IBSP, NMB, SPC24, PDPN, CX3CR1, NES, MKI67, HAS2, UBE2C, RPE65, SPOCD1, CDKN2C, MCM2, SOX1, AC114803.3, KIAA0101, C21orf62, EGFR, TREM2, NUSAP1, HRH1, MCM10, PIGY, TGIF2-C20orf24, RAB42, CCDC109B, CENPA, TLR7, PRR11, CHI3L2, ID3, GPR82, SPC25, CXCL10, GPR34, MEX3A, GBP1.

Head & Neck Squamous Cell Carcinoma : ITGA2, ITGA3, ITGA6, CKS1B, ARTN, FAM64A, PCAT1, RP11-229P13.23, ADAM12, CCNA2, WNT10A, TM4SF19, LAMB3, HN1L, RP11-397A16.1, IL20, DDX60, SERPINB5, RP5-940J5.9, KCTD11, TUBA1C, RP11-334L9.1, BCL2L12, RP13-463N16.6, CEP55, CTSC, AMMECR1, GPR68, OTOP3, TP63, FERMT1, TNFRSF12A, RPSAP52, PTHLH, PI3, EPHA2, RRM2, MXRA5, IGSF3, ITGB4, ITGB6, NEIL3, PMAIP1, CTA-384D8.35, SAMD9, LRRC15, FAM111B, FOXM1, CDCA4, KLK9, RP11-215A21.2, PRDM1, EPGN, COL1A1, C19orf33, KLK10, TMED7-TICAM2, MINOS1-NBL1, IL1A, KRT6B, KRT6C, KRT6A, DSC2, WNT7B, ENTPD7, CGB8, HEPHL1, CKAP4, CTD-2555C10.3, SERINC7, F2RL2, NPBWR1, DEFB4B, DEFB4A, AC007879.7, S100A10, S100A16, CDT1, CST1, VANGL1, IGFL1, PLAU, PHLDA2, SOWAHC, AKR1B15, GNA15, CCL20, CCL22, RND3, LMNA, TMEM102, KRT5, RIPK4, TMEM189-UBE2V1, C1orf74, LGALS3BP, UHRF1, AURKB, CD276, MET, KRT17, KRT16, KRT14, RP4-791C19.1, KPNA7, B4GALT1, FAM83H, LSR, IFIH1, KIF4A, CALML3, CTD-2357A8.3, FZD6, AJUBA, LPAR3, HIST1H3G, RP11-21B23.2, SFN, MMP1, JUP, UBD, CASC9, TNFRSF10A, CLCA2, APOL1, TNPO1P3, COL5A2, PTBP3, KIFC1, RP11-16I16.2, TK1, CELSR1, GSTP1, AC000089.3, RP11-404P21.8, KIF18B, ERCC6L, AC011288.2, ANXA1, ANXA2, ANXA8, PGM2, MMP14, MMP10, MMP11, MMP12, MMP13, ALG1L, CKAP2L, WNT5A, TCF19, GALNT6, GALNT3, KIF14, KIF11, IGF2BP3, IGF2BP2, CD109, LOXL2, SLFN5, CTD-2008L17.1, HMGA2, AREG, IFI27, FAT2, RHOD, SNAI2, AC007389.3, KRTAP4-1, TPRXL, POLE2, RNASE7, RP11-400N13.3, SDC1, CENPI, CENPF, RP4-694A7.2, MELK, MDFI, ITPRIPL2, TENM2, RTP4, S100A7A, HNRNPA1P33, MB21D1, ETV4, SPHK1, SPC24, C10orf99, C10orf91, ADH7, B3GNT5, KRT75, PDPN, FST, TPX2, S100A7, S100A2, KIF23, LY75-CD302, RP11-69L16.6, ARNTL2, FRRS1, RP11-104E19.1, TM4SF19-TCTEX1D2, KIF20A, MKI67, HAS3, ARSI, CXCL9, UBE2C, BIRC5, SPRR1B, DTX3L, ARSJ, TGFBI, AC010677.5, TNIP3, GBP1P1, YWHAZP4, EPSTI1, ARHGAP11A, MFAP2, TNFSF10, ASPM, TUBB6, TNC, ERVMER34-1, DSG2, DSG3, RP11-40C6.2, RAP2B, TABLE 2-continued Cancer signatures CDKN2B, CCL7, RP5-884M6.1, MCM5, MCM2, MICALL1, FAM129B, RASSF10, AC079922.2, CCNB1, LAMC2, HES2, TM4SF1, IER3, KIAA0101, EXT1, EHD4, CTHRC1, TRIM16, LDHAP7, FXYD3, KREMEN2, IL22RA2, CD1B, EXO1, E2F7, LRRC8E, FAM83A, RPL35P1, TP73, CDH1, CDH3, ECT2, ST14, RP1-241P17.4, SLC1A5, INHBA, CD9, NUSAP1, ABCC1, SERPINH1, MCM10, MYBL2, C16orf74, PIGY, TGIF2-C20orf24, RAET1L, ZDHHC12, COL10A1, E2F8, IL36G, IL12RB2, PAPD7, OAS1, OAS3, OAS2, PTGFRN, CDC6, ISG15, IRF6, FOSL1, LAD1, PRRG4, CD44, GAST, IDO1, KRT16P5, ULBP2, ULBP3, F11R, CCDC109B, CXCL11, RPS2P55, CLCA3P, CDK1, CDK2, CENPA, CTC-518P12.6, RP11-44F14.2, PRR11, CCR8, PABPC1, ESRP1, RP11-69G7.1, FGFBP1, PLEK2, GPR87, PROM2, CSF2, GYLTL1B, SPC25, ANXA2P2, LAMA3, LY6D, BBOX1-AS1, AMTN, RAB38, BDKRB1, RP11-483L5.1, TMPRSS4, ANO1, COL3A1, APOBEC3B, KLHDC7B, SLC2A1, SPRR2D, SPRR2A, SPRR2B, EDARADD, BNC1, CXCL10, LCE3D, LCE3E, CDCP1, EFNB1, TGIF1, GBP1, GBP6, GNGT1.
Kidney Chromophobe: RP11-2N1.2, RP11-215A21.2, KLK15, DNTT, CR1L, AC106869.2, AC005255.3, RP4-791C19.1, RP11-459C13.1, NCOA7-AS1, PSG9, KRTAP5-3, RP11-40C6.2, RP11-1E11.1.
Kidney Clear Cell Carcinoma: AP000439.3, RP11-283G6.5, FABP7, RP11-2L8.1, RP11-40C6.2, AC114803.3, RP11-10G12.1, LDHAP7, PI4K2B.
Liver Hepatocellular Carcinoma: GPC3, RP11-334L9.1, RRM2, FAM111B, RP11-215A21.2, FTH1P20, AC005255.3, KIF4A, UBD, ALG1L, SPC24, RP11-40C6.2, RP11-10G12.1, PIGY, CTC-518P12.6, RP11-556E13.1, ACSL4, CXCL10.
Lung Adenocarcinoma: IGKV1-12, RP11-229P13.23, RP5-940J5.9, HMGB3, RP11-334L9.1, HS6ST2, RRM2, LRRC15, FAM111B, RP11-93K22.13, EPCAM, RP11-649E7.5, RP11-350J20.12, AC005255.3, CST1, HMGN2P17, UHRF1, EPYC, KPNA7, BPIFA1, KIF4A, AGR2, ARAP1-AS1, MMP1, UBD, CASC9, RP3-407E4.4, MMP11, MMP12, MMP13, ALG1L, KRTAP4-1, ETV4, PAEP, UBE2C, YWHAZP4, DSG2, RP11-40C6.2, SGPP2, RP11-10G12.1, KIAA0101, CTHRC1, LDHAP7, IL22RA2, RP1-241P17.4, MCM10, RP11-579D7.2, SMPDL3B, RP3-340N1.2, COL10A1, E2F8, PYCR1, RPS2P55, CENPA, CTC-518P12.6, PRR11, LGSN, HTR3A, CEACAM5, AFAP1-AS1, FEZF1-AS1, MEX3A.
Lung Squamous Cell Carcinoma: ARTN, FAM64A, RP11-229P13.23, ADAM12, CCNA2, RP11-397A16.1, RP5-940J5.9, HMGB3, BMP7, RP13-463N16.6, CEP55, TP63, FERMT1, PTHLH, RRM2, PVRL1, TICRR, NEIL3, LRRC15, FAM111B, CHRNA5, FOXM1, CDCA7, RP11-215A21.2, MAD2L1, RP11-649E7.5, RP4-594A5.1, RAD51AP1, CDT1, CST1, IGFBP2, UHRF1, AURKB, ZP3, KRT17, KRT16, AF127577.8, COL11A1, RP11-108M12.3, IGHV1-69, KIF4A, HIST1H3G, ABCA13, MMP1, UBD, CASC9, CLCA2, KIFC1, PARPBP, RP11-161I6.2, TK1, KIF18B, ERCC6L, AC011288.2, MMP10, MMP11, MMP12, MMP13, ALG1L, CKAP2L, KIF14, KIF11, IGF2BP3, CTD-2008L17.1, HMGA2, RP11-8L2.1, FAM83H-AS1, KRTAP4-1, SDC1, MIXL1, CENPI, CENPF, MELK, S100A7A, ETV4, AC005537.2, SPC24, RP11-742B18.1, ADH7, RP11-510J16.5, TPX2, S100A2, KIF23, RP11-69L16.6, RP11-408B11.2, ARNTL2, ADAMTS20, KIF20A, MKI67, HAS3, UBE2C, UBE2T, BIRC5, CCAT1, KC6, YWHAZP4, ARHGAP11A, ASPM, DSG2, RP11-40C6.2, CDKN2A, MCM4, MCM2, CCNB1, RP11-10G12.1, KIAA0101, CTHRC1, LDHAP7, SNRPEP2, AKR1C2, NXPH4, IL22RA2, EXO1, E2F7, TP73, CDH3, ECT2, RP1-241P17.4, SOX2, NUSAP1, MCM10, MYBL2, C16orf74, PIGY, TGIF2-C20orf24, COL10A1, E2F8, PAPD7, PTGFRN, CDC6, RP11-499F3.2, BIK, GAST, RPS2P55, CDK1, CENPM, CENPA, ANLN, CTC-518P12.6, SLAMF9, CTC-480C2.1, PRR11, RP11-657O9.1, CHEK1, GINS4, CYP2S1, GPR87, GYLTL1B, SPC25, BBOX1-AS1, TMPRSS4, APOBEC3B, SLC2A1, EDARADD, NTS, FEZF1-AS1, SAPCD2, MEX3A, GBP6, GNGT1.
Ovarian Serous Cystadenocarcinoma: CKS1B, PHOX2A, KRTAP2-3, SRD5A3, NACC1, FAM64A, CNGB1, RP11-624M8.1, WNT10A, RP5-1065P14.2, CITED4, CRABP2, TTC30B, KLHL14, LDLRAD1, TUBA1C, RNU1-28P, HMGB3, AC144450.2, LYPD1, HIST1H1B, AC004870.4, CEP55, LGALS17A, PNOC, USP18, TNFRSF12A, SCNN1A, RRM2, RIPPLY3, MXRA5, IGSF9, BASP1P1, NEIL3, MESP2, FAM111B, RP11-93K22.13, FOXM1, CTC-513N18.6, ILDR1, PTH2R, KLK6, KLK7, KLK8, MAD2L1, SNORD17, C19orf33, EPCAM, RP11-649E7.5, RP11-350J20.12, AC005255.3, CHI3L1, MUC16, LRRN2, WNT7A, TMEM139, SCGB1D1, KRTCAP3, HIST1H4C, HOXD1, S100A5, WFDC2, RNU1-27P, GLOD5, RPS26P47, LAPTM4B, PGAM1P4, SNORD15B, RAD51AP1, CDT1, CST1, CST5, PART1, STON2, OXGR1, PHLDA2, CDR2L, MSLNL, AC012123.1, RHPN2, RNVU1-18, CCL20, GAL3ST2, TMEM102, KRT8, RP11-806H10.4, TMEM189-UBE2V1, AURKB, RMRP, KRT18, AF127577.8, RN7SL138P, FAM83H, SCGB2A1, FAM84B, LSR, KIF4A, AGRN, RP11-710M11.1, LPAR3, HIST1H3B, HIST1H3G, CMPK2, ATP5J2, VTCN1, MMP7, CASC9, FGF18, TLCD1, SCARNA7, KIFC1, PARPBP, TK1, MSLN, CELSR2, CELSR1, CCDC167, THEM6, RP11-608O21.1, RP11-565P22.6, RP11-565P22.2, KIF18B, ERCC6L, XPR1, HUNK, SBK1, KCNK15, RHPN1-AS1, SNORA12, ARL4C, GALNT6, GALNT3, KIF11, RP11-3K16.2, SPINT1, HMGA2, HMGA1, RP11-283G6.3, RP11-283G6.5, RP11-3J1.1, LYPD6, IFI27, EYA2, HOXB2, HOXB7, HOXB4, NR2F6, FAM72B, AC007389.3, ST8SIA2, PCDH1, NPW, CENPF, RP11-688G15.3, MELK, XAGE2, RTP4, SPON1, ETV4, THSD4, SNORA73B, TMC4, AC005537.2, SPC24, C10orf91, C10orf95, RP11-349N19.2, PARD6B, SNORA47, TPX2, RP11-429J17.7, FOXJ1, RP11-13K12.5, BRI3BP, ZNF695, IFI6, CRIP1, CCNE1, UNC5B-AS1, RP11-408B11.2, RPPH1, PAEP, C1orf233, C2orf48, FAM103A2P, KIF20A, MKI67, RP11-90O23.1, ARSH, CXCL9, RCC2P6, UBE2C, UBE2T, F8A1, HIST1H2BH, VAMP8, RP11-468N14.13, C1orf186, FOLR1, EPHX4, RNU4-2, RNU4-1, UCP2, OVOL2, LRRC55, AP1M2, TLR8-AS1, CDKN2A, CCL7, CCL8, MCM2, SGPP2, ZBTB42, RASSF10, CCNB1, TPD52, LAMC2, SOX17, C2orf15, KIAA0101, C9orf16, CRB2, HPDL, CTD-3051D23.4, CXXC5, CTHRC1, NXPH4, KREMEN2, LRRTM1, CDH6, TREM2, ECT2, ST14, MAL2, CD9, NUSAP1, UPK3B, MCM10, MYBL2, TGIF2-C20orf24, ATP6V1B1, RP11-579D7.2, PIGY, SMPDL3B, HIST1H2AM, ZDHHC12, COL10A1, E2F3, E2F8, RAB42, PAPD7, OAS1, OAS3, OAS2, ISG15, CLDN3, CLDN4, CLDN6, CLDN7, RP11-499F3.2, BIK, CMTM7, RP3-508I15.18, VCAN-AS1, RP11-27M24.1, IDO1, GRB7, TMEM238, KDELR3, CXCL11, GS1-184P14.2, CDK1, CENPA, NHLRC1, PRR11, PRR7, GJD3, FOXI3, OBP2A, RP11-657O9.1, ESRP1, RP11-231N3.1, ABHD11, RNU1-1, SAMD12, SAMD10, RP1-80N2.3, IQGAP3, GYLTL1B, SPC25, HTR3A, BHLHE41, LY6E, BBOX1-AS1, DOK5, FUT8-AS1, KRT87P, TMPRSS3, BCAM, CXCL10, VGLL1, CLDN16, SAPCD2, RP11-323N12.5.
Pancreatic Adenocarcinoma: ITGA2, GCNT3, LIF, ADAM12, LAMB3, TIMP1, RP5-940J5.9, RP13-463N16.6, CTSE, STRA6, RRM2, MXRA5, ITGB6, HLA-DRB6, LRRC15, FAM111B, KLK6, SFRP2, COL1A2, COL1A1, CEMIP, C19orf33, CCL17, WNT7A, CGB8, CGB5, NREP, F2RL2, S100A6, RP11-350J20.12, LCN2, AC005255.3, S100A10, CST2, CST1, CST4, PLAU, PLAT, PHLDA2, IGFBP3, VILL, KCNK1, CCL20, CCL22, SULF1, FNDC1, MATN3, EPYC, GABRP, KRT19, COL11A1, LY75, ONECUT3, KPNA7, RP5-907D15.4, KIF4A, TMSB10, AGR2, F2R, CTD-2357A8.3, ARAP1-AS1, MMP7, MMP1, KIF26B, UBD, CASC9, FGF19, APOL1, COL5A2, COL5A1, DUOXA2, MSLN, ZPLD1, RP11-334E6.12, MMP10, MMP11, MMP12, MMP13, GALNT5, IFI27, ADAMTS12, RP11-400N13.3, OLFML2B, PMCH, MDFI, UGT1A10, GRP, TMC5, BMP4, CTB-191K22.5, GRIN2D, B3GNT3, HLA-DRB5, SLC44A4, LUM, IFI6, KERA, LY75-CD302, UBE2MP1, MKI67, POSTN, CXCL5, CXCL9, UBE2C, CCAT1, YWHAZP4, EPSTI1, TNFSF11, TNFSF18, HLA-DPB2, NPSR1, RP11-40C6.2, RP5-884M6.1, SGPP2, P4HA3, LAMC2, ZNF469, RP11-10G12.1, CTHRC1, TNFRSF6B, FXYD3, WISP1, IL22RA2, CD1B, TREM2, INHBA, PIGY, TGIF2-C20orf24, RP11-579D7.2, TABLE 2-continued Cancer signatures RP11-626H12.1, COL10A1, OAS1, ISG15, CLDN2, BIK, EDAR, FOSL1, CTC-518P12.6, PRR11, CCR8, PLEK2, RP11-462L8.1, CSF2, SYT13, ANXA2P2, LAMA3, CCL19, MYEOV, TRIM31, TMPRSS4, ANO1, COL3A1, CEACAM5, CEACAM6, HTRA3, CXCL10, AFAP1-AS1, FEZF1-AS1, DIAPH2-AS1.
Pheochromocytoma & Paraganglioma: CHST1, PHOX2A, PHOX2B, SEZ6L, BEX1, SLC18A2, SLC18A1, SYT1, SYT2, SYT4, SYT5, CNGB1, UNC5B, VGF, UNC5A, PCSK2, DYNC1I1, ASTN2, PCDHAC2, PCDHAC1, H2AFY2, FAIM2, RP5-940J5.9, AC005944.2, DCX, FLRT1, RP11-334L9.1, BMP7, RP11-124O11.1, RP11-294J22.6, HAND2, PENK, TMEM35, DLX1, DLX2, STRA6, HS6ST2, FAM163A, HAND2-AS1, SMIM18, EPHA8, GLB1L3, TH, CRYBA2, RIPPLY2, C18orf42, CHRNA5, CHRNA7, CHRNA3, PRPH, GDAP1, IGF2, PCDHA11, PCDHA13, RP11-64K12.4, ISL1, LRRN2, TMEM130, AC106869.2, DRD2, MAGEE2, SLC29A4, RP4-607I7.1, CDH18, PCSK1, NPBWR2, FAM163B, RCOR2, RTBDN, TPBGL, GCH1, BSCL2, ADGRA1, SV2C, GPR19, RP4-555D20.4, HDAC9, GABRB3, C14orf132, KCNK9, TMEM132D, LRRC4C, NACAD, TFAP2B, VAX2, RP11-148L24.1, IL13RA2, HS3ST2, ROBO2, RP11-256P1.1, CPE, CHRFAM7A, GNG4, GNG8, RAB39B, GABRQ, MMD, SLC24A2, ARAP1-AS1, HMP19, FBLL1, SCN3A, SCN3B, AMER3, RP11-161D15.3, KIF26A, SEZ6L2, FGF14, SLC8A2, FAM19A3, CACNA2D3, REEP2, FEV, DISP2, KCNH5, KCNH1, KCNH2, MYCN, RP11-334E6.12, NTNG1, GPR176, UCHL1, CDH22, PRCD, RP11-1018N14.5, GALNT6, NEUROD4, NEFM, NRG1, RGS4, DBH, CYGB, RP11-445N20.3, RP11-8L2.1, ST8SIA3, ST8SIA2, SNAP25-AS1, NPY, AP006547.3, CDK5R2, SLC10A4, INA, MFI2, CHRNB2, CHRNB4, TCEAL7, ATP1A3, BEGAIN, PTCHD4, CPLX2, GALR1, RP11-588K22.2, FAM155A, DBN1, B3GNT4, GNAS, SHF, RP11-272L13.3, DRGX, NEFL, UBE2MP1, GLRA1, ALCAM, TUB, NALCN, CACNG2, RP11-248N22.1, ARSF, RET, RP11-12M5.3, GPR22, KCNMB2, CARTPT, ATP1B1, TLX2, TLX3, TUBB3, CHGA, CHGB, RP11-40C6.2, L1CAM, LMO1, MARCH4, TIAM1, VSTM2L, VSTM2A, OPRD1, IPO8P1, KCNB2, KCNB1, CNTNAP5, GNAS-AS1, GPR158, RP11-10G12.1, RAB15, INSM2, INSM1, GFRA2, NXPH4, CTB-158E9.1, CD200, IGF2-AS, LRRTM4, SCG5, SCG3, SCG2, PROKR1, RP1L1, SLC6A2, SPOCK2, SPOCK3, C2orf91, EGFLAM, MLLT11, MYT1, RP11-662M24.2, CAMK4, HMGCLL1, IGFBPL1, NTRK1, PRLHR, PCLO, RP11-579D7.2, NDUFA4L2, TANC2, ELAVL4, GPR162, CTD-2562J17.4, ACOT7, SLC35D3, IL1RAPL2, PTPRN, PCDHB10, TMIE, KIAA2022, STAC, ESM1, PAK3, KCNG4, RP11-21A7A.3, RP11-21A7A.2, HCN1, SCRT2, CYB561, SYP, FAM162B, RP11-269G24.4, MYH15, PLCB4, PRRT4, PCBP3, C1QL1, INSRR, NPFF, TAGLN3, GJD2, TMEM179, PTPRN2, TMEM169, GPR83, TMEM114, KIAA1614, CNTN1, MRAP2, RP11-21A7A.4, GATA2, CXXC1P1, RTL1, RASD2, DOK5, RAB3C, PIRT, PPP1R17, ATCAY, RP11-379F12.4, GRID1, DPP6, DGKK, STMN2, RD3, MGAT4C, MCHR1, DDC, BMPR1B, ARC, APLP1, SLC7A14.
Prostate Adenocarcinoma: GCNT1, RP11-170M17.1, PLA2G7, PCAT1, RP11-229P13.23, WI2-85898F10.1, AC144450.2, DLX1, DLX2, RP11-215A21.2, AMACR, MINOS1-NBL1, TMEFF2, AP006748.1, NPY4R, PODXL2, HMGN2P17, ACSM1, UBD, TRPM8, AC000089.3, TMSB15A, TRGC1, XXbac-BPG308K3.5, MMP10, RPL7P16, LUZP2, RP11-1084J3.3, RP11-40C6.2, VSTM2L, RP11-10G12.1, ABCC4, PIGY, RP11-579D7.2, COL10A1, CLDN8, CXCL11, RPS2P55, DNASE2B, GDF15, GOLM1, PCA3, AP001610.9, SIM2, RP11-483P21.2.
Rectum Adenocarcinoma: POU5F1B, GCNT1, RP11-357H14.17, FAM64A, CHMP4C, RP11-229P13.23, SKA3, LAMB3, GPR143, LY6G6D, RBBP8NL, HMGB3, SEL1L3, CKMT1A, BCL2L15, CEP55, ATP10B, TRABD2A, TDGF1, PRSS33, FERMT1, CDH17, RRM2, RIPPLY3, KRT8P45, NEIL3, MAP7, FAM111B, RP11-93K22.13, ILDR1, CDCA7, RP11-215A21.2, MAD2L1, CEMIP, EPCAM, RNF128, ANKS4B, PPP1R14D, VWA2, MUC13, KRTCAP3, CKAP2, HKDC1, F2RL1, RP11-649E7.5, AP000439.3, AC007099.1, NOX1, AC005255.3, CLRN3, PRSS8, RAD51AP1, CDT1, CST2, CST1, ATP2C2, PHLDA2, EREG, RHPN2, CCL20, GAL3ST2, KRT8, HMGN2P17, UHRF1, AURKA, AURKB, ZP3, MET, KRT18, ABHD17C, LY75, KPNA7, FAM83H, FAM84A, GMDS, LSR, KIF4A, AGR2, MAPK13, PRR15L, FUT3, MMP1, UBD, CASC9, FGF19, TLCD1, NOS2, KIFC1, SQLE, PARPBP, TMEM45B, TK1, LRRC31, CCNF, AC000089.3, KIF18B, ERCC6L, FAM150A, RP11-150O12.3, RP11-150O12.6, MMP10, MMP11, MMP12, KIAA0226L, GGH, GALNT4, GALNT5, GALNT6, GALNT3, KIF11, ASCL2, HMGA1, C6orf222, C6orf223, PLS1, AREG, GRM8, HOXB9, AMELX, MARVELD2, KRTAP4-1, ENC1, CENPF, MACC1, EPHB2, MELK, GPA33, SPAG1, CASC21, RP11-151F5.2, ETV4, LGALS4, CTB-191K22.5, GRIN2D, KRT8P48, B3GNT3, FAM72D, SLC44A3, SLC44A4, TPX2, MISP, LGR5, BRI3BP, LY75-CD302, VIL1, TMEM211, MKI67, GUCY2C, NOTUM, CXCL3, CXCL9, UBE2C, UBE2T, CCAT1, YWHAZP4, ARHGAP11A, TNFSF11, ASPM, EFNA4, CBLC, AP003774.1, RPL36A-HNRNPH2, EPHX4, DSG2, RP11-40C6.2, RNF43, AP1M2, PRR15, MCM2, VDR, FAM105A, PPP1R1B, BLM, RP11-187E13.1, CCNB1, LAMC2, RP11-10G12.1, NOXO1, KIAA0101, DACH1, CRB3, HPDL, TRIM15, LDHAP7, AL163953.2, FXYD3, EXO1, RXFP4, RP11-284F21.7, CDH1, RP11-22L13.1, ABRACL, ECT2, ST14, NFE2L3, SRMS, SOX9, MAL2, NUSAP1, PLEKHG6, MCM10, MYBL2, HNF4A, TGIF2-C20orf24, USH1C, RP11-480I12.5, COL10A1, E2F8, PYCR1, GPR160, CXADR, CDX1, CDX2, CDC6, CLDN3, CLDN4, CLDN7, BIK, EDAR, AC123023.1, TMEM238, CXCL11, RPS2P55, CDK1, CENPA, ANLN, RP11-44F14.2, PRR11, CCR8, RP1-276N6.2, ESRP1, CYP2S1, PLEK2, TRIM31-AS1, FOXP4-AS1, AC021218.2, TOX3, IQGAP3, MYB, SPC25, RP5-881L22.5, IHH, TSPAN8, BBOX1-AS1, MYEOV, ACSL5, TRIM31, TFF3, TMPRSS4, CEACAM1, CEACAM5, CEACAM6, ARHGEF35, STX19, CXCL10, SATB2, GPR39, GPR35, GPX2, CDCP1, SAPCD2, MEX3A, MYO5B, DDC.
Skin Cutaneous Melanoma: PHACTR1, FAM64A, RP11-229P13.23, TRIM51, GPR143, TSPAN10, TYR, RP11-221N13.3, RP5-940J5.9, AC005592.2, PLOD3, NRP2, HSPA8P1, PIR, RRM2, ABCB5, FAM111B, CHRNA6, RP11-215A21.2, PLA1A, ST3GAL6-AS1, CTNNAP1, WARS, RP11-1055B8.3, SLC6A15, ATP6V1B1-AS1, PMEL, PLAT, BANCR, H2AFZP3, CCDC148, RP11-1055B8.2, EDNRB, LGALS3BP, KIF4A, AC144835.1, PRAME, SLC7A5, AP1S2, UBD, MAGEA12, RP11-1070A24.2, BAMBI, RHPN1-AS1, SNX10, EN2, SDC3, CENPF, TRIB2, RPN1, ITIH6, ETV1, ETV5, ETV4, ZNF697, IFI6, NES, CD63, CA14, RP11-104E19.1, GAPLINC, RP11-599J14.2, TRPV2, CXCL9, AC004988.1, BIRC7, FMN1, CTD-2380F24.1, YWHAZP4, STEAP1B, PAX3, CTD-2207A17.1, RP11-40C6.2, BLM, SERPINE2, SOX10, MITF, BACE2, RP11-10G12.1, KIAA0101, MAGEA3, MAGEA6, LDHAP7, EXO1, RHOQP2, TREM2, FAM167B, RENBP, PIGY, TGIF2-C20orf24, MAGEA2, RP11-94H18.1, PKNOX2, RLBP1, TMEM229B, IL12RB2, PAPD7, CDC6, IRF4, HMCN1, KDELR3, GDF15, LEF1, SLC45A2, MIA, LZTS1, PRR11, RGS20, ST3GAL4, GYG2, CSAG3, CSAG2, MLANA, TBC1D7, CNIH3, DUSP4, DUSP6, CXCL10, ALX1, SLC24A5, LHFPL3-AS1.
Stomach Adenocarcinoma: ITGA2, GCNT3, RP11-357H14.17, FAM64A, CCNA2, SKA3, BIVM-ERCC5, RNU1-28P, HIST1H1E, HIST1H1B, CEP55, ATP10B, FERMT1, RRM2, TICRR, MXRA5, NEIL3, FAM111B, RP11-93K22.13, FOXM1, ILDR1, CDCA7, MAD2L1, SNORD17, COL1A1, AC012363.4, RP11-421E14.2, ALPPL2, MUC13, RSC1A1, CKAP2, HIST1H4C, F2RL2, SND1-IT1, LCN2, RNU1-27P, RPS26P47, S100A10, RP4-594A5.1, RAD51AP1, CDT1, CST2, CST1, CST4, PHLDA2, RNVU1-18, CCL20, CCL22, GAL3ST2, HSP90AB4P, TMEM189-UBE2V1, UHRF1, AURKB, RMRP, ONECUT2, KIF4A, CALML4, AGR3, HIST1H3G, UBD, CASC9, SCARNA7, RAET1E-AS1, FOXP3, PARPBP, TK1, CCNF, KIF18B, ERCC6L, RP11-709A23.1, MMP11, MMP12, KIF14, KIF11, ASCL2, PLS1, ADAMTS12, FAM72B, MRPL37P1, CENPF, CENPE, MACC1, EPHB2, MELK, ETV4, GRIN2D, FAM72D, TPX2, MISP, RP11-616K22.1, ZNF695, IFI6, LY75-CD302, MDK, CTB-181H17.1, SGOL1, RPPH1, KCNE3, RP11-404E16.1, KIF20B, KIF20A, MKI67, RP11-90O23.1, CXCL9, UBE2C, UBE2T, HIST1H2BL, CCAT1, NDUFC2-KCTD14, TNIP3, EPSTI1, ARHGAP11A, TNFSF11, ASPM, POU5F1P4, EFNA2, NPSR1, RNU4-2, CCL7, MCM2, BLM, CCNB1, LAMC2,

TABLE 2-continued

Cancer signatures

KIAA0101, AC010761.10, CTHRC1, TRIM15, IL22RA2, EXO1, RP11-284F21.7, TREM2, ECT2, SLC7A5P2, SRMS, INHBA, NUSAP1, FU42393, MCM10, MYBL2, FPR3, HIST1H2AM, RP11-626H12.1, RP11-480I12.5, COL10A1, PAPD7, OAS1, OAS3, CDC6, CLDN3, CLDN4, CLDN7, EDAR, RP3-508I15.18, RP11-157K17.5, RP11-27M24.1, TMEM238, CXCL11, GS1-184P14.2, CDK1, STIL, CENPA, ANLN, RN7SL4P, PRR11, PRR7, GJD3, CCR8, ZNF460, RNU1-1, CHURC1-FNTB, IQGAP3, MYB, SPC25, LY6E, BBOX1-AS1, MYEOV, ZNF724P, TRIM31, TMPRSS4, DEPDC1B, CEACAM5, CEACAM6, ESCO2, CXCL10, FEZF1-AS1, SAPCD2, TNFRSF11A, RP11-323N12.5, ZNRF2P1.
Testicular Germ Cell Tumor: CHST2, ALPP, FAM64A, SYT2, GBX2, AC068134.6, PLA2G2D, SLC7A3, RP5-940J5.9, GLDC, ZFP42, TUBA1C, PQLC3, CTC-260E6.6, PRDM14, MAN1C1, CPXM1, TDGF1, RRM2, AICDA, PMAIP1, TEAD4, VRTN, RP11-215A21.2, PRDM1, MRPL15, NANOGP1, ALPPL2, NANOG, CGB8, CTC-260E6.2, NKX1-2, ZSCAN10, SALL4, HIST1H2AJ, CCR5, CXCR3, KLRG2, TUBB, PHLDA3, BTBD6P1, RP11-148B6.2, CCL26, FOXH1, DACT2, TFAP2C, AURKB, TBPL2, SNHG16, CRYGEP, LIN28A, RPRM, FZD5, RP5-1028K7.2, DLG3, UBD, CASC9, MYCN, TK1, RPS7P11, ERCC6L, RP11-334E6.12, POU5F1, MMP12, TXN, GALNT6, NLRP7, NLRP9, LOXL2, ECEL1P1, OTX2, TET1, ZNF486, AC007389.3, VENTX, MIXL1, MDFI, FBN3, ETV4, AC005682.5, BFSP2, MMP24, PDPN, RP11-13K12.5, SHD, MAGED4, DPPA3, DPPA4, DPPA5, MDK, MX1, RP11-408B11.2, KHDC3L, PRODH, RPL39, ARSI, CXCL9, SUSD2, LIM2, POU5F1P4, HLA-DPB2, RP11-40C6.2, TLR8-AS1, PHB2, DSTNP2, RP11-13K12.1, SOX15, RP11-10G12.1, RAB15, HPDL, FAM46B, BMF, GIP, CDH3, RPL41, NFE2L3, CD9, LDHB, MYBL2, AP000569.9, RP11-855O10.3, ZNF90, FPR3, RPL36A, DNMT3L, ISG15, SLC25A16, CLDN6, FAM124B, BICD1, SNRPFP1, TOR3A, CXCL11, RPS2P55, RP11-87G24.3, FAM162B, CENPA, SLAMF8, ESRG, PRR11, L1TD1, NPFF, FOXI3, CCR8, ESRP1, PPM1N, PPM1H, CYP2S1, GDF3, PIM2, GYLTL1B, CLEC6A, CCND2, RP11-253E3.3, NGEF, CCL19, TSPAN9, RPS4X, MLN, CXCL10, TRPC5, SAPCD2, MEX3A.
Thyroid Carcinoma: NPC2, LAMB3, CYSLTR2, CITED1, RP11-221N13.3, RP5-940J5.9, PSG1, SIGLEC15, TNFRSF12A, RPSAP52, LRP4, FAM111B, RP11-215A21.2, ZCCHC12, ZCCHC16, CCL17, AC018816.3, RP11-649E7.5, RP11-474O21.5, RP11-16K12.1, CST2, GABRB2, TGFA, HMGN2P17, MET, RP4-791C19.1, SLC27A6, LPAR5, DCSTAMP, SLC34A2, HMGA2, AC079630.2, AC079630.4, SDC4, RXRG, ETV4, PTCHD4, FN1, SLC25A47P1, ACTBL2, RP11-40C6.2, PRR15, RP11-542B15.1, AE000661.37, RP11-498C9.3, PDLIM4, RP11-10G12.1, CD1B, CDH3, TREM2, NELL2, PIGY, RP11-579D7.2, RPS2P55, RP11-230G5.2, DTX4, CTC-518P12.6, PNPLA5, CSF2, SYT12, DPP4, DUSP6, TRPC5, CLDN16.
Uterine Carcinosarcoma: FAM64A, C16orf59, WNT10A, CRABP1, CRABP2, CLUL1, RP5-940J5.9, HMGB3, RP11-334L9.1, PLAC1, HSPA8P1, RRM2, RIPPLY3, RNASEH2A, NEIL3, FAM111B, RP11-215A21.2, MAD2L1, MINOS1-NBL1, NREP, SLC29A4, CBX2, RCOR2, RAD51AP1, CDT1, RPL13AP20, HMGN2P17, VAX2, UHRF1, AURKB, KIF4A, PAFAH1B3, KIF26B, KIFC1, PARPBP, TK1, RP11-608O21.1, CCNF, KIF18B, ERCC6L, TMSB15A, MEST, SBK1, RHPN1-AS1, KIF14, KIF11, IGF2BP1, IGF2BP3, HMGA2, HMGA1, TRAF4, FAM72B, MIXL1, COL2A1, CENPF, EPHB2, MELK, MDFI, FBN2, FBN3, ETV4, RAC3, SPC24, TPX2, ZNF695, MDK, DLX4, CCNE1, C2orf48, FSCN1, KIF20A, MKI67, NOTUM, UBE2C, UBE2T, BIRC5, COL26A1, MFAP2, ASPM, ERVMER34-1, RP11-40C6.2, CDKN2A, RP11-360L9.7, NME1, MCM4, MCM2, BLM, AC079922.2, CCNB1, RP11-10G12.1, KIAA0101, CTHRC1, NXPH4, KREMEN2, EXO1, ECT2, RP1-241P17.4, NUSAP1, MCM10, MYBL2, E2F1, E2F8, PYCR1, CDC6, ESM1, RPS2P55, CDK1, CENPM, CENPA, DRAXIN, CTC-518P12.6, PRR11, RP11-657O9.1, CHEK1, GINS4, SPC25, MARCKSL1, BBOX1-AS1, HJURP, SAPCD2, MEX3A, GNGT1.
Uterine Corpus Endometrioid Carcinoma: RP6-65G23.3, FAM64A, C16orf59, RP11-638I2.6, RP5-940J5.9, RBBP8NL, HMGB3, RP11-334L9.1, AC004870.4, RP11-519G16.5, CEP55, DLX5, DLX6, RPSAP52, RRM2, RIPPLY3, KRT8P45, NEIL3, FAM111B, DLX6-AS1, ILDR1, RP11-215A21.2, MAD2L1, EPCAM, ALPPL2, OCIAD2, MUC16, WNT7A, KRTCAP3, HIST1H4J, SERINC2, FEN1, WFDC2, RP11-649E7.5, FTH1P20, PRSS8, CDT1, RHPN2, RPL13AP20, TMEM132A, KRT8, DACT2, HMGN2P17, UHRF1, AURKB, RP11-256P1.1, KRT18, RP11-108M12.3, RP11-465B22.3, SCGB2A1, LSR, KIF4A, ARAP1-AS1, RP11-710M11.1, HIST1H3G, VTCN1, PAFAH1B3, MMP7, UBD, CASC9, FGF18, TLCD1, KIFC1, TK1, CELSR1, RP11-608O21.1, CCNF, KIF18B, ERCC6L, SBK1, MMP11, MMP12, RHPN1-AS1, GALNT6, SPINT2, HMGA2, HMGA1, RP11-3J1.1, IFI27, EYA2, TRAF4, HOXB8, HOXB6, HOXB7, HOXB5, FAM72B, CENPF, MELK, ETV4, RP11-388M20.2, CAPS, SPC24, CTB-191K22.5, TECRP1, TPX2, LGR5, FOXJ1, ZNF695, IFI6, CCNE1, KIF2OA, MKI67, ARSH, UBE2C, UBE2T, BIRC5, HIST1H2BH, COL26A1, CA8, C1orf186, ERVMER34-1, RP11-40C6.2, OVOL2, AP1M2, PRR15, CDKN2A, RP11-360L9.7, NME1, MCM2, BLM, CCNB1, LAMC2, RP11-498C9.3, SOX17, RP11-10G12.1, KIAA0101, EXO1, CDH1, ABRACL, ECT2, ST14, PLEKHG4B, RP1-241P17.4, NUSAP1, MTFP1, MCM10, MYBL2, RP11-579D7.2, SMPDL3B, HIST1H2AM, E2F8, CXADR, CDC6, ISG15, CLDN3, CLDN4, CLDN6, IDO1, F11R, CXCL11, RPS2P55, STXBP6, CDK1, HAPLN1, CENPM, CENPA, CTC-518P12.6, CTD-2531D15.5, PRR11, AP001615.9, ABHD11, RNF183, GYLTL1B, SPC25, MARCKSL1, TMPRSS3, TMPRSS4, MAP2K6, CXCL10, SAPCD2, MEX3A, GNGT1.

Example 4

Analysis of Enhancer and Gene Body Marks

Figure 5C:
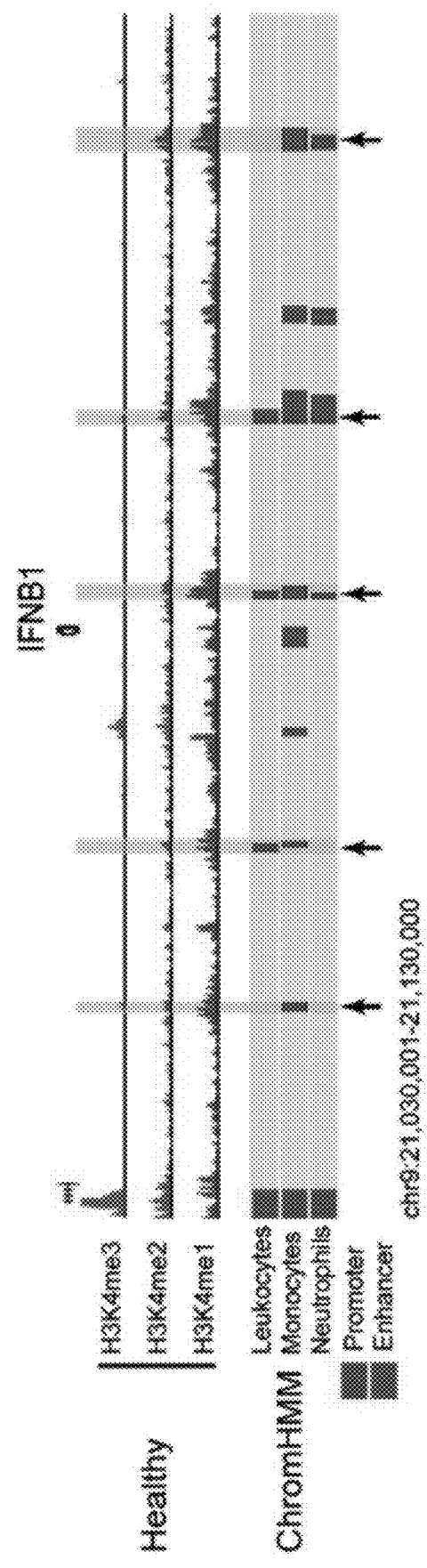
Figure 5D:
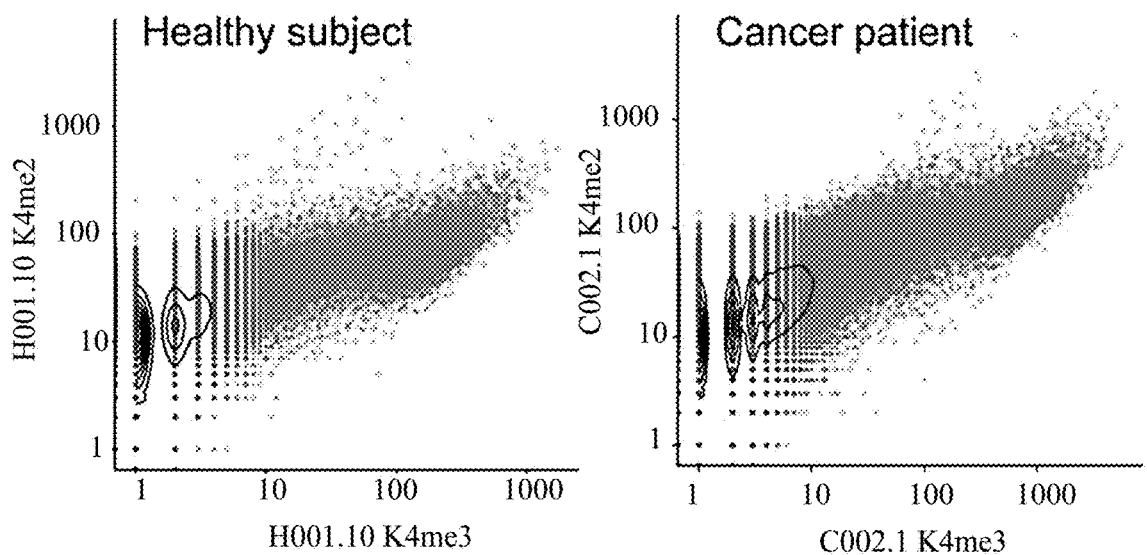

Our analysis of the active promoter mark H3K4me3 provided rich information regarding transcriptional programs in tissue of origin. Can we gain information from chromatin marks that are associated with enhancer and gene activity? Mono and di-methylation of H3 lysine 4 (H3K4me1 and H3K4me2, respectively) are found in two types of genomic regions: 1) promoter flanking regions at the boundaries of regions marked with H3K4me3, or 2) poised/active enhancers, where the H3K4me3 is barely detected. ChIP-seq for these marks in tissues shows H3K4me2 peaks in the near vicinity of enhancers, while H3K4me1 peaks are wider around enhancers (on the order of ~10 kb). cfChIP of these marks recapitulates the expected distribution: Around active promoters, the H3K4me2 and H3K4me1 flank the main H3K4me3 peak (FIG. 5A-B) and correlate with H3K4me3 and RNA level (FIG. 5D). Additionally, in gene-poor regions, such as the IFNB1 locus, we clearly see marks at enhancers, which match experimentally verified enhancers for IFNB1 (Banerjee et al. 2014) (FIG. 5C).

Figure 5E:
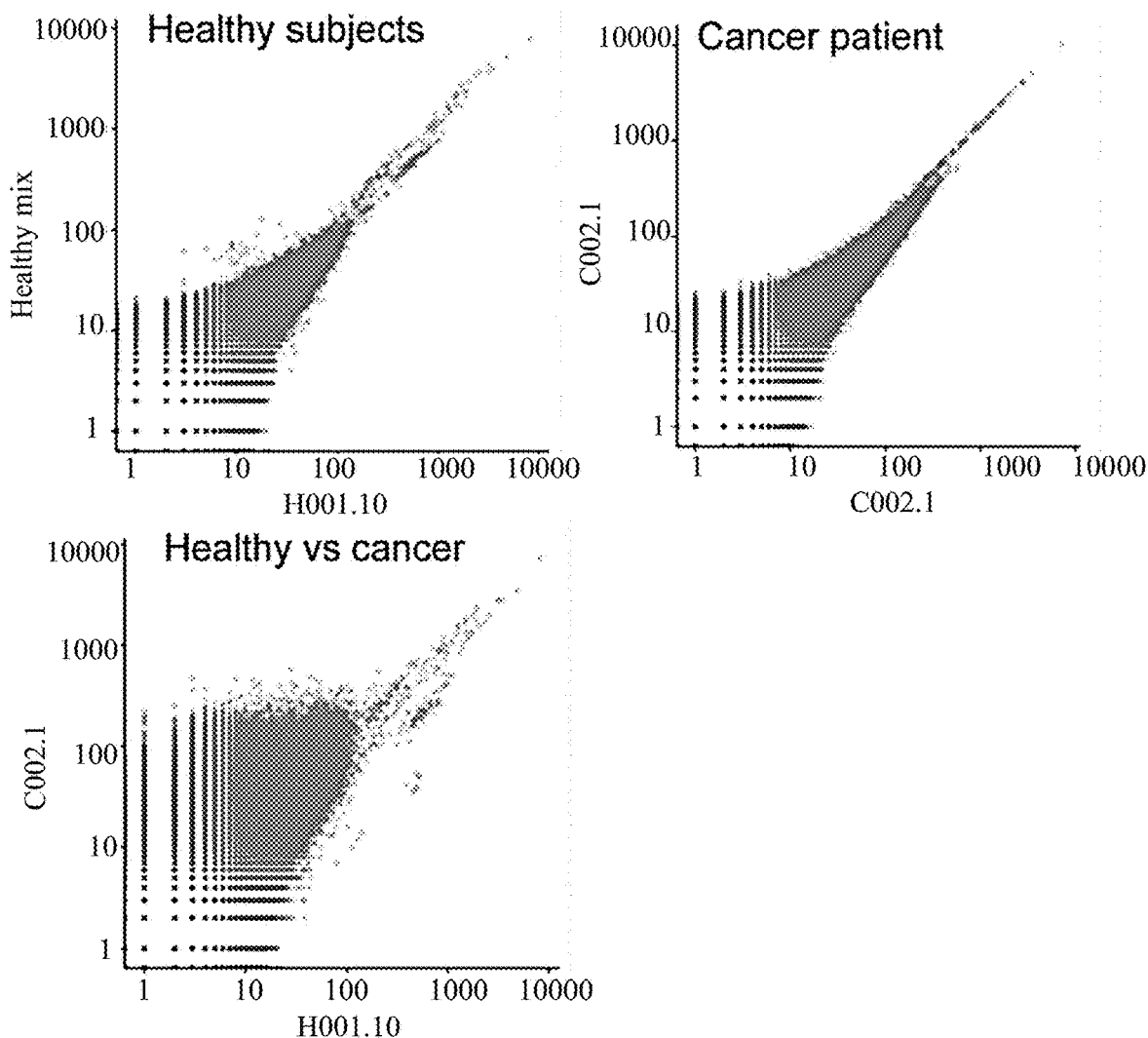
Figure 5F:
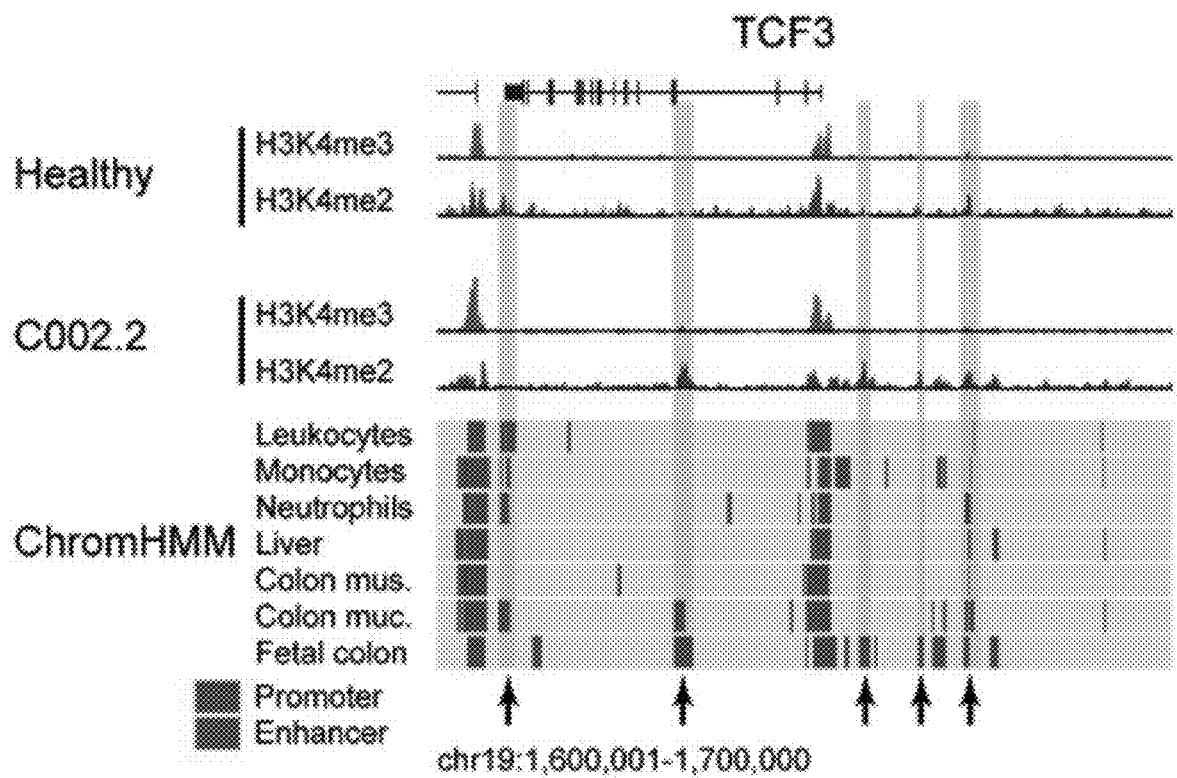
Figure 5G:
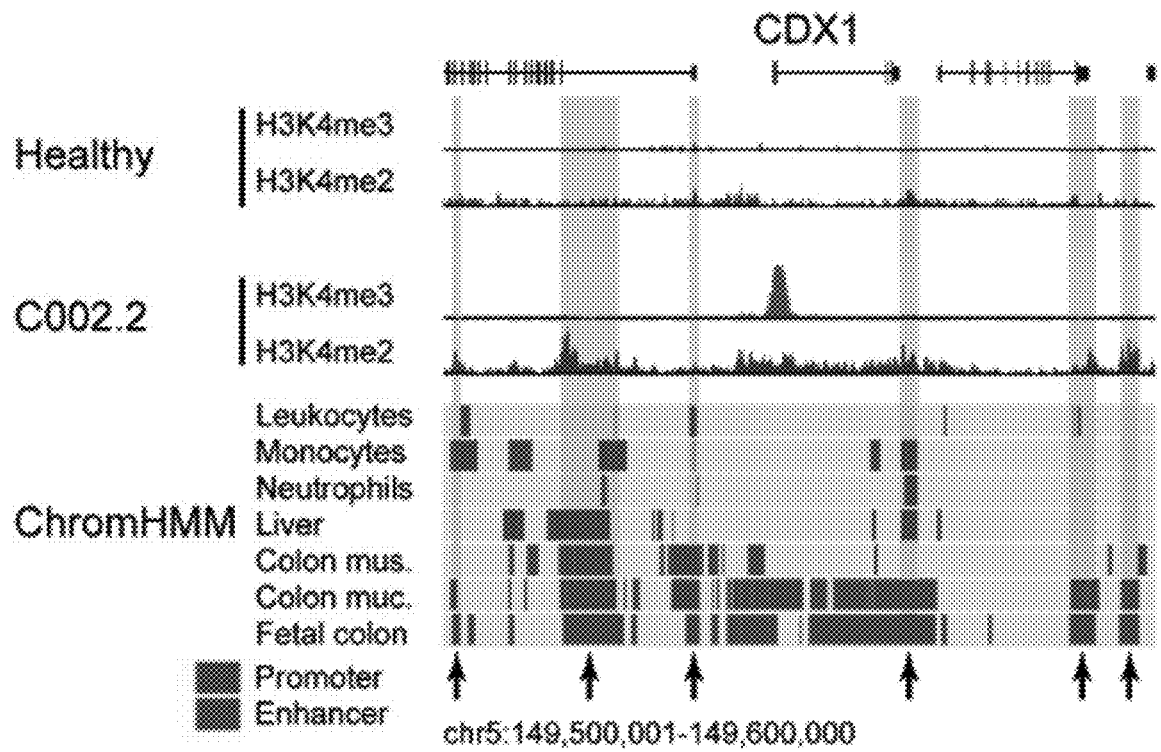
Figure 5H:
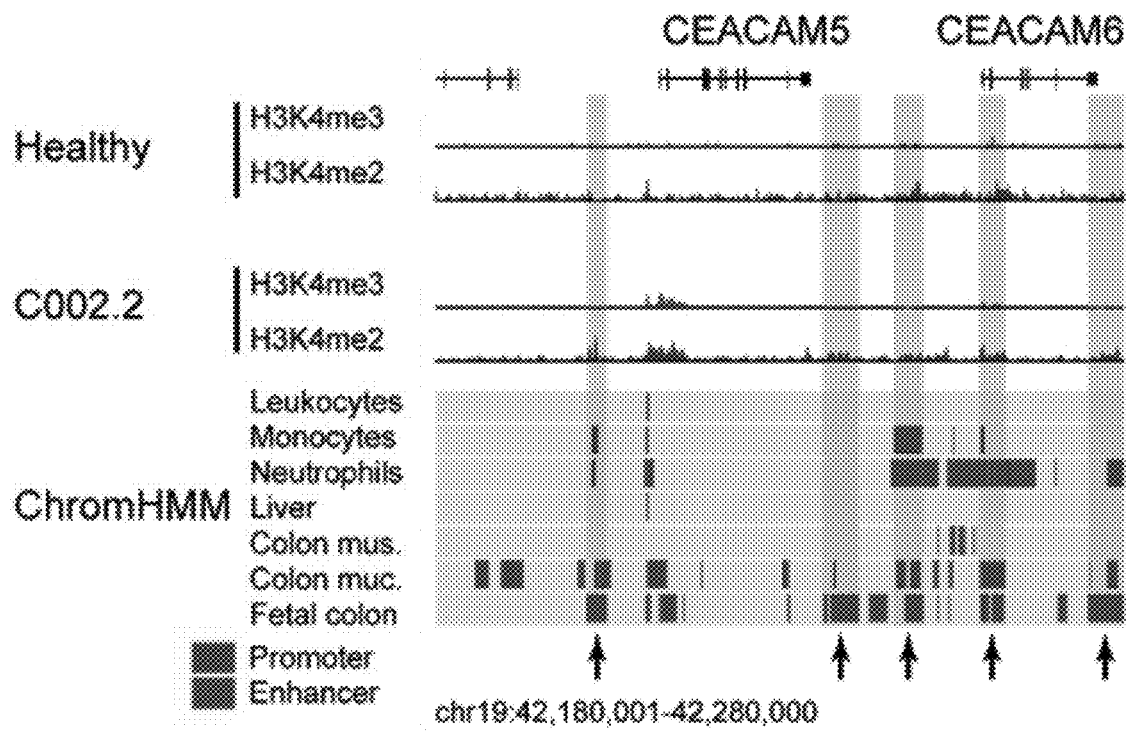
Figure 5I:
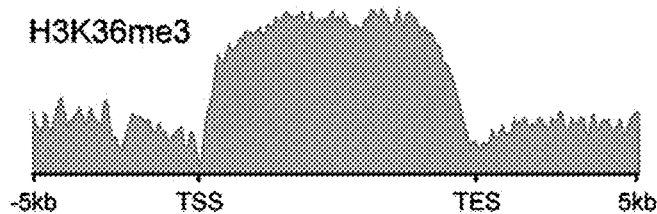

Since the H3K4me2 is more condensed and the signal between healthy subjects is highly similar (FIG. 5E) we chose to focus on this mark for enhancer analysis. To identify enhancers, we looked for H3K4me2 peaks that have low or no H3K4me3 signal. We identified 8,000 putative enhancer peaks in healthy subjects. Of these peaks >90% were at sites predicted to be enhancer regions based on five chromatin marks (ChromHMM) in multiple tissues. Moreover, there is a good agreement between these putative enhancer peaks and ChromHMM annotations in the relevant cell types, e.g., monocytes and neutrophils (FIG. 5C). Applying the same analysis to two samples from a colorectal cancer patient (C002.1 and C002.2) showed strong agreement between these samples with substantial differences from healthy subjects (FIG. 5E). The differences between healthy subjects and cancer samples illustrate the additional information that can be gained from enhancers over promoter signatures. A few examples for cancer-specific enhancers signals include TCF3, CDX1, and CEACAM5 (FIG. 5F-H). The transcription factor TCF3 has promoter H3K4me3 signal in every subject tested. However, the enhancer activity marks in the vicinity of the gene are strikingly different, with the cancer samples showing clear H3K4me2 peaks in regions that correspond to putative colon enhancers (FIG. 5F). These results suggest that the gene is activated by different enhancers in the cells that contributed this signal and are consistent with the patient's clinical condition (FIG. 4A-G). A subset of the H3K4me2 peaks around TCF3 are not observed in adult colon but only in fetal colon, consistent with de-repression of fetal oncogenes. The intestine-specific transcription factor CDX1 does not have H3K4me3 signal in healthy subjects. In the cancer sample it has a clear signal. This activity is accompanied by H3K4me2 peaks over large GI-specific enhancer regions in the vicinity of the gene (FIG. 5G). This suggests that CDX1 is activated through these enhancers. Finally, examining the CEACAM5 locus a more complex picture emerges (FIG. 5H). CEACAM5 has H3K4me3 signal at its promoter in the cancer sample. This is accompanied by a signal in GI-specific enhancers. However, in healthy subjects there is a strong H3K4me2 signal in a neighboring enhancer/promoter region. This suggests that some of these enhancers might be involved in repression of CEACAM5 in monocytes and neutrophils.

Figure 5J:
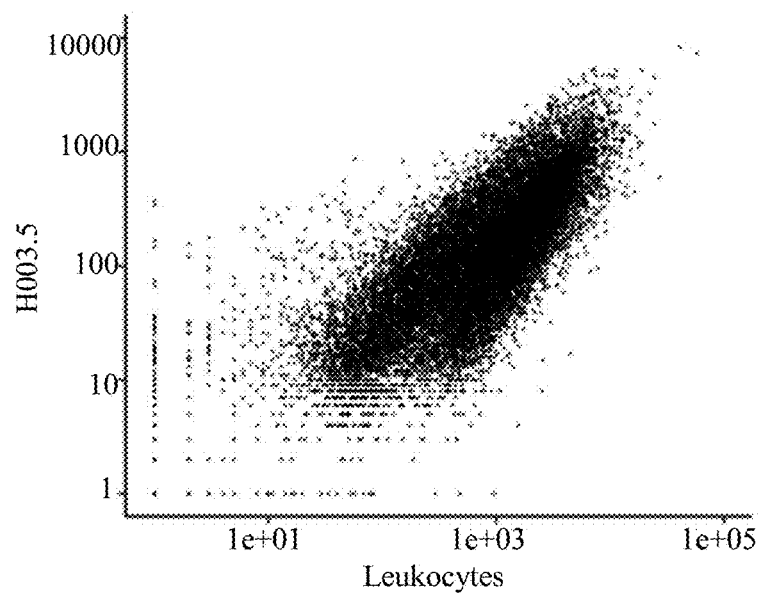
Figure 5K:
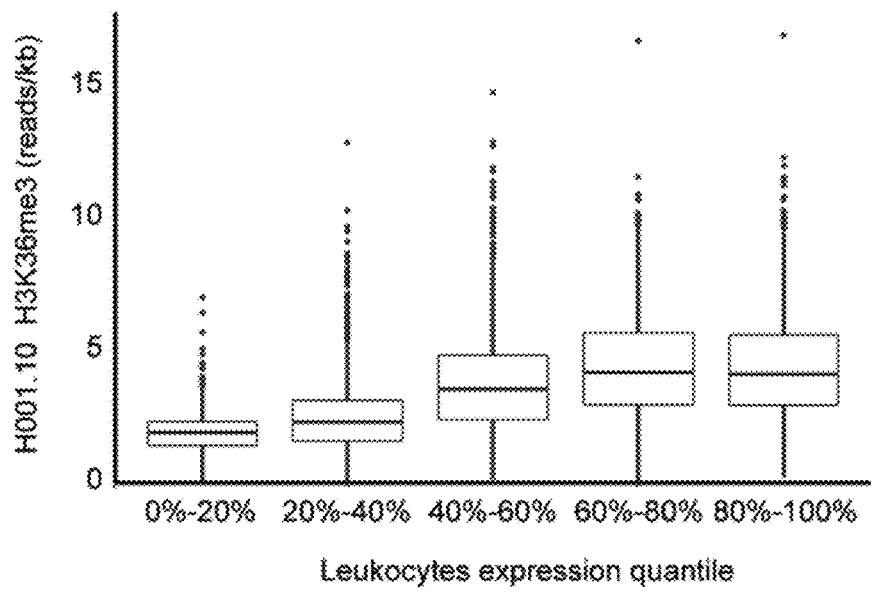
Figure 5L:
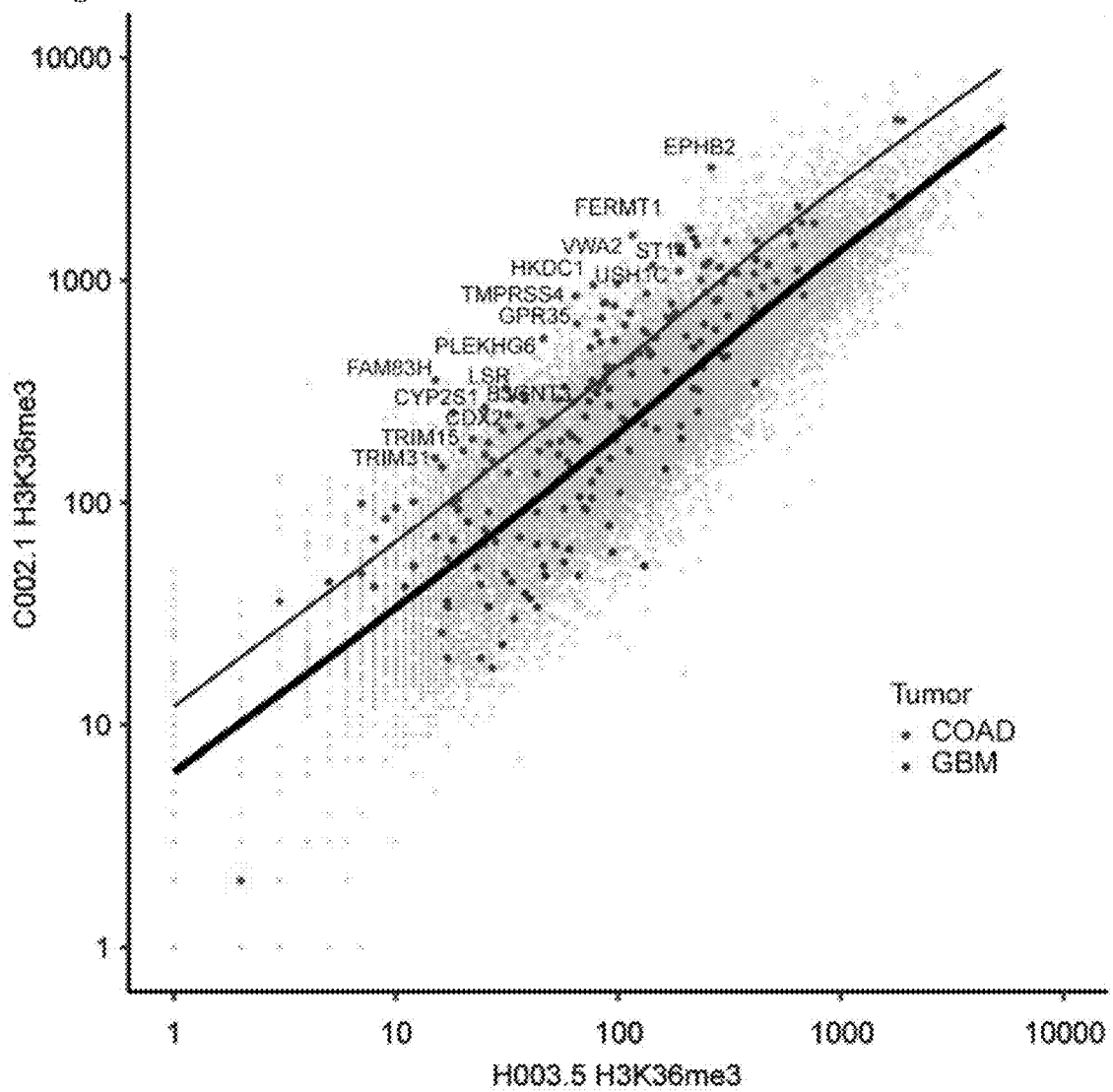
Figure 5M:
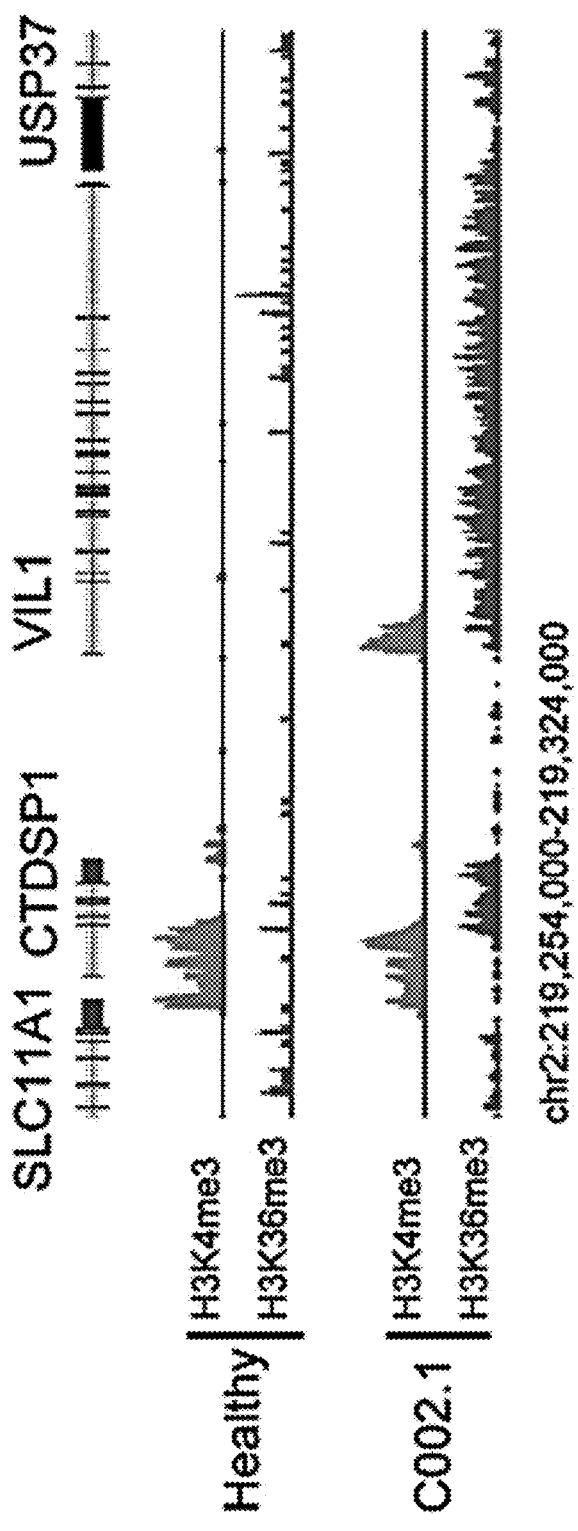

Tri-methylation of H3 lysine 36 (H3K36me3) is found at the body of transcribed genes. Unlike H3K4me3, which marks transcription start sites at both poised and active genes, H3K36me3 requires active transcription elongation to be deposited, and is hence more indicative of gene activity. cfChIP of H3K36me3 results in a typical enrichment at gene bodies (FIG. 5H) and the signal is in correlation to leukocyte H3K36me3 and RNA-seq (FIG. 5J-K). Comparing the H3K36me3 signal from a healthy subject to that of a colorectal adenocarcinoma patient we see 1500 genes that have K36me3 that is increased 2-fold or more in the cancer sample (FIG. 5L). Of these 1500 genes, 60 genes are known to be upregulated in colon adenocarcinoma (60 out of 172 COAD genes, p<10-20; FIG. 5L). Interestingly, while most genes with higher H3K36me3 gene body signal in cancer also show higher H3K4me3 at promotes we find examples of genes that disagree (FIG. 5M), attesting to the increased information that can be obtained by combining data from different histone marks.

Altogether, cf-ChIP-seq can probe the state of various genomic functionalities including promoters, enhancers, and gene bodies, and this information is highly informative on transcriptional activity in cells of origin.

Example 5

Figure 8:
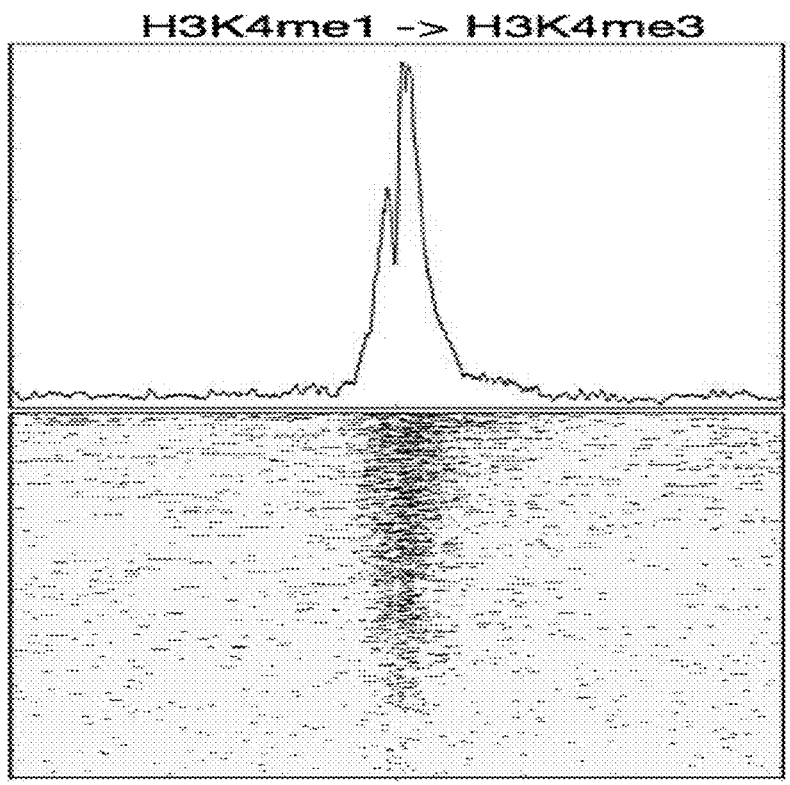
FIG. 8: A meta-plot (top) and heatmap (bottom) for 1,000 highly expressed promoters and the location relative to the transcriptional start site (TSS) of H3K4me3 in cf-nucleosomes from plasma that had already undergone cfChIP with anti-H3K4me1 antibodies.

Successive cfChIP and Additional Proteins for IP. During cf-ChIP most of the material from each blood sample is not captured on beads as it does not carry the target modification/protein. Performing immobilization in successive fashion, where after incubation with one antibody the supernatant is passed to the next one, dramatically increases efficiency in using limited material. Even after multiple cfChIP steps, the remaining material (which still contains most of the original cfDNA) can be used for DNA based assays. To test feasibility, successive cfChIPs for H3K4me1 followed by H3K4me3, and vice versa, were performed (FIG. 8). Good agreement between the results of the two experiments was found.

Figure 9:
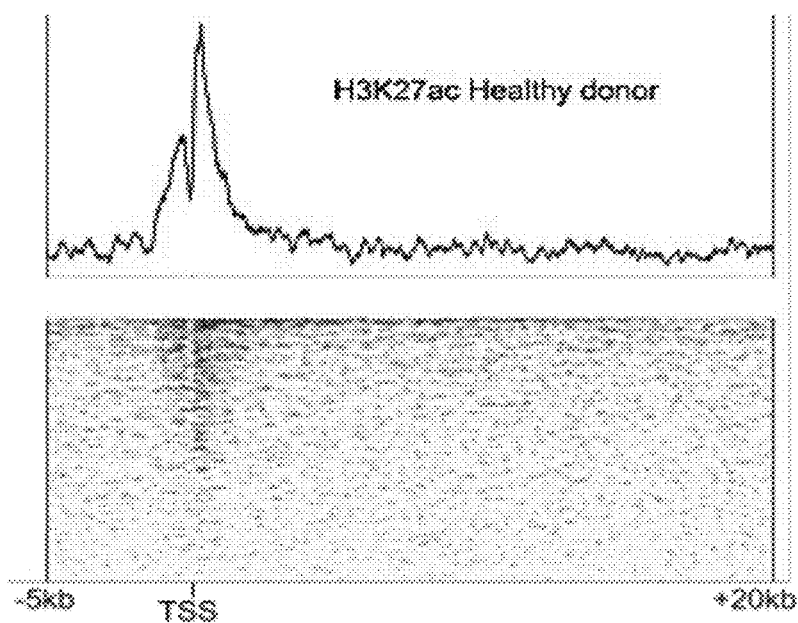
FIG. 9: Meta-plots (above) and heatmaps (below) for 1000 highly expressed promoters and the location relative to the TSS of H3K9Ac, H3K27ac and H2A.Zac in cf-nucleosomes from plasma of healthy patient and one colorectal cancer patient.
Figure 9:
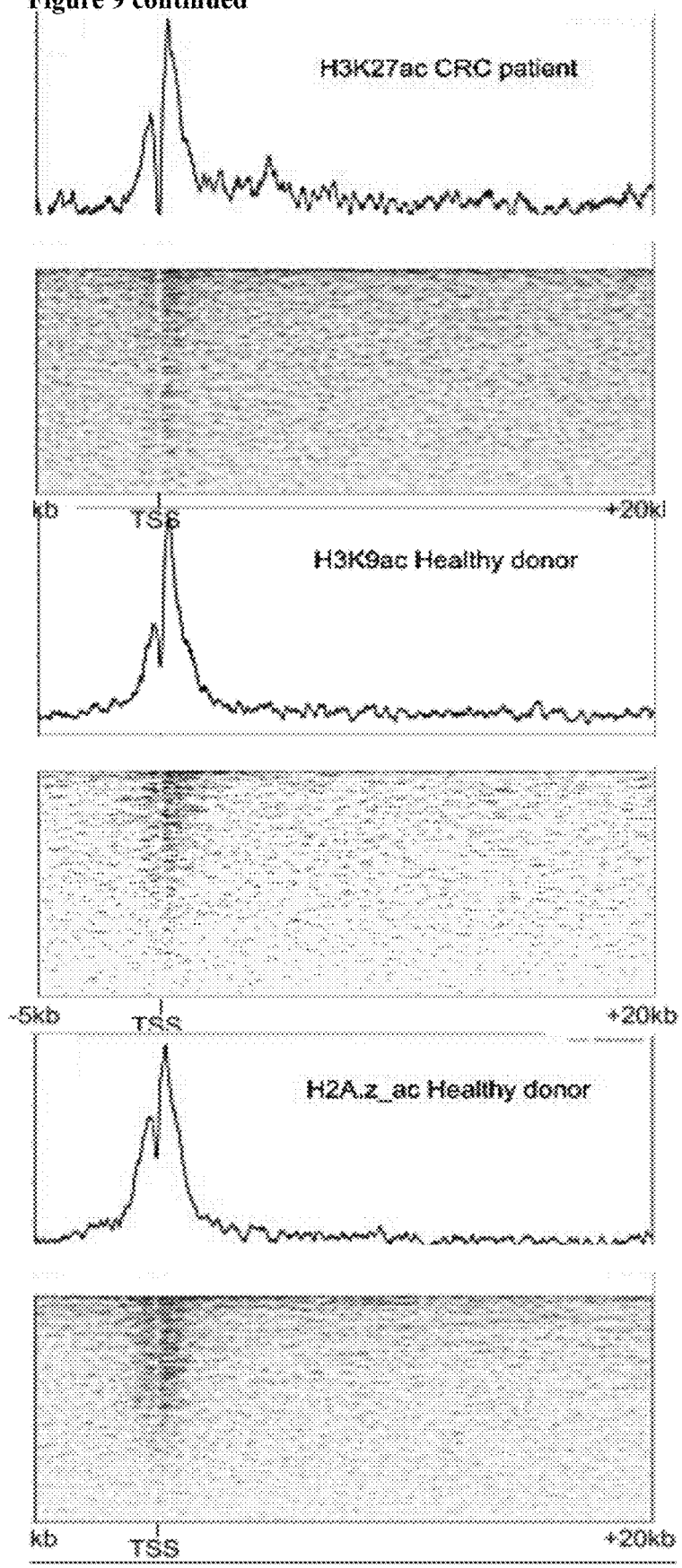

To test the ability of cf-ChIP to target acetylated histones we performed cf-ChIP with antibodies that target different acetylation sites on H3 (H3K9ac, H3K27ac) and acetylation of the H2A histone variant H2A.z (H2A.z_ac). All of these histone marks are associated with active transcription and indeed the histone acetylation marks showed typical patterns of enrichment around the transcription start site (TSS). Following cf-ChIP we aligned the sequenced DNA fragments to the human genome and performed meta gene analysis centered around the TSS of genes. As can be seen in FIG. 9, all acetyl marks showed marked enrichment around the TSS as would be expected. We also used the H3K27ac antibody on a colorectal cancer (CRC) patient and obtained a much higher signal compared to healthy donor suggesting that cf-ChIP of acetylated histones can have diagnostic value as well.

Example 6

Multiplexing by Proximity Ligation (MPL) ChIP

Figure 10A:
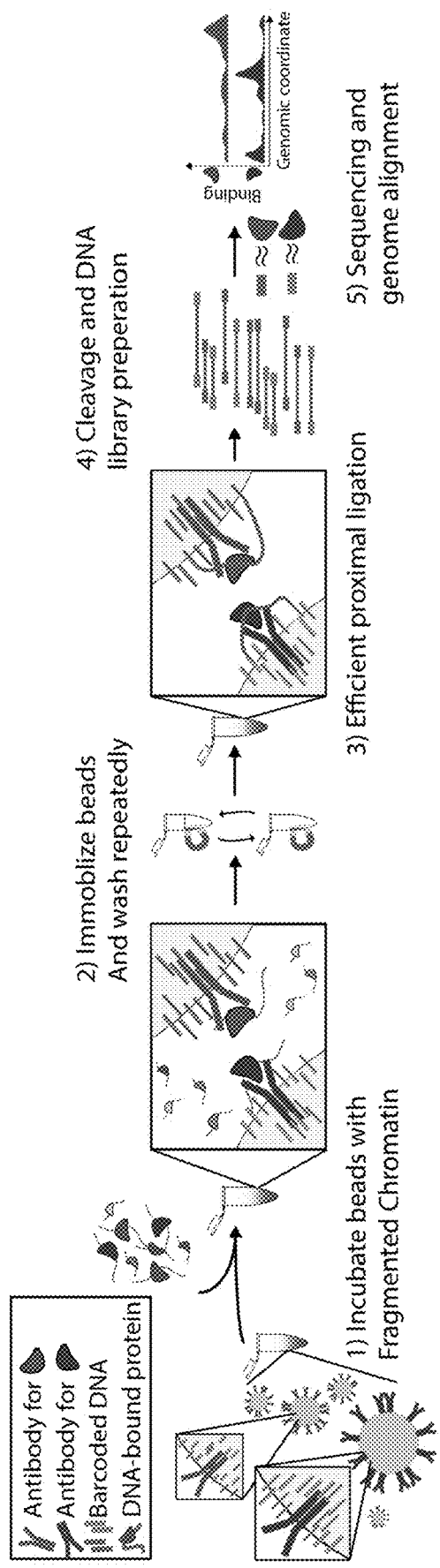
FIGS. 10A-D. (10A) Schematic drawing depicting the scheme of multiplexed ChIP-Seq. (10B) Schematic drawing of the experiment performed to test mixing during MPL based ChIP-Seq. Each rectangle represent an MPL barcoded surface that combines a unique barcode (BC1-BC4) in combination with anti H3K4me3 (K4) or anti H3K36me3 (K36) antibody each targeting a chromatin modification with distinct genomic location. Ellipses are chromatin from two yeast species: *S. cerevisiae* and *K. Lactis*. Various mixing is then performed either before library prep (pink circle in the middle) or after. (10C) A bar graph of the fraction of immobilized chromatin (shown as a % of the input) captured. (10D) A line graph meta-analysis of H3K4me3 and H3K36me3 distribution over a gene body from ChIP-seq signal from MPL barcoded surfaces.

Even more efficient than successive rounds of ChIP, is to perform immobilization for all antibodies in the same tube. Beads are bound by an antibody and a DNA adapter with a matching barcode specific for that antibody. Beads with different antibody/barcode are mixed in the same blood sample and after ChIP a ligation reaction is run on all the beads. Due to the proximity and solid phase immobilization of the cfDNA and adapter/barcode the reaction is specific. The cfDNA on each bead is labeled with the DNA adapter containing a barcode specific to the antibody that pulled it down. Multiplex sequencing is performed on all cfDNA pulled down by any protein together (FIG. 10A). We call this method multiplexing by proximity ligation (MPL). This method minimizes loss of material during subsequent transfers and increases the chance of the antibody finding its target in the sample.

Figure 10B:
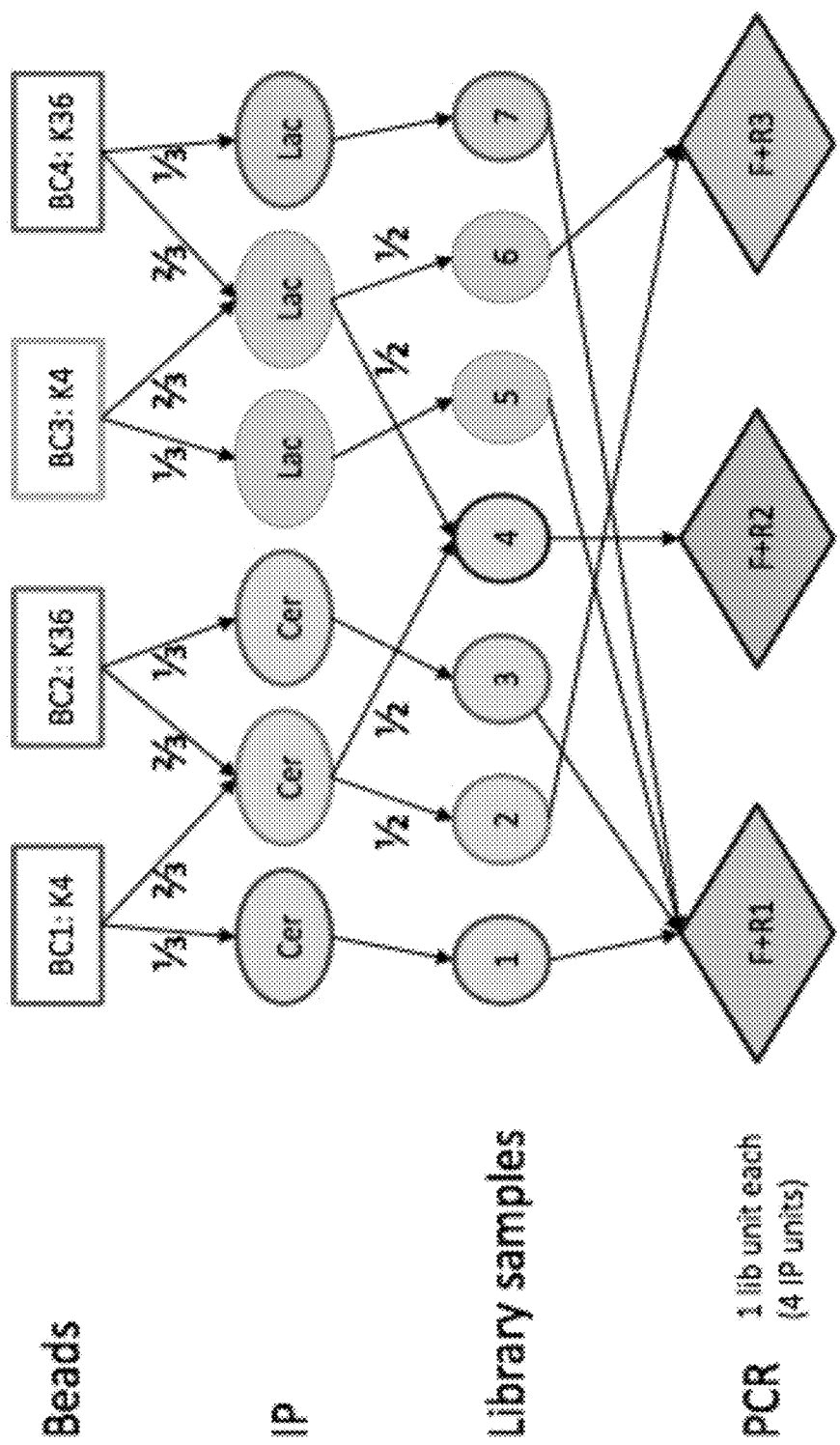

To prove the feasibility of MPL, we show that Chromatin can be Immunoprecipitated on surface containing a mixture of immobilized antibodies and barcoded DNA adapters (MPL barcoded surface, next generation sequencing (NGS) DNA libraries of chromatin immobilized on MPL barcoded surface can be generated and there is minimal mixing of chromatin between MPL barcoded surfaces. To test this, an experiment was devised as shown in FIG. 10B. A unique barcode was combined with a particular pull-down antibody (anti-H3K4me3 or anti-H3K36me3). The MPL barcoded surface were combined to perform ChIP on chromatin derived from two yeast species (S. cerevisiae and K. lactis), that can be differentiated by their genomic sequences. To test whether mixing occurs during IP we mixed K4 and K36 MPL barcoded surface with chromatin from a single source and follow the genomic distribution of the immobilized chromatin. K4 MPL barcoded surface and K36 MPL barcoded surface should ChIP chromatin skewed towards the 5' or 3' end of genes respectively. We also combined MPL barcoded surfaces, which were incubated with different yeast strains, after the IP step to test mixing during library preparation and/or later on in the process. Mixing the outputs of the IPs into a single tube prior to library preparation will reveal mixing that occurs at that stage, for example if *K. Lactis* DNA is sequenced with barcode 1 or barcode 2 we know that undesired mixing occurred during library preparation).

Figure 10C:
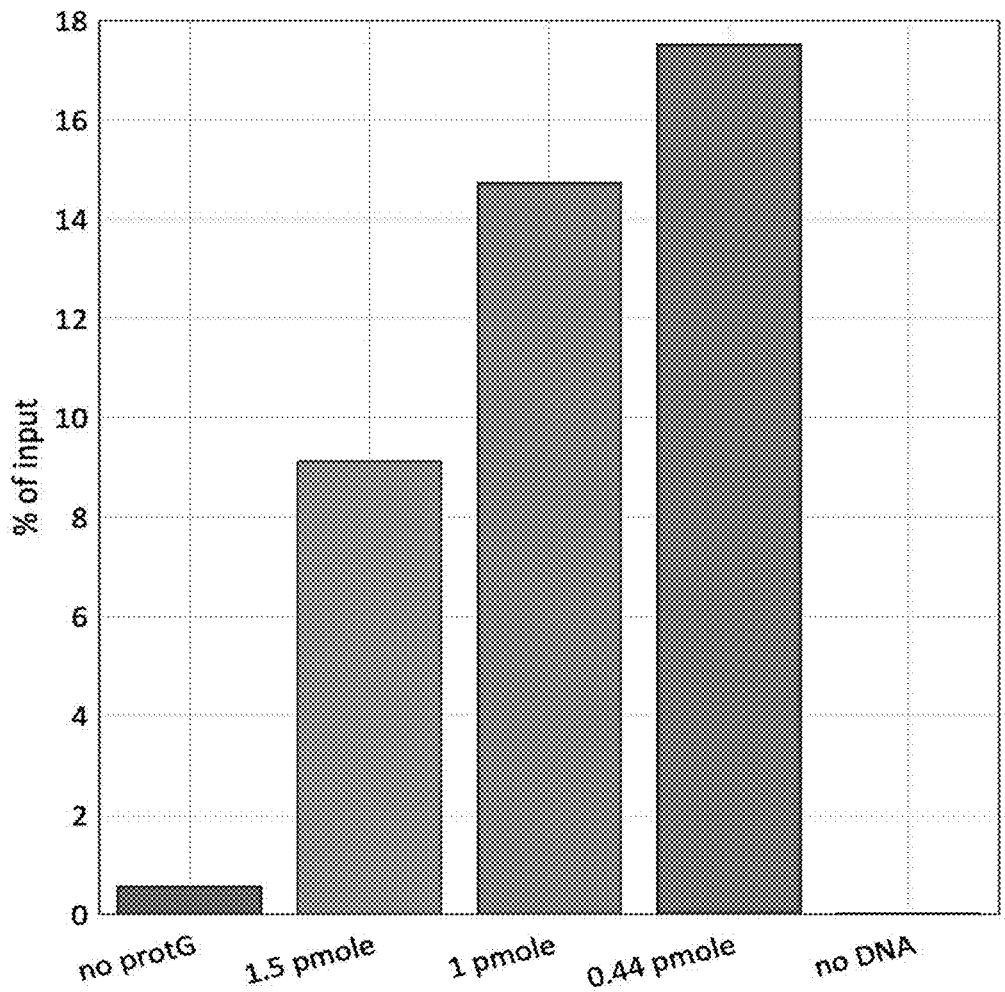

We performed qPCR following ChIP on MPL barcoded surface with decreasing amounts of DNA adapters (and hence increasing amounts of protein G that is used to recruit antibodies to MPL barcoded surface) and calculated the fraction of the chromatin that was immobilized compared to input (FIG. 10C). The fraction of Immunoprecipitated chromatin is comparable to results obtained by standard ChIP and is negatively correlated with the amount of immobilized barcoded DNA adapters (and hence positively correlated with the amount of immobilized antibodies). Note the extremely low levels of background signal (No protein G) proving that ChIP on MPL barcoded surface is dependent on immobilization of the antibody.

Figure 10D:
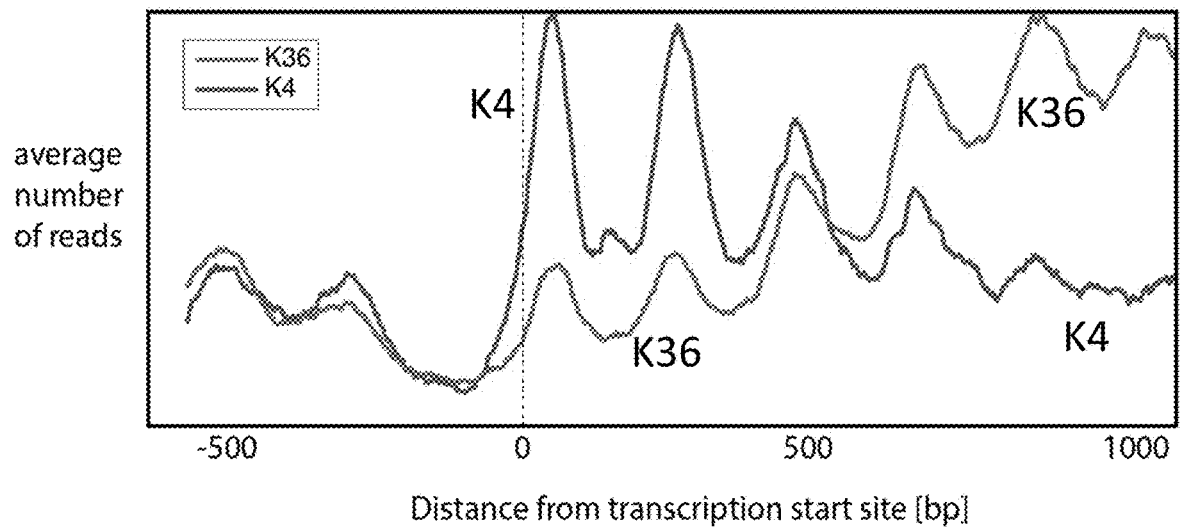

Next, we performed ChIP-seq with MPL barcoded surfaces containing antibodies against H3K4me3 or H3K36me3. Following sequencing the sequenced DNA fragments were aligned to the genome and the signal is presented as a meta plot along a typical gene (FIG. 10D). MPL barcoded surface with H3K4me3 and H3K36me3 yielded typical results, with H3K4me3 concentrated around gene 5', and H3K36me3 spread around gene bodies towards the 3' of the gene.

Finally, to test the amount of mixing, we count the number of reads obtained from MPL barcoded surface that is expected to be ligated only to *K. lactis* chromatin in 5 different samples. It was observed that the majority of the signal is indeed obtained from *K. lactis* DNA while only a small residual fraction is obtained from *S. cerevisiae*, suggesting that mixing is minimal even under conditions where the antibodies are not covalently bound to the MPL barcoded surface (binding is mediated by biotinylated protein G that is bound to the beads by strong biotin Streptavidin interaction). Indeed, mixed samples resulted in 80-90% correct alignment to *S. cerevisiae*.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of determining a cellular state, tissue of origin, cell type or a combination thereof of a cell that released its DNA, comprising:
   a. providing a plamsa or whole blood sample, wherein said sample comprises cell free DNA (cfDNA);
   b. contacting said sample with an antibody covalently immobilized on a paramagnetic bead, wherein said antibody binds to a histone, modified histone or histone variant;
   c. isolating said paramagnetic bead and any thereto bound histones and cfDNA;
   d. ligating a DNA adapter to said cfDNA bound to said protein and bead;
   e. eluting cfDNA ligated to a DNA adapter from said beads;
   f. sequencing said eluted cfDNA; and
   g. designating a cfDNA molecule comprising a DNA sequence of an informative genomic location as originating from a cell in a cellular state, originating from a tissue, originative from a cell type or a combination thereof, wherein association of said DNA-associated protein with said informative genomic location is indicative of said cellular state, tissue of origin, cell type or combination thereof in the cell that released said cfDNA;
   thereby determining a cellular state, tissue of origin cell type or combination thereof of a cell that released its DNA.

2. The method of claim 1, wherein said cell that released its DNA is a dead cell and the method is for detecting death of at least one of:
   a. a cell type in a subject,
   b. a tissue in a subject, and
   c. a cell in a cellular state in a subject.

3. The method of claim 1, wherein said cellular state is a disease state, optionally wherein said disease state is selected from bacteremia, cancer, pre-cancer, infection, neurodegenerative disease, tissue damage, cardiac disease or damage, brain disease or damage, gastrointestinal disease or damage, liver disease, inflammation, autoimmune disease, arthritis, liver disease, damage or inflammation, bowel inflammation, autoimmune disease, tissue damage from drug side effects, tissue necrosis, and diabetes.

4. The method of claim 1, wherein at least 500 genomes of cfDNA are provided or wherein said designating can be performed with as little as 0.1% of said cfDNA in said sample being from said cell type, said tissue, or said cellular state.

5. The method of claim 1, wherein said reagent is selected from an antibody or antigen binding fragment thereof, a protein, or a small molecule.

6. The method of claim 1, wherein said modified histone is selected from Histone 3 monomethylated lysine 4 (H3K4me1), Histone 3 demethylated lysine 4 (H3K4me2), Histone 3 trimethylated lysine 36 (H3K36me3) and Histone 3 trimethylated lysine 4 (H3K4me3), optionally wherein said reagent is an anti-modified histone antibody or fragment thereof.

7. The method of claim 1, wherein at least one of:
   a. association of said histone, modified histone or histone variant with said genomic location is indicative of active transcription and said genomic location is within a tissue, cell type or cellular state specific gene or enhancer element or is at a disease-specific mutation;
   b. wherein said histone, modified histone or histone variant is a marker of active transcription and said designating comprises comparing said sequenced cfDNA to a known transcriptional program of a tissue, cell type or cellular state, wherein a cfDNA with a sequence that is from a gene transcribed in said transcriptional program is from said tissue, cell type or cellular state; and
   c. wherein association of said histone, modified histone or histone variant with said genomic location is indicative of silenced transcription and said genomic location is within a repressor element, or a gene silenced in said tissue, cell-type or cellular state, or is at a disease-specific mutation.

8. The method of claim 1, comprising contacting said sample with at least 2 antibodies, wherein each antibody is covalently immobilized on a paramagnetic bead and said paramagnetic bead comprises a short DNA tag unique to each reagent, wherein upon sequencing said isolated cfDNA said short DNA tag identifies the antibody that isolated said cfDNA, or comprising performing steps a-d again using an antibody that binds to a second histone, modified histone or histone variant, and wherein said second histone, modified histone or histone variant is different from said first histone, modified histone or histone variant.

9. The method of claim 1, wherein said designating comprises at least one of:
  a. comparing said sequenced cfDNA to at least 10 genomic locations with the greatest unique association of said DNA-associated protein in a tissue, cell type or cellular state, and wherein a cfDNA with a sequence that is the same as a DNA sequence within said at least 10 genomic locations is considered to be from said tissue, cell type or cellular state;
  b. comparing the sequenced cfDNA to a DNA-protein association atlas of at least 5 cell types or tissues, wherein said atlas comprises at least 10 genomic location with the greatest unique association of said DNA-associated protein in each of said 5 cell types or tissues, and wherein a cfDNA with a sequence that is the same as a DNA sequence within said at least 10 genomic locations is considered to be from said tissue or cell type; and
  c. comparing the sequenced cfDNA to a transcriptional program atlas of at least 5 transcriptional programs, wherein said atlas comprises at least one genomic location with the greatest unique association of said DNA-associated protein in each of said 5 transcriptional programs and wherein a cfDNA with a sequence that is the same as a DNA sequence within said at least one genomic location indicates activation of said transcriptional program.

10. The method of claim 1, wherein said cellular state is selected from: hypoxia, inflammation, ER stress, mitochondrial stress, interferon response, quiescence, senescence, cycling, malignant, and calcium flux.

11. The method of claim 1, wherein said informative genomic location is selected from a promoter, an enhancer element, a silencer element, a gene body and a disease-associated mutation.

12. The method of claim 11, wherein:
  a. said histone, modified histone or histone variant is a marker of active transcription and said disease associated mutation is within an oncogene or
  b. said histone, modified histone or histone variant is a marker of silenced transcription and said disease associated mutation is within a tumor suppressor gene.

13. The method of claim 1, wherein said sample is from a subject and said method is for use in detecting a disease state in said subject.

14. The method of claim 13, wherein said detecting a disease state comprises at least one of:
  a. early detection of said disease state;
  b. detection of residual metastatic disease; and
  c. monitoring of disease progression with or without treatment.

15. The method of claim 1, further comprising treating said subject with a suitable treatment based on the cellular state, tissue of origin, cell type or a combination thereof of said cell that died in said subject.

16. The method of claim 1, wherein said sequencing is Next Generation Sequencing, High Throughput Sequencing or Massively Parallel Sequencing.

17. The method of claim 1, wherein said adapter is a sequencing adapter.

18. The method of claim 17, wherein said sequencing adapter is a barcoded sequencing adapter.

* * * * *